United States Patent
Harris et al.

(10) Patent No.: US 11,701,115 B2
(45) Date of Patent: Jul. 18, 2023

(54) METHODS OF STAPLING TISSUE

(71) Applicant: Cilag GmbH International, Zug (CH)

(72) Inventors: Jason L. Harris, Lebanon, OH (US);
Mark S. Zeiner, Mason, OH (US);
Janna B. Volz, West Chester, OH (US);
Nichole Y. Kwee, Cincinnati, OH (US);
Frederick E. Shelton, IV, Hillsboro, OH (US)

(73) Assignee: Cilag GmbH International, Zug (CH)

(*) Notice: Subject to any disclaimer, the term of this patent is extended or adjusted under 35 U.S.C. 154(b) by 436 days.

(21) Appl. No.: 16/860,332

(22) Filed: Apr. 28, 2020

(65) Prior Publication Data
US 2020/0275930 A1 Sep. 3, 2020

Related U.S. Application Data

(63) Continuation of application No. 15/385,953, filed on Dec. 21, 2016, now Pat. No. 10,675,026.

(51) Int. Cl.
*A61B 17/072* (2006.01)
*A61B 34/30* (2016.01)
(Continued)

(52) U.S. Cl.
CPC .... *A61B 17/07207* (2013.01); *A61B 17/0644* (2013.01); *A61B 17/0682* (2013.01);
(Continued)

(58) Field of Classification Search
CPC .............. A61B 17/068; A61B 17/072; A61B 17/07207; A61B 2017/07214; A61B 2017/07257; A61B 2017/07271
See application file for complete search history.

(56) References Cited

U.S. PATENT DOCUMENTS 66,052 A 6/1867 Smith
662,587 A 11/1900 Blake
(Continued)

FOREIGN PATENT DOCUMENTS

AU 2012200594 A1 2/2012
AU 2012203035 A1 6/2012
(Continued)

OTHER PUBLICATIONS

ASTM procedure D2240-00, "Standard Test Method for Rubber Property-Durometer Hardness," (Published Aug. 2000).
(Continued)

*Primary Examiner* — Martin T Ton
(74) *Attorney, Agent, or Firm* — Frost Brown Todd LLP

(57) ABSTRACT

A method of stapling tissue is disclosed. The method can include obtaining a staple cartridge including a plurality of staples, wherein each staple has a base and a leg extending from the base. The stapling method can also include firing the staples from the staple cartridge, wherein the staples are fired into tissue in a staple line. The staple line can include a first portion having a first flexibility and a second portion having a second flexibility, wherein the second flexibility is different than the first flexibility. A method of stapling tissue can also include adapting an anvil with an anvil plate having an arrangement of staple-forming pockets that differs from the staple-forming pockets in the anvil.

17 Claims, 74 Drawing Sheets

(51) Int. Cl.
*A61B 90/00* (2016.01)
*A61B 17/064* (2006.01)
*A61B 17/068* (2006.01)
*A61B 17/00* (2006.01)
*A61B 17/29* (2006.01)

(52) U.S. Cl.
CPC ............ *A61B 17/072* (2013.01); *A61B 34/30* (2016.02); *A61B 90/03* (2016.02); *A61B 17/068* (2013.01); *A61B 2017/00017* (2013.01); *A61B 2017/00039* (2013.01); *A61B 2017/0046* (2013.01); *A61B 2017/00398* (2013.01); *A61B 2017/00473* (2013.01); *A61B 2017/00477* (2013.01); *A61B 2017/00734* (2013.01); *A61B 2017/00991* (2013.01); *A61B 2017/0641* (2013.01); *A61B 2017/0725* (2013.01); *A61B 2017/07214* (2013.01); *A61B 2017/07221* (2013.01); *A61B 2017/07228* (2013.01); *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/07285* (2013.01); *A61B 2017/2927* (2013.01); *A61B 2017/2933* (2013.01); *A61B 2090/032* (2016.02); *A61B 2090/0808* (2016.02); *A61B 2090/0811* (2016.02); *A61B 2090/0814* (2016.02)

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 903,739 A | 11/1908 | Lesemann |
| 951,393 A | 3/1910 | Hahn |
| 1,075,556 A | 10/1913 | Fenoughty |
| 1,082,105 A | 12/1913 | Anderson |
| 1,188,721 A | 6/1916 | Bittner |
| 1,306,107 A | 6/1919 | Elliott |
| 1,314,601 A | 9/1919 | McCaskey |
| 1,466,128 A | 8/1923 | Hallenbeck |
| 1,677,337 A | 7/1928 | Grove |
| 1,794,907 A | 3/1931 | Kelly |
| 1,849,427 A | 3/1932 | Hook |
| 1,912,783 A | 6/1933 | Meyer |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | La Chapelle |
| 2,120,951 A | 6/1938 | Hodgman |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,108 A | 12/1940 | Ridgway |
| 2,224,882 A | 12/1940 | Peck |
| 2,256,295 A | 9/1941 | Schmid |
| 2,318,379 A | 5/1943 | Davis et al. |
| 2,329,440 A | 9/1943 | Place |
| 2,377,581 A | 6/1945 | Shaffrey |
| 2,406,389 A | 8/1946 | Lee |
| 2,420,552 A | 5/1947 | Morrill |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,825,178 A | 3/1958 | Hawkins |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse |
| 3,032,769 A | 5/1962 | Palmer |
| 3,035,256 A | 5/1962 | Egbert |
| 3,060,972 A | 10/1962 | Sheldon |
| 3,075,062 A | 1/1963 | Laccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,252,643 A | 5/1966 | Strekopytov et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,315,863 A | 4/1967 | O'Dea |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,604,561 A | 9/1971 | Mallina et al. |
| 3,608,549 A | 9/1971 | Merrill |
| 3,618,842 A | 11/1971 | Bryan |
| 3,635,394 A | 1/1972 | Natelson |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |
| 3,661,666 A | 5/1972 | Foster et al. |
| 3,662,939 A | 5/1972 | Bryan |
| 3,685,250 A | 8/1972 | Henry et al. |
| 3,688,966 A | 9/1972 | Perkins et al. |
| 3,692,224 A | 9/1972 | Astafiev et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |

(56) References Cited

U.S. PATENT DOCUMENTS

| | | |
|---|---|---|
| 3,815,476 A | 6/1974 | Green et al. |
| 3,819,100 A | 6/1974 | Noiles et al. |
| 3,821,919 A | 7/1974 | Knohl |
| 3,822,818 A | 7/1974 | Strekopytov et al. |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |
| 3,894,174 A | 7/1975 | Cartun |
| 3,899,829 A | 8/1975 | Storm et al. |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,047,654 A | 9/1977 | Alvarado |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,149,461 A | 4/1979 | Simeth |
| 4,154,122 A | 5/1979 | Severin |
| 4,160,857 A | 7/1979 | Nardella et al. |
| 4,169,476 A | 10/1979 | Hiltebrandt |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,250,817 A | 2/1981 | Michel |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |

(56) References Cited

U.S. PATENT DOCUMENTS

| | | |
|---|---|---|
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,514,477 A | 4/1985 | Kobayashi |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,726,247 A | 2/1988 | Hormann |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,788,978 A | 12/1988 | Strekopytov et al. |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,495 A | 4/1989 | Hormann |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |

(56) References Cited

U.S. PATENT DOCUMENTS

| | | |
|---|---|---|
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,868,958 A | 9/1989 | Suzuki et al. |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,950,268 A | 8/1990 | Rink |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Arns et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,222 A | 4/1991 | Her |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | Salls et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,100,422 A | 3/1992 | Berguer et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,151 A | 10/1992 | Imran |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,164,652 A | 11/1992 | Johnson et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |

(56) References Cited

U.S. PATENT DOCUMENTS

| | | |
|---|---|---|
| 5,173,133 A | 12/1992 | Morin et al. |
| 5,176,677 A | 1/1993 | Wuchinich |
| 5,176,688 A | 1/1993 | Narayan et al. |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,188,126 A | 2/1993 | Fabian et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,236,629 A | 8/1993 | Mahabadi et al. |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,251,801 A | 10/1993 | Ruckdeschel et al. |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,269,794 A | 12/1993 | Rexroth |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,281,400 A | 1/1994 | Berry, Jr. |
| 5,282,806 A | 2/1994 | Haber et al. |
| 5,282,826 A | 2/1994 | Quadri |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,291,133 A | 3/1994 | Gokhale et al. |
| 5,292,053 A | 3/1994 | Bilotti et al. |
| 5,293,024 A | 3/1994 | Sugahara et al. |
| 5,297,714 A | 3/1994 | Kramer |
| 5,300,087 A | 4/1994 | Knoepfler |
| 5,302,148 A | 4/1994 | Heinz |
| 5,303,606 A | 4/1994 | Kokinda |
| 5,304,204 A | 4/1994 | Bregen |
| D347,474 S | 5/1994 | Olson |
| 5,307,976 A | 5/1994 | Olson et al. |
| 5,308,353 A | 5/1994 | Beurrier |
| 5,308,358 A | 5/1994 | Bond et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,318,589 A | 6/1994 | Lichtman |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,486 A | 7/1994 | Wilk |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,338,317 A | 8/1994 | Hasson et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,104 A | 9/1994 | Main et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |

(56) References Cited

U.S. PATENT DOCUMENTS

| | | |
|---|---|---|
| 5,352,229 A | 10/1994 | Goble et al. |
| 5,352,235 A | 10/1994 | Koros et al. |
| 5,352,238 A | 10/1994 | Green et al. |
| 5,353,798 A | 10/1994 | Sieben |
| 5,354,215 A | 10/1994 | Viracola |
| 5,354,250 A | 10/1994 | Christensen |
| 5,354,303 A | 10/1994 | Spaeth et al. |
| 5,355,897 A | 10/1994 | Pietrafitta et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,368,599 A | 11/1994 | Hirsch et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,072 A | 2/1995 | Imran |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,645 A | 7/1995 | Smith et al. |
| 5,431,654 A | 7/1995 | Nic |
| 5,431,666 A | 7/1995 | Sauer et al. |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avital, I |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,824 A | 10/1995 | Fontayne et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |

(56) References Cited

U.S. PATENT DOCUMENTS

| | | |
|---|---|---|
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,474,738 A | 12/1995 | Nichols et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,308 A | 12/1995 | Cartmell et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,377 A | 1/1996 | Smith et al. |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,507,773 A | 4/1996 | Huitema et al. |
| 5,509,596 A | 4/1996 | Green et al. |
| 5,509,916 A | 4/1996 | Taylor |
| 5,509,918 A | 4/1996 | Romano |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,945 A | 8/1996 | Fritzsch |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,694 A | 10/1996 | Sauer et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A * | 11/1996 | Green .............. A61B 17/07207 227/181.1 |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |

(56) References Cited

U.S. PATENT DOCUMENTS

| | | |
|---|---|---|
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,611,813 A | 3/1997 | Lichtman |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,637,110 A | 6/1997 | Pennybacker et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,656,917 A | 8/1997 | Theobald |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,664,404 A | 9/1997 | Ivanov et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoil |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,704,792 A | 1/1998 | Sobhani |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |

(56) References Cited

U.S. PATENT DOCUMENTS

| | | |
|---|---|---|
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,712 A | 3/1998 | Adair |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,746,770 A | 5/1998 | Zeitels et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |
| 5,766,186 A | 6/1998 | Faraz et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,640 A | 6/1998 | Jacobus et al. |
| 5,769,748 A | 6/1998 | Eyerly et al. |
| 5,769,791 A | 6/1998 | Benaron et al. |
| 5,769,892 A | 6/1998 | Kingwell |
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,798,752 A | 8/1998 | Buxton et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Gelb et al. |
| 5,804,936 A | 9/1998 | Brodsky et al. |
| 5,806,676 A | 9/1998 | Wasgien |
| 5,807,241 A | 9/1998 | Heimberger |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,240 A | 9/1998 | Robertson |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Llvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,664 A | 2/1999 | Speier et al. |
| 5,868,760 A | 2/1999 | McGuckin, Jr. |
| 5,868,790 A | 2/1999 | Vincent et al. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |

(56) References Cited

U.S. PATENT DOCUMENTS

| | | |
|---|---|---|
| 5,878,937 A | 3/1999 | Green et al. |
| 5,878,938 A | 3/1999 | Bittner et al. |
| 5,881,777 A | 3/1999 | Bassi et al. |
| 5,881,943 A | 3/1999 | Heck et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,863 A | 4/1999 | Yoon |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,922,001 A | 7/1999 | Yoon |
| 5,922,003 A | 7/1999 | Anctil et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,275 A | 2/2000 | Horvitz et al. |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |

(56) References Cited

U.S. PATENT DOCUMENTS

| | | | |
|---|---|---|---|
| 6,077,280 A | 6/2000 | Fossum | |
| 6,077,286 A | 6/2000 | Cuschieri et al. | |
| 6,077,290 A | 6/2000 | Marini | |
| 6,079,606 A | 6/2000 | Milliman et al. | |
| 6,080,181 A | 6/2000 | Jensen et al. | |
| 6,082,577 A | 7/2000 | Coates et al. | |
| 6,083,191 A | 7/2000 | Rose | |
| 6,083,223 A | 7/2000 | Baker | |
| 6,083,234 A | 7/2000 | Nicholas et al. | |
| 6,083,242 A | 7/2000 | Cook | |
| 6,086,544 A | 7/2000 | Hibner et al. | |
| 6,086,600 A | 7/2000 | Kortenbach | |
| 6,090,106 A | 7/2000 | Goble et al. | |
| 6,090,123 A | 7/2000 | Culp et al. | |
| 6,093,186 A | 7/2000 | Goble | |
| 6,094,021 A | 7/2000 | Noro et al. | |
| D429,252 S | 8/2000 | Haitani et al. | |
| 6,099,537 A | 8/2000 | Sugai et al. | |
| 6,099,551 A | 8/2000 | Gabbay | |
| 6,102,271 A | 8/2000 | Longo et al. | |
| 6,102,926 A | 8/2000 | Tartaglia et al. | |
| 6,104,162 A | 8/2000 | Sainsbury et al. | |
| 6,104,304 A | 8/2000 | Clark et al. | |
| 6,106,511 A | 8/2000 | Jensen | |
| 6,109,500 A | 8/2000 | Alli et al. | |
| 6,110,187 A | 8/2000 | Donlon | |
| 6,113,618 A | 9/2000 | Nic | |
| 6,117,148 A | 9/2000 | Ravo et al. | |
| 6,117,158 A | 9/2000 | Measamer et al. | |
| 6,119,913 A | 9/2000 | Adams et al. | |
| 6,120,433 A | 9/2000 | Mizuno et al. | |
| 6,120,462 A | 9/2000 | Hibner et al. | |
| 6,123,241 A | 9/2000 | Walter et al. | |
| 6,123,701 A | 9/2000 | Nezhat | |
| H1904 H | 10/2000 | Yates et al. | |
| RE36,923 E | 10/2000 | Hiroi et al. | |
| 6,126,058 A | 10/2000 | Adams et al. | |
| 6,126,359 A | 10/2000 | Dittrich et al. | |
| 6,126,670 A | 10/2000 | Walker et al. | |
| 6,131,789 A | 10/2000 | Schulze et al. | |
| 6,131,790 A | 10/2000 | Piraka | |
| 6,132,368 A | 10/2000 | Cooper | |
| 6,134,962 A | 10/2000 | Sugitani | |
| 6,139,546 A | 10/2000 | Koenig et al. | |
| 6,142,149 A | 11/2000 | Steen | |
| 6,142,933 A | 11/2000 | Longo et al. | |
| 6,147,135 A | 11/2000 | Yuan et al. | |
| 6,149,660 A | 11/2000 | Laufer et al. | |
| 6,151,323 A | 11/2000 | O'Connell et al. | |
| 6,152,935 A | 11/2000 | Kammerer et al. | |
| 6,155,473 A | 12/2000 | Tompkins et al. | |
| 6,156,056 A | 12/2000 | Kearns et al. | |
| 6,157,169 A | 12/2000 | Lee | |
| 6,159,146 A | 12/2000 | El Gazayerli | |
| 6,159,200 A | 12/2000 | Verdura et al. | |
| 6,159,224 A | 12/2000 | Yoon | |
| 6,162,208 A | 12/2000 | Hipps | |
| 6,162,220 A | 12/2000 | Nezhat | |
| 6,162,537 A | 12/2000 | Martin et al. | |
| 6,165,175 A | 12/2000 | Wampler et al. | |
| 6,165,184 A | 12/2000 | Verdura et al. | |
| 6,165,188 A | 12/2000 | Saadat et al. | |
| 6,167,185 A | 12/2000 | Smiley et al. | |
| 6,168,605 B1 | 1/2001 | Measamer et al. | |
| 6,171,305 B1 | 1/2001 | Sherman | |
| 6,171,316 B1 | 1/2001 | Kovac et al. | |
| 6,171,330 B1 | 1/2001 | Benchetrit | |
| 6,173,074 B1 | 1/2001 | Russo | |
| 6,174,308 B1 | 1/2001 | Goble et al. | |
| 6,174,309 B1 | 1/2001 | Wrublewski et al. | |
| 6,174,318 B1 | 1/2001 | Bates et al. | |
| 6,175,290 B1 | 1/2001 | Forsythe et al. | |
| 6,179,195 B1 | 1/2001 | Adams et al. | |
| 6,179,776 B1 | 1/2001 | Adams et al. | |
| 6,181,105 B1 | 1/2001 | Cutolo et al. | |
| 6,182,673 B1 | 2/2001 | Kindermann et al. | |
| 6,185,356 B1 | 2/2001 | Parker et al. | |
| 6,186,142 B1 | 2/2001 | Schmidt et al. | |
| 6,186,957 B1 | 2/2001 | Milam | |
| 6,187,003 B1 | 2/2001 | Buysse et al. | |
| 6,190,386 B1 | 2/2001 | Rydell | |
| 6,193,129 B1 | 2/2001 | Bittner et al. | |
| 6,197,042 B1 | 3/2001 | Ginn et al. | |
| 6,200,311 B1 | 3/2001 | Danek et al. | |
| 6,200,330 B1 | 3/2001 | Benderev et al. | |
| 6,202,914 B1 | 3/2001 | Geiste et al. | |
| 6,206,894 B1 | 3/2001 | Thompson et al. | |
| 6,206,897 B1 | 3/2001 | Jamiolkowski et al. | |
| 6,206,903 B1 | 3/2001 | Ramans | |
| 6,206,904 B1 | 3/2001 | Ouchi | |
| 6,209,414 B1 | 4/2001 | Uneme | |
| 6,210,403 B1 | 4/2001 | Klicek | |
| 6,211,626 B1 | 4/2001 | Lys et al. | |
| 6,213,999 B1 | 4/2001 | Platt, Jr. et al. | |
| 6,214,028 B1 | 4/2001 | Yoon et al. | |
| 6,220,368 B1 | 4/2001 | Ark et al. | |
| 6,221,007 B1 | 4/2001 | Green | |
| 6,221,023 B1 | 4/2001 | Matsuba et al. | |
| 6,223,100 B1 | 4/2001 | Green | |
| 6,223,835 B1 | 5/2001 | Habedank et al. | |
| 6,224,617 B1 | 5/2001 | Saadat et al. | |
| 6,228,080 B1 | 5/2001 | Gines | |
| 6,228,081 B1 | 5/2001 | Goble | |
| 6,228,083 B1 | 5/2001 | Lands et al. | |
| 6,228,084 B1 | 5/2001 | Kirwan, Jr. | |
| 6,228,089 B1 | 5/2001 | Wahrburg | |
| 6,228,098 B1 | 5/2001 | Kayan et al. | |
| 6,231,565 B1 | 5/2001 | Tovey et al. | |
| 6,234,178 B1 | 5/2001 | Goble et al. | |
| 6,235,036 B1 | 5/2001 | Gardner et al. | |
| 6,237,604 B1 | 5/2001 | Burnside et al. | |
| 6,238,384 B1 | 5/2001 | Peer | |
| 6,241,139 B1 | 6/2001 | Milliman et al. | |
| 6,241,140 B1 | 6/2001 | Adams et al. | |
| 6,241,723 B1 | 6/2001 | Heim et al. | |
| 6,245,084 B1 | 6/2001 | Mark et al. | |
| 6,248,116 B1 | 6/2001 | Chevillon et al. | |
| 6,248,117 B1 | 6/2001 | Blatter | |
| 6,249,076 B1 | 6/2001 | Madden et al. | |
| 6,249,105 B1 | 6/2001 | Andrews et al. | |
| 6,250,532 B1 | 6/2001 | Green et al. | |
| 6,251,485 B1 | 6/2001 | Harris et al. | |
| D445,745 S | 7/2001 | Norman | |
| 6,254,534 B1 | 7/2001 | Butler et al. | |
| 6,254,619 B1 | 7/2001 | Garabet et al. | |
| 6,254,642 B1 | 7/2001 | Taylor | |
| 6,258,107 B1 | 7/2001 | Balazs et al. | |
| 6,261,246 B1 | 7/2001 | Pantages et al. | |
| 6,261,286 B1 | 7/2001 | Goble et al. | |
| 6,261,679 B1 | 7/2001 | Chen et al. | |
| 6,264,086 B1 | 7/2001 | McGuckin, Jr. | |
| 6,264,087 B1 | 7/2001 | Whitman | |
| 6,264,617 B1 | 7/2001 | Bales et al. | |
| 6,269,997 B1 | 8/2001 | Balazs et al. | |
| 6,270,508 B1 | 8/2001 | Klieman et al. | |
| 6,270,916 B1 | 8/2001 | Sink et al. | |
| 6,273,252 B1 | 8/2001 | Mitchell | |
| 6,273,876 B1 | 8/2001 | Klima et al. | |
| 6,273,897 B1 | 8/2001 | Dalessandro et al. | |
| 6,277,114 B1 | 8/2001 | Bullivant et al. | |
| 6,280,407 B1 | 8/2001 | Manna et al. | |
| 6,283,981 B1 | 9/2001 | Beaupre | |
| 6,293,927 B1 | 9/2001 | McGuckin, Jr. | |
| 6,293,942 B1 | 9/2001 | Goble et al. | |
| 6,296,640 B1 | 10/2001 | Wampler et al. | |
| 6,302,311 B1 | 10/2001 | Adams et al. | |
| 6,302,743 B1 | 10/2001 | Chiu et al. | |
| 6,305,891 B1 | 10/2001 | Burlingame | |
| 6,306,134 B1 | 10/2001 | Goble et al. | |
| 6,306,149 B1 | 10/2001 | Meade | |
| 6,306,424 B1 | 10/2001 | Vyakarnam et al. | |
| 6,309,397 B1 | 10/2001 | Julian et al. | |
| 6,309,400 B2 | 10/2001 | Beaupre | |
| 6,309,403 B1 | 10/2001 | Minor et al. | |

(56) References Cited

U.S. PATENT DOCUMENTS

| | | |
|---|---|---|
| 6,312,435 B1 | 11/2001 | Wallace et al. |
| 6,315,184 B1 | 11/2001 | Whitman |
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,361,542 B1 | 3/2002 | Dimitriu et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,656 B2 | 9/2002 | Brissette et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,063 B1 | 11/2002 | Frigard |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 | 12/2002 | Lang et al. |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,506,399 B2 | 1/2003 | Donovan |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |

(56) References Cited

U.S. PATENT DOCUMENTS

| | | |
|---|---|---|
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,844 B2 | 4/2003 | Lee et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,569,173 B1 | 5/2003 | Blatter et al. |
| 6,572,629 B2 | 6/2003 | Kalloo et al. |
| 6,575,969 B1 | 6/2003 | Rittman, III et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B2 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,626,938 B1 | 9/2003 | Butaric et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B2 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |

(56) References Cited

U.S. PATENT DOCUMENTS

| | | |
|---|---|---|
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,825 B2 | 6/2004 | Shoenman et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,801,009 B2 | 10/2004 | Makaran et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,860,169 B2 | 3/2005 | Shinozaki |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B1 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,927,315 B2 | 8/2005 | Heinecke et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |

(56) References Cited

U.S. PATENT DOCUMENTS

| | | |
|---|---|---|
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 6,999,821 B2 | 2/2006 | Jenney et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,005,828 B2 | 2/2006 | Karikomi |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,412 B1 | 7/2006 | Reynolds et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |

(56) References Cited

U.S. PATENT DOCUMENTS

| | | |
|---|---|---|
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,363 B2 | 9/2006 | Nishizawa et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,201 B2 | 9/2006 | Truckai et al. |
| 7,112,214 B2 | 9/2006 | Peterson et al. |
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,846 B2 | 1/2007 | Dycus et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,160,311 B2 | 1/2007 | Blatter et al. |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,169,146 B2 | 1/2007 | Truckai et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,197,965 B1 | 4/2007 | Anderson |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,205,959 B2 | 4/2007 | Henriksson |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |

(56) References Cited

U.S. PATENT DOCUMENTS

| | | |
|---|---|---|
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,273,488 B2 | 9/2007 | Nakamura et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,311,709 B2 | 12/2007 | Truckai et al. |
| 7,313,430 B2 | 12/2007 | Urquhart et al. |
| 7,314,473 B2 | 1/2008 | Jinno et al. |
| 7,320,704 B2 | 1/2008 | Lashinski et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,183 B2 | 2/2008 | Reddy et al. |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,398 B2 | 4/2008 | Kanazawa |
| 7,354,440 B2 | 4/2008 | Truckai et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,430,849 B2 | 10/2008 | Coutts et al. |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |

(56) References Cited

U.S. PATENT DOCUMENTS

| | | | |
|---|---|---|---|
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| D580,942 S | 11/2008 | Oshiro et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,572,298 B2 | 8/2009 | Roller et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,605,826 B2 | 10/2009 | Sauer |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| 7,618,427 B2 | 11/2009 | Ortiz et al. |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |
| 7,625,662 B2 | 12/2009 | Vaisnys et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |

(56) References Cited

U.S. PATENT DOCUMENTS

| | | |
|---|---|---|
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,016 B2 | 1/2010 | Nycz et al. |
| 7,644,484 B2 | 1/2010 | Vereschagin |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,670,337 B2 | 3/2010 | Young |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 * | 3/2010 | Shah ............... A61B 17/07207 227/181.1 |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,706,853 B2 | 4/2010 | Hacker et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,735,704 B2 | 6/2010 | Bilotti |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |

(56) References Cited

U.S. PATENT DOCUMENTS

| | | |
|---|---|---|
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,614 B1 | 8/2010 | McGonagle et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,782,382 B2 | 8/2010 | Fujimura |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,076 B2 | 10/2010 | Borovsky et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Offers et al. |
| 7,839,109 B2 | 11/2010 | Carmen, Jr. et al. |
| 7,840,253 B2 | 11/2010 | Tremblay et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,845,912 B2 | 12/2010 | Sung et al. |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,877,869 B2 | 2/2011 | Mehdizadeh et al. |
| 7,879,063 B2 | 2/2011 | Khosravi |
| 7,879,070 B2 | 2/2011 | Ortiz et al. |
| 7,879,367 B2 | 2/2011 | Heublein et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,887,755 B2 | 2/2011 | Mingerink et al. |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |

(56) References Cited

U.S. PATENT DOCUMENTS

| | | |
|---|---|---|
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,300 B2 | 5/2011 | Rethy et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,948,381 B2 | 5/2011 | Lindsay et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,952,464 B2 | 5/2011 | Nikitin et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |
| 7,976,563 B2 | 7/2011 | Summerer |
| 7,979,137 B2 | 7/2011 | Tracey et al. |
| 7,980,443 B2 | 7/2011 | Scheib et al. |
| 7,981,025 B2 | 7/2011 | Pool et al. |
| 7,981,102 B2 | 7/2011 | Patel et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,835 B2 | 10/2011 | Yasuda et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |

(56) References Cited

U.S. PATENT DOCUMENTS

| | | |
|---|---|---|
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,052,697 B2 | 11/2011 | Phillips |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,157,834 B2 | 4/2012 | Conlon |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |

(56) References Cited

U.S. PATENT DOCUMENTS

| | | |
|---|---|---|
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,235,274 B2 | 8/2012 | Cappola |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |

(56) References Cited

U.S. PATENT DOCUMENTS

| | | |
|---|---|---|
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,948 B2 | 1/2013 | Bahney |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,368,327 B2 | 2/2013 | Benning et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,374,723 B2 | 2/2013 | Zhao et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,377,059 B2 | 2/2013 | Deville et al. |
| 8,381,828 B2 | 2/2013 | Whitman et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,972 B2 | 3/2013 | Kostrzewski |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,108 B2 | 3/2013 | Powell et al. |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| D680,646 S | 4/2013 | Hunt et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,211 B2 | 4/2013 | Baroud |
| 8,409,222 B2 | 4/2013 | Whitfield et al. |
| 8,409,223 B2 | 4/2013 | Sorrentino et al. |
| 8,409,234 B2 | 4/2013 | Stabler et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,419,755 B2 | 4/2013 | Deem et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,439,830 B2 | 5/2013 | McKinley et al. |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |

(56) References Cited

U.S. PATENT DOCUMENTS

| | | |
|---|---|---|
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| D686,244 S | 7/2013 | Moriya et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,486,047 B2 | 7/2013 | Stopek |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,852 B2 | 7/2013 | Viola |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,787 B2 | 9/2013 | Ludwin et al. |
| 8,523,881 B2 | 9/2013 | Cabiri et al. |
| 8,523,882 B2 | 9/2013 | Huitema et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,531,153 B2 | 9/2013 | Baarman et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,598 B2 | 11/2013 | Razzaque et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,591,400 B2 | 11/2013 | Sugiyama |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,431 B2 | 12/2013 | Timm et al. |
| 8,617,155 B2 | 12/2013 | Johnson et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |

(56) References Cited

U.S. PATENT DOCUMENTS

| | | |
|---|---|---|
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |

(56) References Cited

U.S. PATENT DOCUMENTS

| | | |
|---|---|---|
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,004 B2 | 9/2014 | Holsten et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,845,622 B2 | 9/2014 | Paik et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,855,822 B2 | 10/2014 | Bartol et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Ro et al. |
| 8,869,913 B2 | 10/2014 | Matthias et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,871,829 B2 | 10/2014 | Gerold et al. |
| 8,875,971 B2 | 11/2014 | Hall et al. |
| 8,875,972 B2 | 11/2014 | Weisenburgh, II et al. |
| 8,876,698 B2 | 11/2014 | Sakamoto et al. |
| 8,876,857 B2 | 11/2014 | Burbank |
| 8,876,858 B2 | 11/2014 | Braun |
| 8,882,660 B2 | 11/2014 | Phee et al. |
| 8,882,792 B2 | 11/2014 | Dietz et al. |
| 8,884,560 B2 | 11/2014 | Ito |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,915,842 B2 | 12/2014 | Weisenburgh, II et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,931,692 B2 | 1/2015 | Sancak |
| 8,936,614 B2 | 1/2015 | Allen, IV |
| 8,937,408 B2 | 1/2015 | Ganem et al. |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |
| 8,945,098 B2 | 2/2015 | Seibold et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,961,542 B2 | 2/2015 | Whitfield et al. |

(56) References Cited

U.S. PATENT DOCUMENTS

| | | |
|---|---|---|
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,004,799 B1 | 4/2015 | Tibbits |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,468 B2 | 5/2015 | Scarfogliero et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,028,529 B2 | 5/2015 | Fox et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,039,736 B2 | 5/2015 | Scirica et al. |
| 9,040,062 B2 | 5/2015 | Maeda et al. |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,070,068 B2 | 6/2015 | Coveley et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,586 B2 | 7/2015 | Hafner et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,095,642 B2 | 8/2015 | Harder et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,359 B2 | 8/2015 | Smith et al. |
| 9,101,385 B2 | 8/2015 | Shelton, IV et al. |
| 9,101,475 B2 | 8/2015 | Wei et al. |
| 9,101,621 B2 | 8/2015 | Zeldis |
| 9,107,663 B2 | 8/2015 | Swensgard |

(56) References Cited

U.S. PATENT DOCUMENTS

| | | |
|---|---|---|
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,875 B2 | 8/2015 | Viola et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,154,189 B2 | 10/2015 | Von Novak et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,167,960 B2 | 10/2015 | Yamaguchi et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,832 B2 | 11/2015 | Diolaiti |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| D746,459 S | 12/2015 | Kaercher et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,686 B2 | 1/2016 | Blair |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,226,799 B2 | 1/2016 | Lightcap et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,268 B2 | 2/2016 | Behnke, II et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,510 B2 | 2/2016 | Dietzel et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |

(56) References Cited

U.S. PATENT DOCUMENTS

| | | |
|---|---|---|
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,283,334 B2 | 3/2016 | Mantell et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | Van Der Walt et al. |
| 9,339,342 B2 | 5/2016 | Prisco et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hall et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,223 B2 | 6/2016 | Scirica |
| 9,364,226 B2 | 6/2016 | Zemlok et al. |
| 9,364,228 B2 | 6/2016 | Straehnz et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,361 B2 | 6/2016 | Viola et al. |
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,385,640 B2 | 7/2016 | Sun et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,369 B1 | 7/2016 | Whitehurst et al. |
| 9,396,669 B2 | 7/2016 | Karkanias et al. |
| 9,398,905 B2 | 7/2016 | Martin |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,402,682 B2 | 8/2016 | Worrell et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |

(56) References Cited

U.S. PATENT DOCUMENTS

| | | |
|---|---|---|
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| 9,429,204 B2 | 8/2016 | Stefan et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Res et al. |
| 9,451,958 B2 | 9/2016 | Shelton, IV et al. |
| 9,452,020 B2 | 9/2016 | Griffiths et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,012 B2 | 10/2016 | Bonutti et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,513 B2 | 10/2016 | Ishida et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,477,649 B1 | 10/2016 | Davidson et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,515,366 B2 | 12/2016 | Herbsommer et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,005 B2 | 12/2016 | Williams et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,549,750 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,554,854 B2 | 1/2017 | Yates et al. |
| 9,559,624 B2 | 1/2017 | Philipp |
| 9,561,013 B2 | 2/2017 | Tsuchiya |
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,561,072 B2 | 2/2017 | Ko |
| 9,561,082 B2 | 2/2017 | Yen et al. |
| 9,566,061 B2 | 2/2017 | Aronhalt et al. |
| 9,566,062 B2 | 2/2017 | Boudreaux |
| 9,566,064 B2 | 2/2017 | Williams et al. |
| 9,566,065 B2 | 2/2017 | Knodel |
| 9,566,067 B2 | 2/2017 | Milliman et al. |
| 9,572,552 B1 | 2/2017 | Bodor et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |

(56) References Cited

U.S. PATENT DOCUMENTS

| | | |
|---|---|---|
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek et al. |
| 9,641,122 B2 | 5/2017 | Romanowich et al. |
| 9,642,620 B2 | 5/2017 | Baxter, III et al. |
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,651,032 B2 | 5/2017 | Weaver et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,661,991 B2 | 5/2017 | Glossop |
| 9,662,108 B2 | 5/2017 | Williams |
| 9,662,110 B2 | 5/2017 | Huang et al. |
| 9,662,111 B2 | 5/2017 | Holsten et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,315 B2 | 7/2017 | Chen et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,700,334 B2 | 7/2017 | Hinman et al. |
| 9,700,381 B2 | 7/2017 | Amat Girbau |
| 9,702,823 B2 | 7/2017 | Maher et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,466 B2 | 7/2017 | Kostrzewski |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,730,757 B2 | 8/2017 | Brudniok |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,298 B2 | 8/2017 | Isbell, Jr. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,323 B2 | 8/2017 | Thapliyal et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |

(56) References Cited

U.S. PATENT DOCUMENTS

| | | |
|---|---|---|
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,839,481 B2 | 12/2017 | Blumenkranz et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,617 B2 | 1/2018 | Ma |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |

(56) References Cited

U.S. PATENT DOCUMENTS

| | | |
|---|---|---|
| 9,901,346 B2 | 2/2018 | Moore et al. |
| 9,901,358 B2 | 2/2018 | Faller et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czemik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,117 B2 | 4/2018 | Hathaway et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,740 B2 | 5/2018 | Krause et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| 10,004,552 B1 | 6/2018 | Kleyman et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,046,904 B2 | 8/2018 | Evans et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,642 B2 | 9/2018 | Marczyk et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |

(56) References Cited

U.S. PATENT DOCUMENTS

| | | |
|---|---|---|
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,126 B2 | 10/2018 | Sauer |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,123,845 B2 | 11/2018 | Yeung |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,146,423 B1 | 12/2018 | Reed et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,161,816 B2 | 12/2018 | Jackson et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,911 B2 | 2/2019 | Miller et al. |
| 10,194,912 B2 | 2/2019 | Scheib et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |

(56) References Cited

U.S. PATENT DOCUMENTS

| | | |
|---|---|---|
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,645 B2 | 4/2019 | Kostrzewski |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,363 B2 | 4/2019 | Worrell et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,700 B2 | 5/2019 | Scheib |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,578 B2 | 6/2019 | Leimbach et al. |
| 10,314,579 B2 | 6/2019 | Chowaniec et al. |
| 10,314,580 B2 | 6/2019 | Scheib et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,866 B2 | 8/2019 | Wang et al. |
| 10,368,867 B2 | 8/2019 | Harris et al. |
| 10,368,892 B2 | 8/2019 | Stulen et al. |
| 10,374,544 B2 | 8/2019 | Yokoyama et al. |
| 10,376,263 B2 | 8/2019 | Morgan et al. |

(56) References Cited

U.S. PATENT DOCUMENTS

| | | |
|---|---|---|
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D859,466 S | 9/2019 | Okada et al. |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,155 B2 | 9/2019 | Inoue |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,551 B2 | 9/2019 | Calderoni |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| D865,174 S | 10/2019 | Auld et al. |
| D865,175 S | 10/2019 | Widenhouse et al. |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,842 B2 | 10/2019 | Amariglio et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,482,292 B2 | 11/2019 | Clouser et al. |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,000 B2 | 12/2019 | Swayze et al. |
| 10,500,004 B2 | 12/2019 | Hanuschik et al. |
| 10,500,309 B2 | 12/2019 | Shah et al. |
| 10,507,034 B2 | 12/2019 | Timm |
| 10,508,720 B2 | 12/2019 | Nicholas |
| 10,512,461 B2 | 12/2019 | Gupta et al. |
| 10,512,462 B2 | 12/2019 | Felder et al. |
| 10,512,464 B2 | 12/2019 | Park et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |

(56) References Cited

U.S. PATENT DOCUMENTS

| | | |
|---|---|---|
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,524,870 B2 | 1/2020 | Saraliev et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderoni et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,493 B2 | 2/2020 | Blase et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,231 B2 | 3/2020 | Sgroi, Jr. et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |
| 10,595,929 B2 | 3/2020 | Boudreaux et al. |
| 10,603,036 B2 | 3/2020 | Hunter et al. |
| 10,603,039 B2 | 3/2020 | Vendely et al. |
| 10,603,041 B2 | 3/2020 | Miller et al. |
| 10,603,117 B2 | 3/2020 | Schings et al. |
| 10,603,128 B2 | 3/2020 | Zergiebel et al. |
| D882,783 S | 4/2020 | Shelton, IV et al. |
| 10,610,224 B2 | 4/2020 | Shelton, IV et al. |
| 10,610,225 B2 | 4/2020 | Reed et al. |
| 10,610,236 B2 | 4/2020 | Baril |
| 10,610,313 B2 | 4/2020 | Bailey et al. |
| 10,610,346 B2 | 4/2020 | Schwartz |
| 10,617,411 B2 | 4/2020 | Williams |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,416 B2 | 4/2020 | Leimbach et al. |
| 10,617,417 B2 | 4/2020 | Baxter, III et al. |
| 10,617,418 B2 | 4/2020 | Barton et al. |
| 10,617,420 B2 | 4/2020 | Shelton, IV et al. |
| 10,617,438 B2 | 4/2020 | O'Keefe et al. |
| 10,624,616 B2 | 4/2020 | Mukherjee et al. |
| 10,624,630 B2 | 4/2020 | Deville et al. |
| 10,624,633 B2 | 4/2020 | Shelton, IV et al. |
| 10,624,634 B2 | 4/2020 | Shelton, IV et al. |
| 10,624,635 B2 | 4/2020 | Harris et al. |
| 10,624,709 B2 | 4/2020 | Remm |
| 10,624,861 B2 | 4/2020 | Widenhouse et al. |
| 10,625,062 B2 | 4/2020 | Matlock et al. |
| 10,631,857 B2 | 4/2020 | Kostrzewski |
| 10,631,858 B2 | 4/2020 | Burbank |
| 10,631,859 B2 | 4/2020 | Shelton, IV et al. |
| 10,631,860 B2 | 4/2020 | Bakos et al. |
| 10,636,104 B2 | 4/2020 | Mazar et al. |
| 10,639,018 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,089 B2 | 5/2020 | Manwaring et al. |
| 10,639,115 B2 | 5/2020 | Shelton, IV et al. |
| 10,642,633 B1 | 5/2020 | Chopra et al. |
| 10,645,905 B2 | 5/2020 | Gandola et al. |
| 10,646,220 B2 | 5/2020 | Shelton, IV et al. |
| 10,646,292 B2 | 5/2020 | Solomon et al. |
| 10,653,413 B2 | 5/2020 | Worthington et al. |
| 10,653,417 B2 | 5/2020 | Shelton, IV et al. |
| 10,653,435 B2 | 5/2020 | Shelton, IV et al. |
| 10,660,640 B2 | 5/2020 | Yates et al. |
| 10,667,408 B2 | 5/2020 | Sgroi, Jr. et al. |
| D888,953 S | 6/2020 | Baxter, III et al. |
| 10,667,808 B2 | 6/2020 | Baxter, III et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,818 B2 | 6/2020 | McLain et al. |
| 10,674,895 B2 | 6/2020 | Yeung et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,028 B2 | 6/2020 | Shelton, IV et al. |
| 10,675,035 B2 | 6/2020 | Zingman |
| 10,675,080 B2 | 6/2020 | Woloszko et al. |
| 10,675,102 B2 | 6/2020 | Forgione et al. |
| 10,677,035 B2 | 6/2020 | Balan et al. |
| 10,682,134 B2 | 6/2020 | Shelton, IV et al. |
| 10,682,136 B2 | 6/2020 | Harris et al. |
| 10,682,137 B2 | 6/2020 | Stokes et al. |
| 10,682,138 B2 | 6/2020 | Shelton, IV et al. |
| 10,682,141 B2 | 6/2020 | Moore et al. |
| 10,682,142 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,812 B2 | 6/2020 | Shelton, IV et al. |
| 10,687,813 B2 | 6/2020 | Shelton, IV et al. |
| 10,687,817 B2 | 6/2020 | Shelton, IV et al. |
| 10,687,819 B2 | 6/2020 | Stokes et al. |
| 10,687,904 B2 | 6/2020 | Harris et al. |
| 10,695,053 B2 | 6/2020 | Hess et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,062 B2 | 6/2020 | Leimbach et al. |
| 10,695,063 B2 | 6/2020 | Morgan et al. |
| 10,695,074 B2 | 6/2020 | Carusillo |
| 10,695,081 B2 | 6/2020 | Shelton, IV et al. |
| 10,695,119 B2 | 6/2020 | Smith |
| 10,695,123 B2 | 6/2020 | Allen, IV |
| 10,695,187 B2 | 6/2020 | Moskowitz et al. |
| D890,784 S | 7/2020 | Shelton, IV et al. |
| 10,702,266 B2 | 7/2020 | Parihar et al. |
| 10,702,267 B2 | 7/2020 | Hess et al. |
| 10,702,270 B2 | 7/2020 | Shelton, IV et al. |
| 10,702,271 B2 | 7/2020 | Aranyi et al. |

(56) References Cited

U.S. PATENT DOCUMENTS

| | | |
|---|---|---|
| 10,705,660 B2 | 7/2020 | Xiao |
| 10,709,446 B2 | 7/2020 | Harris et al. |
| 10,709,468 B2 | 7/2020 | Shelton, IV et al. |
| 10,709,469 B2 | 7/2020 | Shelton, IV et al. |
| 10,709,496 B2 | 7/2020 | Moua et al. |
| 10,716,563 B2 | 7/2020 | Shelton, IV et al. |
| 10,716,565 B2 | 7/2020 | Shelton, IV et al. |
| 10,716,568 B2 | 7/2020 | Hall et al. |
| 10,716,614 B2 | 7/2020 | Yates et al. |
| 10,717,179 B2 | 7/2020 | Koenig et al. |
| 10,722,232 B2 | 7/2020 | Yates et al. |
| 10,722,233 B2 | 7/2020 | Wellman |
| 10,722,292 B2 | 7/2020 | Arya et al. |
| 10,722,293 B2 | 7/2020 | Arya et al. |
| 10,722,317 B2 | 7/2020 | Ward et al. |
| D893,717 S | 8/2020 | Messerly et al. |
| 10,729,432 B2 | 8/2020 | Shelton, IV et al. |
| 10,729,434 B2 | 8/2020 | Harris et al. |
| 10,729,435 B2 | 8/2020 | Richard |
| 10,729,436 B2 | 8/2020 | Shelton, IV et al. |
| 10,729,443 B2 | 8/2020 | Cabrera et al. |
| 10,729,458 B2 | 8/2020 | Stoddard et al. |
| 10,729,501 B2 | 8/2020 | Leimbach et al. |
| 10,729,509 B2 | 8/2020 | Shelton, IV et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,630 B2 | 8/2020 | Huang et al. |
| 10,736,633 B2 | 8/2020 | Vendely et al. |
| 10,736,634 B2 | 8/2020 | Shelton, IV et al. |
| 10,736,636 B2 | 8/2020 | Baxter, III et al. |
| 10,736,644 B2 | 8/2020 | Windolf et al. |
| 10,736,702 B2 | 8/2020 | Harris et al. |
| 10,737,398 B2 | 8/2020 | Remirez et al. |
| 10,743,849 B2 | 8/2020 | Shelton, IV et al. |
| 10,743,850 B2 | 8/2020 | Hibner et al. |
| 10,743,851 B2 | 8/2020 | Swayze et al. |
| 10,743,868 B2 | 8/2020 | Shelton, IV et al. |
| 10,743,870 B2 | 8/2020 | Hall et al. |
| 10,743,872 B2 | 8/2020 | Leimbach et al. |
| 10,743,873 B2 | 8/2020 | Overmyer et al. |
| 10,743,874 B2 | 8/2020 | Shelton, IV et al. |
| 10,743,875 B2 | 8/2020 | Shelton, IV et al. |
| 10,743,877 B2 | 8/2020 | Shelton, IV et al. |
| 10,743,930 B2 | 8/2020 | Nagtegaal |
| 10,751,048 B2 | 8/2020 | Whitman et al. |
| 10,751,053 B2 | 8/2020 | Harris et al. |
| 10,751,076 B2 | 8/2020 | Laurent et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,233 B2 | 9/2020 | Scheib et al. |
| 10,758,259 B2 | 9/2020 | Demmy et al. |
| 10,765,425 B2 | 9/2020 | Yates et al. |
| 10,765,427 B2 | 9/2020 | Shelton, IV et al. |
| 10,765,429 B2 | 9/2020 | Leimbach et al. |
| 10,765,430 B2 | 9/2020 | Wixey |
| 10,765,432 B2 | 9/2020 | Moore et al. |
| 10,765,442 B2 | 9/2020 | Strobl |
| 10,772,625 B2 | 9/2020 | Shelton, IV et al. |
| 10,772,628 B2 | 9/2020 | Chen et al. |
| 10,772,629 B2 | 9/2020 | Shelton, IV et al. |
| 10,772,630 B2 | 9/2020 | Wixey |
| 10,772,631 B2 | 9/2020 | Zergiebel et al. |
| 10,772,632 B2 | 9/2020 | Kostrzewski |
| 10,772,651 B2 | 9/2020 | Shelton, IV et al. |
| 10,779,818 B2 | 9/2020 | Zemlok et al. |
| 10,779,820 B2 | 9/2020 | Harris et al. |
| 10,779,821 B2 | 9/2020 | Harris et al. |
| 10,779,822 B2 | 9/2020 | Yates et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,826 B2 | 9/2020 | Shelton, IV et al. |
| 10,779,903 B2 | 9/2020 | Wise et al. |
| 10,780,539 B2 | 9/2020 | Shelton, IV et al. |
| 10,786,248 B2 | 9/2020 | Rousseau et al. |
| 10,786,253 B2 | 9/2020 | Shelton, IV et al. |
| 10,786,255 B2 | 9/2020 | Hodgkinson et al. |
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,939 B2 | 11/2020 | Sartor |
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| D904,612 S | 12/2020 | Wynn et al. |
| D904,613 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,663 B2 | 12/2020 | Shelton, IV et al. |
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti, III et al. |
| 10,874,396 B2 | 12/2020 | Moore et al. |
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| D908,216 S | 1/2021 | Messerly et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, IV et al. |
| 10,888,322 B2 | 1/2021 | Morgan et al. |
| 10,888,323 B2 | 1/2021 | Chen et al. |

(56) References Cited

U.S. PATENT DOCUMENTS

| | | |
|---|---|---|
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Blasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,919,156 B2 | 2/2021 | Roberts et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,726 B2 | 3/2021 | Chowaniec |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,726 B2 | 3/2021 | Williams et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| 10,959,797 B2 | 3/2021 | Licht et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 10,973,515 B2 | 4/2021 | Harris et al. |
| 10,973,516 B2 | 4/2021 | Shelton, IV et al. |
| 10,973,517 B2 | 4/2021 | Wixey |
| 10,973,519 B2 | 4/2021 | Weir et al. |
| 10,973,520 B2 | 4/2021 | Shelton, IV et al. |
| 10,980,534 B2 | 4/2021 | Yates et al. |
| 10,980,535 B2 | 4/2021 | Yates et al. |
| 10,980,536 B2 | 4/2021 | Weaner et al. |
| 10,980,537 B2 | 4/2021 | Shelton, IV et al. |
| 10,980,538 B2 | 4/2021 | Nalagatla et al. |
| 10,980,539 B2 | 4/2021 | Harris et al. |
| 10,980,560 B2 | 4/2021 | Shelton, IV et al. |
| 10,983,646 B2 | 4/2021 | Yoon et al. |
| 10,987,102 B2 | 4/2021 | Gonzalez et al. |
| 10,987,178 B2 | 4/2021 | Shelton, IV et al. |
| 10,993,713 B2 | 5/2021 | Shelton, IV et al. |
| 10,993,715 B2 | 5/2021 | Shelton, IV et al. |
| 10,993,716 B2 | 5/2021 | Shelton, IV et al. |
| 10,993,717 B2 | 5/2021 | Shelton, IV et al. |
| 11,000,274 B2 | 5/2021 | Shelton, IV et al. |
| 11,000,275 B2 | 5/2021 | Shelton, IV et al. |
| 11,000,277 B2 | 5/2021 | Giordano et al. |
| 11,000,278 B2 | 5/2021 | Shelton, IV et al. |
| 11,000,279 B2 | 5/2021 | Shelton, IV et al. |
| 11,005,291 B2 | 5/2021 | Calderoni |
| 11,006,951 B2 | 5/2021 | Giordano et al. |
| 11,006,955 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,511 B2 | 5/2021 | Huang et al. |
| 11,013,552 B2 | 5/2021 | Widenhouse et al. |
| 11,013,563 B2 | 5/2021 | Shelton, IV et al. |
| 11,020,016 B2 | 6/2021 | Wallace et al. |
| 11,020,112 B2 | 6/2021 | Shelton, IV et al. |
| 11,020,113 B2 | 6/2021 | Shelton, IV et al. |
| 11,020,114 B2 | 6/2021 | Shelton, IV et al. |
| 11,020,115 B2 | 6/2021 | Scheib et al. |
| 11,026,678 B2 | 6/2021 | Overmyer et al. |
| 11,026,680 B2 | 6/2021 | Shelton, IV et al. |
| 11,026,684 B2 | 6/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,033,267 B2 | 6/2021 | Shelton, IV et al. |
| 11,039,834 B2 | 6/2021 | Harris et al. |
| 11,039,836 B2 | 6/2021 | Shelton, IV et al. |
| 11,039,837 B2 | 6/2021 | Shelton, IV et al. |
| 11,039,849 B2 | 6/2021 | Bucciaglia et al. |
| 11,045,189 B2 | 6/2021 | Yates et al. |
| 11,045,191 B2 | 6/2021 | Shelton, IV et al. |
| 11,045,192 B2 | 6/2021 | Harris et al. |
| 11,045,196 B2 | 6/2021 | Olson et al. |
| 11,045,197 B2 | 6/2021 | Shelton, IV et al. |
| 11,045,199 B2 | 6/2021 | Mozdzierz et al. |
| 11,045,270 B2 | 6/2021 | Shelton, IV et al. |
| 11,051,807 B2 | 7/2021 | Shelton, IV et al. |
| 11,051,810 B2 | 7/2021 | Harris et al. |
| 11,051,811 B2 | 7/2021 | Shelton, IV et al. |
| 11,051,813 B2 | 7/2021 | Shelton, IV et al. |
| 11,051,836 B2 | 7/2021 | Shelton, IV et al. |
| 11,051,840 B2 | 7/2021 | Shelton, IV et al. |
| 11,051,873 B2 | 7/2021 | Wiener et al. |
| 11,058,418 B2 | 7/2021 | Shelton, IV et al. |
| 11,058,420 B2 | 7/2021 | Shelton, IV et al. |
| 11,058,422 B2 | 7/2021 | Harris et al. |
| 11,058,423 B2 | 7/2021 | Shelton, IV et al. |
| 11,058,424 B2 | 7/2021 | Shelton, IV et al. |
| 11,058,425 B2 | 7/2021 | Widenhouse et al. |
| 11,058,426 B2 | 7/2021 | Nalagatla et al. |
| 11,058,498 B2 | 7/2021 | Shelton, IV et al. |
| 11,064,997 B2 | 7/2021 | Shelton, IV et al. |
| 11,064,998 B2 | 7/2021 | Shelton, IV |
| 11,065,048 B2 | 7/2021 | Messerly et al. |
| 11,069,012 B2 | 7/2021 | Shelton, IV et al. |
| 11,071,542 B2 | 7/2021 | Chen et al. |
| 11,071,543 B2 | 7/2021 | Shelton, IV et al. |
| 11,071,545 B2 | 7/2021 | Baber et al. |
| 11,071,554 B2 | 7/2021 | Parfett et al. |
| 11,071,560 B2 | 7/2021 | Deck et al. |
| 11,076,853 B2 | 8/2021 | Parfett et al. |
| 11,076,854 B2 | 8/2021 | Baber et al. |
| 11,076,921 B2 | 8/2021 | Shelton, IV et al. |

(56) References Cited

U.S. PATENT DOCUMENTS

| | | |
|---|---|---|
| 11,076,929 B2 | 8/2021 | Shelton, IV et al. |
| 11,083,452 B2 | 8/2021 | Schmid et al. |
| 11,083,453 B2 | 8/2021 | Shelton, IV et al. |
| 11,083,454 B2 | 8/2021 | Harris et al. |
| 11,083,455 B2 | 8/2021 | Shelton, IV et al. |
| 11,083,456 B2 | 8/2021 | Shelton, IV et al. |
| 11,083,457 B2 | 8/2021 | Shelton, IV et al. |
| 11,083,458 B2 | 8/2021 | Harris et al. |
| 11,090,045 B2 | 8/2021 | Shelton, IV |
| 11,090,046 B2 | 8/2021 | Shelton, IV et al. |
| 11,090,047 B2 | 8/2021 | Shelton, IV et al. |
| 11,090,048 B2 | 8/2021 | Fanelli et al. |
| 11,090,049 B2 | 8/2021 | Bakos et al. |
| 11,090,075 B2 | 8/2021 | Hunter et al. |
| 11,096,688 B2 | 8/2021 | Shelton, IV et al. |
| 11,096,689 B2 | 8/2021 | Overmyer et al. |
| 11,100,631 B2 | 8/2021 | Yates et al. |
| 11,103,241 B2 | 8/2021 | Yates et al. |
| 11,103,248 B2 | 8/2021 | Shelton, IV et al. |
| 11,103,268 B2 | 8/2021 | Shelton, IV et al. |
| 11,103,269 B2 | 8/2021 | Shelton, IV et al. |
| 11,109,858 B2 | 9/2021 | Shelton, IV et al. |
| 11,109,859 B2 | 9/2021 | Overmyer et al. |
| 11,109,860 B2 | 9/2021 | Shelton, IV et al. |
| 11,109,866 B2 | 9/2021 | Shelton, IV et al. |
| 11,109,878 B2 | 9/2021 | Shelton, IV et al. |
| 11,109,925 B2 | 9/2021 | Cooper et al. |
| 11,116,485 B2 | 9/2021 | Scheib et al. |
| 11,116,502 B2 | 9/2021 | Shelton, IV et al. |
| 11,116,594 B2 | 9/2021 | Beardsley |
| 11,123,069 B2 | 9/2021 | Baxter, III et al. |
| 11,123,070 B2 | 9/2021 | Shelton, IV et al. |
| 11,129,611 B2 | 9/2021 | Shelton, IV et al. |
| 11,129,613 B2 | 9/2021 | Harris et al. |
| 11,129,615 B2 | 9/2021 | Scheib et al. |
| 11,129,616 B2 | 9/2021 | Shelton, IV et al. |
| 11,129,634 B2 | 9/2021 | Scheib et al. |
| 11,129,636 B2 | 9/2021 | Shelton, IV et al. |
| 11,129,666 B2 | 9/2021 | Messerly et al. |
| 11,129,680 B2 | 9/2021 | Shelton, IV et al. |
| 11,132,462 B2 | 9/2021 | Shelton, IV et al. |
| 11,133,106 B2 | 9/2021 | Shelton, IV et al. |
| 11,134,938 B2 | 10/2021 | Timm et al. |
| 11,134,940 B2 | 10/2021 | Shelton, IV et al. |
| 11,134,942 B2 | 10/2021 | Harris et al. |
| 11,134,943 B2 | 10/2021 | Giordano et al. |
| 11,134,944 B2 | 10/2021 | Wise et al. |
| 11,134,947 B2 | 10/2021 | Shelton, IV et al. |
| 11,135,352 B2 | 10/2021 | Shelton, IV et al. |
| 11,141,153 B2 | 10/2021 | Shelton, IV et al. |
| 11,141,154 B2 | 10/2021 | Shelton, IV et al. |
| 11,141,155 B2 | 10/2021 | Shelton, IV |
| 11,141,156 B2 | 10/2021 | Shelton, IV |
| 11,141,159 B2 | 10/2021 | Scheib et al. |
| 11,141,160 B2 | 10/2021 | Shelton, IV et al. |
| 11,147,547 B2 | 10/2021 | Shelton, IV et al. |
| 11,147,549 B2 | 10/2021 | Timm et al. |
| 11,147,551 B2 | 10/2021 | Shelton, IV |
| 11,147,553 B2 | 10/2021 | Shelton, IV |
| 11,147,554 B2 | 10/2021 | Aronhalt et al. |
| 11,154,296 B2 | 10/2021 | Aronhalt et al. |
| 11,154,297 B2 | 10/2021 | Swayze et al. |
| 11,154,298 B2 | 10/2021 | Timm et al. |
| 11,154,299 B2 | 10/2021 | Shelton, IV et al. |
| 11,154,300 B2 | 10/2021 | Nalagatla et al. |
| 11,154,301 B2 | 10/2021 | Beckman et al. |
| 11,160,551 B2 | 11/2021 | Shelton, IV et al. |
| 11,160,553 B2 | 11/2021 | Simms et al. |
| 11,160,601 B2 | 11/2021 | Worrell et al. |
| 11,166,716 B2 | 11/2021 | Shelton, IV et al. |
| 11,166,717 B2 | 11/2021 | Shelton, IV et al. |
| 11,166,720 B2 | 11/2021 | Giordano et al. |
| 11,166,772 B2 | 11/2021 | Shelton, IV et al. |
| 11,166,773 B2 | 11/2021 | Ragosta et al. |
| 11,172,580 B2 | 11/2021 | Gaertner, II |
| 11,172,927 B2 | 11/2021 | Shelton, IV |
| 11,172,929 B2 | 11/2021 | Shelton, IV |
| 11,179,150 B2 | 11/2021 | Yates et al. |
| 11,179,152 B2 | 11/2021 | Morgan et al. |
| 11,179,155 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,191,543 B2 | 12/2021 | Overmyer et al. |
| 11,191,545 B2 | 12/2021 | Vendely et al. |
| 11,197,668 B2 | 12/2021 | Shelton, IV et al. |
| 11,197,670 B2 | 12/2021 | Shelton, IV et al. |
| 11,197,671 B2 | 12/2021 | Shelton, IV et al. |
| 11,197,672 B2 | 12/2021 | Dunki-Jacobs et al. |
| 11,202,570 B2 | 12/2021 | Shelton, IV et al. |
| 11,202,631 B2 | 12/2021 | Shelton, IV et al. |
| 11,202,633 B2 | 12/2021 | Harris et al. |
| 11,207,064 B2 | 12/2021 | Shelton, IV et al. |
| 11,207,065 B2 | 12/2021 | Harris et al. |
| 11,207,067 B2 | 12/2021 | Shelton, IV et al. |
| 11,207,089 B2 | 12/2021 | Kostrzewski et al. |
| 11,207,090 B2 | 12/2021 | Shelton, IV et al. |
| 11,207,146 B2 | 12/2021 | Shelton, IV et al. |
| 11,213,293 B2 | 1/2022 | Worthington et al. |
| 11,213,294 B2 | 1/2022 | Shelton, IV et al. |
| 11,213,302 B2 | 1/2022 | Parfett et al. |
| 11,213,359 B2 | 1/2022 | Shelton, IV et al. |
| 11,219,453 B2 | 1/2022 | Shelton, IV et al. |
| 11,219,455 B2 | 1/2022 | Shelton, IV et al. |
| 11,224,423 B2 | 1/2022 | Shelton, IV et al. |
| 11,224,426 B2 | 1/2022 | Shelton, IV et al. |
| 11,224,427 B2 | 1/2022 | Shelton, IV et al. |
| 11,224,428 B2 | 1/2022 | Scott et al. |
| 11,224,454 B2 | 1/2022 | Shelton, IV et al. |
| 11,224,497 B2 | 1/2022 | Shelton, IV et al. |
| 11,229,436 B2 | 1/2022 | Shelton, IV et al. |
| 11,229,437 B2 | 1/2022 | Shelton, IV et al. |
| 11,234,698 B2 | 2/2022 | Shelton, IV et al. |
| 11,234,700 B2 | 2/2022 | Ragosta et al. |
| 11,241,229 B2 | 2/2022 | Shelton, IV et al. |
| 11,241,230 B2 | 2/2022 | Shelton, IV et al. |
| 11,241,235 B2 | 2/2022 | Shelton, IV et al. |
| 11,246,590 B2 | 2/2022 | Swayze et al. |
| 11,246,592 B2 | 2/2022 | Shelton, IV et al. |
| 11,246,616 B2 | 2/2022 | Shelton, IV et al. |
| 11,246,618 B2 | 2/2022 | Hall et al. |
| 11,246,678 B2 | 2/2022 | Shelton, IV et al. |
| 11,253,254 B2 | 2/2022 | Kimball et al. |
| 11,253,256 B2 | 2/2022 | Harris et al. |
| 11,259,799 B2 | 3/2022 | Overmyer et al. |
| 11,259,803 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,304,697 B2 | 4/2022 | Fanelli et al. |
| 11,304,704 B2 | 4/2022 | Thomas et al. |
| 11,311,295 B2 | 4/2022 | Wingardner et al. |
| D950,728 S | 5/2022 | Bakos et al. |
| D952,144 S | 5/2022 | Boudreaux |
| 11,317,912 B2 | 5/2022 | Jenkins et al. |
| 11,317,978 B2 | 5/2022 | Cameron et al. |
| 11,376,082 B2 | 7/2022 | Shelton, IV et al. |
| D964,564 S | 9/2022 | Boudreaux |
| 11,439,391 B2 | 9/2022 | Bruns et al. |
| D966,512 S | 10/2022 | Shelton, IV et al. |
| D967,421 S | 10/2022 | Shelton, IV et al. |
| D971,232 S | 11/2022 | Siebel et al. |
| 11,484,309 B2 | 11/2022 | Harris et al. |
| 11,484,312 B2 | 11/2022 | Shelton, IV et al. |
| 11,517,390 B2 | 12/2022 | Baxter, III |
| 11,534,259 B2 | 12/2022 | Leimbach et al. |
| D974,560 S | 1/2023 | Shelton, IV et al. |
| D975,278 S | 1/2023 | Shelton, IV et al. |
| D975,850 S | 1/2023 | Shelton, IV et al. |
| D975,851 S | 1/2023 | Shelton, IV et al. |
| D976,401 S | 1/2023 | Shelton, IV et al. |
| 11,553,911 B2 | 1/2023 | Shelton, IV et al. |
| 2001/0000531 A1 | 4/2001 | Casscells et al. |

(56) References Cited

U.S. PATENT DOCUMENTS

| | | |
|---|---|---|
| 2001/0025183 A1 | 9/2001 | Shahid! |
| 2001/0025184 A1 | 9/2001 | Messerly |
| 2001/0030219 A1 | 10/2001 | Green et al. |
| 2001/0034530 A1 | 10/2001 | Malackowski et al. |
| 2001/0045442 A1 | 11/2001 | Whitman |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0023126 A1 | 2/2002 | Flavin |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0054158 A1 | 5/2002 | Asami |
| 2002/0082612 A1 | 6/2002 | Moll et al. |
| 2002/0087048 A1 | 7/2002 | Brock et al. |
| 2002/0087148 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0111621 A1 | 8/2002 | Wallace et al. |
| 2002/0111624 A1 | 8/2002 | Witt et al. |
| 2002/0116063 A1 | 8/2002 | Giannetti et al. |
| 2002/0117533 A1 | 8/2002 | Milliman et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0133236 A1 | 9/2002 | Rousseau |
| 2002/0134811 A1 | 9/2002 | Napier et al. |
| 2002/0135474 A1 | 9/2002 | Sylliassen |
| 2002/0138086 A1 | 9/2002 | Sixto et al. |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0161277 A1 | 10/2002 | Boone et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0018323 A1 | 1/2003 | Wallace et al. |
| 2003/0028236 A1 | 2/2003 | Gillick et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0047582 A1 | 3/2003 | Sonnenschein et al. |
| 2003/0050628 A1 | 3/2003 | Whitman et al. |
| 2003/0050654 A1 | 3/2003 | Whitman et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0105475 A1 | 6/2003 | Sancoff et al. |
| 2003/0114851 A1 | 6/2003 | Truckai et al. |
| 2003/0121586 A1 | 7/2003 | Mitra et al. |
| 2003/0135204 A1 | 7/2003 | Lee et al. |
| 2003/0139741 A1 | 7/2003 | Goble et al. |
| 2003/0144660 A1 | 7/2003 | Mollenauer |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163029 A1 | 8/2003 | Sonnenschein et al. |
| 2003/0163085 A1 | 8/2003 | Tanner et al. |
| 2003/0164172 A1 | 9/2003 | Chumas et al. |
| 2003/0181800 A1 | 9/2003 | Bonutti |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034287 A1 | 2/2004 | Hickle |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093020 A1 | 5/2004 | Sinton |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0231870 A1 | 11/2004 | McCormick et al. |
| 2004/0232201 A1 | 11/2004 | Wenchell et al. |
| 2004/0236352 A1 | 11/2004 | Wang et al. |
| 2004/0239582 A1 | 12/2004 | Seymour |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254680 A1 | 12/2004 | Sunaoshi |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0023325 A1 | 2/2005 | Gresham et al. |
| 2005/0032511 A1 | 2/2005 | Malone et al. |
| 2005/0033352 A1 | 2/2005 | Zepf et al. |
| 2005/0044489 A1 | 2/2005 | Yamagami et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |

(56) References Cited

U.S. PATENT DOCUMENTS

| | | |
|---|---|---|
| 2005/0059997 A1 | 3/2005 | Bauman et al. |
| 2005/0067548 A1 | 3/2005 | Inoue |
| 2005/0070929 A1 | 3/2005 | Dalessandro et al. |
| 2005/0075561 A1 | 4/2005 | Golden |
| 2005/0079088 A1 | 4/2005 | Wirth et al. |
| 2005/0080342 A1 | 4/2005 | Gilreath et al. |
| 2005/0085693 A1 | 4/2005 | Belson et al. |
| 2005/0085838 A1 | 4/2005 | Thompson et al. |
| 2005/0090709 A1 | 4/2005 | Okada et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0120836 A1 | 6/2005 | Anderson |
| 2005/0124855 A1 | 6/2005 | Jaffe et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0145672 A1 | 7/2005 | Schwemberger et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0191936 A1 | 9/2005 | Marine et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0256546 A1 | 11/2005 | Vaisnys et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0267464 A1 | 12/2005 | Truckai et al. |
| 2005/0267529 A1 | 12/2005 | Crockett et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0008787 A1 | 1/2006 | Hayman et al. |
| 2006/0011698 A1 | 1/2006 | Okada et al. |
| 2006/0015009 A1 | 1/2006 | Jaffe et al. |
| 2006/0020167 A1 | 1/2006 | Sitzmann |
| 2006/0020258 A1 | 1/2006 | Strauss et al. |
| 2006/0020272 A1 | 1/2006 | Gildenberg |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226957 A1 | 10/2006 | Miller et al. |
| 2006/0235368 A1 | 10/2006 | Oz |
| 2006/0241666 A1 | 10/2006 | Briggs et al. |
| 2006/0241691 A1 | 10/2006 | Wilk |
| 2006/0244460 A1 | 11/2006 | Weaver |
| 2006/0247584 A1 | 11/2006 | Sheetz et al. |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289600 A1 | 12/2006 | Wales et al. |
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027459 A1 | 2/2007 | Horvath et al. |
| 2007/0027468 A1 | 2/2007 | Wales et al. |
| 2007/0027551 A1 | 2/2007 | Farnsworth et al. |
| 2007/0043338 A1 | 2/2007 | Moll et al. |
| 2007/0043387 A1 | 2/2007 | Vargas et al. |
| 2007/0049951 A1 | 3/2007 | Menn |
| 2007/0049966 A1 | 3/2007 | Bonadio et al. |

(56) References Cited

U.S. PATENT DOCUMENTS

| | | |
|---|---|---|
| 2007/0051375 A1 | 3/2007 | Milliman |
| 2007/0055228 A1 | 3/2007 | Berg et al. |
| 2007/0055305 A1 | 3/2007 | Schnyder et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0152829 A1 | 7/2007 | Lindsay et al. |
| 2007/0155010 A1 | 7/2007 | Farnsworth et al. |
| 2007/0162056 A1 | 7/2007 | Gerbi et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0191915 A1 | 8/2007 | Strother et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0221701 A1 | 9/2007 | Ortiz et al. |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0260132 A1 | 11/2007 | Sterling |
| 2007/0260242 A1 | 11/2007 | Dycus et al. |
| 2007/0262592 A1 | 11/2007 | Hwang et al. |
| 2007/0270660 A1 | 11/2007 | Caylor et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0290027 A1 | 12/2007 | Maatta et al. |
| 2007/0296286 A1 | 12/2007 | Avenell |
| 2008/0000941 A1 | 1/2008 | Sonnenschein et al. |
| 2008/0003196 A1 | 1/2008 | Jonn et al. |
| 2008/0007237 A1 | 1/2008 | Nagashima et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0046000 A1 | 2/2008 | Lee et al. |
| 2008/0051833 A1 | 2/2008 | Gramuglia et al. |
| 2008/0064920 A1 | 3/2008 | Bakos et al. |
| 2008/0064921 A1 | 3/2008 | Larkin et al. |
| 2008/0065153 A1 | 3/2008 | Allard et al. |
| 2008/0069736 A1 | 3/2008 | Mingerink et al. |
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0081948 A1 | 4/2008 | Weisenburgh et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0083811 A1 | 4/2008 | Marczyk |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0094228 A1 | 4/2008 | Welch et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0126984 A1 | 5/2008 | Fleishman et al. |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0216704 A1 | 9/2008 | Eisenbeis et al. |
| 2008/0234709 A1 | 9/2008 | Houser |
| 2008/0234866 A1 | 9/2008 | Kishi et al. |
| 2008/0242939 A1 | 10/2008 | Johnston |
| 2008/0243088 A1 | 10/2008 | Evans |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255421 A1 | 10/2008 | Hegeman et al. |
| 2008/0255663 A1 | 10/2008 | Akpek et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0296347 A1 | 12/2008 | Shelton, IV et al. |
| 2008/0297287 A1 | 12/2008 | Shachar et al. |
| 2008/0298784 A1 | 12/2008 | Kastner |
| 2008/0308504 A1 | 12/2008 | Hallan et al. |
| 2008/0308602 A1 | 12/2008 | Timm et al. |
| 2008/0308603 A1 | 12/2008 | Shelton et al. |
| 2008/0308607 A1 | 12/2008 | Timm et al. |
| 2008/0308807 A1 | 12/2008 | Yamazaki et al. |
| 2008/0312686 A1 | 12/2008 | Ellingwood |
| 2008/0312687 A1 | 12/2008 | Blier |
| 2008/0315829 A1 | 12/2008 | Jones et al. |

(56) References Cited

U.S. PATENT DOCUMENTS

| | | |
|---|---|---|
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0007014 A1 | 1/2009 | Coomer et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0114701 A1 | 5/2009 | Zemlok et al. |
| 2009/0118762 A1 | 5/2009 | Crainch et al. |
| 2009/0119011 A1 | 5/2009 | Kondo et al. |
| 2009/0120994 A1 | 5/2009 | Murray et al. |
| 2009/0131819 A1 | 5/2009 | Ritchie et al. |
| 2009/0132400 A1 | 5/2009 | Conway |
| 2009/0135280 A1 | 5/2009 | Johnston et al. |
| 2009/0138003 A1 | 5/2009 | Deville et al. |
| 2009/0143797 A1 | 6/2009 | Smith et al. |
| 2009/0143855 A1 | 6/2009 | Weber et al. |
| 2009/0149871 A9 | 6/2009 | Kagan et al. |
| 2009/0167548 A1 | 7/2009 | Sugahara |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0204126 A1 | 8/2009 | Le |
| 2009/0204925 A1 | 8/2009 | Bhat et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |
| 2009/0262078 A1 | 10/2009 | Pizzi |
| 2009/0270895 A1 | 10/2009 | Churchill et al. |
| 2009/0273353 A1 | 11/2009 | Kroh et al. |
| 2009/0277288 A1 | 11/2009 | Doepker et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0002013 A1 | 1/2010 | Kagaya |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016853 A1 | 1/2010 | Burbank |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0036441 A1 | 2/2010 | Procter |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069833 A1 | 3/2010 | Wenderow et al. |
| 2010/0069942 A1 | 3/2010 | Shelton, IV |
| 2010/0072257 A1* | 3/2010 | Farascioni ....... A61B 17/07207 227/180.1 |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094312 A1 | 4/2010 | Ruiz Morales et al. |
| 2010/0094340 A1 | 4/2010 | Stopek et al. |
| 2010/0094400 A1 | 4/2010 | Bolduc et al. |
| 2010/0100123 A1 | 4/2010 | Bennett |
| 2010/0100124 A1 | 4/2010 | Calabrese et al. |
| 2010/0116519 A1 | 5/2010 | Garels |
| 2010/0122339 A1 | 5/2010 | Boccacci |
| 2010/0125786 A1 | 5/2010 | Ozawa et al. |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0168741 A1 | 7/2010 | Sanai et al. |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0194541 A1 | 8/2010 | Stevenson et al. |
| 2010/0198159 A1 | 8/2010 | Voss et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267525 A1 | 10/2010 | Tanner |
| 2010/0267662 A1 | 10/2010 | Fielder et al. |
| 2010/0274160 A1 | 10/2010 | Yachi et al. |
| 2010/0291184 A1 | 11/2010 | Clark et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0325568 A1 | 12/2010 | Pedersen et al. |
| 2010/0327041 A1 | 12/2010 | Milliman et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0028991 A1 | 2/2011 | Ikeda et al. |

(56) References Cited

U.S. PATENT DOCUMENTS

| | | |
|---|---|---|
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0095067 A1 | 4/2011 | Ohdaira |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118708 A1 | 5/2011 | Burbank et al. |
| 2011/0118754 A1 | 5/2011 | Dachs, II et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0198381 A1 | 8/2011 | McCardle et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0224543 A1 | 9/2011 | Johnson et al. |
| 2011/0225105 A1 | 9/2011 | Scholer et al. |
| 2011/0230713 A1 | 9/2011 | Kleemann et al. |
| 2011/0235168 A1 | 9/2011 | Sander |
| 2011/0238044 A1 | 9/2011 | Main et al. |
| 2011/0241597 A1 | 10/2011 | Zhu et al. |
| 2011/0251606 A1 | 10/2011 | Kerr |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278035 A1 | 11/2011 | Chen |
| 2011/0278343 A1 | 11/2011 | Knodel et al. |
| 2011/0279268 A1 | 11/2011 | Konishi et al. |
| 2011/0285507 A1 | 11/2011 | Nelson |
| 2011/0290856 A1 | 12/2011 | Shelton, IV et al. |
| 2011/0290858 A1 | 12/2011 | Whitman et al. |
| 2011/0292258 A1 | 12/2011 | Adler et al. |
| 2011/0293690 A1 | 12/2011 | Griffin et al. |
| 2011/0295295 A1 | 12/2011 | Shelton, IV et al. |
| 2011/0295299 A1 | 12/2011 | Braithwaite et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0008880 A1 | 1/2012 | Toth |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0029550 A1 | 2/2012 | Forsell |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080474 A1 * | 4/2012 | Farascioni ........... A61B 17/068 227/175.1 |
| 2012/0080478 A1 | 4/2012 | Morgan et al. |
| 2012/0080491 A1 | 4/2012 | Shelton, IV et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0101488 A1 | 4/2012 | Aldridge et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0132663 A1 | 5/2012 | Kasvikis et al. |
| 2012/0143175 A1 | 6/2012 | Hermann et al. |
| 2012/0171539 A1 | 7/2012 | Rejman et al. |
| 2012/0175398 A1 | 7/2012 | Sandborn et al. |
| 2012/0190964 A1 | 7/2012 | Hyde et al. |
| 2012/0197239 A1 | 8/2012 | Smith et al. |
| 2012/0197272 A1 | 8/2012 | Oray et al. |
| 2012/0203213 A1 | 8/2012 | Kimball et al. |
| 2012/0211542 A1 | 8/2012 | Racenet |
| 2012/0220990 A1 | 8/2012 | Mckenzie et al. |
| 2012/0233298 A1 | 9/2012 | Verbandt et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0241494 A1 | 9/2012 | Marczyk |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0256494 A1 | 10/2012 | Kesler et al. |
| 2012/0271327 A1 | 10/2012 | West et al. |
| 2012/0283707 A1 | 11/2012 | Giordano et al. |
| 2012/0286019 A1 | 11/2012 | Hueil et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296316 A1 | 11/2012 | Imuta |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0310254 A1 | 12/2012 | Manzo et al. |
| 2012/0316424 A1 | 12/2012 | Stopek |
| 2012/0330329 A1 | 12/2012 | Harris et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0069088 A1 | 3/2013 | Speck et al. |
| 2013/0075447 A1 | 3/2013 | Weisenburgh, II et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0106352 A1 | 5/2013 | Nagamine |
| 2013/0112729 A1 | 5/2013 | Beardsley et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |

(56) References Cited

U.S. PATENT DOCUMENTS

| | | |
|---|---|---|
| 2013/0153639 A1 | 6/2013 | Hodgkinson et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172713 A1 | 7/2013 | Kirschenman |
| 2013/0172878 A1 | 7/2013 | Smith |
| 2013/0175315 A1 | 7/2013 | Milliman |
| 2013/0175317 A1 | 7/2013 | Yates et al. |
| 2013/0183769 A1 | 7/2013 | Tajima |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0231681 A1 | 9/2013 | Robinson et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267950 A1 | 10/2013 | Rosa et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0284792 A1 | 10/2013 | Ma |
| 2013/0289565 A1 | 10/2013 | Hassler, Jr. |
| 2013/0293353 A1 | 11/2013 | McPherson et al. |
| 2013/0303845 A1 | 11/2013 | Skula et al. |
| 2013/0306704 A1 | 11/2013 | Balbierz et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0002322 A1 | 1/2014 | Kanome et al. |
| 2014/0005550 A1 | 1/2014 | Lu et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0008289 A1 | 1/2014 | Williams et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0041191 A1 | 2/2014 | Knodel |
| 2014/0048580 A1 | 2/2014 | Merchant et al. |
| 2014/0069240 A1 | 3/2014 | Dauvin et al. |
| 2014/0078715 A1 | 3/2014 | Pickard et al. |
| 2014/0081176 A1 | 3/2014 | Hassan |
| 2014/0088614 A1 | 3/2014 | Blumenkranz |
| 2014/0094681 A1 | 4/2014 | Valentine et al. |
| 2014/0100558 A1 | 4/2014 | Schmitz et al. |
| 2014/0107697 A1 | 4/2014 | Patani et al. |
| 2014/0110453 A1 | 4/2014 | Wingardner et al. |
| 2014/0115229 A1 | 4/2014 | Kothamasu et al. |
| 2014/0131418 A1 | 5/2014 | Kostrzewski |
| 2014/0131419 A1 | 5/2014 | Bettuchi |
| 2014/0135832 A1 | 5/2014 | Park et al. |
| 2014/0148803 A1 | 5/2014 | Taylor |
| 2014/0151433 A1 | 6/2014 | Shelton, IV et al. |
| 2014/0155916 A1 | 6/2014 | Hodgkinson et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0183244 A1 | 7/2014 | Duque et al. |
| 2014/0188091 A1 | 7/2014 | Vidal et al. |
| 2014/0188101 A1 | 7/2014 | Bales, Jr. et al. |
| 2014/0188159 A1 | 7/2014 | Steege |
| 2014/0203063 A1* | 7/2014 | Hessler ............ A61B 17/07207 227/176.1 |
| 2014/0207124 A1 | 7/2014 | Aldridge et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch et al. |
| 2014/0249573 A1 | 9/2014 | Arav |
| 2014/0262408 A1 | 9/2014 | Woodard |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0287703 A1 | 9/2014 | Herbsommer et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0358163 A1 | 12/2014 | Farin et al. |
| 2014/0367445 A1 | 12/2014 | Ingmanson et al. |
| 2014/0373003 A1 | 12/2014 | Grez et al. |
| 2014/0374130 A1 | 12/2014 | Nakamura et al. |
| 2014/0378950 A1 | 12/2014 | Chiu |
| 2015/0001272 A1 | 1/2015 | Sniffin et al. |
| 2015/0002089 A1 | 1/2015 | Rejman et al. |
| 2015/0022012 A1 | 1/2015 | Kim et al. |
| 2015/0025549 A1 | 1/2015 | Kilroy et al. |
| 2015/0025571 A1 | 1/2015 | Suzuki et al. |
| 2015/0034697 A1 | 2/2015 | Mastri et al. |
| 2015/0039010 A1 | 2/2015 | Beardsley et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060516 A1 | 3/2015 | Collings et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0067582 A1 | 3/2015 | Donnelly et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0080883 A1 | 3/2015 | Haverkost et al. |
| 2015/0082624 A1 | 3/2015 | Craig et al. |
| 2015/0083781 A1 | 3/2015 | Giordano et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |

(56) References Cited

U.S. PATENT DOCUMENTS

| | | |
|---|---|---|
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209045 A1 | 7/2015 | Hodgkinson et al. |
| 2015/0216605 A1 | 8/2015 | Baldwin |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0230794 A1 | 8/2015 | Wellman et al. |
| 2015/0230861 A1 | 8/2015 | Woloszko et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272606 A1 | 10/2015 | Nobis |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297824 A1 | 10/2015 | Cabiri et al. |
| 2015/0303417 A1 | 10/2015 | Koeder et al. |
| 2015/0305743 A1 | 10/2015 | Casasanta et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366585 A1 | 12/2015 | Lemay et al. |
| 2015/0367497 A1 | 12/2015 | Ito et al. |
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0029998 A1 | 2/2016 | Brister et al. |
| 2016/0030042 A1 | 2/2016 | Heinrich et al. |
| 2016/0030043 A1 | 2/2016 | Fanelli et al. |
| 2016/0030076 A1 | 2/2016 | Faller et al. |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074035 A1 | 3/2016 | Whitman et al. |
| 2016/0074040 A1 | 3/2016 | Widenhouse et al. |
| 2016/0081678 A1 | 3/2016 | Kappel et al. |
| 2016/0082161 A1 | 3/2016 | Zilberman et al. |
| 2016/0089175 A1 | 3/2016 | Hibner et al. |
| 2016/0118201 A1 | 4/2016 | Nicholas et al. |
| 2016/0132026 A1 | 5/2016 | Wingardner et al. |
| 2016/0135835 A1 | 5/2016 | Onuma |
| 2016/0135895 A1 | 5/2016 | Faasse et al. |
| 2016/0139666 A1 | 5/2016 | Rubin et al. |
| 2016/0174969 A1 | 6/2016 | Kerr et al. |
| 2016/0174983 A1 | 6/2016 | Shelton, IV et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192927 A1 | 7/2016 | Kostrzewski |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0220150 A1 | 8/2016 | Sharonov |
| 2016/0235494 A1 | 8/2016 | Shelton, IV et al. |
| 2016/0242783 A1 | 8/2016 | Shelton, IV et al. |
| 2016/0242855 A1 | 8/2016 | Fichtinger et al. |
| 2016/0249910 A1 | 9/2016 | Shelton, IV et al. |
| 2016/0249922 A1 | 9/2016 | Morgan et al. |
| 2016/0249929 A1 | 9/2016 | Cappola et al. |
| 2016/0256159 A1 | 9/2016 | Pinjala et al. |
| 2016/0256184 A1 | 9/2016 | Shelton, IV et al. |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0270781 A1 | 9/2016 | Scirica |
| 2016/0287265 A1 | 10/2016 | Macdonald et al. |
| 2016/0287279 A1 | 10/2016 | Bovay et al. |
| 2016/0302820 A1 | 10/2016 | Hibner et al. |
| 2016/0310143 A1 | 10/2016 | Bettuchi |
| 2016/0314716 A1 | 10/2016 | Grubbs |
| 2016/0314717 A1 | 10/2016 | Grubbs |
| 2016/0345972 A1 | 12/2016 | Beardsley et al. |
| 2016/0367122 A1 | 12/2016 | Ichimura et al. |
| 2016/0374669 A1 | 12/2016 | Overmyer et al. |
| 2016/0374716 A1 | 12/2016 | Kessler |
| 2017/0007234 A1 | 1/2017 | Chin et al. |
| 2017/0007244 A1 | 1/2017 | Shelton, IV et al. |
| 2017/0007245 A1 | 1/2017 | Shelton, IV et al. |
| 2017/0007347 A1 | 1/2017 | Jaworek et al. |
| 2017/0020616 A1 | 1/2017 | Vale et al. |
| 2017/0055819 A1 | 3/2017 | Hansen et al. |
| 2017/0055980 A1 | 3/2017 | Vendely et al. |
| 2017/0056008 A1 | 3/2017 | Shelton, IV et al. |
| 2017/0056015 A1* | 3/2017 | Harris ................ A61B 17/068 |
| 2017/0056016 A1 | 3/2017 | Barton et al. |
| 2017/0056018 A1 | 3/2017 | Zeiner et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086842 A1 | 3/2017 | Shelton, IV et al. |
| 2017/0086930 A1 | 3/2017 | Thompson et al. |
| 2017/0086932 A1 | 3/2017 | Auld et al. |
| 2017/0095922 A1 | 4/2017 | Licht et al. |
| 2017/0105727 A1 | 4/2017 | Scheib et al. |
| 2017/0105733 A1 | 4/2017 | Scheib et al. |
| 2017/0105786 A1 | 4/2017 | Scheib et al. |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0168187 A1 | 6/2017 | Calderon et al. |
| 2017/0172382 A1 | 6/2017 | Nir et al. |
| 2017/0172549 A1 | 6/2017 | Smaby et al. |
| 2017/0172662 A1 | 6/2017 | Panescu et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196648 A1* | 7/2017 | Ward ................ A61B 18/085 |
| 2017/0196649 A1 | 7/2017 | Yates et al. |
| 2017/0202607 A1 | 7/2017 | Shelton, IV et al. |
| 2017/0202770 A1 | 7/2017 | Friedrich et al. |
| 2017/0209145 A1 | 7/2017 | Swayze et al. |
| 2017/0224332 A1 | 8/2017 | Hunter et al. |
| 2017/0231628 A1 | 8/2017 | Shelton, IV et al. |
| 2017/0231629 A1 | 8/2017 | Stopek et al. |
| 2017/0238962 A1 | 8/2017 | Hansen et al. |
| 2017/0242455 A1 | 8/2017 | Dickens |
| 2017/0245949 A1 | 8/2017 | Randle |
| 2017/0249431 A1 | 8/2017 | Shelton, IV et al. |
| 2017/0252060 A1 | 9/2017 | Ellingson et al. |
| 2017/0255799 A1 | 9/2017 | Zhao et al. |
| 2017/0262110 A1 | 9/2017 | Polishchuk et al. |
| 2017/0265774 A1 | 9/2017 | Johnson et al. |
| 2017/0281186 A1 | 10/2017 | Shelton, IV et al. |
| 2017/0281189 A1 | 10/2017 | Nalagatla et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0312042 A1 | 11/2017 | Giordano et al. |
| 2017/0319047 A1 | 11/2017 | Poulsen et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |

(56) References Cited

U.S. PATENT DOCUMENTS

| | | |
|---|---|---|
| 2018/0042610 A1 | 2/2018 | Sgroi, Jr. |
| 2018/0042689 A1 | 2/2018 | Mozdzierz et al. |
| 2018/0049738 A1 | 2/2018 | Meloul et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0067004 A1 | 3/2018 | Sgroi, Jr. |
| 2018/0085116 A1 | 3/2018 | Yates et al. |
| 2018/0085117 A1 | 3/2018 | Shelton, IV et al. |
| 2018/0085120 A1 | 3/2018 | Viola |
| 2018/0092710 A1 | 4/2018 | Bosisio et al. |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125590 A1 | 5/2018 | Giordano et al. |
| 2018/0125594 A1 | 5/2018 | Beardsley |
| 2018/0132845 A1 | 5/2018 | Schmid et al. |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0133521 A1 | 5/2018 | Frushour et al. |
| 2018/0140299 A1 | 5/2018 | Weaner et al. |
| 2018/0146960 A1 | 5/2018 | Shelton, IV et al. |
| 2018/0153542 A1 | 6/2018 | Shelton, IV et al. |
| 2018/0153634 A1 | 6/2018 | Zemlok et al. |
| 2018/0161034 A1 | 6/2018 | Scheib et al. |
| 2018/0168572 A1 | 6/2018 | Burbank |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0168754 A1 | 6/2018 | Overmyer |
| 2018/0228490 A1 | 8/2018 | Richard et al. |
| 2018/0231475 A1 | 8/2018 | Brown et al. |
| 2018/0235609 A1 | 8/2018 | Harris et al. |
| 2018/0235617 A1 | 8/2018 | Shelton, IV et al. |
| 2018/0235618 A1 | 8/2018 | Kostrzewski |
| 2018/0235626 A1 | 8/2018 | Shelton, IV et al. |
| 2018/0236181 A1 | 8/2018 | Marlin et al. |
| 2018/0242970 A1 | 8/2018 | Mozdzierz |
| 2018/0247711 A1 | 8/2018 | Terry |
| 2018/0250002 A1 | 9/2018 | Eschbach |
| 2018/0271520 A1 | 9/2018 | Shelton, IV et al. |
| 2018/0271604 A1 | 9/2018 | Grout et al. |
| 2018/0273597 A1 | 9/2018 | Stimson |
| 2018/0280073 A1 | 10/2018 | Sanai et al. |
| 2018/0289371 A1 | 10/2018 | Wang et al. |
| 2018/0296216 A1 | 10/2018 | Shelton, IV et al. |
| 2018/0296290 A1 | 10/2018 | Namiki et al. |
| 2018/0317905 A1 | 11/2018 | Olson et al. |
| 2018/0317915 A1 | 11/2018 | McDonald, II |
| 2018/0325514 A1 | 11/2018 | Harris et al. |
| 2018/0333169 A1 | 11/2018 | Leimbach et al. |
| 2018/0353176 A1 | 12/2018 | Shelton, IV et al. |
| 2018/0360446 A1 | 12/2018 | Shelton, IV et al. |
| 2018/0360456 A1 | 12/2018 | Shelton, IV et al. |
| 2018/0360472 A1 | 12/2018 | Harris et al. |
| 2018/0360473 A1 | 12/2018 | Shelton, IV et al. |
| 2018/0368066 A1 | 12/2018 | Howell et al. |
| 2018/0368833 A1 | 12/2018 | Shelton, IV et al. |
| 2018/0368839 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0372806 A1 | 12/2018 | Laughery et al. |
| 2018/0375165 A1 | 12/2018 | Shelton, IV et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000481 A1 | 1/2019 | Harris et al. |
| 2019/0000535 A1 | 1/2019 | Messerly et al. |
| 2019/0000536 A1 | 1/2019 | Yates et al. |
| 2019/0008515 A1 | 1/2019 | Beardsley et al. |
| 2019/0015102 A1 | 1/2019 | Baber et al. |
| 2019/0015165 A1 | 1/2019 | Giordano et al. |
| 2019/0017311 A1 | 1/2019 | McGettrick et al. |
| 2019/0021733 A1 | 1/2019 | Burbank |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038285 A1 | 2/2019 | Mozdzierz |
| 2019/0059986 A1 | 2/2019 | Shelton, IV et al. |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0099179 A1 | 4/2019 | Leimbach et al. |
| 2019/0099181 A1 | 4/2019 | Shelton, IV et al. |
| 2019/0099229 A1 | 4/2019 | Spivey et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0110779 A1 | 4/2019 | Gardner et al. |
| 2019/0110791 A1 | 4/2019 | Shelton, IV et al. |
| 2019/0110792 A1 | 4/2019 | Shelton, IV et al. |
| 2019/0117224 A1 | 4/2019 | Setser et al. |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125342 A1 | 5/2019 | Beardsley et al. |
| 2019/0125344 A1 | 5/2019 | DiNardo et al. |
| 2019/0125357 A1 | 5/2019 | Shelton, IV et al. |
| 2019/0125358 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133422 A1 | 5/2019 | Nakamura |
| 2019/0133577 A1 | 5/2019 | Weadock et al. |
| 2019/0138770 A1 | 5/2019 | Compaijen et al. |
| 2019/0142421 A1 | 5/2019 | Shelton, IV |

(56) References Cited

U.S. PATENT DOCUMENTS

| | | |
|---|---|---|
| 2019/0142423 A1 | 5/2019 | Satti, III et al. |
| 2019/0150925 A1 | 5/2019 | Marczyk et al. |
| 2019/0151029 A1 | 5/2019 | Robinson |
| 2019/0159778 A1 | 5/2019 | Shelton, IV et al. |
| 2019/0175847 A1 | 6/2019 | Pocreva, III et al. |
| 2019/0183502 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192156 A1 | 6/2019 | Simms et al. |
| 2019/0192157 A1 | 6/2019 | Scott et al. |
| 2019/0192235 A1 | 6/2019 | Harris et al. |
| 2019/0192236 A1 | 6/2019 | Shelton, IV et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200989 A1 | 7/2019 | Burbank et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201079 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201158 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206003 A1 | 7/2019 | Harris et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0261982 A1 | 8/2019 | Holsten |
| 2019/0261983 A1 | 8/2019 | Granger et al. |
| 2019/0261984 A1 | 8/2019 | Nelson et al. |
| 2019/0261987 A1 | 8/2019 | Viola et al. |
| 2019/0269400 A1 | 9/2019 | Mandakolathur Vasudevan et al. |
| 2019/0269402 A1 | 9/2019 | Murray et al. |
| 2019/0269407 A1 | 9/2019 | Swensgard et al. |
| 2019/0269428 A1 | 9/2019 | Allen et al. |
| 2019/0274677 A1 | 9/2019 | Shelton, IV |
| 2019/0274679 A1 | 9/2019 | Shelton, IV |
| 2019/0274685 A1 | 9/2019 | Olson et al. |
| 2019/0282233 A1 | 9/2019 | Burbank et al. |
| 2019/0290263 A1 | 9/2019 | Morgan et al. |
| 2019/0290264 A1 | 9/2019 | Morgan et al. |
| 2019/0290266 A1 | 9/2019 | Scheib et al. |
| 2019/0290267 A1 | 9/2019 | Baxter, III et al. |
| 2019/0290297 A1 | 9/2019 | Haider et al. |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298357 A1 | 10/2019 | Shelton, IV et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0298381 A1 | 10/2019 | Kreidler et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307456 A1 | 10/2019 | Shelton, IV et al. |
| 2019/0307479 A1 | 10/2019 | Shelton, IV et al. |
| 2019/0314015 A1 | 10/2019 | Shelton, IV et al. |
| 2019/0314016 A1 | 10/2019 | Huitema et al. |
| 2019/0314017 A1 | 10/2019 | Huitema et al. |
| 2019/0314018 A1 | 10/2019 | Huitema et al. |
| 2019/0321040 A1 | 10/2019 | Shelton, IV |
| 2019/0321062 A1 | 10/2019 | Williams |
| 2019/0328387 A1 | 10/2019 | Overmyer et al. |
| 2019/0328390 A1 | 10/2019 | Harris et al. |
| 2019/0343515 A1 | 11/2019 | Morgan et al. |
| 2019/0343525 A1 | 11/2019 | Shelton, IV et al. |
| 2019/0350581 A1 | 11/2019 | Baxter, III et al. |
| 2019/0350582 A1 | 11/2019 | Shelton, IV et al. |
| 2019/0357909 A1 | 11/2019 | Huitema et al. |
| 2019/0365384 A1 | 12/2019 | Baxter, III et al. |
| 2019/0374224 A1 | 12/2019 | Huitema et al. |
| 2019/0388091 A1 | 12/2019 | Eschbach et al. |
| 2020/0000471 A1 | 1/2020 | Shelton, IV et al. |
| 2020/0000531 A1 | 1/2020 | Giordano et al. |
| 2020/0008800 A1 | 1/2020 | Shelton, IV et al. |
| 2020/0008802 A1 | 1/2020 | Aronhalt et al. |
| 2020/0008809 A1 | 1/2020 | Shelton, IV et al. |
| 2020/0008827 A1 | 1/2020 | Dearden et al. |
| 2020/0015817 A1 | 1/2020 | Harris et al. |
| 2020/0015819 A1 | 1/2020 | Shelton, IV et al. |
| 2020/0015915 A1 | 1/2020 | Swayze et al. |
| 2020/0037939 A1 | 2/2020 | Castagna et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0046348 A1 | 2/2020 | Shelton, IV et al. |
| 2020/0046355 A1 | 2/2020 | Harris et al. |
| 2020/0046356 A1 | 2/2020 | Baxter, III et al. |
| 2020/0054320 A1 | 2/2020 | Harris et al. |
| 2020/0054321 A1 | 2/2020 | Harris et al. |
| 2020/0054324 A1 | 2/2020 | Shelton, IV et al. |
| 2020/0054329 A1 | 2/2020 | Shelton, IV et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060523 A1 | 2/2020 | Matsuda et al. |
| 2020/0060680 A1 | 2/2020 | Shelton, IV et al. |
| 2020/0060681 A1 | 2/2020 | Shelton, IV et al. |
| 2020/0060713 A1 | 2/2020 | Leimbach et al. |
| 2020/0061385 A1 | 2/2020 | Schwarz et al. |

(56) References Cited

U.S. PATENT DOCUMENTS

| | | |
|---|---|---|
| 2020/0077994 A1 | 3/2020 | Shelton, IV et al. |
| 2020/0078015 A1 | 3/2020 | Miller et al. |
| 2020/0085427 A1 | 3/2020 | Giordano et al. |
| 2020/0085431 A1 | 3/2020 | Swayze et al. |
| 2020/0085435 A1 | 3/2020 | Shelton, IV et al. |
| 2020/0085436 A1 | 3/2020 | Beckman et al. |
| 2020/0085518 A1 | 3/2020 | Giordano et al. |
| 2020/0093484 A1 | 3/2020 | Shelton, IV et al. |
| 2020/0093485 A1 | 3/2020 | Shelton, IV et al. |
| 2020/0093506 A1 | 3/2020 | Leimbach et al. |
| 2020/0093550 A1 | 3/2020 | Spivey et al. |
| 2020/0100699 A1 | 4/2020 | Shelton, IV et al. |
| 2020/0100783 A1 | 4/2020 | Yates et al. |
| 2020/0107829 A1 | 4/2020 | Shelton, IV et al. |
| 2020/0114505 A1 | 4/2020 | Kikuchi |
| 2020/0138434 A1 | 5/2020 | Miller et al. |
| 2020/0138435 A1 | 5/2020 | Shelton, IV et al. |
| 2020/0138436 A1 | 5/2020 | Yates et al. |
| 2020/0138534 A1 | 5/2020 | Garcia Kilroy et al. |
| 2020/0146676 A1 | 5/2020 | Yates et al. |
| 2020/0146678 A1 | 5/2020 | Leimbach et al. |
| 2020/0146741 A1 | 5/2020 | Long et al. |
| 2020/0155155 A1 | 5/2020 | Shelton, IV et al. |
| 2020/0187943 A1 | 6/2020 | Shelton, IV et al. |
| 2020/0197027 A1 | 6/2020 | Hershberger et al. |
| 2020/0205810 A1 | 7/2020 | Posey et al. |
| 2020/0205811 A1 | 7/2020 | Posey et al. |
| 2020/0205823 A1 | 7/2020 | Vendely et al. |
| 2020/0214706 A1 | 7/2020 | Vendely et al. |
| 2020/0214731 A1 | 7/2020 | Shelton, IV et al. |
| 2020/0222047 A1 | 7/2020 | Shelton, IV et al. |
| 2020/0229812 A1 | 7/2020 | Parihar et al. |
| 2020/0229814 A1 | 7/2020 | Amariglio et al. |
| 2020/0229816 A1 | 7/2020 | Bakos et al. |
| 2020/0237371 A1 | 7/2020 | Huitema et al. |
| 2020/0246001 A1 | 8/2020 | Ming et al. |
| 2020/0253605 A1 | 8/2020 | Swayze et al. |
| 2020/0261075 A1 | 8/2020 | Boudreaux et al. |
| 2020/0261076 A1 | 8/2020 | Boudreaux et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0261106 A1 | 8/2020 | Hess et al. |
| 2020/0268377 A1 | 8/2020 | Schmid et al. |
| 2020/0275926 A1 | 9/2020 | Shelton, IV et al. |
| 2020/0275927 A1 | 9/2020 | Shelton, IV et al. |
| 2020/0275928 A1 | 9/2020 | Shelton, IV et al. |
| 2020/0280219 A1 | 9/2020 | Laughery et al. |
| 2020/0281585 A1 | 9/2020 | Timm et al. |
| 2020/0281587 A1 | 9/2020 | Schmid et al. |
| 2020/0281590 A1 | 9/2020 | Shelton, IV et al. |
| 2020/0289112 A1 | 9/2020 | Whitfield et al. |
| 2020/0297340 A1 | 9/2020 | Hess et al. |
| 2020/0297341 A1 | 9/2020 | Yates et al. |
| 2020/0297346 A1 | 9/2020 | Shelton, IV et al. |
| 2020/0297438 A1 | 9/2020 | Shelton, IV et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305870 A1 | 10/2020 | Shelton, IV |
| 2020/0305871 A1 | 10/2020 | Shelton, IV et al. |
| 2020/0305872 A1 | 10/2020 | Weidner et al. |
| 2020/0305874 A1 | 10/2020 | Huitema et al. |
| 2020/0315612 A1 | 10/2020 | Shelton, IV et al. |
| 2020/0315623 A1 | 10/2020 | Eisinger et al. |
| 2020/0315625 A1 | 10/2020 | Hall et al. |
| 2020/0315983 A1 | 10/2020 | Widenhouse et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330094 A1 | 10/2020 | Baxter, III et al. |
| 2020/0330096 A1 | 10/2020 | Shelton, IV et al. |
| 2020/0330181 A1 | 10/2020 | Junger et al. |
| 2020/0337693 A1 | 10/2020 | Shelton, IV et al. |
| 2020/0337702 A1 | 10/2020 | Shelton, IV et al. |
| 2020/0337703 A1 | 10/2020 | Shelton, IV et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345354 A1 | 11/2020 | Leimbach et al. |
| 2020/0345355 A1 | 11/2020 | Baxter, III et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345360 A1 | 11/2020 | Leimbach et al. |
| 2020/0345363 A1 | 11/2020 | Shelton, IV et al. |
| 2020/0345435 A1 | 11/2020 | Traina |
| 2020/0345446 A1 | 11/2020 | Kimball et al. |
| 2020/0352562 A1 | 11/2020 | Timm et al. |
| 2020/0367885 A1 | 11/2020 | Yates et al. |
| 2020/0367886 A1 | 11/2020 | Shelton, IV et al. |
| 2020/0375585 A1 | 12/2020 | Swayze et al. |
| 2020/0375592 A1 | 12/2020 | Hall et al. |
| 2020/0375593 A1 | 12/2020 | Hunter et al. |
| 2020/0375597 A1 | 12/2020 | Shelton, IV et al. |
| 2020/0390444 A1 | 12/2020 | Harris et al. |
| 2020/0397430 A1 | 12/2020 | Patel et al. |
| 2020/0397433 A1 | 12/2020 | Lytle, IV et al. |
| 2020/0397434 A1 | 12/2020 | Overmyer et al. |
| 2020/0405290 A1 | 12/2020 | Shelton, IV et al. |
| 2020/0405292 A1 | 12/2020 | Shelton, IV et al. |
| 2020/0405293 A1 | 12/2020 | Shelton, IV et al. |
| 2020/0405294 A1 | 12/2020 | Shelton, IV |
| 2020/0405295 A1 | 12/2020 | Shelton, IV et al. |
| 2020/0405296 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405304 A1 | 12/2020 | Mozdzierz et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405309 A1 | 12/2020 | Shelton, IV et al. |
| 2020/0405312 A1 | 12/2020 | Shelton, IV et al. |
| 2020/0405313 A1 | 12/2020 | Shelton, IV |
| 2020/0405314 A1 | 12/2020 | Shelton, IV et al. |
| 2020/0405316 A1 | 12/2020 | Shelton, IV et al. |
| 2020/0405341 A1 | 12/2020 | Hess et al. |
| 2020/0405403 A1 | 12/2020 | Shelton, IV et al. |
| 2020/0405404 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405416 A1 | 12/2020 | Shelton, IV et al. |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0000466 A1 | 1/2021 | Leimbach et al. |
| 2021/0000467 A1 | 1/2021 | Shelton, IV et al. |
| 2021/0000470 A1 | 1/2021 | Leimbach et al. |
| 2021/0015480 A1 | 1/2021 | Shelton, IV et al. |
| 2021/0022741 A1 | 1/2021 | Baxter, III et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059666 A1 | 3/2021 | Schmid et al. |
| 2021/0059669 A1 | 3/2021 | Yates et al. |
| 2021/0059670 A1 | 3/2021 | Overmyer et al. |
| 2021/0059671 A1 | 3/2021 | Shelton, IV et al. |

(56) References Cited

U.S. PATENT DOCUMENTS

| | | |
|---|---|---|
| 2021/0059672 A1 | 3/2021 | Giordano et al. |
| 2021/0059673 A1 | 3/2021 | Shelton, IV et al. |
| 2021/0068817 A1 | 3/2021 | Shelton, IV et al. |
| 2021/0068818 A1 | 3/2021 | Overmyer et al. |
| 2021/0068820 A1 | 3/2021 | Parihar et al. |
| 2021/0068829 A1 | 3/2021 | Miller et al. |
| 2021/0068830 A1 | 3/2021 | Baber et al. |
| 2021/0068831 A1 | 3/2021 | Baber et al. |
| 2021/0068832 A1 | 3/2021 | Yates et al. |
| 2021/0068835 A1 | 3/2021 | Shelton, IV et al. |
| 2021/0077092 A1 | 3/2021 | Parihar et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085317 A1 | 3/2021 | Miller et al. |
| 2021/0085318 A1 | 3/2021 | Swayze et al. |
| 2021/0085319 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0085326 A1 | 3/2021 | Vendely et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100550 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0128153 A1 | 5/2021 | Sgroi |
| 2021/0137522 A1 | 5/2021 | Shelton, IV et al. |
| 2021/0153866 A1 | 5/2021 | Knapp et al. |
| 2021/0177401 A1 | 6/2021 | Abramek et al. |
| 2021/0177411 A1 | 6/2021 | Williams |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186506 A1 | 6/2021 | Shelton, IV et al. |
| 2021/0186507 A1 | 6/2021 | Shelton, IV et al. |
| 2021/0204941 A1 | 7/2021 | Dewaele et al. |
| 2021/0204951 A1 | 7/2021 | Sgroi et al. |
| 2021/0212671 A1 | 7/2021 | Ramadan et al. |
| 2021/0212691 A1 | 7/2021 | Smith et al. |
| 2021/0212776 A1 | 7/2021 | Schmitt et al. |
| 2021/0219976 A1 | 7/2021 | DiNardo et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244411 A1 | 8/2021 | Smith et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267592 A1 | 9/2021 | Baxter, III et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275175 A1 | 9/2021 | Vadali et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0290322 A1 | 9/2021 | Traina |
| 2021/0298745 A1 | 9/2021 | Leimbach et al. |
| 2021/0298746 A1 | 9/2021 | Leimbach et al. |
| 2021/0307744 A1 | 10/2021 | Walcott et al. |
| 2021/0307748 A1 | 10/2021 | Harris et al. |
| 2021/0307754 A1 | 10/2021 | Shelton, IV et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0338260 A1 | 11/2021 | Le Rolland et al. |
| 2021/0353284 A1 | 11/2021 | Yang et al. |
| 2021/0369271 A1 | 12/2021 | Schings et al. |
| 2021/0369273 A1 | 12/2021 | Yates et al. |
| 2021/0378669 A1 | 12/2021 | Shelton, IV et al. |
| 2021/0393260 A1 | 12/2021 | Shelton, IV et al. |
| 2021/0393261 A1 | 12/2021 | Harris et al. |
| 2021/0393262 A1 | 12/2021 | Shelton, IV et al. |
| 2021/0393268 A1 | 12/2021 | Shelton, IV et al. |
| 2021/0393366 A1 | 12/2021 | Shelton, IV et al. |
| 2022/0000478 A1 | 1/2022 | Shelton, IV et al. |
| 2022/0000479 A1 | 1/2022 | Shelton, IV et al. |
| 2022/0015760 A1 | 1/2022 | Beardsley et al. |
| 2022/0031313 A1 | 2/2022 | Bakos et al. |
| 2022/0031314 A1 | 2/2022 | Bakos et al. |
| 2022/0031315 A1 | 2/2022 | Bakos et al. |
| 2022/0031319 A1 | 2/2022 | Witte et al. |
| 2022/0031320 A1 | 2/2022 | Hall et al. |
| 2022/0031322 A1 | 2/2022 | Parks |
| 2022/0031323 A1 | 2/2022 | Witte |
| 2022/0031324 A1 | 2/2022 | Hall et al. |
| 2022/0031345 A1 | 2/2022 | Witte |
| 2022/0031346 A1 | 2/2022 | Parks |
| 2022/0031350 A1 | 2/2022 | Witte |
| 2022/0031351 A1 | 2/2022 | Moubarak et al. |
| 2022/0049593 A1 | 2/2022 | Groover et al. |
| 2022/0054125 A1 | 2/2022 | Ji et al. |
| 2022/0054130 A1 | 2/2022 | Overmyer et al. |
| 2022/0061836 A1 | 3/2022 | Parihar et al. |
| 2022/0061843 A1 | 3/2022 | Vendely et al. |
| 2022/0061845 A1 | 3/2022 | Shelton, IV et al. |
| 2022/0061862 A1 | 3/2022 | Shelton, IV et al. |
| 2022/0071630 A1 | 3/2022 | Swayze et al. |
| 2022/0071631 A1 | 3/2022 | Harris et al. |
| 2022/0071632 A1 | 3/2022 | Patel et al. |
| 2022/0071635 A1 | 3/2022 | Shelton, IV et al. |
| 2022/0079580 A1 | 3/2022 | Vendely et al. |
| 2022/0079586 A1 | 3/2022 | Shelton, IV et al. |
| 2022/0079588 A1 | 3/2022 | Harris et al. |
| 2022/0079589 A1 | 3/2022 | Harris et al. |
| 2022/0079590 A1 | 3/2022 | Harris et al. |
| 2022/0079595 A1 | 3/2022 | Huitema et al. |
| 2022/0079596 A1 | 3/2022 | Huitema et al. |
| 2022/0087676 A1 | 3/2022 | Shelton, IV et al. |
| 2022/0104816 A1 | 4/2022 | Fernandes et al. |
| 2022/0117602 A1 | 4/2022 | Wise et al. |

(56) References Cited

U.S. PATENT DOCUMENTS

| | | |
|---|---|---|
| 2022/0133299 A1 | 5/2022 | Baxter, III |
| 2022/0133300 A1 | 5/2022 | Leimbach et al. |
| 2022/0133301 A1 | 5/2022 | Leimbach |
| 2022/0133302 A1 | 5/2022 | Zerkle et al. |
| 2022/0133303 A1 | 5/2022 | Huang |
| 2022/0133304 A1 | 5/2022 | Leimbach et al. |
| 2022/0133310 A1 | 5/2022 | Ross |
| 2022/0133311 A1 | 5/2022 | Huang |
| 2022/0133312 A1 | 5/2022 | Huang |
| 2022/0142643 A1 | 5/2022 | Shelton, IV et al. |
| 2022/0151611 A1 | 5/2022 | Shelton, IV et al. |
| 2022/0151613 A1 | 5/2022 | Vendely et al. |
| 2022/0151614 A1 | 5/2022 | Vendely et al. |
| 2022/0151615 A1 | 5/2022 | Shelton, IV et al. |
| 2022/0151616 A1 | 5/2022 | Shelton, IV et al. |
| 2022/0160358 A1 | 5/2022 | Wixey |
| 2022/0167968 A1 | 6/2022 | Worthington et al. |
| 2022/0167970 A1 | 6/2022 | Aronhalt et al. |
| 2022/0167971 A1 | 6/2022 | Shelton, IV et al. |
| 2022/0167972 A1 | 6/2022 | Shelton, IV et al. |
| 2022/0167973 A1 | 6/2022 | Shelton, IV et al. |
| 2022/0167974 A1 | 6/2022 | Shelton, IV et al. |
| 2022/0167975 A1 | 6/2022 | Shelton, IV et al. |
| 2022/0167977 A1 | 6/2022 | Shelton, IV et al. |
| 2022/0167979 A1 | 6/2022 | Yates et al. |
| 2022/0167980 A1 | 6/2022 | Shelton, IV et al. |
| 2022/0167981 A1 | 6/2022 | Shelton, IV et al. |
| 2022/0167982 A1 | 6/2022 | Shelton, IV et al. |
| 2022/0167983 A1 | 6/2022 | Shelton, IV et al. |
| 2022/0167984 A1 | 6/2022 | Shelton, IV et al. |
| 2022/0167995 A1 | 6/2022 | Parfett et al. |
| 2022/0168038 A1 | 6/2022 | Shelton, IV et al. |
| 2022/0175370 A1 | 6/2022 | Shelton, IV et al. |
| 2022/0175371 A1 | 6/2022 | Hess et al. |
| 2022/0175372 A1 | 6/2022 | Shelton, IV et al. |
| 2022/0175375 A1 | 6/2022 | Harris et al. |
| 2022/0175378 A1 | 6/2022 | Leimbach et al. |
| 2022/0175381 A1 | 6/2022 | Scheib et al. |
| 2022/0183685 A1 | 6/2022 | Shelton, IV et al. |
| 2022/0211367 A1 | 7/2022 | Schmid et al. |
| 2022/0218332 A1 | 7/2022 | Shelton, IV et al. |
| 2022/0218333 A1 | 7/2022 | Parihar et al. |
| 2022/0218334 A1 | 7/2022 | Parihar et al. |
| 2022/0218336 A1 | 7/2022 | Timm et al. |
| 2022/0218337 A1 | 7/2022 | Timm et al. |
| 2022/0218338 A1 | 7/2022 | Shelton, IV et al. |
| 2022/0218340 A1 | 7/2022 | Harris et al. |
| 2022/0218344 A1 | 7/2022 | Leimbach et al. |
| 2022/0218345 A1 | 7/2022 | Shelton, IV et al. |
| 2022/0218346 A1 | 7/2022 | Shelton, IV et al. |
| 2022/0218347 A1 | 7/2022 | Shelton, IV et al. |
| 2022/0218348 A1 | 7/2022 | Swensgard et al. |
| 2022/0218349 A1 | 7/2022 | Shelton, IV et al. |
| 2022/0218350 A1 | 7/2022 | Shelton, IV et al. |
| 2022/0218351 A1 | 7/2022 | Shelton, IV et al. |
| 2022/0218376 A1 | 7/2022 | Shelton, IV et al. |
| 2022/0218378 A1 | 7/2022 | Shelton, IV et al. |
| 2022/0218381 A1 | 7/2022 | Leimbach et al. |
| 2022/0218382 A1 | 7/2022 | Leimbach et al. |
| 2022/0225980 A1 | 7/2022 | Shelton, IV et al. |
| 2022/0225982 A1 | 7/2022 | Yates et al. |
| 2022/0225986 A1 | 7/2022 | Shelton, IV et al. |
| 2022/0225992 A1 | 7/2022 | Smith et al. |
| 2022/0225993 A1 | 7/2022 | Huitema et al. |
| 2022/0225994 A1 | 7/2022 | Setser et al. |
| 2022/0226012 A1 | 7/2022 | Shelton, IV et al. |
| 2022/0226013 A1 | 7/2022 | Hall et al. |
| 2022/0233184 A1 | 7/2022 | Parihar et al. |
| 2022/0233185 A1 | 7/2022 | Parihar et al. |
| 2022/0233186 A1 | 7/2022 | Timm et al. |
| 2022/0233187 A1 | 7/2022 | Timm et al. |
| 2022/0233188 A1 | 7/2022 | Timm et al. |
| 2022/0233194 A1 | 7/2022 | Baxter, III et al. |
| 2022/0233195 A1 | 7/2022 | Shelton, IV et al. |
| 2022/0233257 A1 | 7/2022 | Shelton, IV et al. |
| 2022/0240927 A1 | 8/2022 | Timm et al. |
| 2022/0240928 A1 | 8/2022 | Timm et al. |
| 2022/0240929 A1 | 8/2022 | Timm et al. |
| 2022/0240930 A1 | 8/2022 | Yates et al. |
| 2022/0240936 A1 | 8/2022 | Huitema et al. |
| 2022/0240937 A1 | 8/2022 | Shelton, IV et al. |
| 2022/0249095 A1 | 8/2022 | Shelton, IV et al. |
| 2022/0265272 A1 | 8/2022 | Li et al. |
| 2022/0273291 A1 | 9/2022 | Shelton, IV et al. |
| 2022/0273292 A1 | 9/2022 | Shelton, IV et al. |
| 2022/0273293 A1 | 9/2022 | Shelton, IV et al. |
| 2022/0273294 A1 | 9/2022 | Creamer et al. |
| 2022/0273299 A1 | 9/2022 | Shelton, IV et al. |
| 2022/0273300 A1 | 9/2022 | Shelton, IV et al. |
| 2022/0273301 A1 | 9/2022 | Creamer et al. |
| 2022/0273302 A1 | 9/2022 | Shelton, IV et al. |
| 2022/0273303 A1 | 9/2022 | Creamer et al. |
| 2022/0273304 A1 | 9/2022 | Shelton, IV et al. |
| 2022/0273305 A1 | 9/2022 | Shelton, IV et al. |
| 2022/0273306 A1 | 9/2022 | Shelton, IV et al. |
| 2022/0273307 A1 | 9/2022 | Shelton, IV et al. |
| 2022/0273308 A1 | 9/2022 | Shelton, IV et al. |
| 2022/0278438 A1 | 9/2022 | Shelton, IV et al. |
| 2022/0287711 A1 | 9/2022 | Ming et al. |
| 2022/0296230 A1 | 9/2022 | Adams et al. |
| 2022/0296231 A1 | 9/2022 | Adams et al. |
| 2022/0296232 A1 | 9/2022 | Adams et al. |
| 2022/0296233 A1 | 9/2022 | Morgan et al. |
| 2022/0296234 A1 | 9/2022 | Shelton, IV et al. |
| 2022/0296235 A1 | 9/2022 | Morgan et al. |
| 2022/0296236 A1 | 9/2022 | Bakos et al. |
| 2022/0296237 A1 | 9/2022 | Bakos et al. |
| 2022/0304679 A1 | 9/2022 | Bakos et al. |
| 2022/0304680 A1 | 9/2022 | Shelton, IV et al. |
| 2022/0304681 A1 | 9/2022 | Shelton, IV et al. |
| 2022/0304682 A1 | 9/2022 | Shelton, IV et al. |
| 2022/0304683 A1 | 9/2022 | Shelton, IV et al. |
| 2022/0304684 A1 | 9/2022 | Bakos et al. |
| 2022/0304685 A1 | 9/2022 | Bakos et al. |
| 2022/0304686 A1 | 9/2022 | Shelton, IV et al. |
| 2022/0304687 A1 | 9/2022 | Shelton, IV et al. |
| 2022/0304688 A1 | 9/2022 | Shelton, IV et al. |
| 2022/0304689 A1 | 9/2022 | Shelton, IV |
| 2022/0304690 A1 | 9/2022 | Baxter, III et al. |
| 2022/0304714 A1 | 9/2022 | Shelton, IV et al. |
| 2022/0304715 A1 | 9/2022 | Shelton, IV |
| 2022/0313253 A1 | 10/2022 | Shelton, IV et al. |
| 2022/0313263 A1 | 10/2022 | Huitema et al. |
| 2022/0313619 A1 | 10/2022 | Schmid et al. |
| 2022/0323067 A1 | 10/2022 | Overmyer et al. |
| 2022/0323070 A1 | 10/2022 | Ross et al. |
| 2022/0330940 A1 | 10/2022 | Shelton, IV et al. |
| 2022/0338870 A1 | 10/2022 | Swayze et al. |
| 2022/0346774 A1 | 11/2022 | Hess et al. |
| 2022/0346775 A1 | 11/2022 | Hess et al. |
| 2022/0354493 A1 | 11/2022 | Shelton, IV et al. |
| 2022/0354495 A1 | 11/2022 | Baxter, III et al. |
| 2022/0361879 A1 | 11/2022 | Baxter, III et al. |
| 2022/0370069 A1 | 11/2022 | Simms et al. |

FOREIGN PATENT DOCUMENTS

| | | |
|---|---|---|
| AU | 2012268848 A1 | 1/2013 |
| AU | 2011218702 B2 | 6/2013 |
| AU | 2012200178 B2 | 7/2013 |
| BR | 112013007744 A2 | 6/2016 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |

(56) References Cited

FOREIGN PATENT DOCUMENTS

| | | | |
|---|---|---|---|
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |

(56) References Cited

FOREIGN PATENT DOCUMENTS

| | | | |
|---|---|---|---|
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 2153793 A2 | 2/2010 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2529671 A2 | 12/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2878274 A1 | 6/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135225 A2 | 3/2017 |
| EP | 2789299 B1 | 5/2017 |
| EP | 3225190 A2 | 10/2017 |
| EP | 3235445 A1 | 10/2017 |
| EP | 3326548 A1 | 5/2018 |
| EP | 3363378 A1 | 8/2018 |
| EP | 3409216 A1 | 12/2018 |
| EP | 3476334 A1 | 5/2019 |
| EP | 3275378 B1 | 7/2019 |
| EP | 3505095 A1 | 7/2019 |
| EP | 3791810 A1 | 3/2021 |
| ES | 1070456 U | 9/2009 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S6333137 A | 2/1988 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |
| JP | H0385009 U | 8/1991 |
| JP | H0489041 A | 3/1992 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H0636757 A | 2/1994 |
| JP | H06237937 A | 8/1994 |
| JP | H06304176 A | 11/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H0950795 A | 2/1997 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |

(56) References Cited

FOREIGN PATENT DOCUMENTS

| | | |
|---|---|---|
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008154804 A | 7/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | 2011200665 A | 10/2011 |
| JP | D1432094 | 12/2011 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541982 A | 11/2013 |
| JP | 2013541983 A | 11/2013 |
| JP | 2013541997 A | 11/2013 |
| JP | 2014018667 A | 2/2014 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015516838 A | 6/2015 |
| JP | 2015521524 A | 7/2015 |
| JP | 2015521525 A | 7/2015 |
| JP | 2016007800 A | 1/2016 |
| JP | 2016508792 A | 3/2016 |
| JP | 2016512057 A | 4/2016 |
| JP | 2016530949 A | 10/2016 |
| JP | 2017513563 A | 6/2017 |
| JP | 1601498 S | 4/2018 |
| JP | 2019513530 A | 5/2019 |
| JP | 2020501797 A | 1/2020 |
| JP | D1677030 S | 1/2021 |
| JP | D1696539 S | 10/2021 |
| KR | 20100110134 A | 10/2010 |
| KR | 20110003229 A | 1/2011 |
| KR | 300631507 | 3/2012 |
| KR | 300747646 | 6/2014 |
| KR | 20180053811 A | 5/2018 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1042742 A1 | 9/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0036690 A2 | 6/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |

(56) References Cited

FOREIGN PATENT DOCUMENTS

| | | |
|---|---|---|
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A1 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |
| WO | WO-2016107448 A1 | 7/2016 |
| WO | WO-2018011664 A1 | 1/2018 |
| WO | WO-2019036490 A1 | 2/2019 |
| WO | WO-2019130087 A1 | 7/2019 |
| WO | WO-2019130089 A1 | 7/2019 |
| WO | WO-2019208902 A1 | 10/2019 |
| WO | WO-2021189234 A1 | 9/2021 |

OTHER PUBLICATIONS

ASTM procedure D2240-05, "Standard Test Method for Rubber Property-Durometer Hardness," (Published Apr. 2010).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. Wit Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~ /media/Files/Datasheets/A3941-Datasheet.ashx?la=en.
Data Sheet of LM4F230H5QR, 2007.
Seiis et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).

(56) References Cited

OTHER PUBLICATIONS

The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3AI-2. 5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Meeh. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DSO0710C, Microchip Technology Inc., Available: http://ww1.microchip.com/downloads/en/AppNotes/00710c.pdf.

Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 9, 2017], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/desiqn/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, Article ID 879294, *Hindawi Publishing Corporation*.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/

(56) References Cited

OTHER PUBLICATIONS

20170522174710/http:/rotarysystems.com: 80/slip-rings/sealed/, retrieved on Aug. 12, 2020, pp. 1-2.
IEEE Std 802.Mar. 2012 (Revision of IEEE Std 802.Mar. 2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.

\* cited by examiner

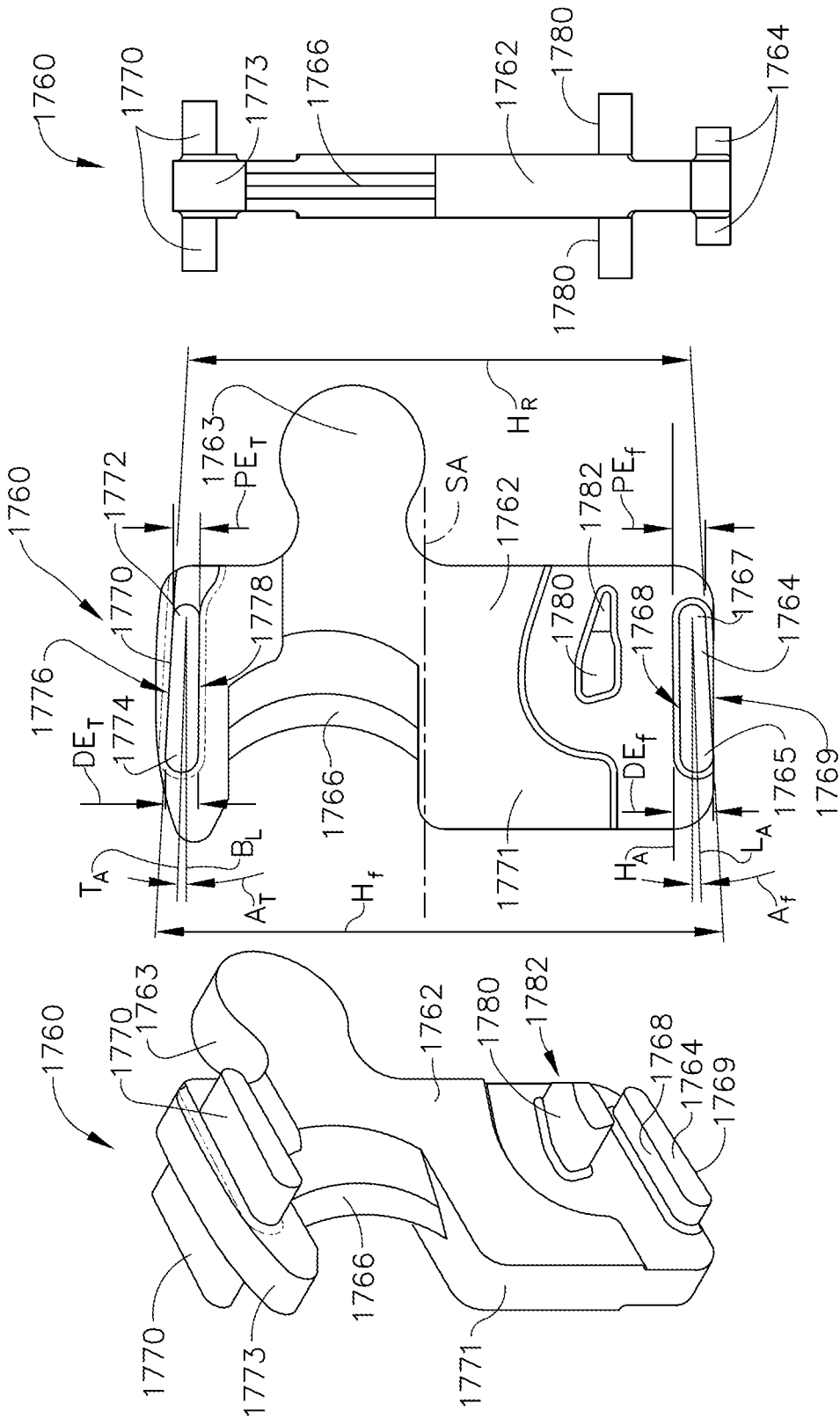

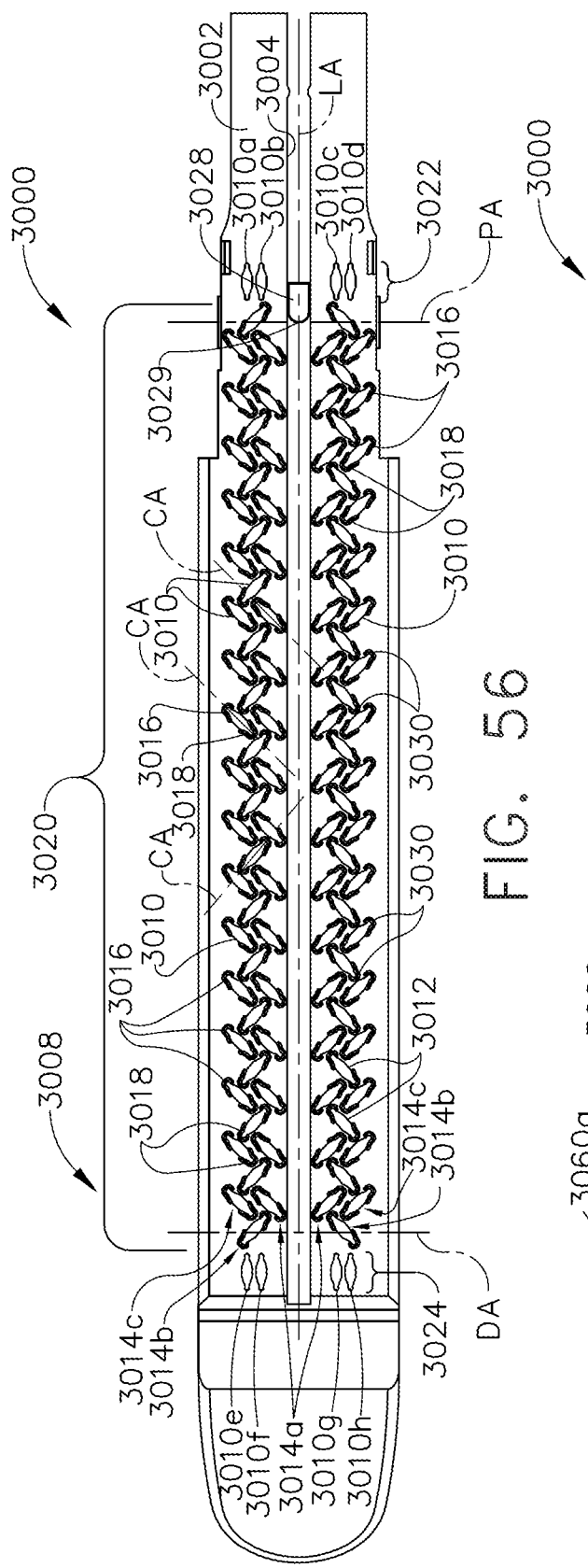
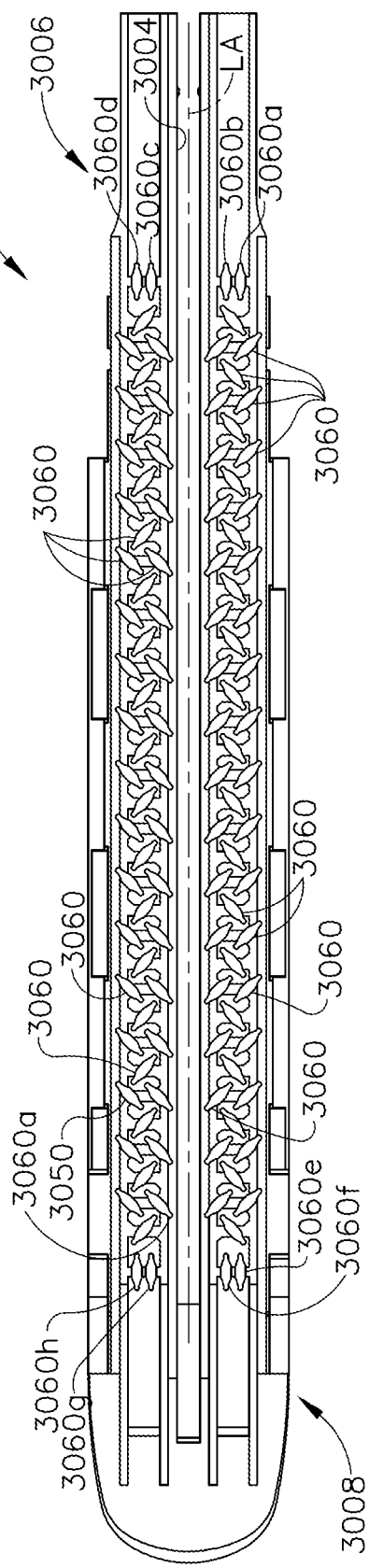
FIG. 56
FIG. 57

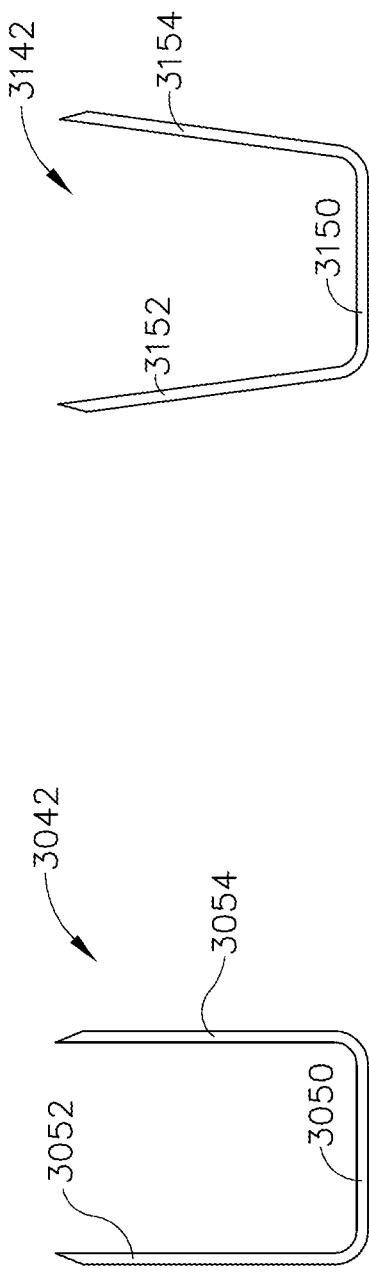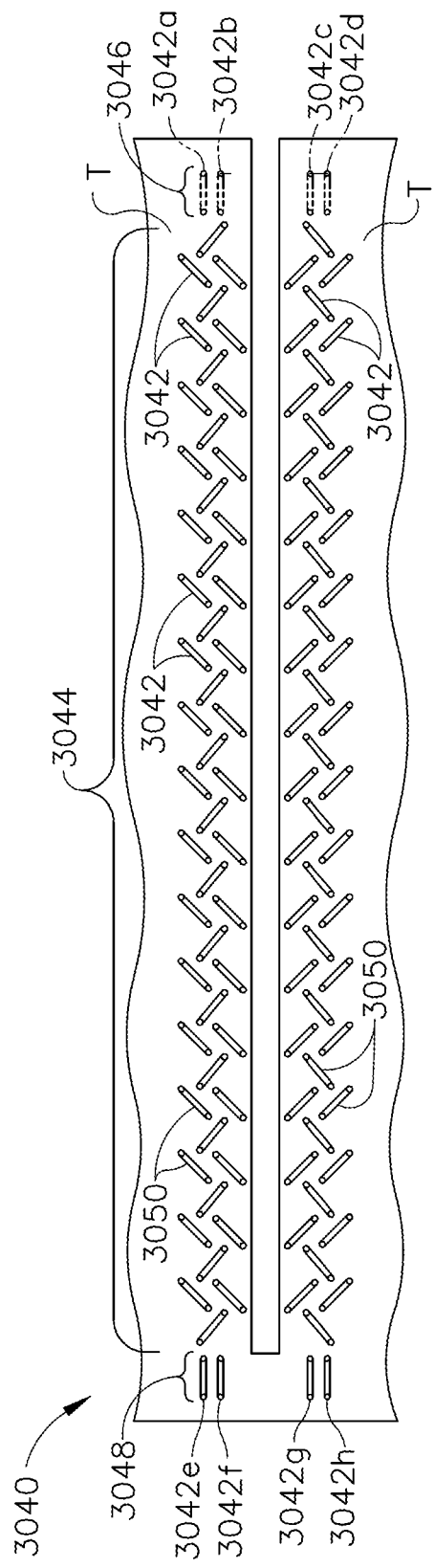

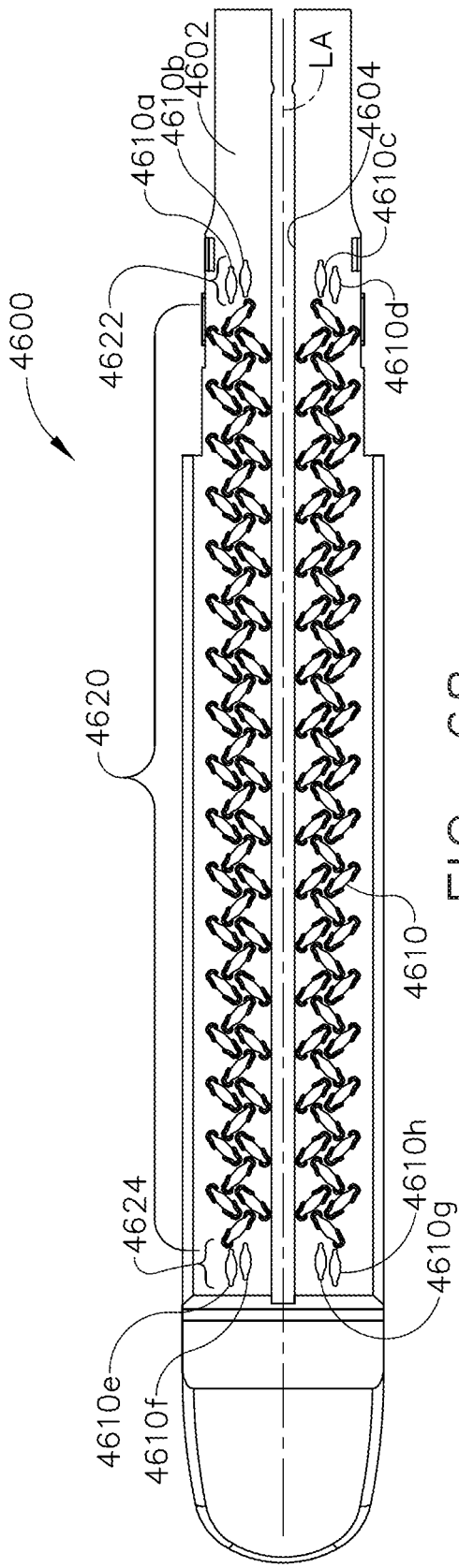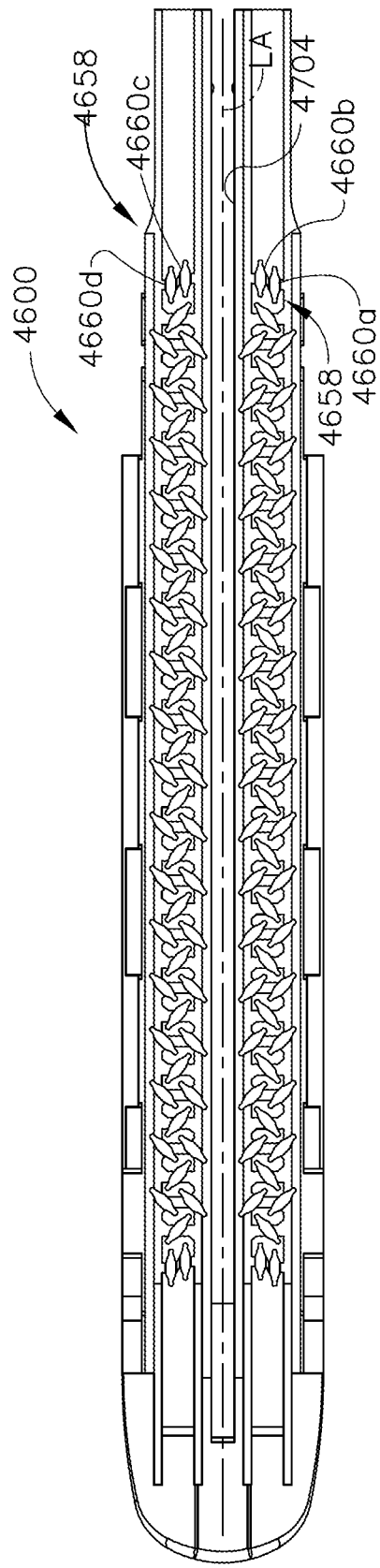

METHODS OF STAPLING TISSUE

CROSS-REFERENCE TO RELATED APPLICATION

This application is a continuation application that claims priority under 35 U.S.C. § 120 to U.S. patent application Ser. No. 15/385,953, filed Dec. 21, 2016, which issued on Jun. 9, 2020 as U.S. Pat. No. 10,675,026, the entire disclosure of which is hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 30 is a perspective view of a firing member embodiment;

FIG. 31 is a side elevational view of the firing member of FIG. 30;

FIG. 32 is a front view of the firing member of FIG. 30;

FIG. 56 is a top plan view of the staple cartridge body of FIG. 54 depicting a cutting element positioned in a longitudinal slot of the cartridge body;

FIG. 57 is a bottom plan view of the staple cartridge body of FIG. 54 depicting drivers positioned in the staple cavities;

FIG. 58 is a staple line implanted in stapled tissue and generated by the staple cartridge body of FIG. 54 and depicting certain staples that are likely to be missing from the staple line with phantom lines;

FIG. 59 is a side elevation view of a staple in the staple line of FIG. 58;

FIG. 60 is a side elevation view of a staple;

FIG. 68 is a top plan view of a staple cartridge body having a plurality of staple cavities defined therein;

FIG. 69 is a bottom plan view of the staple cartridge body of FIG. 68 depicting drivers positioned in the staple cavities;

FIG. 126 is an exploded perspective view of an end effector and an adaptor assembly;

FIG. 127 is a cross-sectional perspective view of a portion of the end effector and the adaptor assembly of FIG. 126;

FIG. 128 is a cross-sectional perspective view of a portion of the end effector of FIG. 126 and an adaptor assembly; and FIG. 129 is a plan view of a portion of an anvil having a plurality of staple-forming pockets defined therein.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
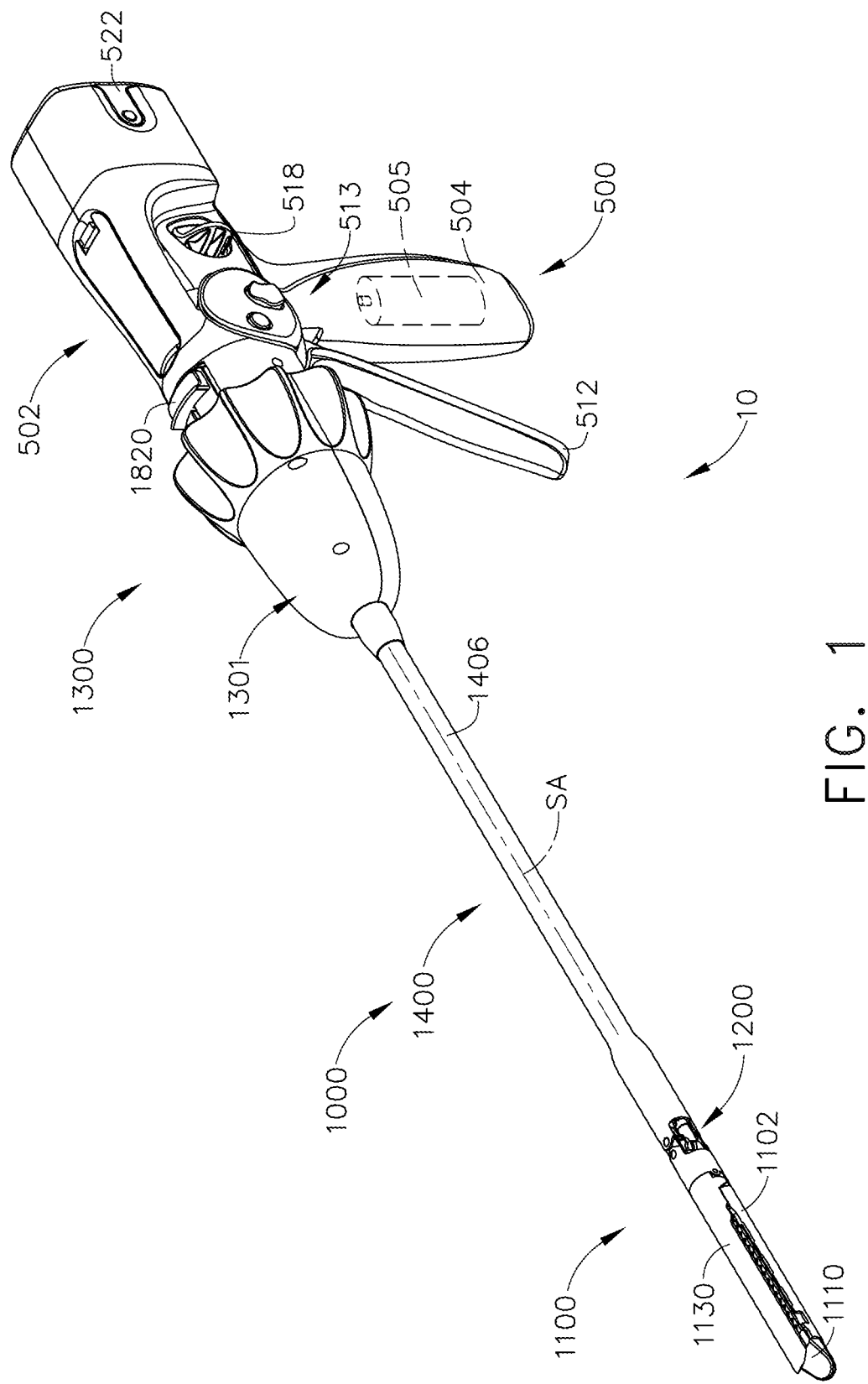
FIG. 1 is a perspective view of an interchangeable surgical tool assembly embodiment operably coupled to a handle assembly embodiment.

Applicant of the present application owns the following U.S. Patent Applications that were filed on Dec. 21, 2016, and which are each herein incorporated by reference in their respective entireties:

- U.S. patent application Ser. No. 15/386,185, entitled SURGICAL STAPLING INSTRUMENTS AND REPLACEABLE TOOL ASSEMBLIES THEREOF, now U.S. Pat. No. 10,639,035;
- U.S. patent application Ser. No. 15/386,230, entitled ARTICULATABLE SURGICAL STAPLING INSTRUMENTS, now U.S. Patent Application Publication No. 2018/0168649, issued as U.S. Pat. No. 11,160,551 on Nov. 2, 2021;
- U.S. patent application Ser. No. 15/386,221, entitled LOCKOUT ARRANGEMENTS FOR SURGICAL END EFFECTORS, now U.S. Patent Application Publication No. 2018/0168646, issued as U.S. Pat. No. 10,835,247 on Nov. 17, 2020;
- U.S. patent application Ser. No. 15/386,209, entitled SURGICAL END EFFECTORS AND FIRING MEMBERS THEREOF, now U.S. Pat. No. 10,588,632;
- U.S. patent application Ser. No. 15/386,198, entitled LOCKOUT ARRANGEMENTS FOR SURGICAL END EFFECTORS AND REPLACEABLE TOOL ASSEMBLIES, now U.S. Pat. No. 10,610,224; and
- U.S. patent application Ser. No. 15/386,240, entitled SURGICAL END EFFECTORS AND ADAPTABLE FIRING MEMBERS THEREFOR, now U.S. Patent Application Publication No. 2018/0168651, issued as U.S. Pat. No. 10,973,516 on Apr. 13, 2021.

Applicant of the present application owns the following U.S. Patent Applications that were filed on Dec. 21, 2016, and which are each herein incorporated by reference in their respective entireties:

- U.S. patent application Ser. No. 15/385,939, entitled STAPLE CARTRIDGES AND ARRANGEMENTS OF STAPLES AND STAPLE CAVITIES THEREIN, now U.S. Patent Application Publication No. 2018/0168629, issued as U.S. Pat. No. 10,835,246 on Nov. 17, 2020;
- U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630, issued as U.S. Pat. No. 10,736,629 on Aug. 11, 2020;
- U.S. patent application Ser. No. 15/385,943, entitled SURGICAL STAPLING INSTRUMENTS AND STAPLE-FORMING ANVILS, now U.S. Patent Application Publication No. 2018/0168631, issued as U.S. Pat. No. 10,667,811 on Jun. 2, 2020;
- U.S. patent application Ser. No. 15/385,950, entitled SURGICAL TOOL ASSEMBLIES WITH CLOSURE STROKE REDUCTION FEATURES, now U.S. Pat. No. 10,588,630;
- U.S. patent application Ser. No. 15/385,945, entitled STAPLE CARTRIDGES AND ARRANGEMENTS OF STAPLES AND STAPLE CAVITIES THEREIN, now U.S. Patent Application Publication No. 2018/0168632, issued as U.S. Pat. No. 10,893,864 on Jan. 19, 2021;

U.S. patent application Ser. No. 15/385,946, entitled SURGICAL STAPLING INSTRUMENTS AND STAPLE-FORMING ANVILS, now U.S. Patent Application Publication No. 2018/0168633, now abandoned;

U.S. patent application Ser. No. 15/385,951, entitled SURGICAL INSTRUMENTS WITH JAW OPENING FEATURES FOR INCREASING A JAW OPENING DISTANCE, now U.S. Pat. No. 10,568,626;

U.S. patent application Ser. No. 15/385,954, entitled FIRING MEMBERS WITH NON-PARALLEL JAW ENGAGEMENT FEATURES FOR SURGICAL END EFFECTORS, now U.S. Pat. No. 10,624,635;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639, issued as U.S. Pat. No. 10,813,638 on Oct. 27, 2020;

U.S. patent application Ser. No. 15/385,948, entitled SURGICAL STAPLING INSTRUMENTS AND STAPLE-FORMING ANVILS, now U.S. Patent Application Publication No. 2018/0168584, issued as U.S. Pat. No. 11,134,942 on Oct. 5, 2021;

U.S. patent application Ser. No. 15/385,956, entitled SURGICAL INSTRUMENTS WITH POSITIVE JAW OPENING FEATURES, now U.S. Pat. No. 10,588,631;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Pat. No. 10,639,034; and U.S. patent application Ser. No. 15/385,947, entitled STAPLE CARTRIDGES AND ARRANGEMENTS OF STAPLES AND STAPLE CAVITIES THEREIN, now U.S. Pat. No. 10,568,625.

Applicant of the present application owns the following U.S. Patent Applications that were filed on Dec. 21, 2016, and which are each herein incorporated by reference in their respective entireties:

U.S. patent application Ser. No. 15/385,896, entitled METHOD FOR RESETTING A FUSE OF A SURGICAL INSTRUMENT SHAFT, now U.S. Patent Application Publication No. 2018/0168597, issued as U.S. Pat. No. 11,090,048 on Aug. 17, 2021;

U.S. patent application Ser. No. 15/385,898, entitled STAPLE FORMING POCKET ARRANGEMENT TO ACCOMMODATE DIFFERENT TYPES OF STAPLES, now U.S. Pat. No. 10,537,325;

U.S. patent application Ser. No. 15/385,899 entitled SURGICAL INSTRUMENT COMPRISING IMPROVED JAW CONTROL, now U.S. Patent Application Publication No. 2018/0168600, issued as U.S. Pat. No. 10,758,229 on Sep. 1, 2020;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602, issued as U.S. Pat. No. 10,667,809 on Jun. 2, 2020;

U.S. patent application Ser. No. 15/385,902, entitled SURGICAL INSTRUMENT COMPRISING A CUTTING MEMBER, now U.S. Patent Application Publication No. 2018/0168603, issued as U.S. Pat. No. 10,888,322 on Jan. 12, 2021;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605, issued as U.S. Pat. No. 10,881,401 on Jan. 5, 2021;

U.S. patent application Ser. No. 15/385,905, entitled FIRING ASSEMBLY COMPRISING A LOCKOUT, now U.S. Patent Application Publication No. 2018/0168606, issued as U.S. Pat. No. 10,695,055 on Jun. 30, 2020;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608, now abandoned;

U.S. patent application Ser. No. 15/385,908, entitled FIRING ASSEMBLY COMPRISING A FUSE, now U.S. Patent Application Publication No. 2018/0168609, now abandoned; and U.S. patent application Ser. No. 15/385,909, entitled FIRING ASSEMBLY COMPRISING A MULTIPLE FAILED-STATE FUSE, now U.S. Patent Application Publication No. 2018/0168610, issued as U.S. Pat. No. 11,571,201 on Feb. 7, 2023.

Applicant of the present application owns the following U.S. Patent Applications that were filed on Dec. 21, 2016, and which are each herein incorporated by reference in their respective entireties:

U.S. patent application Ser. No. 15/385,920, entitled STAPLE FORMING POCKET ARRANGEMENTS, now U.S. Pat. No. 10,499,914;

U.S. patent application Ser. No. 15/385,913, entitled ANVIL ARRANGEMENTS FOR SURGICAL STAPLERS, now U.S. Patent Application Publication No. 2018/0168614, issued as U.S. Pat. No. 11,179,155 on Nov. 23, 2021;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615, now abandoned;

U.S. patent application Ser. No. 15/385,893, entitled BILATERALLY ASYMMETRIC STAPLE FORMING POCKET PAIRS, now U.S. Patent Application Publication No. 2018/0168594, issued as U.S. Pat. No. 10,682,138 on Jun. 16, 2020;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626, issued as U.S. Pat. No. 10,667,810 on Jun. 2, 2020;

U.S. patent application Ser. No. 15/385,911, entitled SURGICAL STAPLERS WITH INDEPENDENTLY ACTUATABLE CLOSING AND FIRING SYSTEMS, now U.S. Pat. No. 10,448,950;

U.S. patent application Ser. No. 15/385,927, entitled SURGICAL STAPLING INSTRUMENTS WITH SMART STAPLE CARTRIDGES, now U.S. Patent Application Publication No 2018/0168625, now abandoned;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617, issued as U.S. Pat. No. 10,993,715 on May 4, 2021;

U.S. patent application Ser. No. 15/385,900, entitled STAPLE FORMING POCKET ARRANGEMENTS COMPRISING PRIMARY SIDEWALLS AND POCKET SIDEWALLS, now U.S. Patent Application Publication No. 2018/0168601, issued as U.S. Pat. No. 10,898,168 on Jan. 26, 2021;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627, issued as U.S. Pat. No. 10,980,536 on Apr. 20, 2021;

U.S. patent application Ser. No. 15/385,915, entitled FIRING MEMBER PIN ANGLE, now U.S. Patent Application Publication No. 2018/0168616, issued as U.S. Pat. No. 10,779,823 on Sep. 22, 2020;

U.S. patent application Ser. No. 15/385,897, entitled STAPLE FORMING POCKET ARRANGEMENTS COMPRISING ZONED FORMING SURFACE GROOVES, now U.S. Patent Application Publication No. 2018/0168598, now abandoned;

U.S. patent application Ser. No. 15/385,922, entitled SURGICAL INSTRUMENT WITH MULTIPLE FAILURE RESPONSE MODES, now U.S. Pat. No. 10,426,471;

U.S. patent application Ser. No. 15/385,924, entitled SURGICAL INSTRUMENT WITH PRIMARY AND SAFETY PROCESSORS, now U.S. Patent Application Publication No. 2018/0168624, issued as U.S. Pat. No. 10,758,230 Sep. 1, 2020;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, now U.S. Pat. No. 10,568,624;

U.S. patent application Ser. No. 15/385,910, entitled ANVIL HAVING A KNIFE SLOT WIDTH, now U.S. Pat. No. 10,485,543;

U.S. patent application Ser. No. 15/385,903, entitled CLOSURE MEMBER ARRANGEMENTS FOR SURGICAL INSTRUMENTS, now U.S. Pat. No. 10,617,414; and U.S. patent application Ser. No. 15/385,906, entitled FIRING MEMBER PIN CONFIGURATIONS, now U.S. Patent Application Publication No. 2018/0168607, issued as U.S. Pat. No. 10,856,868 on Dec. 8, 2020.

Applicant of the present application owns the following U.S. Patent Applications that were filed on Dec. 21, 2016, and which are each herein incorporated by reference in their respective entireties:

U.S. patent application Ser. No. 15/386,188, entitled STEPPED STAPLE CARTRIDGE WITH ASYMMETRICAL STAPLES, now U.S. Pat. No. 10,537,324;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643, issued as U.S. Pat. No. 10,687,810 Jun. 23, 2020;

U.S. patent application Ser. No. 15/386,206, entitled STAPLE CARTRIDGE WITH DEFORMABLE DRIVER RETENTION FEATURES, now U.S. Patent Application Publication No. 2018/0168586, issued as U.S. Pat. No. 10,945,727 on Mar. 16, 2021;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648, now abandoned;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647, now abandoned; and U.S. patent application Ser. No. 15/386,236, entitled CONNECTION PORTIONS FOR DISPOSABLE LOADING UNITS FOR SURGICAL STAPLING INSTRUMENTS, now U.S. Patent Application Publication No. 2018/0168650, now abandoned.

Applicant of the present application owns the following U.S. Patent Applications that were filed on Dec. 21, 2016, and which are each herein incorporated by reference in their respective entireties:

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589, issued as U.S. Pat. No. 10,835,245 on Nov. 17, 2020;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590, issued as U.S. Pat. No. 11,191,539 on Dec. 7, 2021;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591, issued as U.S. Pat. No. 10,675,025 on Jun. 9, 2020;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592, issued as U.S. Pat. No. 11,419,606 on Aug. 23, 2022;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593, issued as U.S. Pat. No. 10,918,358 on Feb. 16, 2021;

U.S. patent application Ser. No. 15/385,894, entitled SHAFT ASSEMBLY COMPRISING A LOCKOUT, now U.S. Pat. No. 10,492,785; and U.S. patent application Ser. No. 15/385,895, entitled SHAFT ASSEMBLY COMPRISING FIRST AND SECOND ARTICULATION LOCKOUTS, now U.S. Pat. No. 10,542,982.

Applicant of the present application owns the following U.S. Patent Applications that were filed on Dec. 21, 2016 and which are each herein incorporated by reference in their respective entireties:

U.S. patent application Ser. No. 15/385,916, entitled SURGICAL STAPLING SYSTEMS, now U.S. Patent Application Publication No. 2018/0168575, now abandoned;

U.S. patent application Ser. No. 15/385,918, entitled SURGICAL STAPLING SYSTEMS, now U.S. Patent Application Publication No. 2018/0168618, now abandoned;

U.S. patent application Ser. No. 15/385,919, entitled SURGICAL STAPLING SYSTEMS, now U.S. Patent Application Publication No. 2018/0168619, now abandoned;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Patent Application Publication No. 2018/0168621, issued as U.S. Pat. No. 10,687,809 on Jun. 23, 2020;

U.S. patent application Ser. No. 15/385,923, entitled SURGICAL STAPLING SYSTEMS, now U.S. Patent Application Publication No. 2018/0168623, now abandoned;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Pat. No. 10,517,595;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577, now abandoned;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578, issued as U.S. Pat. No. 11,191,540 on Dec. 7, 2021;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579, now abandoned;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628, issued as U.S. Pat. No. 10,959,727 on Mar. 30, 2021;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Pat. No. 10,603,036;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Pat. No. 10,582,928;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Patent Application Publication No. 10,524,789; and U.S. patent application Ser. No. 15/385,936, entitled ARTICULATABLE SURGICAL INSTRUMENTS WITH ARTICULATION STROKE AMPLIFICATION FEATURES, now U.S. Pat. No. 10,517,596.

Applicant of the present application owns the following U.S. Patent Applications that were filed on Jun. 24, 2016, and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695, issued as U.S. Pat. No. 11,000,278 on May 11, 2021;

U.S. patent application Ser. No. 15/191,807, entitled STAPLING SYSTEM FOR USE WITH WIRE STAPLES AND STAMPED STAPLES, now U.S. Patent Application Publication No. 2017/0367696, issued as U.S. Pat. No. 10,702,270 on Jul. 7, 2020;

U.S. patent application Ser. No. 15/191,834, entitled STAMPED STAPLES AND STAPLE CARTRIDGES USING THE SAME, now U.S. Pat. No. 10,542,979;

U.S. patent application Ser. No. 15/191,788, entitled STAPLE CARTRIDGE COMPRISING OVERDRIVEN STAPLES, now U.S. Patent Application Publication No. 2017/0367698, issued as U.S. Pat. No. 10,675,024 on Jun. 9, 2020; and U.S. patent application Ser. No. 15/191,818, entitled STAPLE CARTRIDGE COMPRISING OFFSET LONGITUDINAL STAPLE ROWS, now U.S. Patent Application Publication No. 2017/0367697, issued as U.S. Pat. No. 10,893,863 on Jan. 19, 2021.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER, now U.S. Pat. No. D826,405;

U.S. Design patent application Ser. No. 29/569,227, entitled SURGICAL FASTENER, now U.S. Pat. No. D822,206;

U.S. Design patent application Ser. No. 29/569,259, entitled SURGICAL FASTENER CARTRIDGE, now U.S. Pat. No. D847,989; and U.S. Design patent application Ser. No. 29/569,264, entitled SURGICAL FASTENER CARTRIDGE, now U.S. Pat. No. D850,617.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171, issued as U.S. Pat. No. 11,045,191 on Jun. 29, 2021;

U.S. patent application Ser. No. 15/089,321, entitled MODULAR SURGICAL STAPLING SYSTEM COMPRISING A DISPLAY, now U.S. Pat. No. 10,271,851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Pat. No. 10,433,849;

U.S. patent application Ser. No. 15/089,263, entitled SURGICAL INSTRUMENT HANDLE ASSEMBLY WITH RECONFIGURABLE GRIP PORTION, now U.S. Pat. No. 10,307,159;

U.S. patent application Ser. No. 15/089,262, entitled ROTARY POWERED SURGICAL INSTRUMENT WITH MANUALLY ACTUATABLE BAILOUT SYSTEM, now U.S. Pat. No. 10,357,246;

U.S. patent application Ser. No. 15/089,277, entitled SURGICAL CUTTING AND STAPLING END EFFECTOR WITH ANVIL CONCENTRIC DRIVE MEMBER, now U.S. Pat. No. 10,531,874;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Pat. No. 10,413,293;

U.S. patent application Ser. No. 15/089,258, entitled SURGICAL STAPLING SYSTEM COMPRISING A SHIFTABLE TRANSMISSION, now U.S. Pat. No. 10,342,543;

U.S. patent application Ser. No. 15/089,278, entitled SURGICAL STAPLING SYSTEM CONFIGURED TO PROVIDE SELECTIVE CUTTING OF TISSUE, now U.S. Pat. No. 10,420,552;

U.S. patent application Ser. No. 15/089,284, entitled SURGICAL STAPLING SYSTEM COMPRISING A CONTOURABLE SHAFT, now U.S. Patent Application Publication No. 2017/0281186, now abandoned;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187, issued as U.S. Pat. No. 10,856,867 on Dec. 8, 2020;

U.S. patent application Ser. No. 15/089,300, entitled SURGICAL STAPLING SYSTEM COMPRISING AN UNCLAMPING LOCKOUT, now U.S. Pat. No. 10,456,140;

U.S. patent application Ser. No. 15/089,196, entitled SURGICAL STAPLING SYSTEM COMPRISING A JAW CLOSURE LOCKOUT, now U.S. Pat. No. 10,568,632;

U.S. patent application Ser. No. 15/089,203, entitled SURGICAL STAPLING SYSTEM COMPRISING A JAW ATTACHMENT LOCKOUT, now U.S. Pat. No. 10,542,991;

U.S. patent application Ser. No. 15/089,210, entitled SURGICAL STAPLING SYSTEM COMPRISING A SPENT CARTRIDGE LOCKOUT, now U.S. Pat. No. 10,478,190;

U.S. patent application Ser. No. 15/089,324, entitled SURGICAL INSTRUMENT COMPRISING A SHIFTING MECHANISM, now U.S. Pat. No. 10,314,582;

U.S. patent application Ser. No. 15/089,335, entitled SURGICAL STAPLING INSTRUMENT COMPRISING MULTIPLE LOCKOUTS, now U.S. Pat. No. 10,485,542;

U.S. patent application Ser. No. 15/089,339, entitled SURGICAL STAPLING INSTRUMENT, now U.S. Patent Application Publication No. 2017/0281173, issued as U.S. Pat. No. 11,064,997 on Jul. 20, 2021;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Pat. No. 10,413,297;

U.S. patent application Ser. No. 15/089,304, entitled SURGICAL STAPLING SYSTEM COMPRISING A GROOVED FORMING POCKET, now U.S. Pat. No. 10,285,705;

U.S. patent application Ser. No. 15/089,331, entitled ANVIL MODIFICATION MEMBERS FOR SURGICAL STAPLERS, now U.S. Pat. No. 10,376,263;

U.S. patent application Ser. No. 15/089,336, entitled STAPLE CARTRIDGES WITH ATRAUMATIC FEATURES, now U.S. Patent Application Publication No. 2017/0281164, issued as U.S. Pat. No. 10,709,446 on Jul. 14, 2020;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189, issued as U.S. Pat. No. 11,284,890 on Mar. 29, 2022;

U.S. patent application Ser. No. 15/089,309, entitled CIRCULAR STAPLING SYSTEM COMPRISING ROTARY FIRING SYSTEM, now U.S. Patent Application Publication No. 2017/0281169, issued as U.S. Pat. No. 10,675,021 on Jun. 9, 2020; and U.S. patent application Ser. No. 15/089,349, entitled CIRCULAR STAPLING SYSTEM COMPRISING LOAD CONTROL, now U.S. Patent Application Publication No. 2017/0281174, issued as U.S. Pat. No. 10,682,136 Jun. 16, 2020.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Pat. No. 10,292,704;

U.S. patent application Ser. No. 14/984,525, entitled MECHANISMS FOR COMPENSATING FOR DRIVETRAIN FAILURE IN POWERED SURGICAL INSTRUMENTS, now U.S. Pat. No. 10,368,865; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Pat. No. 10,433,837;

U.S. patent application Ser. No. 15/019,196, entitled SURGICAL INSTRUMENT ARTICULATION MECHANISM WITH SLOTTED SECONDARY CONSTRAINT, now U.S. Pat. No. 10,413,291;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEM- BLY, now U.S. Patent Application Publication No. 2017/0224331, issued as U.S. Pat. No. 10,653,413 on May 19, 2020;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332, now abandoned;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334, issued as U.S. Pat. No. 11,213,293 on Jan. 4, 2022;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Pat. No. 10,588,625; and U.S. patent application Ser. No. 15/019,245, entitled SURGICAL INSTRUMENTS WITH CLOSURE STROKE REDUCTION ARRANGEMENTS, now U.S. Pat. No. 10,470,764.

Applicant of the present application also owns the U.S. Patent Applications identified below which were filed on Feb. 12, 2016, which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Pat. No. 10,448,948;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627, issued as U.S. Pat. No. 11,224,426 on Jan. 18, 2022; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628, now abandoned.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015, and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154, issued as U.S. Pat. No. 10,687,806 on Jun. 23, 2020;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Pat. No. 10,617,412;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910, now abandoned;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013, and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557, now abandoned;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475, now abandoned;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541, now abandoned;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014, and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582, now abandoned;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580, now abandoned;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571, now abandoned;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557, now abandoned;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014, and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO DETECT MIS-LOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913, now abandoned.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application also owns the following patent applications that were filed on Sep. 2, 2015 and which are each herein incorporated by reference in their respective entirety:

U.S. patent application Ser. No. 14/843,168, entitled SURGICAL STAPLE CARTRIDGE WITH IMPROVED STAPLE DRIVER CONFIGURATIONS, now U.S. Pat. No. 10,314,587;

U.S. patent application Ser. No. 14/843,196, entitled SURGICAL STAPLE DRIVER ARRAYS, now U.S. Pat. No. 10,172,619;

U.S. patent application Ser. No. 14/843,216, entitled SURGICAL STAPLE CARTRIDGE STAPLE DRIVERS WITH CENTRAL SUPPORT FEATURES, now U.S. Pat. No. 10,251,648;

U.S. patent application Ser. No. 14/843,243, entitled SURGICAL STAPLE CONFIGURATIONS WITH CAMMING SURFACES LOCATED BETWEEN PORTIONS SUPPORTING SURGICAL STAPLES, now U.S. Pat. No. 10,357,252; and U.S. patent application Ser. No. 14/843,267, entitled SURGICAL STAPLE CARTRIDGES WITH DRIVER ARRANGEMENTS FOR ESTABLISHING HERRINGBONE STAPLE PATTERNS, now U.S. Pat. No. 10,238,390.

Applicant of the present application also owns the following patent applications that were filed on Sep. 26, 2014 and which are each herein incorporated by reference in their respective entirety:

U.S. patent application Ser. No. 14/498,070, entitled CIRCULAR FASTENER CARTRIDGES FOR APPLYING RADIALLY EXPANDABLE FASTENER LINES; now U.S. Pat. No. 10,426,476;

U.S. patent application Ser. No. 14/498,087, entitled SURGICAL STAPLE AND DRIVER ARRANGEMENTS FOR STAPLE CARTRIDGES; now U.S. Pat. No. 10,206,677;

U.S. patent application Ser. No. 14/498,105, entitled SURGICAL STAPLE AND DRIVER ARRANGEMENTS FOR STAPLE CARTRIDGES; now U.S. Pat. No. 9,801,628;

U.S. patent application Ser. No. 14/498,121, entitled FASTENER CARTRIDGE FOR CREATING A FLEXIBLE STAPLE LINE; now U.S. Pat. No. 9,801,627;

U.S. patent application Ser. No. 14/498,145, entitled METHOD FOR CREATING A FLEXIBLE STAPLE LINE; now U.S. Pat. No. 10,327,764; and U.S. patent application Ser. No. 14/498,107, entitled SURGICAL STAPLING BUTTRESSES AND ADJUNCT MATERIALS; now U.S. Pat. No. 9,943,310.

Applicant of the present application also owns U.S. Pat. No. 8,590,762, which issued Nov. 26, 2013, entitled STAPLE CARTRIDGE CAVITY CONFIGURATIONS, which is herein incorporated by reference in its respective entirety.

Applicant of the present application also owns U.S. Pat. No. 8,727,197, which issued May 20, 2014, entitled STAPLE CARTRIDGE CAVITY CONFIGURATION WITH COOPERATIVE SURGICAL STAPLE, which is herein incorporated by reference in its respective entirety.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts one form of an interchangeable surgical tool assembly 1000 that is operably coupled to a motor driven handle assembly 500. The tool assembly 1000 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety. The handle assembly 500, as well as the tool drive assembly of a robotic system may also be referred to herein as "control systems" or "control units".

Figure 2:
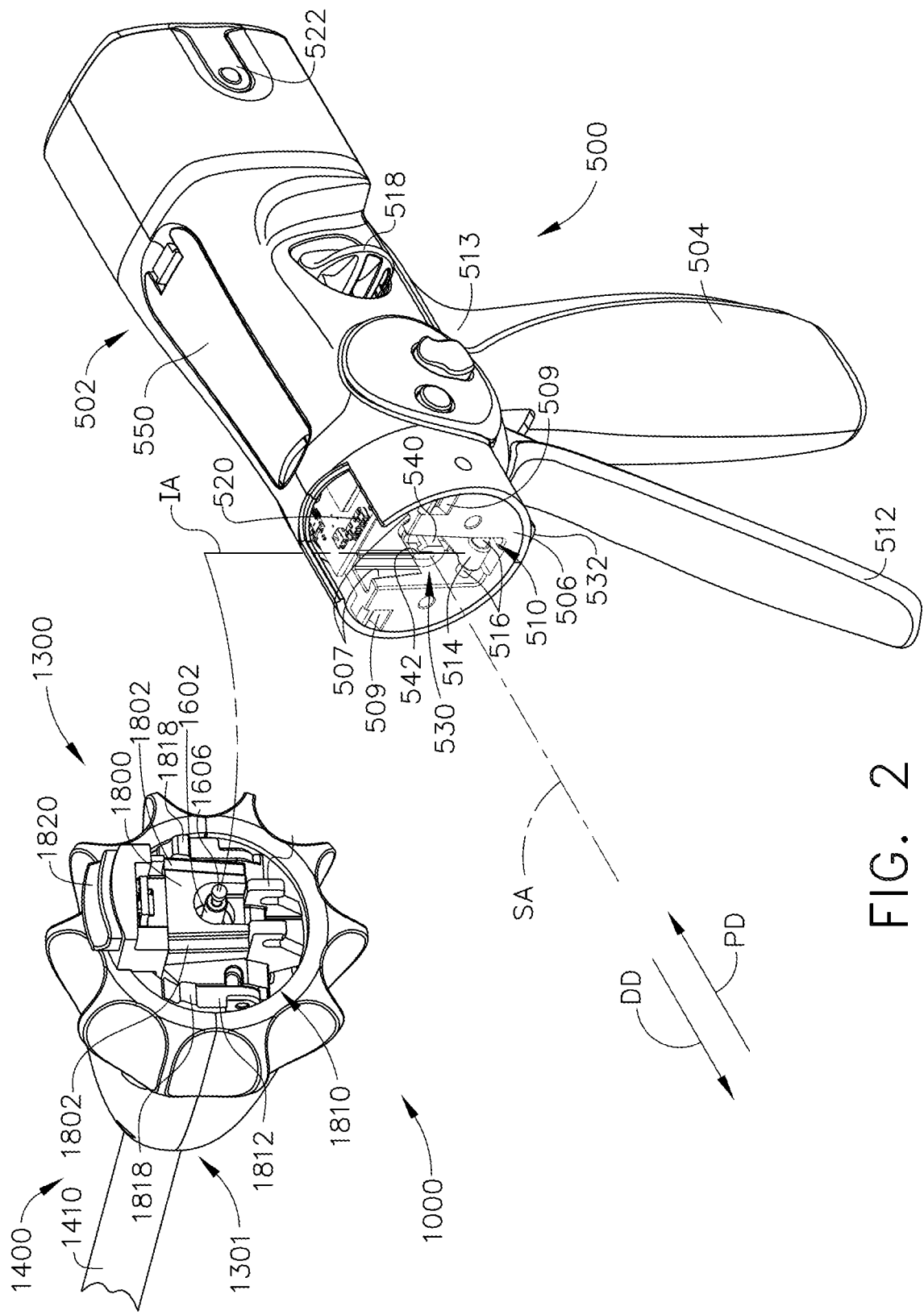
FIG. 2 is an exploded assembly view of portions of the handle assembly and interchangeable surgical tool assembly of FIG. 1.

FIG. 2 illustrates attachment of the interchangeable surgical tool assembly 1000 to the handle assembly 500. The handle assembly 500 may comprise a handle housing 502 that includes a pistol grip portion 504 that can be gripped and manipulated by the clinician. The handle assembly 500 may further include a frame 506 that operably supports the plurality of drive systems. For example, the frame 506 can operably support a "first" or closure drive system, generally designated as 510, which may be employed to apply closing and opening motions to the interchangeable surgical tool assembly 1000 that is operably attached or coupled to the handle assembly 500. In at least one form, the closure drive system 510 may include an actuator in the form of a closure trigger 512 that is pivotally supported by the frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly, to a fully compressed or fully actuated position. In various forms, the closure drive system 510 further includes a closure linkage assembly 514 that is pivotally coupled to the closure trigger 512 or otherwise operably interfaces therewith. As will be discussed in further detail below, in the illustrated example, the closure linkage assembly 514 includes a transverse attachment pin 516 that facilitates attachment to a corresponding drive system on the surgical tool assembly. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Pat. No. 9,913,642, which is hereby incorporated by reference in its entirety herein, when the clinician fully depresses the closure trigger 512 to attain a "full" closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger 512 to return to the unactuated position. The closure release button assembly 518 may also be configured to interact with various sensors that communicate with a microcontroller 520 in the handle assembly 500 for tracking the position of the closure trigger 512. Further details concerning the configuration and operation of the closure release button assembly 518 may be found in U.S. Pat. No. 9,913,642.

In at least one form, the handle assembly 500 and the frame 506 may operably support another drive system referred to herein as a firing drive system 530 that is configured to apply firing motions to corresponding portions of the interchangeable surgical tool assembly that is attached thereto. As was described in detail in U.S. Pat. No. 9,913,642, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries may be connected in series and may be used as the power source 522 for the handle assembly 500. In addition, the power source 522 may be replaceable and/or rechargeable.

The electric motor 505 is configured to axially drive a longitudinally movable drive member 540 in distal and proximal directions depending upon the polarity of the motor. For example, when the motor 505 is driven in one rotary direction, the longitudinally movable drive member 540 will be axially driven in the distal direction "DD". When the motor 505 is driven in the opposite rotary direction, the longitudinally movable drive member 540 will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member 540 and/or the direction in which the drive member 540 is being moved. Actuation of the motor 505 can be controlled by a firing trigger 532 that is pivotally supported on the handle assembly 500. The firing trigger 532 may be pivoted between an unactuated position and an actuated position. The firing trigger 532 may be biased into the unactuated position by a spring (not shown) or other biasing arrangement such that when the clinician releases the firing trigger 532, it may be pivoted or otherwise returned to the unactuated position by the spring or biasing arrangement. In at least one form, the firing trigger 532 can be positioned "outboard" of the closure trigger 512 as was discussed above. As discussed in U.S. Pat. No. 9,913,642, the handle assembly 500 may be equipped with a firing trigger safety button (not shown) to prevent inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 may pivot down wherein they can then be manipulated by the clinician.

In at least one form, the longitudinally movable drive member 540 may have a rack of teeth (not shown) formed thereon for meshing engagement with a corresponding drive gear arrangement (not shown) that interfaces with the motor 505. Further details regarding those features may be found in U.S. Pat. No. 9,913,642. At least one form also includes a manually-actuatable "bailout" assembly that is configured to enable the clinician to manually retract the longitudinally movable drive member 540 should the motor 505 become disabled. The bailout assembly may include a lever or bailout handle assembly that is stored within the handle assembly 500 under a releasable door 550. The lever is configured to be manually pivoted into ratcheting engagement with the teeth in the drive member 540. Thus, the clinician can manually retract the drive member 540 by using the bailout handle assembly to ratchet the drive member 540 in the proximal direction "PD". U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, the entire disclosure of which is hereby incorporated by reference herein, discloses bailout arrangements and other components, arrangements and systems that may also be employed with the tool assembly 1000.

Figure 3:
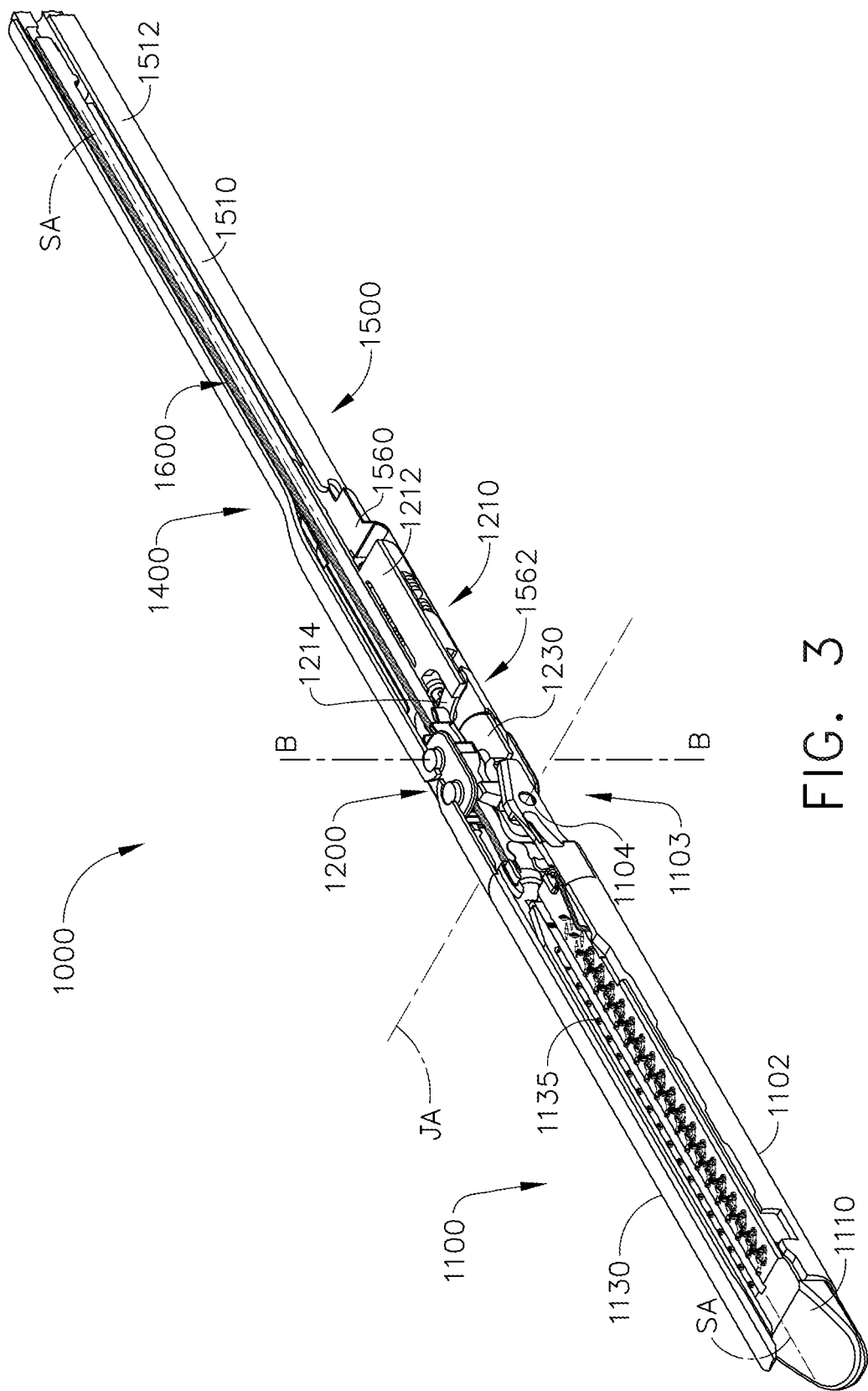
FIG. 3 is a perspective view of a distal portion of the interchangeable surgical tool assembly embodiment depicted in FIGS. 1 and 2 with portions thereof omitted for clarity.
Figure 4:
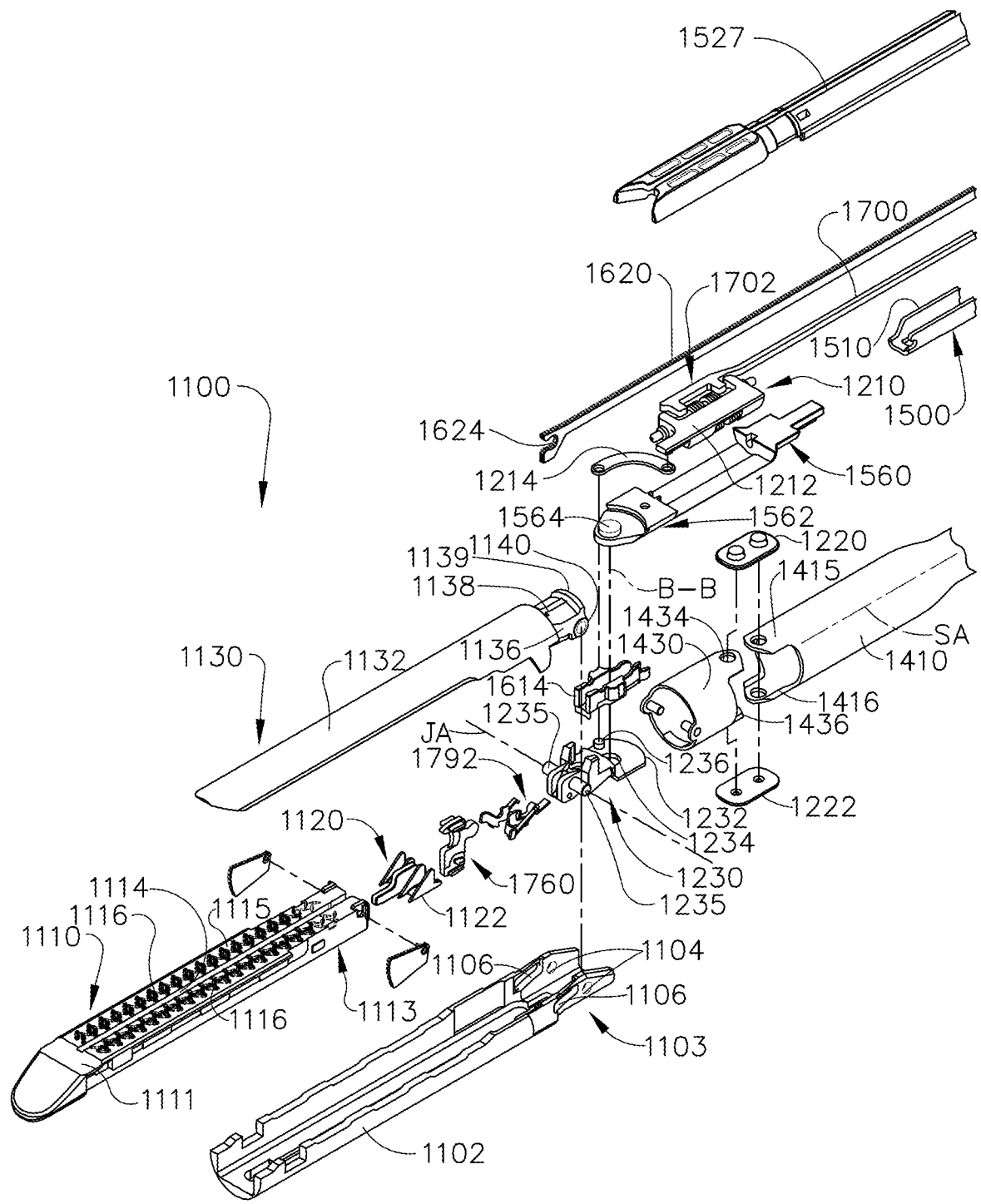
FIG. 4 is an exploded assembly view of a distal portion of the interchangeable surgical tool assembly of FIG. 1.
Figure 5:
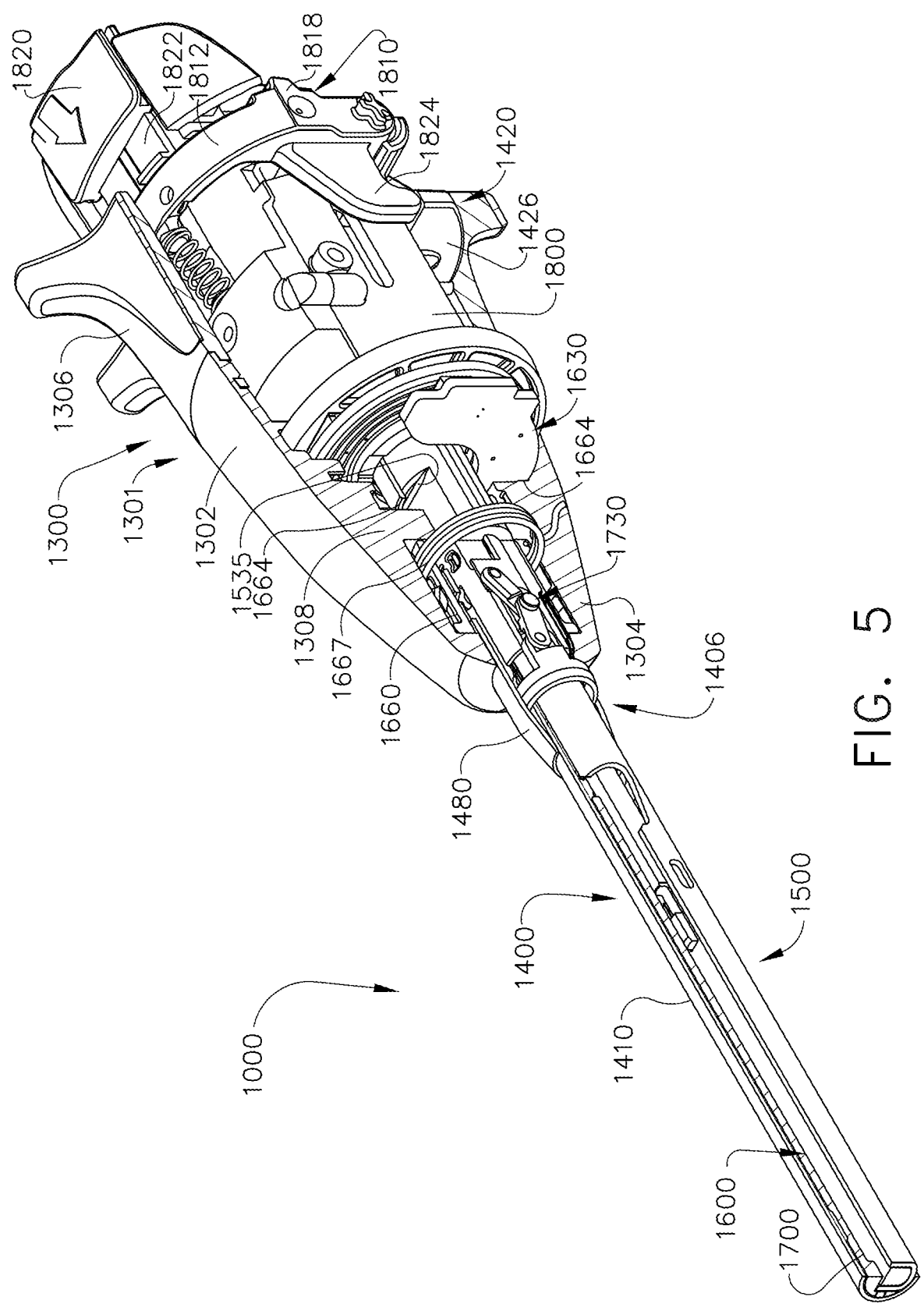
FIG. 5 is a partial cross-sectional perspective view of a proximal portion of the interchangeable surgical tool assembly of FIG. 1.
Figure 6:
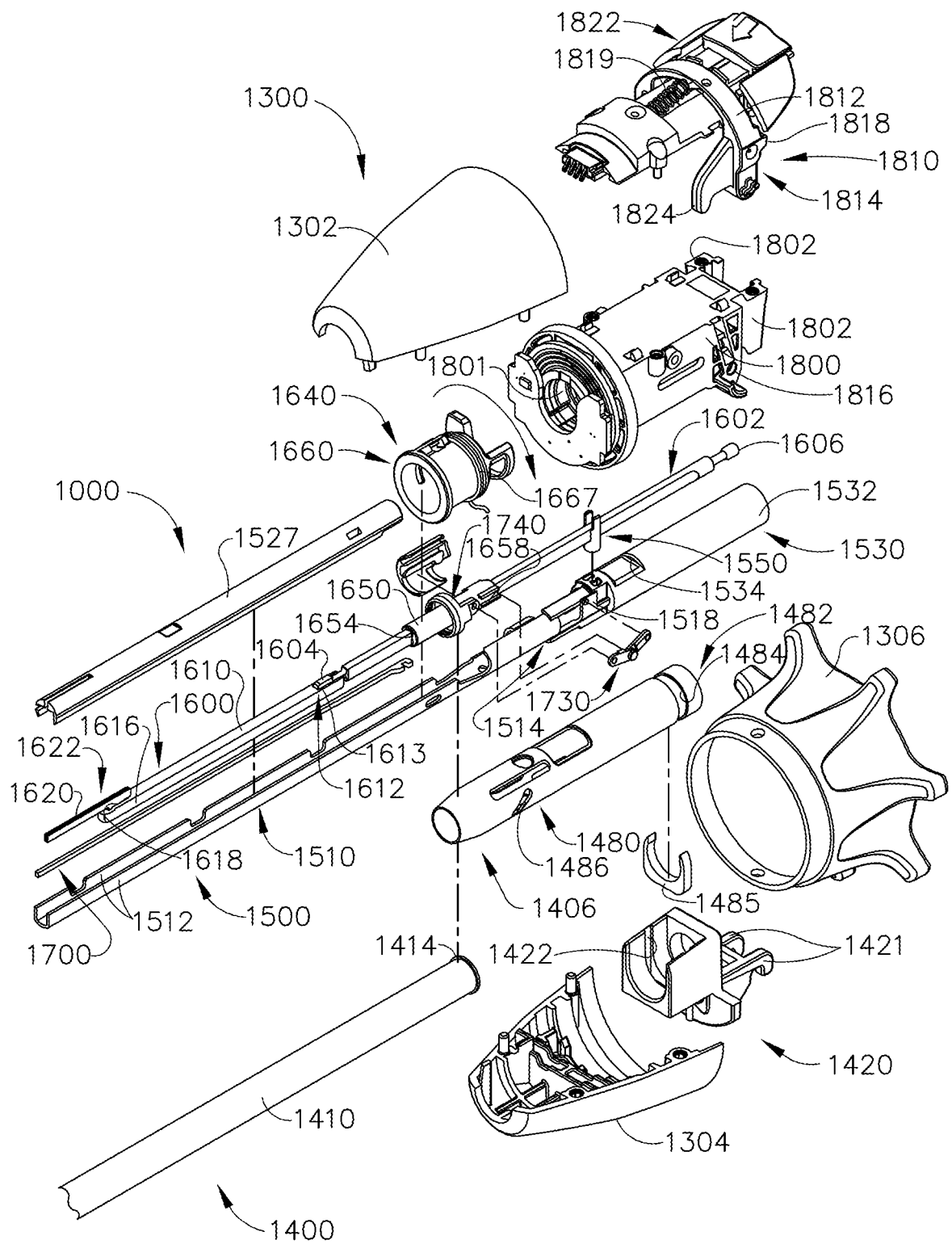
FIG. 6 is an exploded assembly view of the proximal portion of the interchangeable surgical tool assembly of FIG. 5.

Turning now to FIGS. 4, 5 and 6, the interchangeable surgical tool assembly 1000 includes a shaft mounting portion 1300 that is operably attached to an elongate shaft assembly 1400. A surgical end effector 1100 that comprises an elongate channel 1102 that is configured to operably support a staple cartridge 1110 therein is operably attached to the elongate shaft assembly 1400. See FIGS. 3 and 4. The end effector 1100 may further include an anvil 1130 that is pivotally supported relative to the elongate channel 1102. The elongate channel 1102 staple cartridge assembly 1110 and the anvil 1130 may also be referred to as "jaws". The interchangeable surgical tool assembly 1000 may further include an articulation joint 1200 and an articulation lock 1210 (FIGS. 3 and 4) which can be configured to releasably hold the end effector 1100 in a desired articulated position about an articulation axis B-B which is transverse to a shaft axis SA. Details regarding the construction and operation of the articulation lock 1210 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 1210 may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosure of which is hereby incorporated by reference herein.

As can be seen in FIGS. 5 and 6, the shaft mounting portion 1300 includes a proximal housing or nozzle 1301 comprised of nozzle portions 1302, 1304 as well as an actuator wheel portion 1306 that is configured to be coupled to the assembled nozzle portions 1302, 1304 by snaps, lugs, screws etc. In the illustrated embodiment, the interchangeable surgical tool assembly 1000 further includes a closure assembly 1406 which can be utilized to close and/or open the anvil 1130 and the elongate channel 1102 of the end effector 1100 as will be discussed in further detail below. In addition, the illustrated interchangeable surgical tool assembly 1000 includes a spine assembly 1500 which is operably supports the articulation lock 1210. The spine assembly 1500 is configured to, one, slidably support a firing member assembly 1600 therein and, two, slidably support the closure assembly 1406 which extends around the spine assembly 1500 or is otherwise movably supported thereby.

In the illustrated arrangement, the surgical end effector 1100 is operably coupled to the elongate shaft assembly 1400 by an articulation joint 1200 that facilitates selective articulation of the surgical end effector 1100 about an articulation axis B-B that is transverse to the shaft axis SA. See FIG. 3. As can be seen in FIG. 4, the spine assembly 1500 slidably supports a proximal articulation driver 1700 that operably interfaces with an articulation lock 1210. The articulation lock 1210 is supported on a distal frame segment 1560 that also comprises a portion of the spine assembly 1500. As can be seen in FIG. 4, the distal frame segment 1560 is pivotally coupled to the elongate channel 1102 by an end effector mounting assembly 1230. In one arrangement, for example, a distal end 1562 of the distal frame segment 1560 has an articulation pin 1564 formed thereon. The articulation pin 1564 is adapted to be pivotally received within an articulation pivot hole 1234 formed in a pivot base portion 1232 of the end effector mounting assembly 1230. The end effector mounting assembly 1230 is pivotally attached to a proximal end 1103 of the elongate channel 1102 by a pair of laterally extending jaw attachment pins 1235 that are rotatably received within jaw pivot holes 1104 that are provided in the proximal end 1103 of the elongate channel 1102. The jaw attachment pins 1235 define a jaw pivot axis JA that is substantially traverse to the shaft axis SA. See FIG. 3. The articulation pivot pin 1564 defines an articulation axis B-B that is transverse to the shaft axis SA. Such arrangement facilitates pivotal travel (i.e., articulation) of the end effector 1100 about the articulation axis B-B relative to the spine assembly 1500.

Referring again to FIG. 4, in the illustrated embodiment, the articulation driver 1700 has a distal end 1702 that is configured to operably engage the articulation lock 1210. The articulation lock 1210 includes an articulation frame 1212 that is pivotally coupled to an articulation link 1214 that is adapted to operably engage an articulation drive pin 1236 on the pivot base portion 1232 of the end effector mounting assembly 1230. As indicated above, further details regarding the operation of the articulation lock 1210 and the articulation frame 1212 may be found in U.S. patent application Ser. No. 13/803,086, U.S. Patent Application Publication No. 2014/0263541. Further details regarding the end effector mounting assembly and articulation link 1214 may be found in U.S. patent application Ser. No. 15/019,245, filed Feb. 9, 2016, entitled SURGICAL INSTRUMENTS WITH CLOSURE STROKE REDUCTION ARRANGEMENTS, the entire disclosure of which is hereby incorporated by reference herein.

Figure 7:
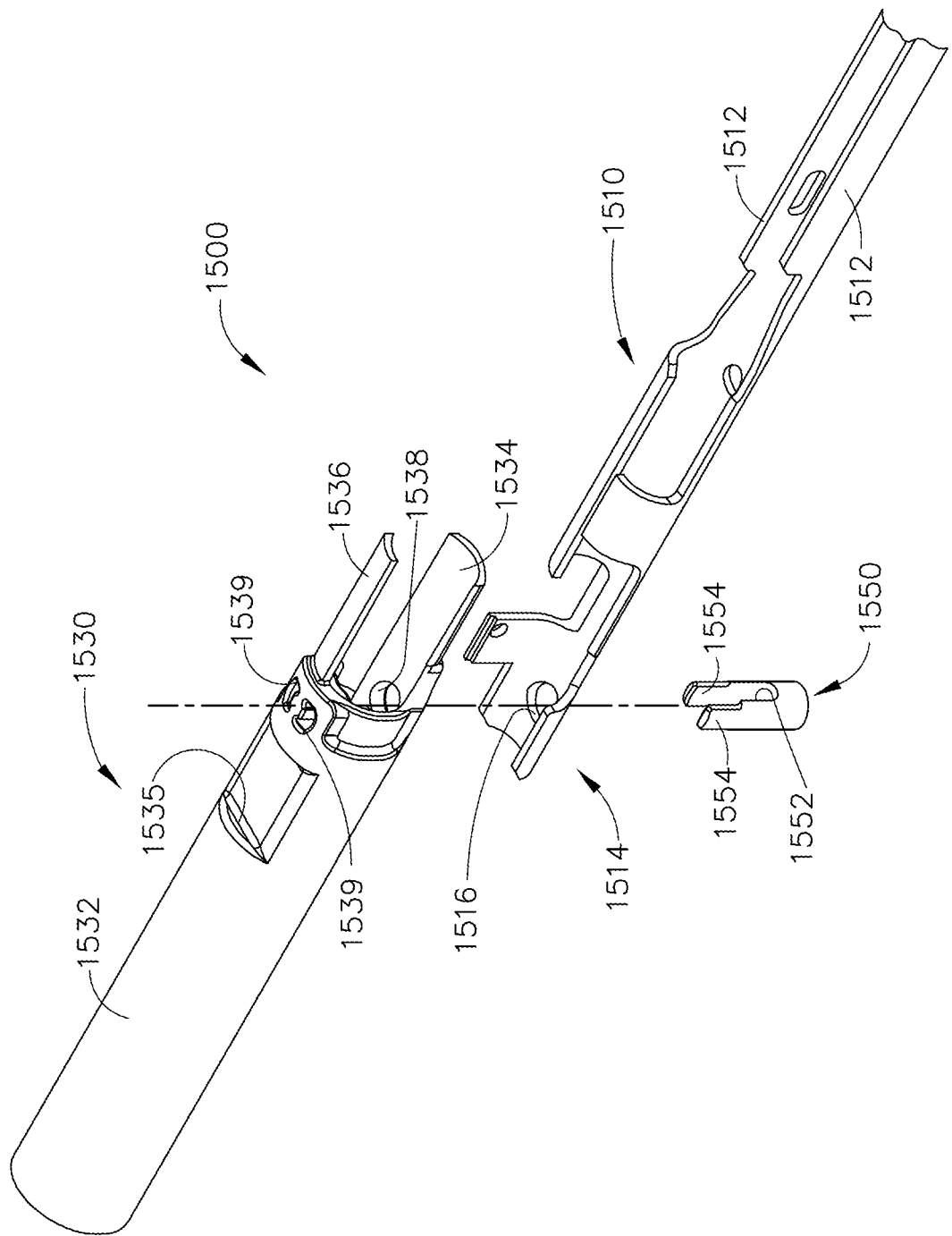
FIG. 7 is a partial exploded assembly view of a portion of a spine assembly embodiment of the interchangeable surgical tool assembly of FIG. 1.

In various circumstances, the spine assembly 1500 further includes a proximal spine channel 1510 that may be fabricated out of pressed, bent or machined material. As can be seen in FIG. 6, the proximal spine channel 1510 is essentially C-shaped (when viewed from a distal end) and is configured to operably support the firing member assembly 1600 between side wall portions 1512 thereof. As can be seen in FIGS. 6 and 7, the spine assembly 1500 further comprises a proximal spine mounting segment 1530 that is rotatably pinned to a distal end 1514 of the proximal spine channel 1510 by a spine pin 1550. The proximal spine mounting segment 1530 comprises a proximal end portion 1532 that has opposing notches 1535 (only one can be seen in FIG. 7) for receiving a corresponding mounting lug 1308 (shown in FIG. 5) that protrude inwardly from each of the nozzle portions 1302, 1304. Such arrangement facilitates rotation of the proximal spine mounting segment 1530 about the shaft axis SA by rotating the nozzle 1301 about the shaft axis SA. In the illustrated arrangement, the proximal spine mounting segment 1530 further comprises a distally protruding lower shaft segment 1534 and a distally protruding upper shaft segment 1536 that is spaced from the lower shaft segment 1534. See FIG. 7. Each of the shaft segments 1534, 1536 has an arcuate cross-sectional shape. The lower shaft segment 1534 is received within the proximal end 1514 of the proximal spine channel 1510. The spine pin 1550 extends through a pivot hole 1516 in the proximal end of the proximal spine channel 1510 and a pivot hole 1538 in the lower shaft segment 1534. The spine pin 1550 includes a vertical groove 1552 that forms two upstanding sidewall portions 1554. The upper ends of the side wall portions 1554 are received within corresponding pockets 1539 that are formed in the proximal spine mounting segment 1530.

The interchangeable surgical tool assembly 1000 includes a chassis 1800 that rotatably supported the shaft assembly 1400. The proximal end portion 1532 of the proximal spine mounting segment is rotatably supported in a central shaft hole 1801 that is formed in the chassis 1800. See FIG. 6. In one arrangement, for example, the proximal end portion 1532 may be threaded for attachment to a spine bearing (not shown) or other wise supported in a spine bearing that is mounted within the chassis 1800. Such an arrangement facilitates rotatable attachment of the spine assembly 1500 to the chassis 1800 such that the spine assembly 1500 may be selectively rotated about a shaft axis SA relative to the chassis 1800.

The closure assembly 1406 comprises an elongate intermediate closure member 1410, a distal closure member 1430 and a proximal closure member 1480. In the illustrated arrangement, the proximal closure member 1480 comprises a hollow tubular member that is slidably supported on a portion of the spine assembly 1500. Hence, the proximal closure member 1480 may also be referred to herein as the proximal closure tube. Similarly, the intermediate closure member 1410 may also be referred to herein as the intermediate closure tube and the distal closure member 1430 may also be referred to as the distal closure tube. Referring primarily to FIG. 6, the interchangeable surgical tool assembly 1000 includes a closure shuttle 1420 that is slidably supported within the chassis 1800 such that it may be axially moved relative thereto. In one form, the closure shuttle 1420 includes a pair of proximally-protruding hooks 1421 that are configured for attachment to the attachment pin 516 (FIG. 2) that is attached to the closure linkage assembly 514 of the handle assembly 500. Thus, when the hooks 1421 are hooked over the pin 516, actuation of the closure trigger 512 will result in the axial movement of the closure shuttle 1420 and ultimately, the closure assembly 1406 on the spine assembly 1500. A closure spring (not shown) may also be journaled on the closure assembly 1406 and serves to bias the closure member assembly 1406 in the proximal direction "PD" which can serve to pivot the closure trigger 512 into the unactuated position when the tool assembly 1000 is operably coupled to the handle assembly 500. In use, the closure member assembly 1406 is translated distally (direction DD) to close the anvil 1130, for example, in response to the actuation of the closure trigger 512.

The closure linkage 514 may also be referred to herein as a "closure actuator" and the closure linkage 514 and the closure shuttle 1420 may be collectively referred to herein as a "closure actuator assembly". A proximal end 1482 of the proximal closure member 1480 is coupled to the closure shuttle 1420 for relative rotation thereto. For example, a U-shaped connector 1485 is inserted into an annular slot 1484 in the proximal end 1482 of the proximal closure member 1480 and is retained within vertical slots 1422 in the closure shuttle 1420. See FIG. 6. Such arrangement serves to attach the proximal closure member 1480 to the closure shuttle 1420 for axial travel therewith while enabling the closure assembly 1406 to rotate relative to the closure shuttle 1420 about the shaft axis SA.

As indicated above, the illustrated interchangeable surgical tool assembly 1000 includes an articulation joint 1200. As can be seen in FIG. 4, upper and lower tangs 1415, 1416 protrude distally from a distal end of the intermediate closure member 1410 to be movably coupled to the distal closure member 1430. As can be seen in FIG. 4, the distal closure member 1430 includes upper and lower tangs 1434, 1436 that protrude proximally from a proximal end thereof. The intermediate closure member 1410 and the distal closure member 1430 are coupled together by an upper double pivot link 1220. The upper double pivot link 1220 includes proximal and distal pins that engage corresponding holes in the upper tangs 1415, 1434 of the proximal closure member 1410 and distal closure member 1430, respectively. The intermediate closure member 1410 and the distal closure member 1430 are also coupled together by a lower double pivot link 1222. The lower double pivot link 1222 includes proximal and distal pins that engage corresponding holes in the lower tangs 1416 and 1436 of the intermediate closure member 1410 and distal closure member 1430, respectively. As will be discussed in further detail below, distal and proximal axial translation of the closure assembly 1406 will result in the closing and opening of the anvil 1130 and the elongate channel 1102.

As mentioned above, the interchangeable surgical tool assembly 1000 further includes a firing member assembly 1600 that is supported for axial travel within the spine assembly 1500. In the illustrated embodiment, the firing member assembly 1600 includes a proximal firing shaft segment 1602, an intermediate firing shaft segment 1610 and a distal cutting portion or distal firing bar 1620. The firing member assembly 1600 may also be referred to herein as a "second shaft" and/or a "second shaft assembly". As can be seen in FIG. 6, the proximal firing shaft segment 1602 may be formed with a distal mounting lug 1604 that is configured to be received with a corresponding cradle or groove 1613 in the proximal end 1612 of the intermediate firing shaft segment 1610. A proximal attachment lug 1606 is protrudes proximally from a proximal end of the proximal firing shaft segment 1602 and is configured to be operably received within the firing shaft attachment cradle 542 in the longitudinally movable drive member 540 that is supported in the handle assembly 500. See FIG. 2.

Referring again to FIG. 6, a distal end 1616 of the intermediate firing shaft segment 1610 includes a longitudinal slot 1618 which is configured to receive a tab (not shown) on the proximal end of the distal firing bar 1620. The longitudinal slot 1618 and the proximal end of the distal firing bar 1620 can be sized and configured to permit relative movement therebetween and can comprise a slip joint 1622. The slip joint 1622 can permit the proximal firing shaft segment 1602 and the intermediate firing shaft segment 1610 of the firing member assembly 1600 to move as a unit during the articulation action without moving, or at least substantially moving, the distal firing bar 1620. Once the end effector 1100 has been suitably oriented, the proximal firing shaft segment 1602 and the intermediate firing shaft segment 1610 can be advanced distally until a proximal end wall of the longitudinal slot 1618 comes into contact with the tab on the distal firing bar 1620 to advance the distal firing bar 1620 and fire the staple cartridge 1110 that is positioned within the elongate channel 1102. As can be further seen in FIG. 6, to facilitate assembly, the proximal firing shaft segment 1602, the intermediate firing shaft segment 1610 and the distal firing bar 1620 may be inserted as a unit into the proximal spine channel 1510 and a top spine cover 1527 may be engaged with the proximal spine channel 1510 to enclose those portions of the firing member assembly 1600 therein.

Further to the above, the interchangeable surgical tool assembly 1000 includes a clutch assembly 1640 which can be configured to selectively and releasably couple the articulation driver 1700 to the firing member assembly 1600. In one form, the clutch assembly 1640 includes a rotary lock assembly that in at least one embodiment comprises a lock collar, or lock sleeve 1650 that is positioned around the firing member assembly 1600. The lock sleeve 1650 is configured to be rotated between an engaged position in which the lock sleeve 1650 couples the articulation driver 1700 to the firing member assembly 1600 and a disengaged position in which the articulation driver 1700 is not operably coupled to the firing member assembly 1600. When lock sleeve 1650 is in its engaged position, distal movement of the firing member assembly 1600 can move the articulation driver 1700 distally and, correspondingly, proximal movement of the firing member assembly 1600 can move the articulation driver 1700 proximally. When lock sleeve 1650 is in its disengaged position, movement of the firing member assembly 1600 is not transmitted to the articulation driver 1700 and, as a result, the firing member assembly 1600 can move independently of the articulation driver 1700. In various circumstances, the articulation driver 1700 can be held in position by the articulation lock 1210 when the articulation driver 1700 is not being moved in the proximal or distal directions by the firing member assembly 1600.

Figure 8:
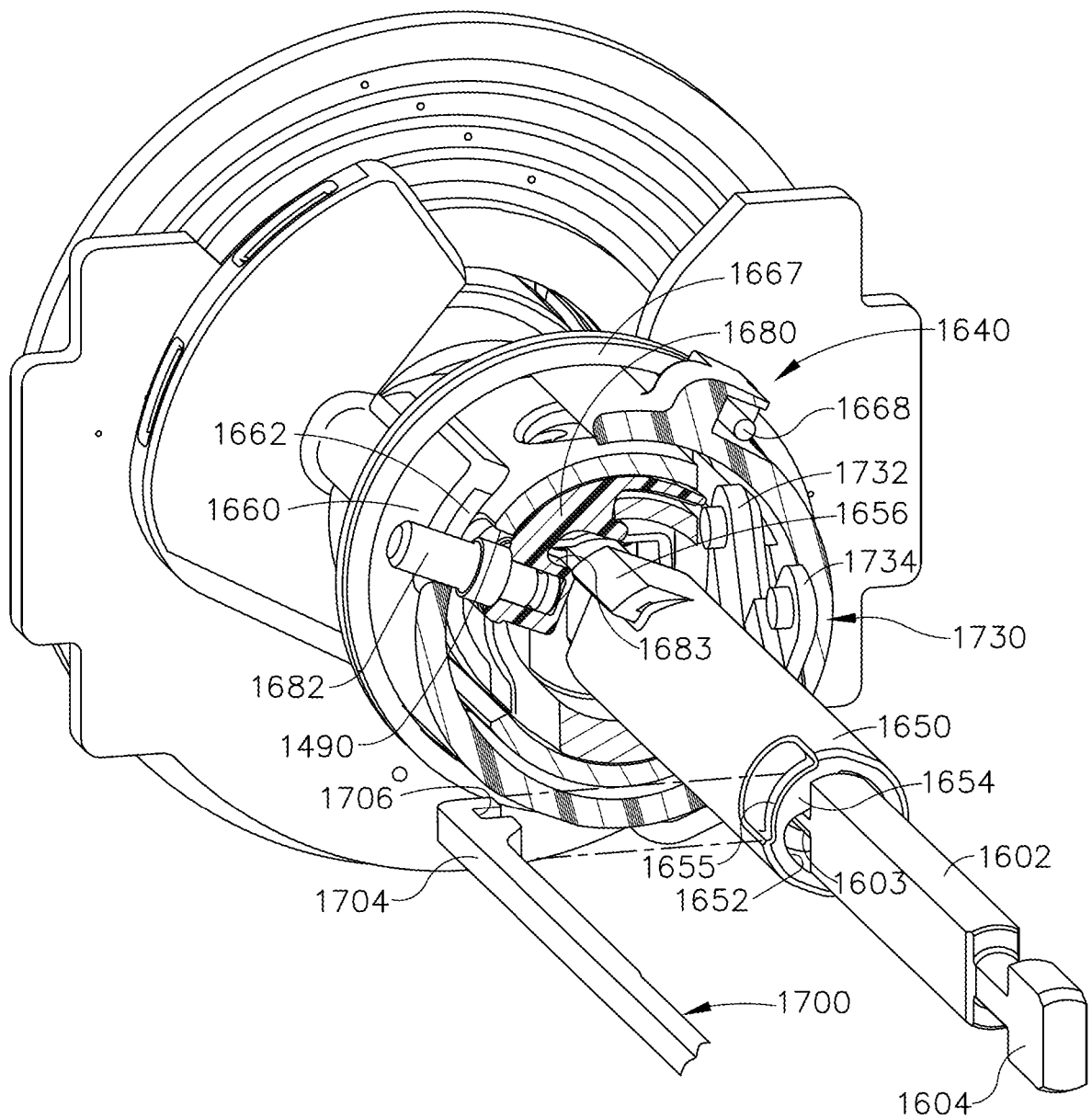
FIG. 8 is a partial cross-sectional end view of the proximal portion of the interchangeable surgical tool assembly of FIG. 5 with a clutch assembly thereof shown in an articulation mode.
Figure 9:
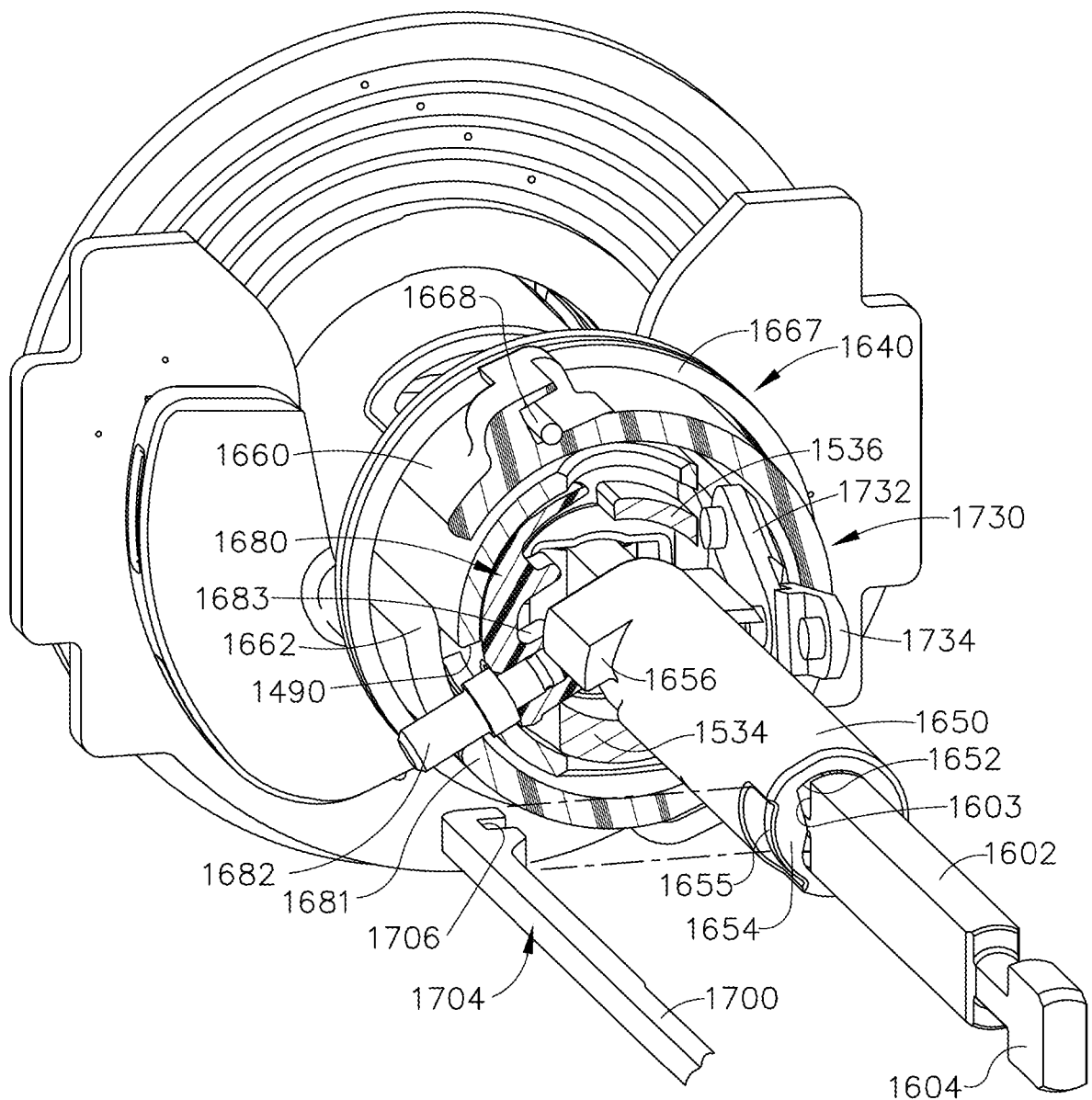
FIG. 9 is another partial cross-sectional end view of the proximal portion of the interchangeable surgical tool assembly of FIG. 5 with the clutch assembly thereof shown in a firing mode.

Referring primarily to FIGS. 8 and 9, the lock sleeve 1650 comprises a cylindrical, or an at least substantially cylindrical, body including a longitudinal aperture 1652 defined therein configured to receive the proximal firing shaft segment 1602 of the firing member assembly 1600. The lock sleeve 1650 also has two diametrically-opposed, inwardly-facing lock protrusions 1654 formed thereon. Only one lock protrusion 1654 can be seen in FIGS. 8 and 9. The lock protrusions 1654 can be configured to be selectively engaged with the proximal firing shaft segment 1602 of the firing member assembly 1600. More particularly, when the lock sleeve 1650 is in its engaged position (FIG. 8), the lock protrusions 1654 are positioned within a drive notch 1603 that is provided in the proximal firing shaft segment 1602 such that a distal pushing force and/or a proximal pulling force can be transmitted from the firing member assembly 1600 to the lock sleeve 1650. As can be seen in FIGS. 8 and 9, an articulation drive notch 1655 is provided in a distal end portion of the lock sleeve 1650 for attachment to a proximal end 1704 of the proximal articulation driver 1700. In the illustrated arrangement, for example, the proximal end 1704 includes a driver notch 1706 that is configured to engage the drive notch 1655 in the lock sleeve 1650. Such attachment arrangement enables the lock sleeve 1650 to be rotated relative to the proximal articulation driver 1700 while remaining attached thereto. When the lock sleeve 1650 is in an "articulation mode" or orientation (FIG. 8), a distal pushing force and/or a proximal pulling force that is applied to the proximal firing shaft segment 1602 is also transmitted to the lock sleeve 1650 and the proximal articulation driver 1700 that is coupled thereto. In effect, the firing member assembly 1600, the lock sleeve 1650, and the proximal articulation driver 1700 will move together when the lock sleeve 1650 is in the articulation mode. On the other hand, when the lock sleeve 1650 is in its "firing mode" (FIG. 9), the lock protrusions 1654 are not positioned within the drive notch 1603 in the proximal firing shaft segment 1602 of the firing member assembly 1600. When in that position, a distal pushing force and/or a proximal pulling force applied to the proximal firing shaft segment 1602 is not transmitted to the lock sleeve 1650 and the proximal articulation driver 1700. In such circumstances, the firing member assembly 1600 can move proximally and/or distally relative to the lock sleeve 1650 and the proximal articulation driver 1700.

The illustrated clutch assembly 1640 further includes a switch drum 1660 that interfaces with the lock sleeve 1650. The switch drum 1660 comprises a hollow shaft segment that operably interfaces with a shift plate assembly 1680 that is supported therein. The shift plate assembly 1680 comprises a body portion 1681 that has a shift pin 1682 that protrudes laterally therefrom. The shift pin 1682 extends into a shift pin slot 1662 that is provided through a wall portion of the shift drum 1660. The body portion 1681 of the shift plate assembly 1680 has a slide slot 1683 formed therein that is sized and configured to interface with a slide boss 1656 that protrudes from a proximal end of the slide lock 1650. The switch drum 1660 can further include openings 1664 which permit the inwardly extending mounting lugs 1308 that extend from the nozzle halves 1302, 1304 to extend therethrough to be seating received within the corresponding notches 1535 in the proximal spine mounting segment 1530. See FIG. 5. Such arrangement facilitates rotation of the shaft assembly 1400 about the shaft axis SA by rotating the nozzle 1301.

Also in the illustrated embodiment, the switch drum 1660 includes a magnet support arm 1665 that supports an articulation magnet 1708 and a firing magnet 1611 therein. The articulation magnet 1708 and firing magnet 1611 are configured to operably interface with a Hall effect sensor 1632 that interfaces with a slip ring assembly 1630 that is operably mounted to the chassis 1800. The slip ring assembly 1630 is configured to conduct electrical power to and/or from the interchangeable surgical shaft assembly 1000 and/or communicate signals to and/or from the interchangeable shaft assembly 1000 components back to the microcontroller 520 in the handle assembly 500 (FIG. 2) or robotic system controller, for example. Further details concerning the slip ring assembly 1630 and associated connectors may be found in U.S. patent application Ser. No. 13/803,086 and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety. The articulation magnet 1708 and the firing magnet 1611 cooperate with the Hall effect sensor 1632 or other sensor arrangement to detect the rotary position of the switch drum 1660 and convey that information to the microcontroller 520 which may serve to provide an indication or indications to the user in the various manners discussed in the aforementioned incorporated references. Other sensor arrangements may also be employed.

In various circumstances, the handle assembly 500 may be used to control a variety of different interchangeable surgical tool assemblies that are configured to perform various surgical procedures. As briefly mentioned above, the interchangeable surgical tool assembly 1000 may also be effectively used in connection with robotic systems and automated surgical systems that each may be referred to herein as "control systems" or "control units". Such control systems or control units may operably support firing systems and closure systems that are configured upon actuation to move a firing actuation component or "firing actuator" (in the case of the firing system) and a closure actuation component or "closure actuator" (in the case of the closure system) a corresponding axial distance to apply control motions to corresponding components within the interchangeable tool assembly. In one arrangement, when a closure system in the handle assembly (or robotic system) is fully actuated, a closure actuator may move axially from an unactuated position to its fully actuated position. The axial distance that the closure component moves between its unactuated position to its fully actuated position may be referred to herein as its "closure stroke length" or a "first closure distance". Similarly, when a firing system in the handle assembly or robotic system is fully actuated, one of the firing system components may move axially from its unactuated position to its fully actuated or fired position. The axial distance that the firing member component moves between its unactuated position and its fully fired position may be referred to herein as its "firing stroke length" or "first firing distance". For those surgical tool assemblies that employ articulatable end effector arrangements, the handle assembly or robotic system may employ articulation control components that move axially through an "articulation drive stroke length" or a "first articulation distance". In many circumstances, the closure stroke length, the firing stroke length and the articulation drive stroke length are fixed for a particular handle assembly or robotic system. Thus, each of the interchangeable surgical tool assemblies that are configured to be used in connection with such control units or systems must be able to accommodate control movements of the closure, firing and/or articulation components/actuators through each of their entire stroke lengths without placing undue stress on the surgical tool components which might lead to damage or catastrophic failure of surgical tool assembly. Examples of surgical tool assemblies that have arrangements for reducing the axial closure stroke of an actuator system are disclosed in U.S. patent application Ser. No. 15/019,245, filed Feb. 9, 2016, entitled SURGICAL INSTRUMENTS WITH CLOSURE STROKE REDUCTION ARRANGEMENTS, the entire disclosure of which is hereby incorporated by reference herein. U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER discloses arrangements for adjusting the firing stroke of a firing member.

Depending upon the jaw arrangement of the end effector portion of the interchangeable surgical tool assembly that is operably coupled to the handle assembly 500, the closure drive system 510 in the handle assembly 500, when fully actuated, may generate a closure stroke or first axial closure distance that is too long for such a jaw arrangement. The illustrated embodiment of the interchangeable surgical tool assembly 1000 employs a closure stroke reduction assembly generally designated as 1720 to reduce the amount of closure stroke that is applied to the end effector when the closure drive system 510 is fully actuated. For example, the closure drive system 510 in one form of the handle assembly 500 may generate axial closure motions so as to move the closure actuator (e.g., the closure linkage 514—FIG. 2) or closure actuator assembly (e.g., the closure linkage 514, and the closure shuttle 1420) axially forward and backward about 0.240"-0.260". Such axial control travel may be well-suited for surgical end effectors that are equipped with an anvil or jaw arrangement that moves distally relative to the channel or jaw arrangements to which they are attached. Because the jaws are pivotally coupled together about a fixed jaw axis JA, they may be better suited for a shorter closure stroke. Stated another way, the anvil 1130 does not move distally relative to the elongate channel 1102. For example, such arrangement may be better suited for a closure stroke range of approximately 0.1"-0.150". As will be discussed in further detail below, upon full actuation of the closure drive system 510 in the handle assembly 500, the closure shuttle 1420 and the proximal closure member 1480 may move approximately the 0.260" in the distal direction DD ("first closure stroke distance"). However, the closure stroke reduction assembly 1720 reduces the amount of closure stroke that is applied to the intermediate closure member 1410 and ultimately to the distal closure member 1430 ("second closure stroke distance"). In some arrangements, for example, the closure stroke reduction assembly 1720 may reduce the magnitude of the closure stroke that is applied to the intermediate closure member 1410 and distal closure member 1430 to approximately 0.1", for example. It will be appreciated that other amounts of closure stroke reduction could conceivably be achieved.

Figure 12B:
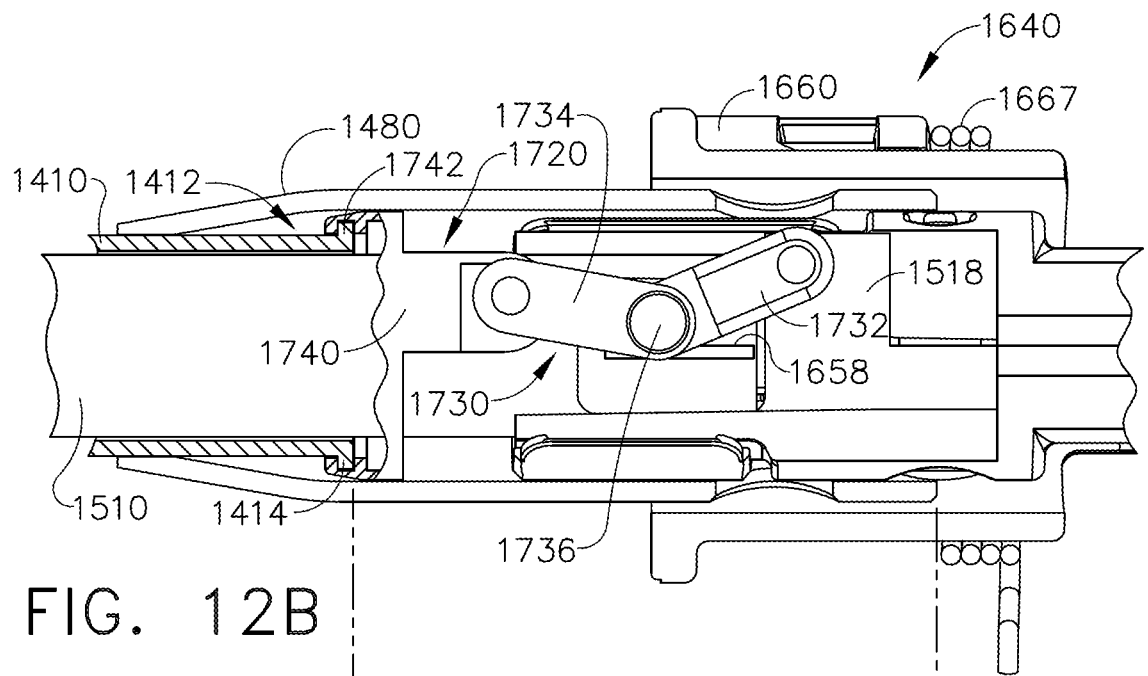
FIG. 12B is a partial side cross-sectional view of the interchangeable surgical tool assembly of FIG. 12A with the closure stroke reduction assembly embodiment in an extended orientation corresponding to the firing mode.
Figure 12A:
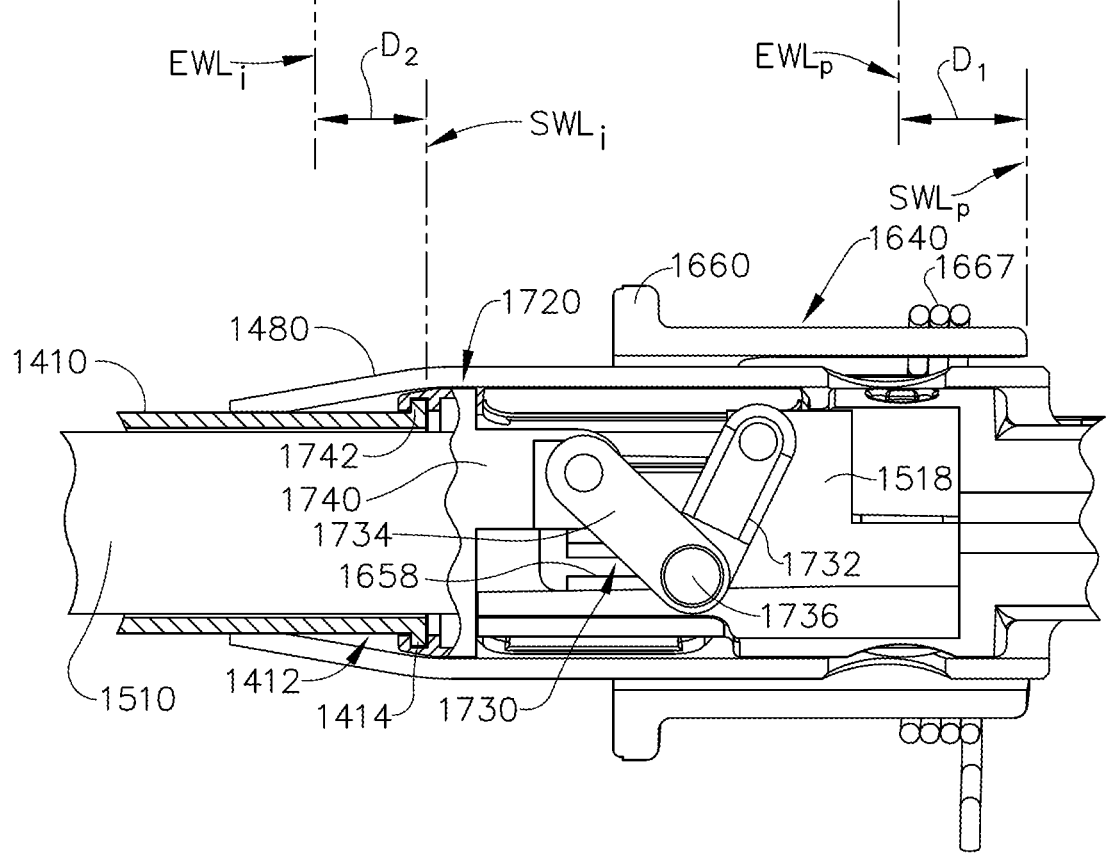
FIG. 12A is a partial side cross-sectional view of the interchangeable surgical tool assembly of FIG. 1 with a closure stroke reduction assembly embodiment in a retracted orientation corresponding to the articulation mode.
Figure 14:
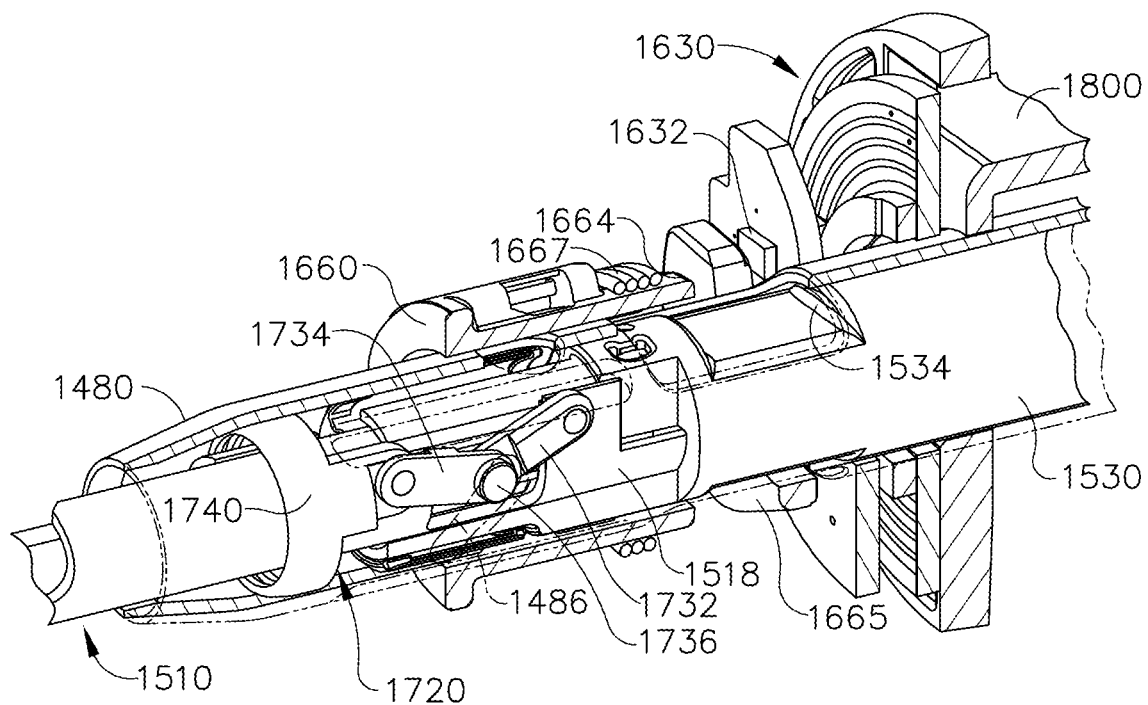
FIG. 14 is a perspective view of a portion of the interchangeable surgical tool assembly of FIG. 12B showing the closure stroke reduction assembly embodiment in the extended orientation corresponding to the firing mode.
Figure 13:
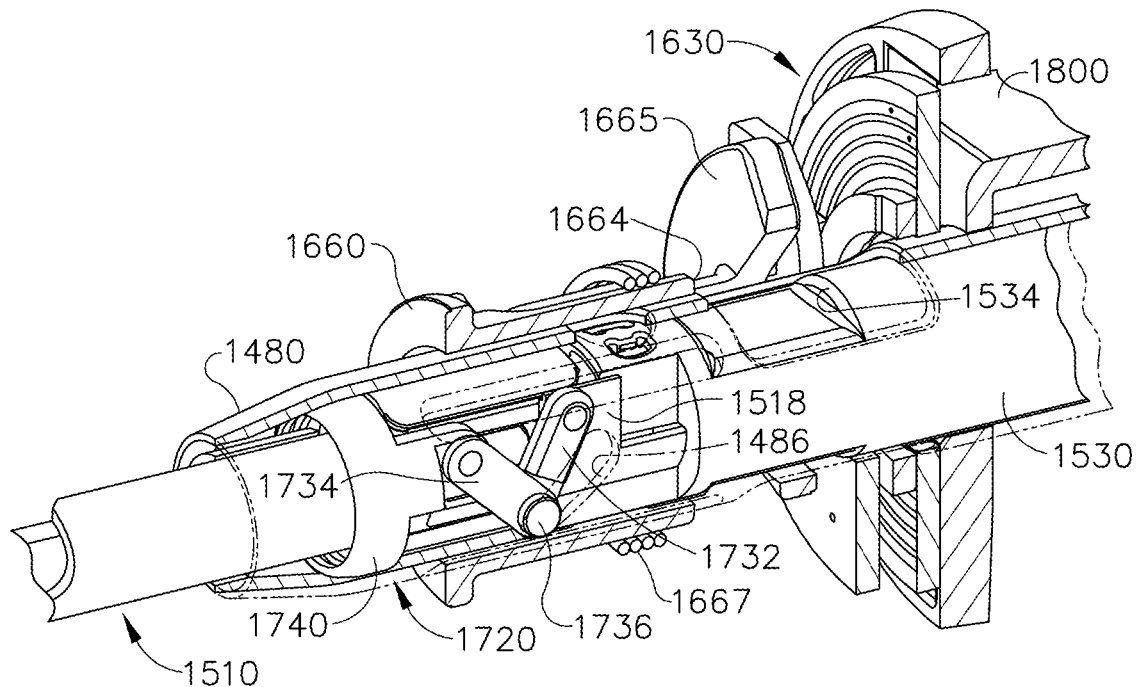
FIG. 13 is a perspective view of a portion of the interchangeable surgical tool assembly of FIG. 12A showing the closure stroke reduction assembly embodiment in the retracted orientation corresponding to the articulation mode.

Referring now to FIGS. 12A and 12B, in one form, the closure stroke reduction assembly 1720 includes a closure reduction linkage 1730 that is attached to a closure member mounting member or mounting ring 1740. As can be seen in FIGS. 6, 12A and 12B, the intermediate closure member 1410 has a proximal attachment flange 1414 that is formed on a proximal end portion 1412. The mounting ring 1740 is sized to slidably move within the proximal closure member 1480 and includes a mounting groove 1742 for receiving the attachment flange 1414 therein. Such arrangement serves to attach the mounting ring 1740 to the intermediate closure member 1410. In the illustrated embodiment, the closure reduction linkage 1730 comprises a proximal link 1732 and a distal link 1734 that are pivotally attached together by an actuator pin 1736. The proximal link 1732 is pivotally pinned to an upstanding attachment wall 1518 that is formed on the proximal spine channel 1510. The distal link 1734 is pivotally pinned to the mounting ring 1740. The closure reduction linkage 1730 is actuated by axially moving the proximal closure member 1480. In at least one arrangement, for example, the actuator pin 1736 is slidably journaled in a cam slot 1486 that is provided in the proximal closure member 1480. The actuator pin 1736 also extends inwardly to be slidably received within a slide track 1658 that is formed on a proximal end portion of the lock sleeve 1650. Thus, when the proximal closure member 1480 is moved to its distal-most position, the actuator pin 1736 is in the proximal end of the cam slot 1486 such that the closure reduction linkage 1730 is in its fully extended position as shown in FIGS. 12B and 14. When the proximal closure member 1480 is in its proximal-most position, the closure reduction linkage 1730 is in its retracted position (FIGS. 12A and 13).

As was briefly discussed above, the shift plate assembly 1680 comprises a body portion 1681 that has a shift pin 1682 that laterally protrudes therefrom. The shift pin 1682 extends into a shift pin slot 1662 that is provided through a wall portion of the switch drum 1660. The shift pin 1682 also extends through a cam opening 1490 that is provided in the proximal closure member 1480. See FIGS. 10 and 11. The cam opening 1490 in the illustrated arrangement includes a travel portion 1492 that is sufficiently long enough so as to permit a predetermined amount of axial travel of the proximal closure member assembly 1480 relative to the shift pin 1682 and a firing portion 1494. In at least one arrangement, the shift plate 1680 is constrained to only rotate a short distance around the shaft axis SA and is constrained not to move axially within the switch drum 1660. This rotary travel of the shift plate 1680 and the shift pin 1682 may be observed from reference to FIGS. 8-11.

Figure 11:
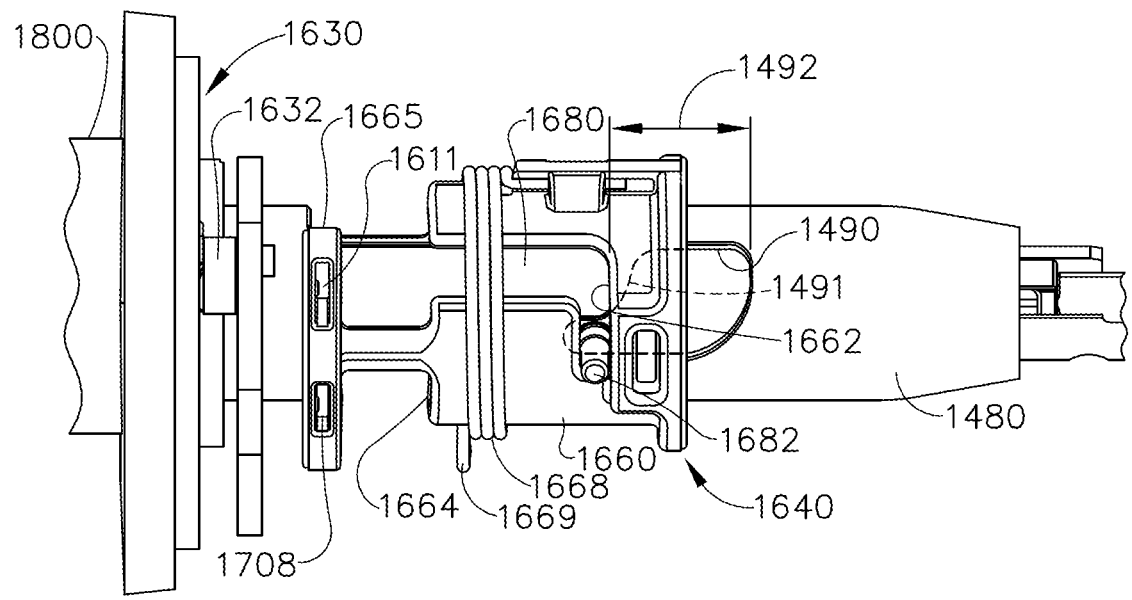
FIG. 11 is a partial side view of a portion of the interchangeable surgical tool assembly of FIG. 1 with the clutch assembly thereof shown in the firing mode.
Figure 10:
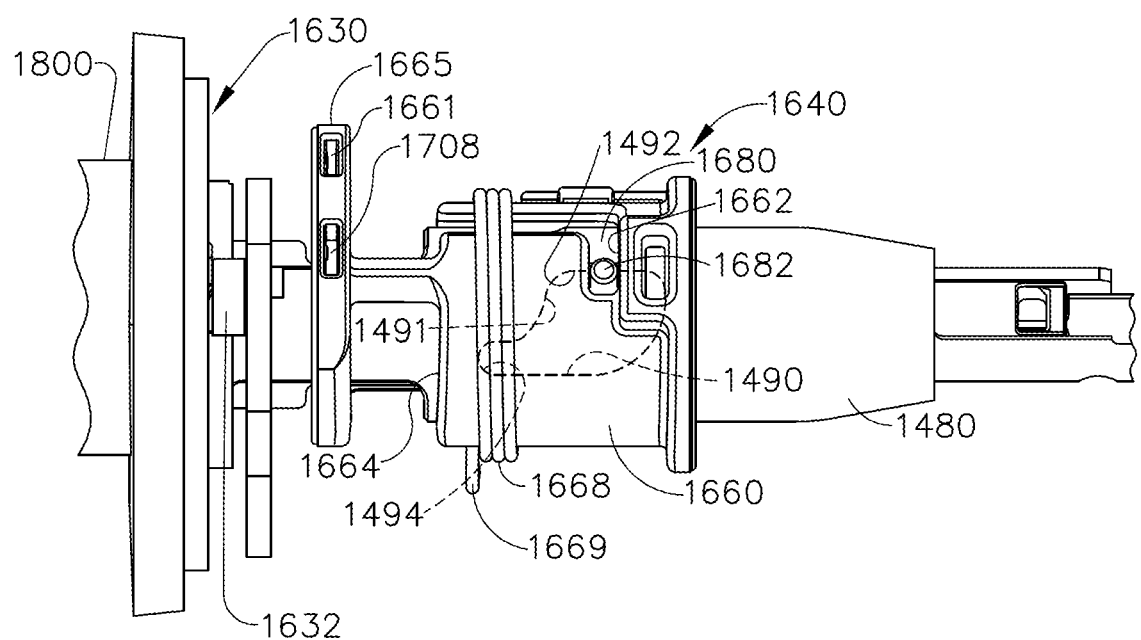
FIG. 10 is a partial side view of the proximal portion of the interchangeable surgical tool assembly of FIG. 1 with a clutch assembly thereof shown in the articulation mode.

FIGS. 8, 10 and 12A illustrate the clutch assembly 1640 in the articulation mode and FIGS. 9, 11 and 12B, illustrate the clutch assembly 1640 in the firing mode. The clutch assembly 1640 is moved from the articulation mode to the firing mode by moving the proximal closure member 1480 to it distal-most position which corresponds to a "fully closed" position of the end effector jaws (elongate channel 1102 and anvil 1130). The proximal closure member 1480 is moved distally by depressing the closure trigger 512 on the handle assembly 500. As discussed above, when the closure trigger 512 is depressed, the closure shuttle 1420 is advanced distally. Because the proximal closure member 1480 is supported in the closure shuttle 1420, the proximal closure member 1480 moves distally as well. When the clutch assembly 1640 is in the articulation mode, the shift pin 1682 is located about midway (lengthwise) within the travel portion 1492 of the cam opening 1490 in the proximal closure member 1480. Thus, the proximal closure member 1480 can be moved back and forth axially (by means of depressing and at least partially releasing the closure trigger 512) a short distance to effectively move the jaws (anvil 1130 and elongate channel 1102) between open and closed positions without moving the clutch assembly 1640 into the firing mode. Thus, the clinician can use the jaws to grasp and manipulate tissue without moving the jaws to a fully closed position and without shifting the clutch assembly 1640 to the firing mode. However, when the clinician desires to fully close the jaws, the clinician fully depresses the closure trigger 512 to the fully actuated position. This action causes the proximal closure member 1480 to move to its distal-most axial position. See FIGS. 9, 11 and 12B. When the proximal closure member 1480 moves to this position, the proximal cam wall 1491 of the cam opening 1490 contacts the shift pin 1682 and cams the shift pin 1682 (and the shift plate 1680) to the firing orientation shown in FIGS. 9 and 11. In the illustrated embodiment, a torsional shift spring 1667 is journaled on the switch drum 1660 and is configured to bias the switch drum 1660 into the position corresponding to the articulation mode. See FIG. 10. The shift pin 1682 is in the bottom of the shift pin slot 1662 in the switch drum 1660 and is thereby moved to the articulation position shown in FIG. 10. To apply the torsional biasing force to the switch drum 1660, one end 1668 of the torsion spring 1667 is attached to the switch drum 1660 and the other end 1669 is attached to nozzle 1301. Further details concerning the operation of the clutch assembly 1640 and the closure stroke reduction assembly 1720 are provided below.

FIG. 12A illustrates the positions of the closure stroke reduction assembly 1730 and the intermediate closure member 1410 when the proximal closure member 1480 is in an unactuated position. This "unactuated" position may correspond to the orientations of the jaws of the surgical end effector when the jaws are in their respective "fully opened" positions. For reference purposes, the unactuated position of the proximal closure member 1480 is represented by a starting witness line $SWL_p$ and the unactuated position of the intermediate closure member 1410 is represented by starting witness line $SWL_i$. FIG. 12B illustrates the positions of the of the closure stroke reduction assembly 1730 and the intermediate closure member 1410 when the proximal closure member 1480 is in a fully actuated position which may correspond to the orientations of the jaws of the surgical end effector when the jaws are in their respective "fully closed" positions. As was briefly discussed above, when the proximal closure member 1480 is in the fully actuated position, actuation of the firing trigger 532 will cause the firing member assembly 1600 to be advanced distally. For reference purposes, the fully actuated position of the proximal closure segment 1480 is represented by an ending witness line $EWL_p$. The fully actuated position of the intermediate closure member 1410 is represented by a ending witness line $EWL_i$. The axial distance that the proximal closure member 1480 traveled between the unactuated position and the fully actuated position is represented by distance $D_1$. In one example, $D_1$ may be approximately 0.260". The axial distance that the intermediate closure member 1410 (and ultimately the distal closure member 1430) traveled between the unactuated position and the fully actuated position is represented by distance $D_2$. As can be seen in FIGS. 12A and 12B, $D_1 > D_2$. In the above-referenced example, $D_2$ may be approximately 0.1". Thus, the intermediate closure member 1410 and the distal closure member 1430 traveled a shorter axial distance than did the proximal closure member 1480. Such arrangement permits the jaw arrangements of the surgical end effector 1100 to better utilize the closure motions generated by the closure drive system 510 in the handle assembly 500 and avoid potential damage that might otherwise result if the full range of closure motions were applied to the end effector.

Referring again to FIGS. 2 and 6, the chassis 1800 includes at least one, and preferably two, tapered attachment portions 1802 that are formed thereon and are adapted to be received within corresponding dovetail slots 507 that are formed within the distal end portion of the frame 506 of the handle assembly 500. As can be further seen in FIG. 2, a shaft attachment lug 1606 is formed on the proximal end of the proximal firing shaft segment 1602. As will be discussed in further detail below, when the interchangeable surgical tool assembly 1000 is coupled to the handle assembly 500, the shaft attachment lug 1606 is received in a firing shaft attachment cradle 542 that is formed in the distal end of the longitudinal drive member 540. See FIG. 2.

The interchangeable surgical tool assembly 1000 employs a latch system 1810 for removably coupling the interchangeable surgical tool assembly 1000 to the frame 506 of the handle assembly 500. As can be seen in FIG. 5, for example, in at least one form, the latch system 1810 includes a lock member or lock yoke 1812 that is movably coupled to the chassis 1800. In the illustrated embodiment, for example, the lock yoke 1812 has a U-shape and includes two downwardly extending legs 1814. The legs 1814 each have a pivot lug (not shown) formed thereon that is adapted to be received in corresponding holes 1816 that are formed in the chassis 1800. Such arrangement facilitates pivotal attachment of the lock yoke 1812 to the chassis 1800. See FIG. 6. The lock yoke 1812 may include two proximally protruding lock lugs 1818 that are configured for releasable engagement with corresponding lock detents or grooves 509 in the distal end of the frame 506 of the handle assembly 500. See FIG. 2. In various forms, the lock yoke 1812 is biased in the proximal direction by a spring or biasing member 1819. Actuation of the lock yoke 1812 may be accomplished by a latch button 1820 that is slidably mounted on a latch actuator assembly 1822 that is mounted to the chassis 1800. The latch button 1820 may be biased in a proximal direction relative to the lock yoke 1812. The lock yoke 1812 may be moved to an unlocked position by biasing the latch button 1820 the in distal direction which also causes the lock yoke 1812 to pivot out of retaining engagement with the distal end of the frame 506. When the lock yoke 1812 is in "retaining engagement" with the distal end of the frame 506, the lock lugs 1818 are retainingly seated within the corresponding lock detents or grooves 509 in the distal end of the frame 506.

In the illustrated arrangement, the lock yoke 1812 includes at least one and preferably two lock hooks 1824 that are adapted to contact corresponding lock lug portions 1426 that are formed on the closure shuttle 1420. When the closure shuttle 1420 is in an unactuated position, the lock yoke 1812 may be pivoted in a distal direction to unlock the interchangeable surgical tool assembly 1000 from the handle assembly 500. When in that position, the lock hooks 1824 do not contact the lock lug portions 1426 on the closure shuttle 1420. However, when the closure shuttle 1420 is moved to an actuated position, the lock yoke 1812 is prevented from being pivoted to an unlocked position. Stated another way, if the clinician were to attempt to pivot the lock yoke 1812 to an unlocked position or, for example, the lock yoke 1812 was in advertently bumped or contacted in a manner that might otherwise cause it to pivot distally, the lock hooks 1824 on the lock yoke 1812 will contact the lock lugs 1426 on the closure shuttle 1420 and prevent movement of the lock yoke 1812 to an unlocked position. See FIG. 5. Further details concerning the latching system may be found in U.S. Patent Application Publication No. 2014/0263541.

Attachment of the interchangeable surgical tool assembly 1000 to the handle assembly 500 will now be described with reference to FIG. 2. To commence the coupling process, the clinician may position the chassis 1800 of the interchangeable surgical tool assembly 1000 above or adjacent to the distal end of the frame 506 such that the tapered attachment portions 1802 formed on the chassis 1800 are aligned with the dovetail slots 507 in the frame 506. The clinician may then move the surgical tool assembly 1000 along an installation axis IA that is perpendicular to the shaft axis SA to seat the tapered attachment portions 1802 in "operable engagement" with the corresponding dovetail receiving slots 507 in the distal end of the frame 506. In doing so, the shaft attachment lug 1606 on the proximal firing shaft segment 1602 will also be seated in the cradle 542 in the longitudinally movable drive member 540 and the portions of pin 516 on the closure link 514 will be seated in the corresponding hooks 1421 in the closure shuttle 1420. As used herein, the term "operable engagement" in the context of two components means that the two components are sufficiently engaged with each other so that upon application of an actuation motion thereto, the components may carry out their intended action, function and/or procedure.

Referring again to FIG. 4, the distal firing bar 1620 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the distal firing bar 1620 to be sufficiently flexible to accommodate articulation of the end effector. Various laminated knife bar arrangements are disclosed in U.S. patent application Ser. No. 15/019,245. As can also be seen in FIG. 4, a middle support member 1614 is employed to provide lateral support to the distal firing bar 1620 as it flexes to accommodate articulation of the surgical end effector 1100. Further details concerning the middle support member and alternative knife bar support arrangements are disclosed in U.S. patent application Ser. No. 15/019,245.

After the interchangeable surgical tool assembly 1000 has been operably coupled to the handle assembly 500 (FIG. 1), the clinician may operate the surgical tool assembly 10 as follows. As discussed above, when the closure drive system 510 is in its unactuated position (i.e., the closure trigger 512 has not been actuated), the torsion spring 1667 has biased the clutch assembly 1640 and, more particularly, the switch pin 1682 and the lock sleeve 1650 into the articulation position. See FIGS. 8, 10 and 12A. As can be seen in FIG. 8, when in that position, the lock protrusions 1654 on the lock sleeve 1650 are received within the drive notch 1603 in the proximal firing shaft segment 1602. As can be seen in FIG. 10, when in that mode, the articulation magnet 1708 is in position relative to the Hall effect sensor 1632 so as to indicate to the microcontroller 520 that the tool assembly 1000 is in the articulation mode. When the clinician actuates the firing trigger 512, the motor drives the proximal firing shaft segment 1602 distally. As mentioned above, however, the slip joint 1622 facilitates movement of the proximal firing shaft segment 1602 and the intermediate firing shaft segment 1610 without moving, or at least substantially moving, the distal firing bar 1620. Because the lock sleeve 1650 is in operable engagement with the proximal firing shaft segment 1602 and the proximal articulation driver 1700 is in engagement with the lock sleeve 1650, actuation of the proximal firing shaft segment 1602 results in the distal movement of the articulation driver 1700. Distal movement of the articulation driver 1700 causes the surgical end effector 1000 to articulate around the articulation axis B-B. During this time, the clinician can also partially close the jaws of the end effector 1100 by partially depressing the closure trigger. Such axial movement of the proximal closure member 1480 without automatically shifting the clutch assembly 1640 to the firing mode is accommodated by the travel portion 1492 of the cam opening 1490 in the proximal closure member 1480. See FIG. 10. This feature enables the clinician to use the jaws to grasp and manipulate tissue prior to clamping onto the target tissue.

Once the clinician has articulated the end effector 1100 into a desired position and the jaws have been positioned in a desired orientation relative to the target tissue, the clinician releases the firing trigger 532 which will discontinue the motorized movement of the proximal firing shaft segment 1602 as well as the proximal articulation driver 1700. The articulation lock 1210 will lock the proximal articulation driver 1700 in that position to prevent further articulation of the end effector 1100. The clinician may clamp the target tissue between the jaws by depressing the closure trigger 512 to the fully depressed position. Such action moves the proximal closure member 1480 distally. Such distal movement of the proximal closure member 1480 causes the switch pin 1682 to rotate downward within the cam opening 1490 as it is contacted by the cam wall 1491. See FIG. 11. Referring now to FIG. 11, movement of the shift pin 1682 downwardly within cam opening 1490 causes the shift plate 1680 to rotate the lock sleeve 1650 to rotate to a disengaged position with the proximal firing shaft segment 1602. When in that position, the lock protrusions 1654 have disengaged from the drive notch 1603 in the proximal firing shaft segment 1602. Thus, the proximal firing shaft segment 1602 can move axially without moving the lock sleeve 1650 and the proximal articulation driver 1700. As the proximal closure member 1480 is moved distally to the fully actuated position (by depressing the closure trigger 512), the closure stroke reduction assembly 1730 moves the intermediate closure member 1410 distally a reduced axial distance as was discussed above. This axial motion is applied to the distal closure member 1430 and ultimately moves the jaws to the fully closed position. When in this position, the closure drive system 510 system in the handle assembly 500 may be locked and the clinician can release the closure trigger 512. When the clutch assembly 1640 has been moved to this firing mode, the firing magnet 1611 is in communication with the Hall effect sensor 1632 to indicate the position of the clutch assembly 1640 to the microcontroller 520. See FIG. 11. The microcontroller 520 may provide the clinician with an indication of the position of the distal firing bar 1620 as it is advanced distally through the target tissue that is clamped between the end effector jaws. Once the distal firing bar 1620 and, more specifically, the firing member or knife member attached thereto has been advanced to a fully fired position, the microcontroller 520, by means of sensor arrangements, detects the position of a portion of the firing member assembly 1600 and may then reverse the motor to retract the distal firing bar 1620 to its starting position. This action may be automatic or the clinician may have to depress the firing trigger 532 during the retraction process. Once the distal firing bar 1620 has been fully retracted to its starting position, the microcontroller 520 may provide the clinician with an indication that the distal firing bar 1620 has been fully retracted and the closure trigger 512 may be unlocked to enable the closure assembly 1406 to be returned to the unactuated position which thereby moves the jaws to the open position.

Figure 15A:
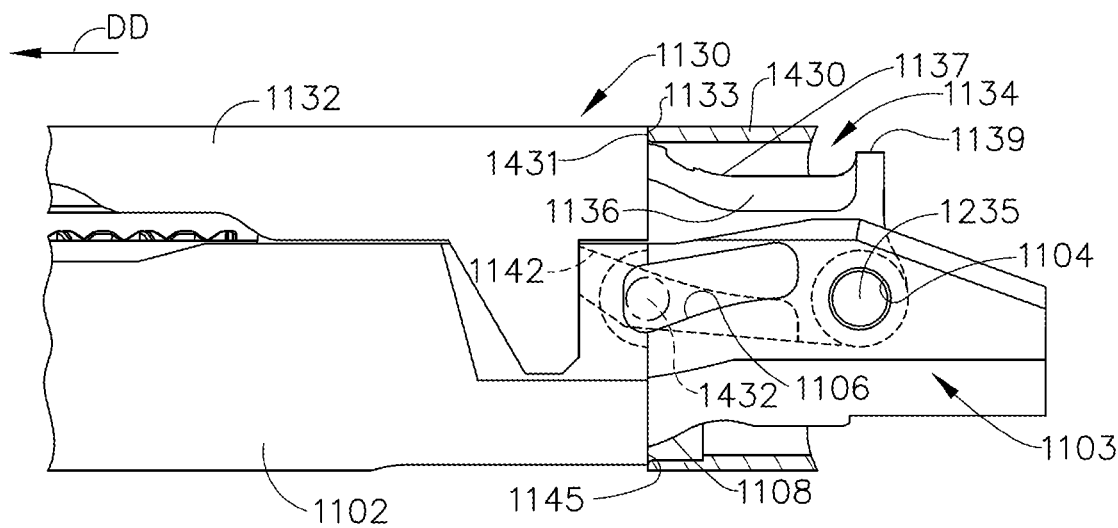
FIG. 15A is a side elevational view of a portion of a surgical end effector embodiment with the jaws thereof in a fully closed orientation.
Figure 15B:
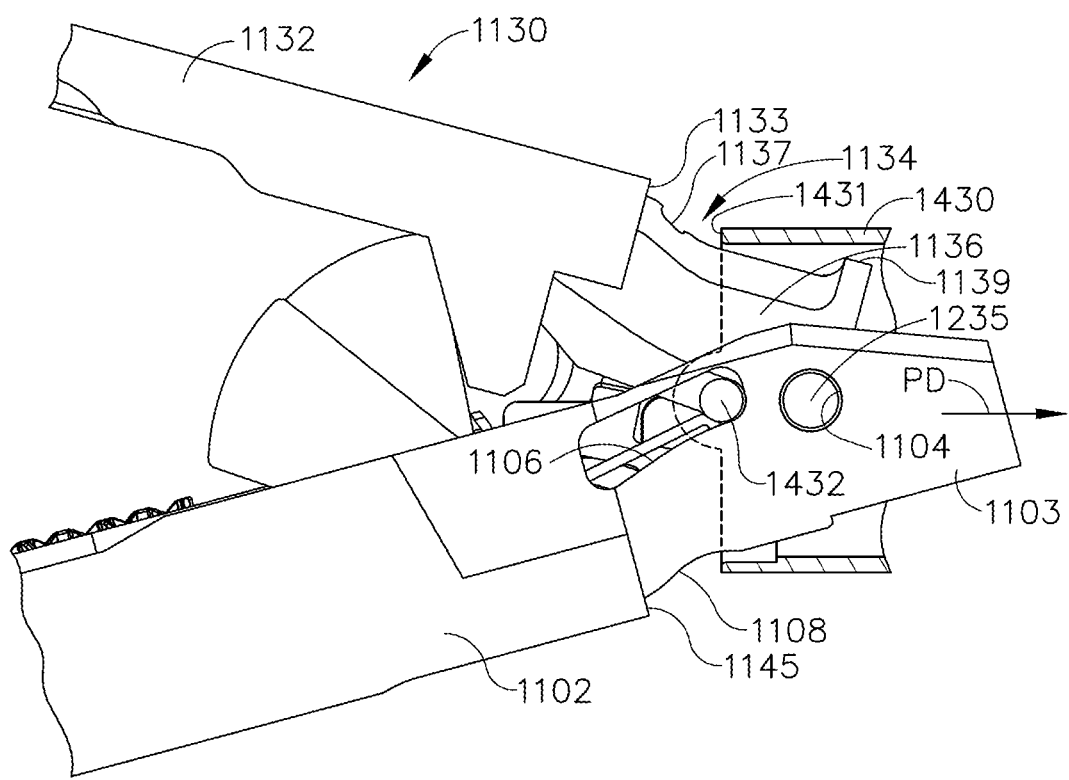
FIG. 15B is another side elevational view of the surgical end effector embodiment of FIG. 15A with the jaws thereof in a fully open orientation.
Figure 17:
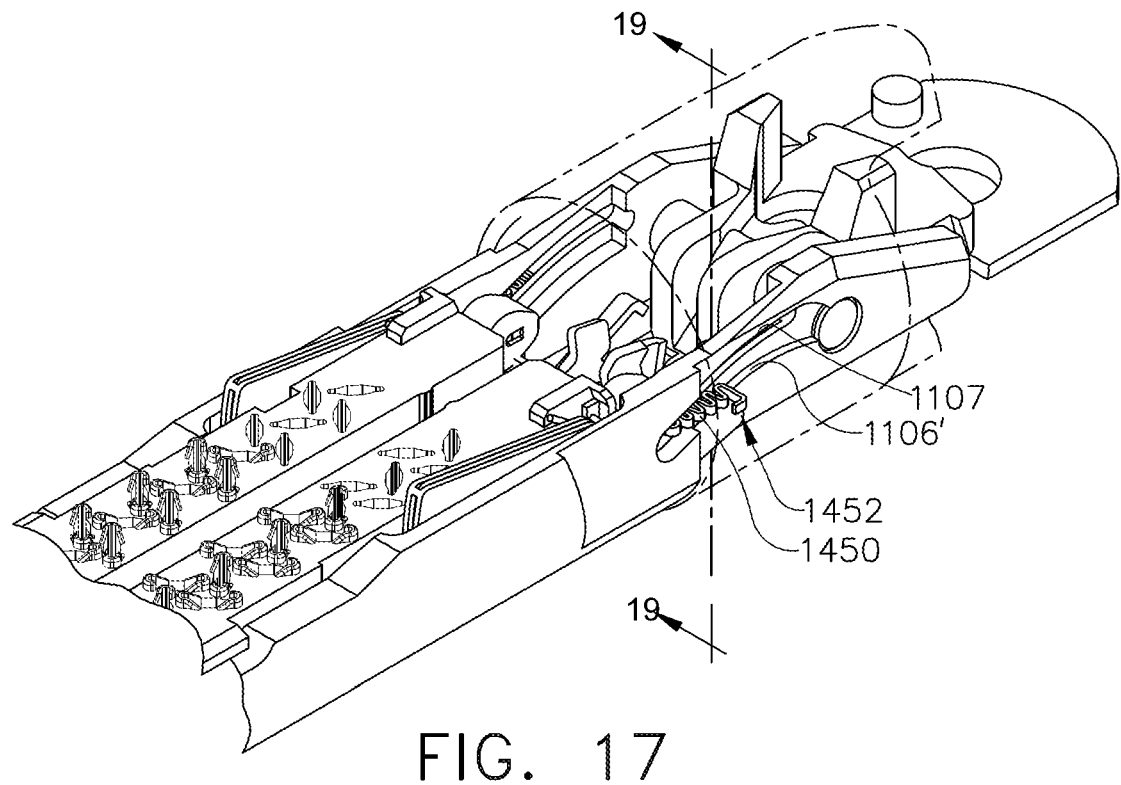
FIG. 17 is a perspective view of a portion of a surgical end effector embodiment that is configured to be used in connection with the distal closure member of FIG. 16.

In the embodiment illustrated in FIGS. 15A and 15B, the anvil assembly 1130 includes an anvil body portion 1132 and an anvil mounting portion 1134. The anvil mounting portion 1134 comprises a pair of anvil mounting walls 1136 that are separated by a slot 1138 (FIG. 4). The anvil mounting walls 1136 are interconnected or bridged by an upstanding tab portion 1139. As discussed above, the end effector mounting assembly 1230 is pivotally attached to the proximal end 1103 of the elongate channel 1102 by a pair of laterally extending jaw attachment pins 1235 that are rotatably received within jaw pivot holes 1104 that are provided in the proximal end 1103 of the elongate channel 1102. The jaw attachment pins 1235 define a fixed jaw pivot axis JA that is substantially traverse to the shaft axis SA. See FIG. 4. Each of the anvil mounting walls 1136 has a mounting hole 1140 extending therethrough to enable the anvil mounting portion 1134 to be pivotally journaled on the jaw attachment pins 1235. Thus, in such arrangement, the anvil 1130 and the elongate channel 1102 are independently pivotable about the fixed jaw pivot axis JA. Such arrangement may permit the anvil 1130 and elongate channel 1102 (the "jaws") to be opened to positions that may be wider than those open positions that may be attained by the jaws of other end effector arrangements wherein only one of the jaws moves relative to the other jaw.

Still referring to FIGS. 15A and 15B, the distal closure member 1430 includes two inwardly extending jaw opening pins 1432 that are adapted to extend through corresponding channel opening cam slots 1106 provided in the proximal end 1103 of the elongate channel 1102. Each jaw opening pin 1432 is configured to engage a corresponding anvil opening cam surface 1142 that is formed on each anvil mounting wall 1136. As can be seen in FIGS. 15A and 15B, the anvil opening cam surfaces 1142 are opposed or arranged in an opposite configuration as the corresponding channel opening cam slots 1106. Stated another way, the channel opening cam slots 1106 and the anvil opening cam surfaces 1142 curve in opposite directions from each other.

FIG. 15A illustrates the anvil 1130 and the elongate channel 1102 (the "jaws") in the fully closed position. As the distal closure member 1430 is advanced distally, the distal end 1431 of the distal closure member 1430 travels up closure cam surfaces 1137 formed on each of the anvil mounting walls 1136 as well as up closure cam surfaces 1108 formed on the proximal end 1103 of the elongate channel 1102. As the distal end 1431 of the distal closure member 1430 cammingly contacts the closure cam surfaces 1137, 1108, the anvil 1130 as well as the elongate channel 1102 are both pivoted about the jaw pivot axis JA to the closed position at which point the distal end 1431 of the distal closure member 1430 contacts a ledge portion 1133 that is formed between the anvil mounting portion 1134 and the anvil body portion 1132 as well as a ledge 1145 on the elongate channel. See FIG. 15A. When the closure member assembly 1400 is locked in position, the distal closure member 1430 retains the anvil 1130 and elongate channel 1102 in that closed position. When the clinician desires to move the anvil 1130 and the elongate channel 1102 to the open position, the distal closure member 1430 is moved in the proximal direction PD. As the distal closure member 1430 is moved in the proximal direction PD, the jaw opening pins 1432 engage the corresponding channel opening cam slots 1106 and the anvil opening cam surfaces 1142 and pivots the anvil 1130 and elongate channel about the fixed jaw axis JA to the open position shown in FIG. 15B. Such use of pins of features on the distal closure member to effectuate movement of both jaws from a fully closed position to a fully open position may be referred to herein as "positive jaw opening" features. Other positive jaw opening arrangements are disclosed in U.S. patent application Ser. No. 14/742,925, entitled SURGICAL END EFFECTORS WITH POSITIVE JAW OPENING ARRANGEMENTS, which has been incorporated by reference in its entirety herein.

Figure 16:
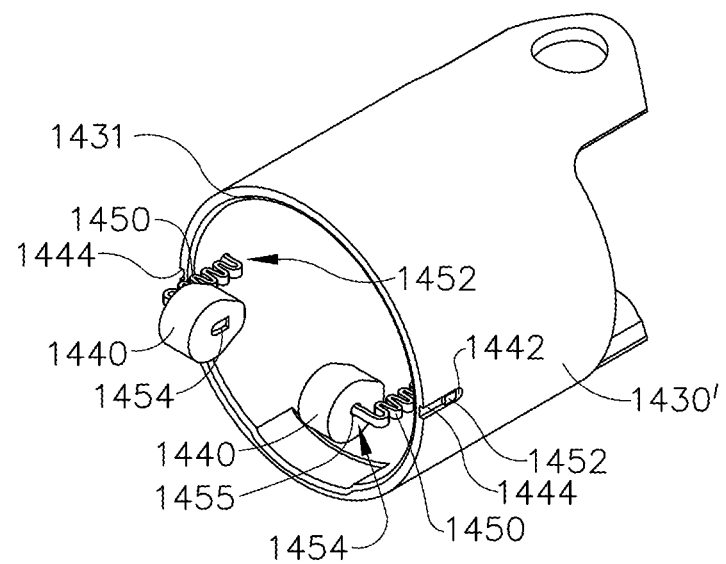
FIG. 16 is a perspective view of a distal closure member embodiment with positive jaw opening features.
Figure 18:
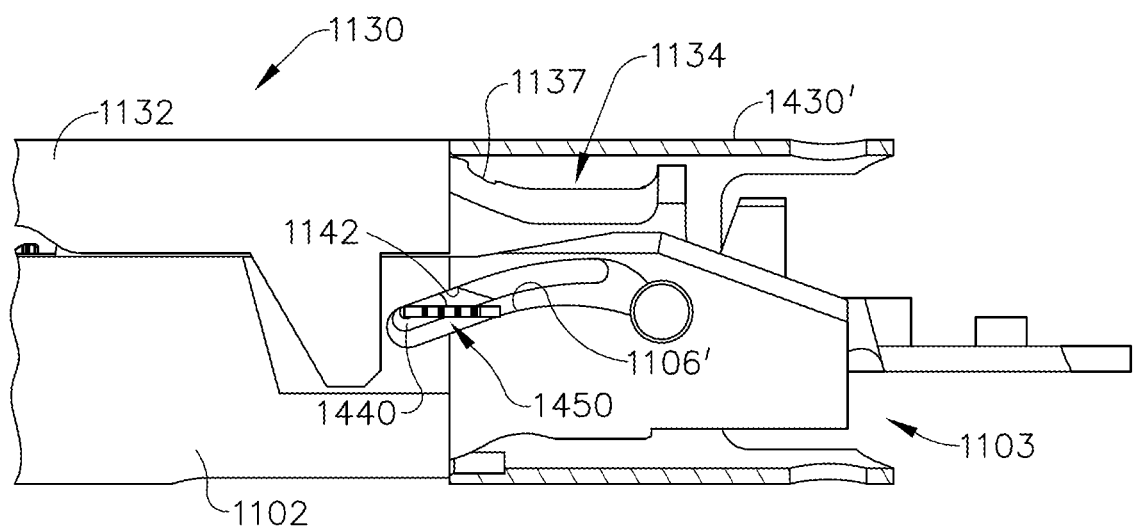
FIG. 18 is a side elevational view of portions of the surgical end effector of FIG. 17 with jaws thereof in a fully closed position and the distal closure member of FIG. 16 shown in cross-section.
Figure 19:
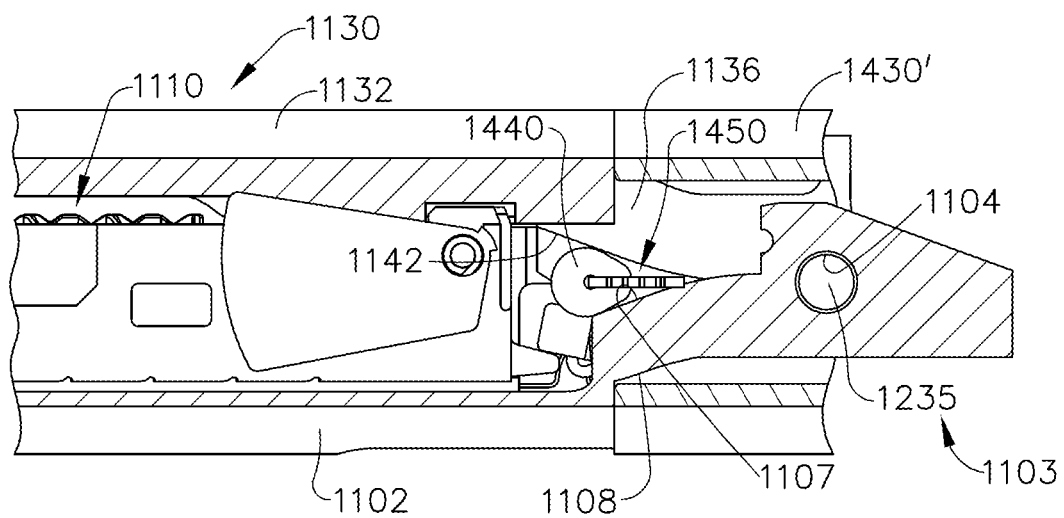
FIG. 19 is a cross-sectional side view of the surgical end effector and distal closure member of FIG. 17, taken along line 19-19 of FIG. 17, with the jaws thereof in the fully closed position.

FIGS. 16-21 Illustrate an alternative distal closure member 1430' that employs alternative positive jaw opening features in the form of, for example, movable jaw opening cams 1440 that are attached to the distal closure member 1430' in place of the jaw opening pins. At least one and preferably two jaw opening cams 1440 are movably attached to the distal closure member 1430' by a corresponding stretchable coupler 1450. In the illustrated embodiment, the coupler 1450 comprises a cam or tension spring. In the illustrated arrangement, the tension spring 1454 comprises flat spring to save space. A proximal end of each tension spring 1450 has a hook 1452 formed thereon that extends through an opening 1442 in the distal closure member 1430'. An end of each hook 1452 may be seated in a corresponding slot or groove 1444 that is formed in the distal closure member 1430' as shown in FIG. 16. A distal end 1455 of each tension spring 1454 is attached to the corresponding jaw opening cam 1440. The proximal end 1103 of the elongate channel 1102 includes a pair of spring clearance slots 1106' and channel opening cam surfaces 1107 that are configured to be engaged by the jaw opening cams 1440. In alternative arrangements, the spring could include maximum extension features that only allow a predetermined amount of compliance and then assure jaw opening that is proportionate to the remaining closure trigger travel and therefore closure shuttle motion. As indicated above, each of the anvil mounting walls 1136 has an anvil opening cam surface 1142 formed thereon. As can be seen in FIG. 19, the anvil opening cam surfaces 1142 are opposed or arranged in an opposite configuration as the corresponding channel opening cam surface 1107. Stated another way, the channel opening cam surface 1107 and the anvil opening cam surfaces 1142 are arcuate and curve in opposite directions.

Figure 20:
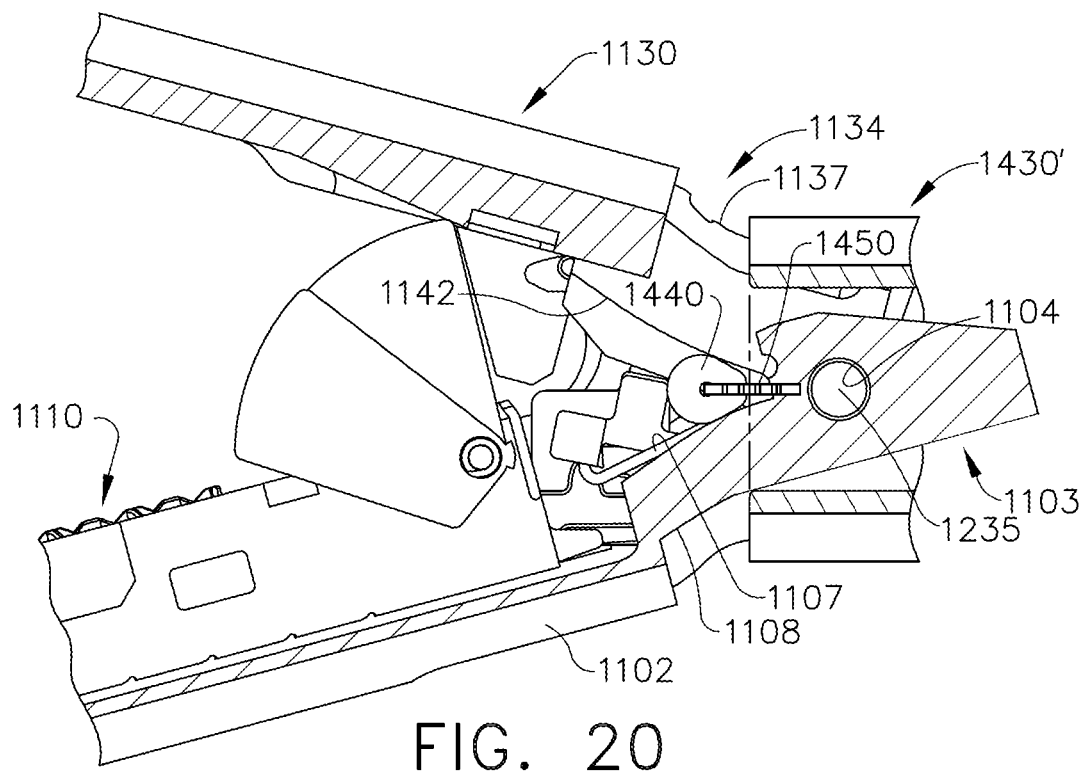
FIG. 20 is another cross-sectional side view of the surgical end effector and distal closure member of FIG. 18 with the jaws thereof in the fully open position.
Figure 21:
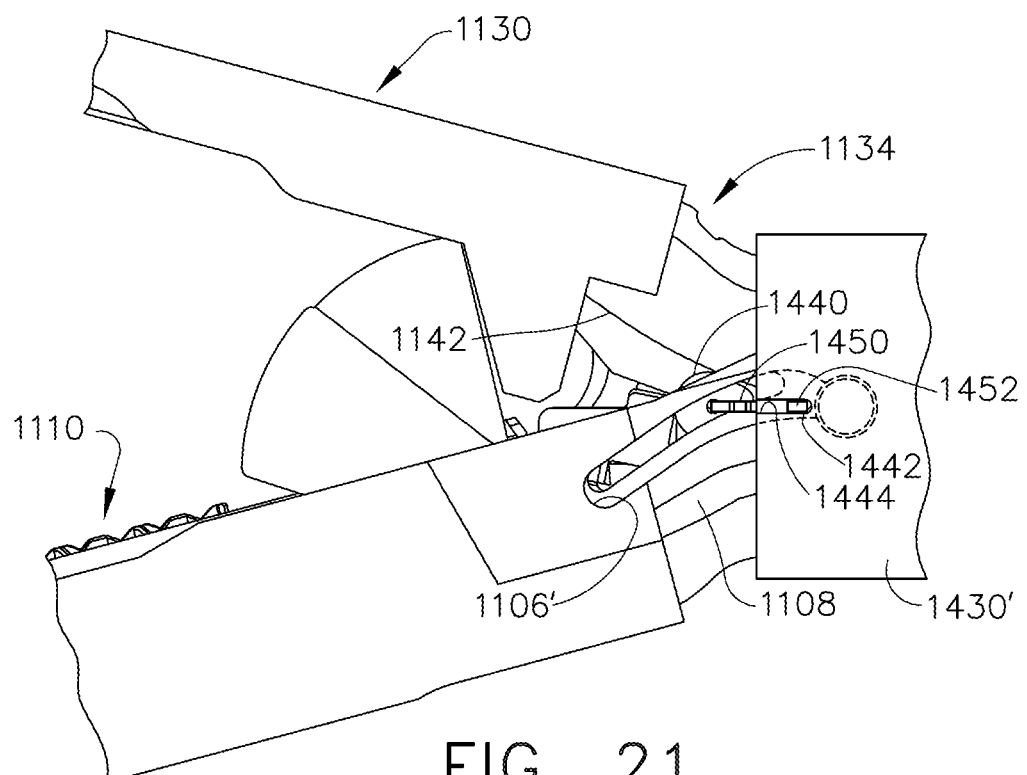
FIG. 21 is a side view of the surgical end effector and distal closure member of FIG. 18 with the jaws thereof in the fully open position.

FIGS. 20 and 21 illustrate the anvil 1130 and elongate channel 1102 in their respective fully opened positions. As can be seen in each of those Figures, the jaw opening cams 1440 are oriented between the corresponding anvil opening cam surface 1142 and the channel opening cam surface 1107 and are in their proximal-most positions. When in the fully opened positions, the jaw opening cams 1440 are located distal to the distal end of the distal closure member 1430'. As can be seen in FIGS. 19 and 20, the jaw opening cams 1440 may be wedge-shaped. In at least one arrangement, the wedge geometry has a gradual cam surface on the proximal side to prevent biding between the jaws. When in that fully open position, the tension springs 1454 are in their starting position wherein the tension springs 1454 are applying their smallest amount of biasing force to each of the jaw opening cams 1440. Upon commencement of the closing process, the distal closure member 1430' is advanced distally in the various manners described herein. As the distal closure member 1430' is advanced distally, the distal end 1431 contacts the closure cam surfaces 1137 on the anvil mounting portion 1134 and closure cam surfaces 1108 that are formed on the proximal end 1103 of the elongate channel 1102 to pivot the anvil 1130 and the elongate channel 1102 toward each other about the pivot jaw axis JA. As the anvil 1130 and the elongate channel 1102 are pivoted toward each other, the jaw opening cams 1440 that are riding on cam surfaces 1142 and 1104 are driven in the distal direction. As the jaw opening cams 1440 are driven distally, the tension springs 1454 are elongated and "loaded".

FIGS. 18 and 19 depict the anvil 1130 and elongate channel 1102 in their fully closed positions. When the clinician desires to return the anvil 1130 and elongate channel 1102 to their fully open positions (FIGS. 20 and 21), the distal closure member 1430' is withdrawn in the proximal direction which permits the anvil 1130 and the elongate channel 1102 to pivot away from each other about the pivot jaw axis JA. Because the tension springs 1454 are elongated and loaded, they draw each of the jaw opening cams 1440 in the proximal direction. As the jaw opening cams 1440 move in the proximal direction PD between the cam surfaces 1142 and 1107, the anvil 1130 and the elongate channel 1102 are positively moved to the fully opened position and retained therein by the jaw opening cams 1440. The more that the distal closure member is moved proximally, the more the jaws are urged away from each other. Such compliant positive jaw opening arrangements may assure direct one-to-one final pull open to provide more opening force if stuck.

Figure 23:
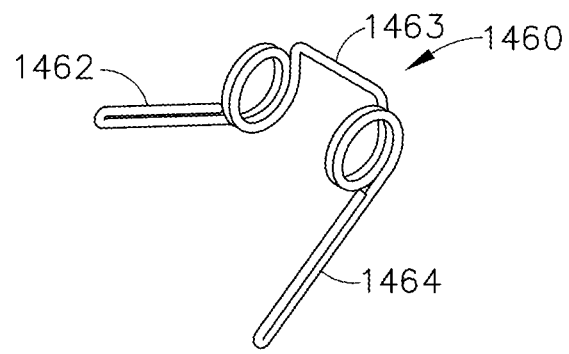
FIG. 23 is perspective view the positive jaw opening spring of FIG. 22.
Figure 24:
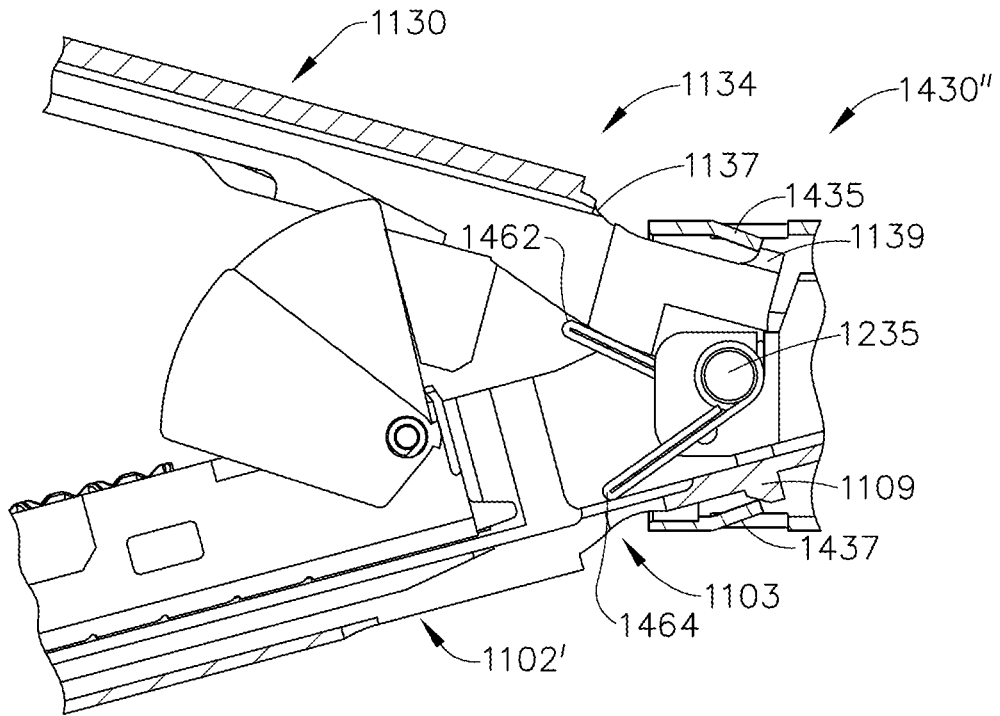
FIG. 24 is a cross-sectional side view of the surgical end effector of FIG. 22 with jaws thereof in a fully open position.
Figure 25:
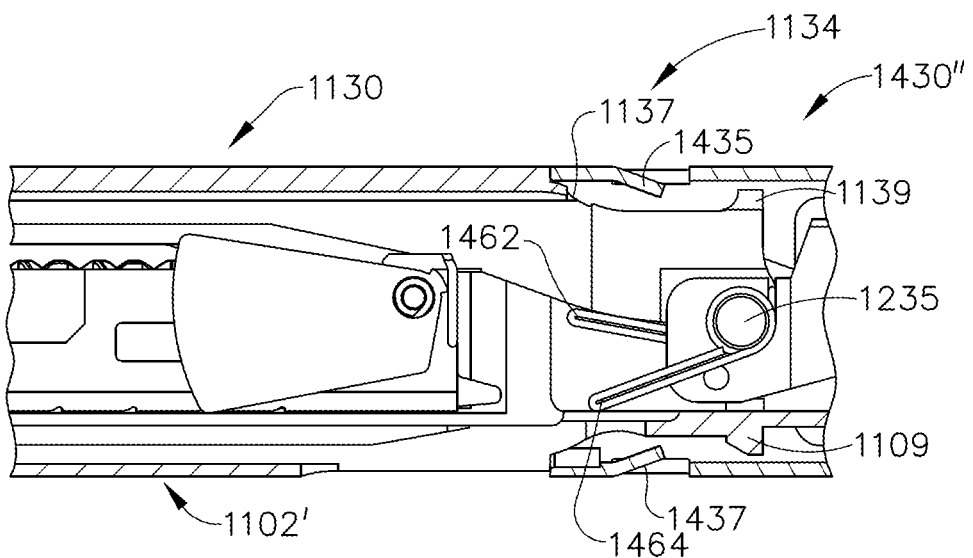
FIG. 25 is another cross-sectional side view of the surgical end effector of FIG. 22 with jaws thereof in a fully closed position.

FIGS. 22-25 Illustrate an alternative distal closure member 1430" that employs jaw opening tabs as well as at least one jaw opening spring 1460 to move the anvil 1130 and the elongate channel 1102' into their respective fully opened positions. As can be seen in FIGS. 24 and 25, the distal closure member 1430" is similar to distal closure member 1430 as described above, except that distal closure member 1430" additionally includes an anvil open tab 1435 and a channel open tab 1437. As shown in FIG. 24, when the distal closure member 1430" has been moved to its proximal most position corresponding to the fully opened position, the anvil open tab 1435 is in contact with the tab 1139 on the anvil mounting portion 1134 and the channel opening tab is in contact with a channel tab 1109 protruding from the underside of the proximal end portion 1103 of the elongate channel 1102'.

Figure 22:
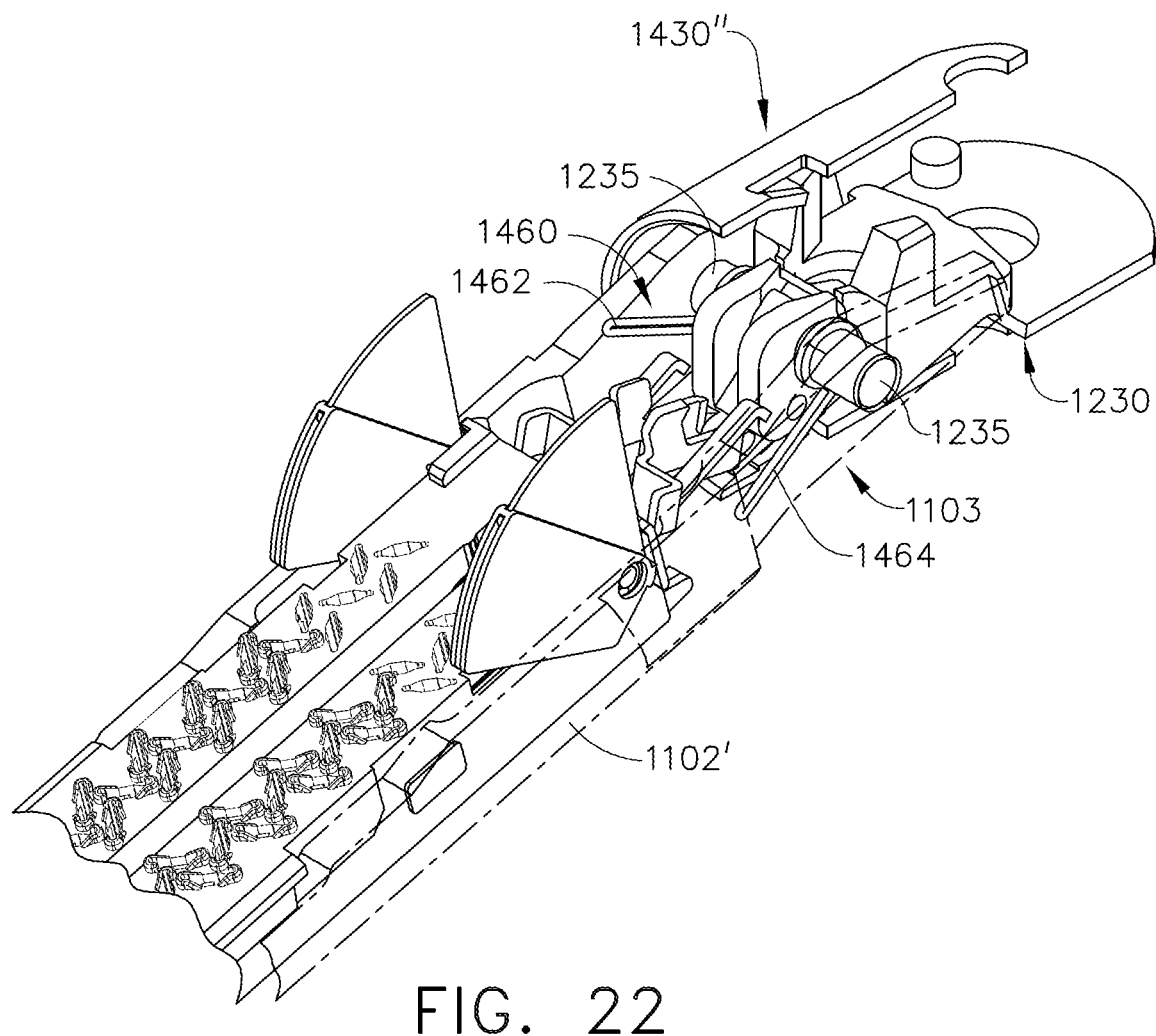
FIG. 22 is a perspective view of a portion of another surgical end effector embodiment with the anvil omitted for clarity that employs a positive jaw opening spring.

The embodiment depicted in FIGS. 22, 24 and 25 also employs a positive jaw opening member which may comprise a jaw opening spring 1460. As can be seen in FIG. 23, in the illustrated arrangement, the jaw opening spring 1460 includes an anvil opening leg 1462 and a channel opening leg 1464 that are attached by a bridge portion 1463. The spring 1460 may be journaled on the jaw attachment pins 1235 as shown in FIGS. 22, 24 and 25 such that the anvil opening leg 1462 bears on a bottom surface of the anvil mounting portion 1134 and the channel opening leg 1464 bears on a bottom surface of the proximal end 1103 of the elongate channel 1102'. Thus, the jaw opening spring 1460 serves to apply biasing forces to the anvil 1130 and the elongate channel 1102' to pivot them away from each other to open positions. FIG. 25 illustrates the anvil 1130 and the elongate channel 1102' in the fully closed position. As can be seen in FIG. 25, the jaw opening spring 1460 is in its fully compressed state. To open the anvil and channel 1102', the distal closure member 1430" is moved in the proximal direction PD in the various manners disclosed herein. As the distal closure member 1430" moves proximally, the jaw opening spring 1460 positively biases the anvil 1130 and the elongate channel 1102' away from each other about the pivot axis JA to the fully open position wherein the anvil opening tab 1435 engages the tab 1139 on the anvil mounting portion 1134 and the channel opening tab 1437 engages the channel tab 1109. See FIG. 24. In at least one arrangement, the jaw opening spring is mounted proximal to the firing member parking area (i.e., the area where the firing member resides when in the starting position).

FIGS. 26-29 Illustrate an alternative distal closure member 1470 that employs slot arrangements in the elongate channel and closure member that are configured to move an anvil 1130" between a fully open position and a fully closed position. In the illustrated arrangement, the distal closure member 1470 is similar to distal closure member 1430 as described above, except for the differences discussed below. In this arrangement, however, only the anvil 1130" moves relative to the elongate channel 1102". As can be seen in FIGS. 26-29, the anvil mounting portion 1134 of the anvil 1130" includes two outwardly extending anvil pins 1150 that extend through corresponding channel slots 1472 provided in the proximal end 1103 of the elongate channel 1102". Each anvil pin 1150 also extends into corresponding closure slots 1474 in the distal closure member 1470. In the illustrated arrangement, each of the channel slots 1472 extends along a vertical axis VA. The anvil pins 1150 define a pivot axis PA about which the anvil 1130" may pivot. Because the anvil pins 1150 are constrained to only move within the vertically extending channel slots 1472, the pivot axis PA is constrained to only move along the vertical axis VA. Each closure slot 1474 has a proximal portion 1476 and a distal portion 1478. The proximal portion 1476 lies along a first horizontal axis $HA_1$ and the distal portion 1478 lies along a second horizontal axis $HA_2$ that is offset from the first horizontal axis $HA_1$. See FIG. 26. Vertical axis VA is transverse to the first and second horizontal axes $HA_1$ and $HA_2$.

Figure 26:
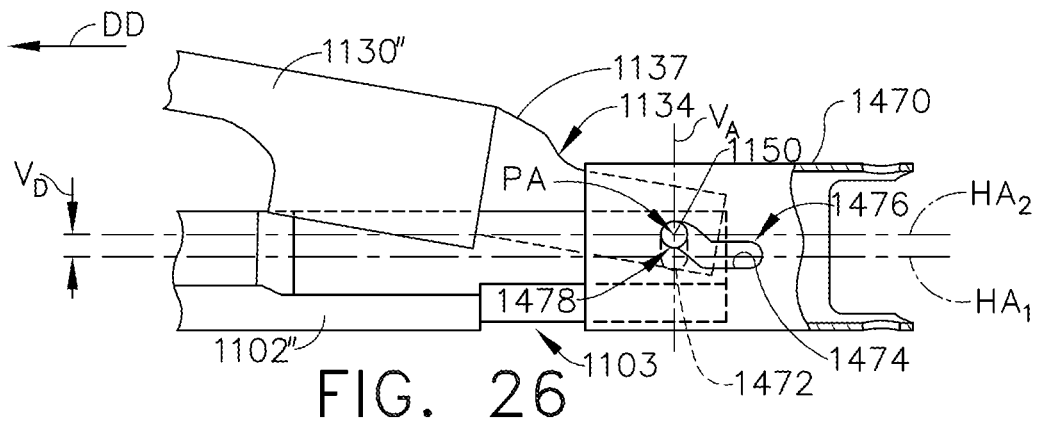
FIG. 26 is a side view of a portion of another surgical end effector embodiment and a distal closure member embodiment with the jaws of the surgical end effector in a fully open position.
Figure 27:
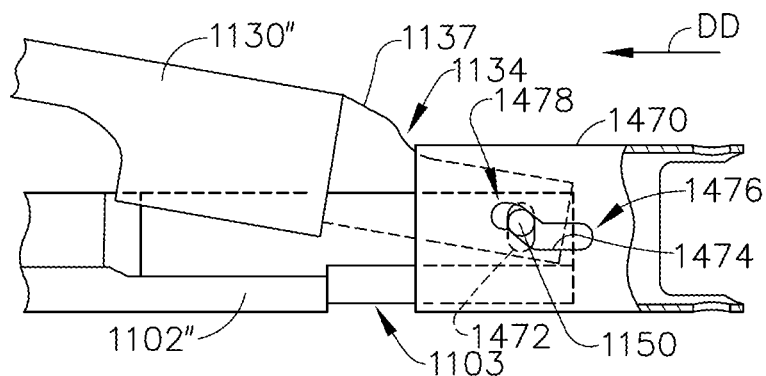
FIG. 27 is another side view of the surgical end effector and distal closure member of FIG. 26 at the beginning of a jaw closure sequence.
Figure 28:
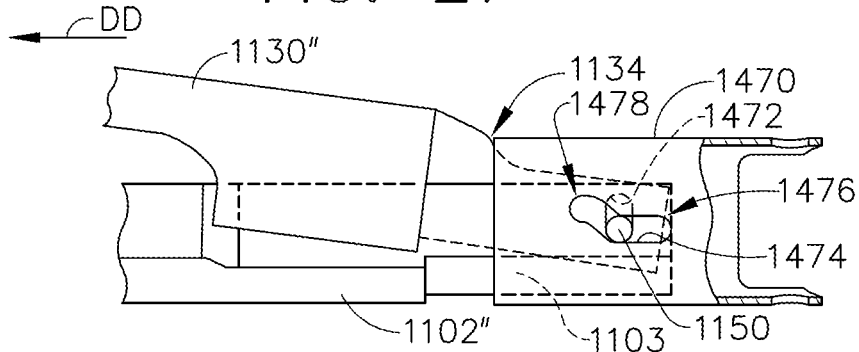
FIG. 28 is another side view of the surgical end effector and distal closure member of FIG. 26 during the jaw closure sequence.

FIG. 26 illustrates the positions of the anvil 1130" and the elongate channel 1102" when in the fully open position. As can be seen in FIG. 26, when in that position, the anvil pins 1150 are located at the top end of the channel slot 1472 ("first vertical positions") as well as in the distal portion 1478 of the closure slots 1474. FIG. 27 illustrates the positions of the anvil 1130" and the elongate channel 1102" after the closure process has been commenced. As can be seen in FIG. 27, the distal closure member 1470 has begun to move distally so that the anvil pins 1150 are just about to enter the proximal portion 1476 of the closure slots and the pins have begun to move downward in the channel slots 1472. In FIG. 28, the distal closure member 1470 has moved distally to a point wherein the anvil pins 1150 are at the bottom ends of the channel slots 1472 and the anvil pins 1150 have now entered the proximal portions 1476 of the closure slots 1474. Thus the anvil mounting portion 1134 has moved downward toward the elongate channel 1102". FIG.

Figure 29:
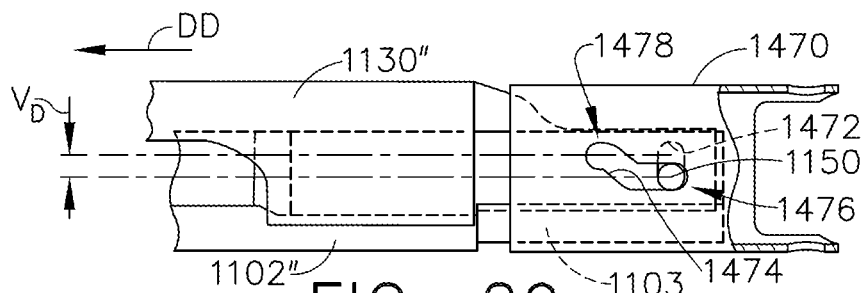
FIG. 29 is another side view of the surgical end effector and distal closure member of FIG. 26 with the jaws thereof in a fully closed position.

29 illustrates the anvil 1130" and the elongate channel anvil 1102" in their fully closed positions. As can be seen in FIG. 29, the anvil pins 1150 are retained in the bottom ends of the channel slots 1472 ("second vertical positions") and are also received within the proximal portions 1476 of the closure slots 1474. The anvil 1130" and elongate channel 1102" are retained in that fully closed position while the distal closure member 1470 is retained in that position. As can be seen in FIG. 29, such arrangement facilitates the vertical travel of the anvil mounting portion 1134 relative to the channel 1102" thereby increasing the distance between the underside of the anvil and the cartridge deck when in the fully opened position. Such redundant linkage arrangement may allow for the adjustment of the proximal distance between the anvil and the cartridge deck adjacent the tissue stops. Another cartridge embodiment may include a metallic camming termination feature proximal to the sled start location. Such metallic feature may support or hold the sled in the "ready-to-use" position while preventing the collapse of the tail.

FIGS. 30-32 illustrate one form of a firing member 1760 that may be employed with the interchangeable tool assembly 1000. In one exemplary form, the firing member 1760 comprises a body portion 1762 that includes a proximally extending connector member 1763 that is configured to be received in a correspondingly shaped connector opening 1624 (FIG. 4) in the distal end of the distal firing bar 1620. The connector 1763 may be retained within the connector opening 1624 by friction and/or welding or suitable adhesive, etc. In use, the body portion 1762 protrudes through an elongate slot 1160 in the elongate channel 1102. A laterally extending foot tab 1764 extends from each lateral side of the body portion 1762. Each foot tab 1764 includes a proximal end 1765 that has a thickness $PE_f$ and a distal end 1767 that has a thickness $DE_f$. Such configuration also defines an upper foot surface 1768 and a lower foot surface 1769. In the illustrated reference the upper foot surface 1768 and the lower foot surface 1769 angle away from each other. In FIG. 31, the upper foot surface 1768 is parallel to the upper axis $U_A$ and the lower foot surface 1769 is parallel to lower axis $U_L$ with an angle $A_F$ therebetween. Stated another way, the distal thickness $DE_f >$ the proximal thickness $PE_f$. Thus, each of the foot tabs 1764 taper in thickness from their respective distal end 1767 to their proximal end 1765 with the proximal end being thinner.

Still referring primarily to FIG. 31, the illustrated firing member 1760 also includes a pair of laterally extending top tabs 1770. Each top tab 1770 includes a proximal end 1772 that has a thickness $PE_T$ and a distal end 1774 that has a thickness $DE_T$. Such configuration also defines a top surface 1776 and a bottom surface 1778. In the illustrated reference the top surface 1776 and the bottom surface 1778 angle away from each other. In FIG. 31, the top surface 1776 is parallel to an upper axis $T_A$ and the bottom surface 1778 is parallel to a bottom axis $B_L$ with an angle $A_T$ therebetween. Stated another way, a distal thickness $DE_T$ of each top tab 1770 is greater than proximal thickness $PE_T$ thereof. Thus, each of the top tabs 1770 taper in thickness from their respective distal end 1774 to their proximal end 1772 with the proximal end 1772 being thinner. In the illustrated arrangement angle $A_F$ may be approximately equal to angle $A_T$. In addition, the top surface 1776 of each of the top tabs 1770 may be a distance $H_F$ from the lower foot surface 1769 of each corresponding foot tab 1764 between the distal ends 1774, 1765, respectively and also be a distance $H_R$ from each other at their respective proximal ends 1772, 1767. In the illustrated arrangement, $H_F > H_R$. Thus, the top surface 1776 of each top tab 1770 angles away from the shaft axis SA and each lower foot surface 1769 of each foot tab 1764 angles away from the shaft axis SA. The illustrated firing member 1760 further includes laterally protruding central lock lugs 1780 which will be discussed in further detail below. The body portion 1762 of the firing member 1760 further includes a tissue cutting edge or feature 1766 that is disposed between a distally protruding bottom portion 1771 and a distally protruding top nose portion 1773.

In the illustrated example, the cartridge body 1111 operably supports therein a plurality of staple drivers that are aligned in rows on each side of a centrally disposed slot 1114. FIGS. 33A-33C illustrate one example of a staple driver 1170 that may be employed to support staples on one side of a surgical staple cartridge. The drivers located on the opposite side of the centrally disposed slot 1114 may comprise mirror images of drivers 1170. Other staple driver configurations may also be effectively employed as well. As can be seen in FIGS. 33A-33C, one form of a staple driver 1700 comprises a staple driver body 1172. The driver body 1172 includes a first or innermost staple support portion 1174 that is configured to support a staple (not shown) thereon. A second or central staple support portion 1176 is configured to support another staple (not shown) thereon and a third support portion 1870 that is configured to support a third staple (not shown) thereon. The first staple support portion 1174, the second staple support portion 1176 and the third staple support portion 1178 are all coupled together by a connector portion 1180. In at least one arrangement, the connector portion 1180 is formed with a centrally disposed opening or aperture 1182 that is configured to slidably receive a corresponding first driver guide (not shown) that is formed in the cartridge body. The connector portion 1180 includes a first cam portion 1184 that has a first camming surface or ramp 1186 formed thereon. The connector portion 1180 also includes a second cam portion 1188 that has a second a second camming surface 1190 formed thereon. The camming surfaces 1186, 1190 have the same slope or angle or they may have different slopes/angles. In at least one embodiment, each staple driver 1170 is integrally formed from or molded from, for example, Ultem®, with no fill. However, other materials such as, for example, Ultem® with a glass or mineral fill or Nylon or Nylon with a glass file could be used. In other arrangements, the various portions of the staple drivers 1170 may be separately fabricated from other materials and be attached together by adhesive, solder, etc. Further details concerning the staple drivers 1170 as well as other driver embodiments that may be effectively employed with the various embodiments disclosed herein may be found in U.S. patent application Ser. No. 14/843, 243, filed Sep. 2, 2015, entitled SURGICAL STAPLE CONFIGURATIONS WITH CAMMING SURFACES LOCATED BETWEEN PORTIONS SUPPORTING SURGICAL STAPLES, the entire disclosure of which is hereby incorporated by reference herein.

Figure 33:
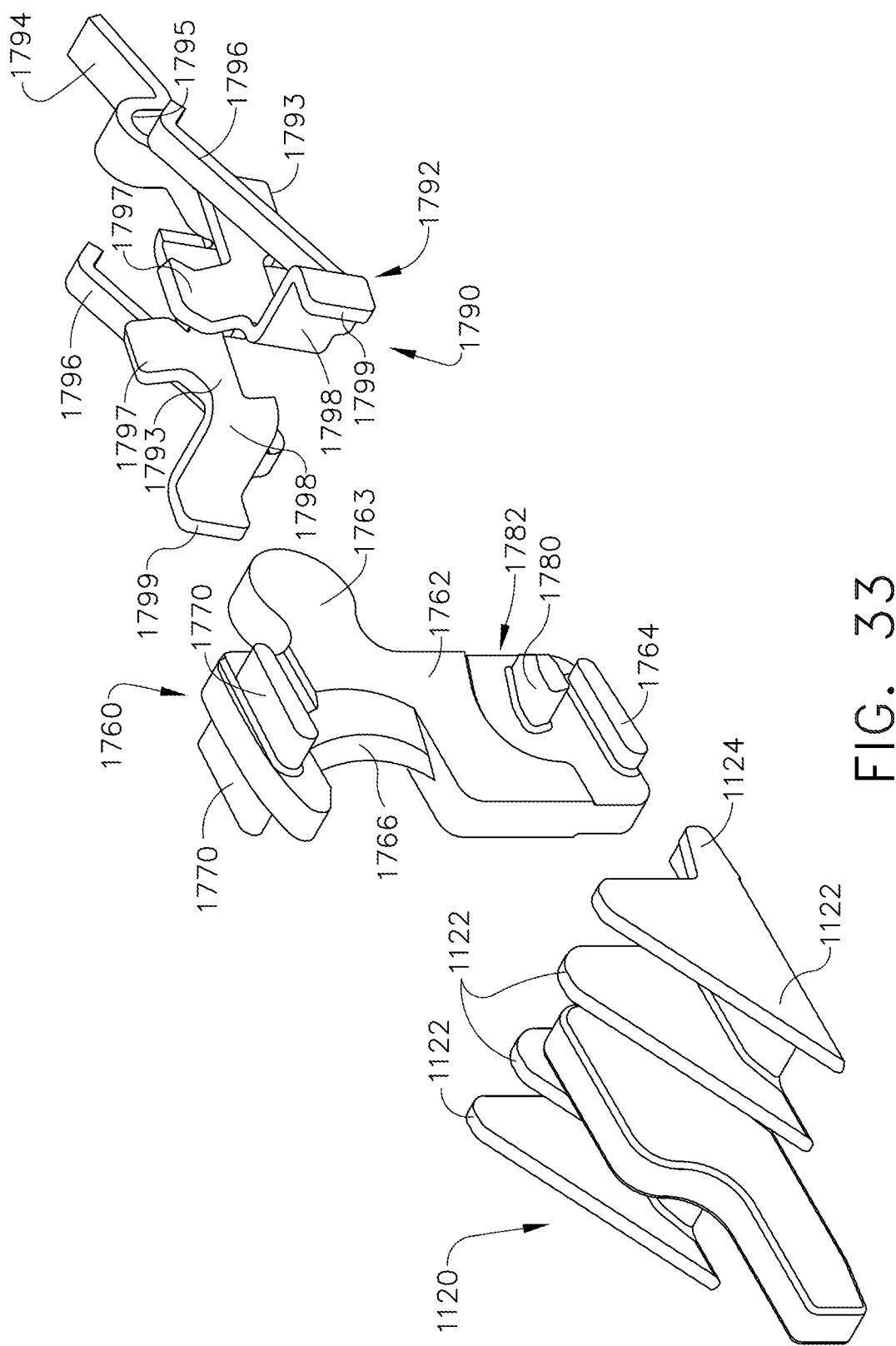
FIG. 33 is a perspective view of the firing member of FIG. 30 in relation to a sled assembly embodiment and a firing member lock embodiment.
Figure 33A:
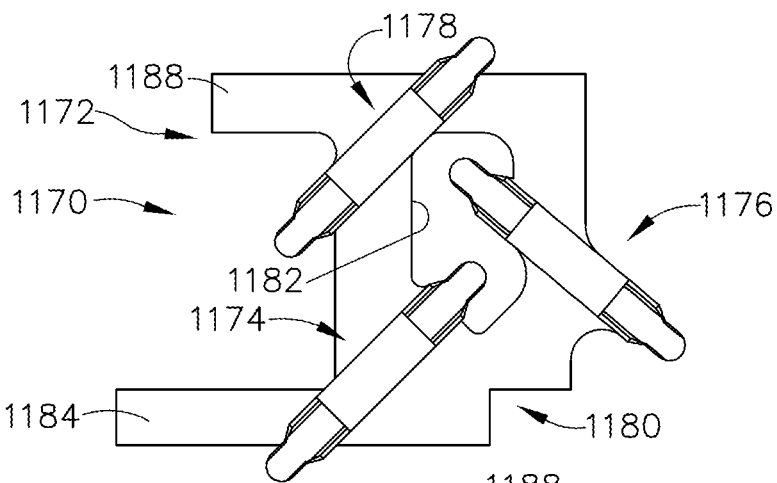
FIG. 33A is a top view of a staple driver embodiment.
Figure 33B:
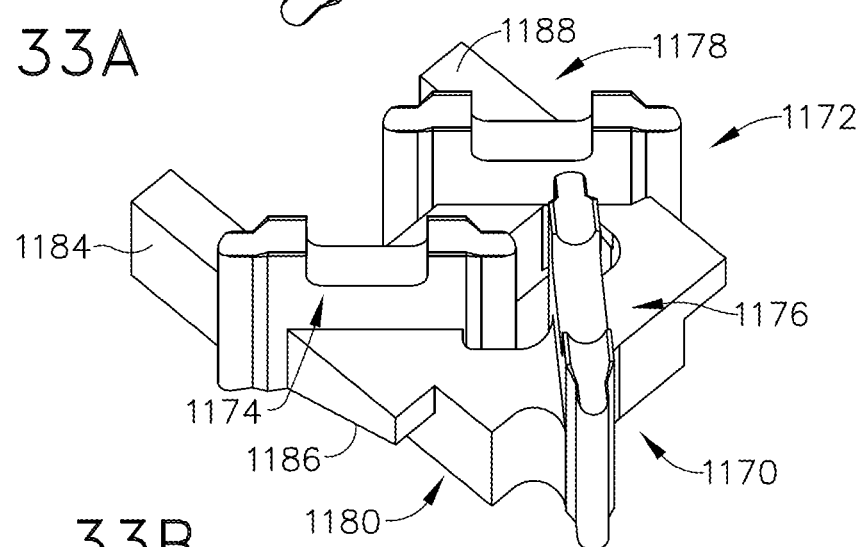
FIG. 33B is a top perspective view of the staple driver embodiment of FIG. 33A.
Figure 33C:
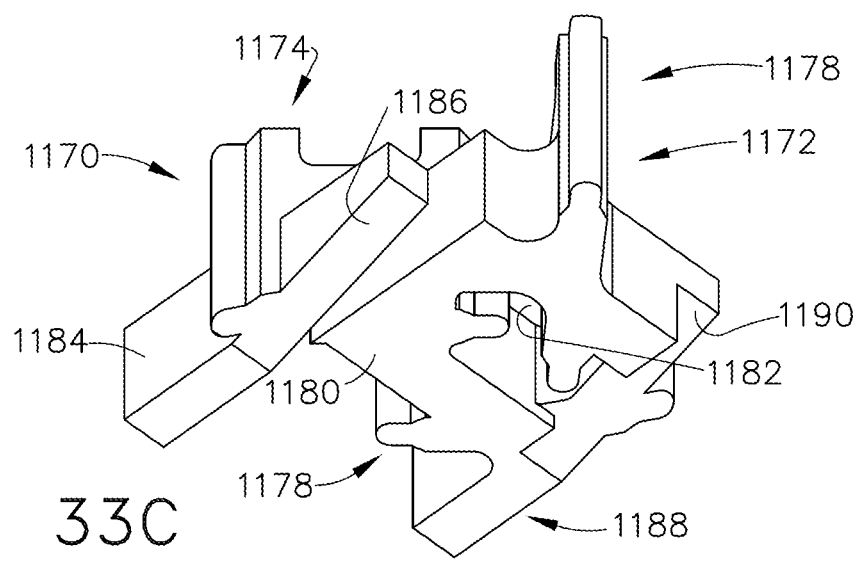
FIG. 33C is a bottom perspective view of the staple driver embodiment of FIGS. 33A and 33B.
Figure 34:
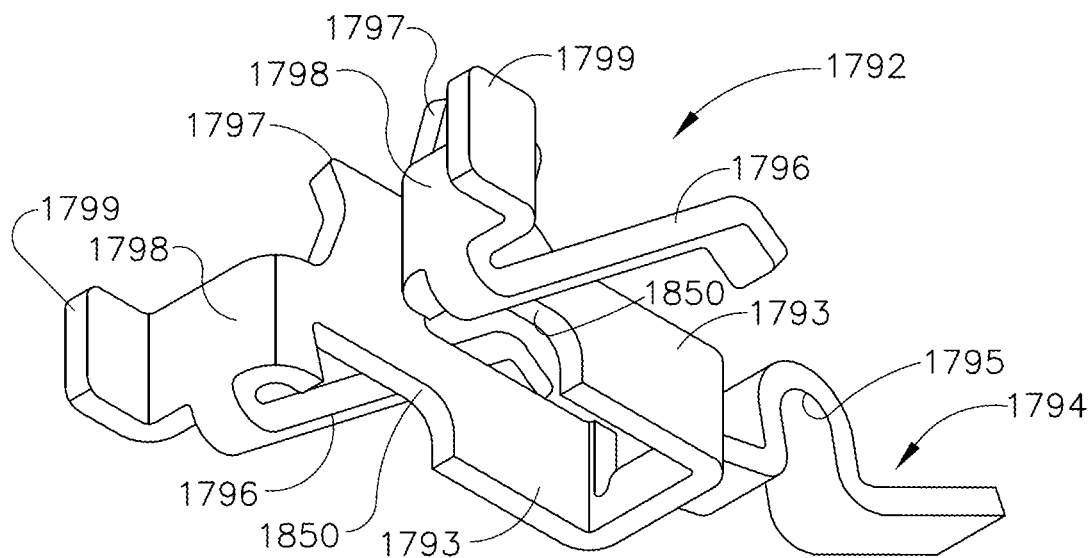
FIG. 34 is a bottom perspective view of the firing member lock of FIG. 33.
Figure 36:
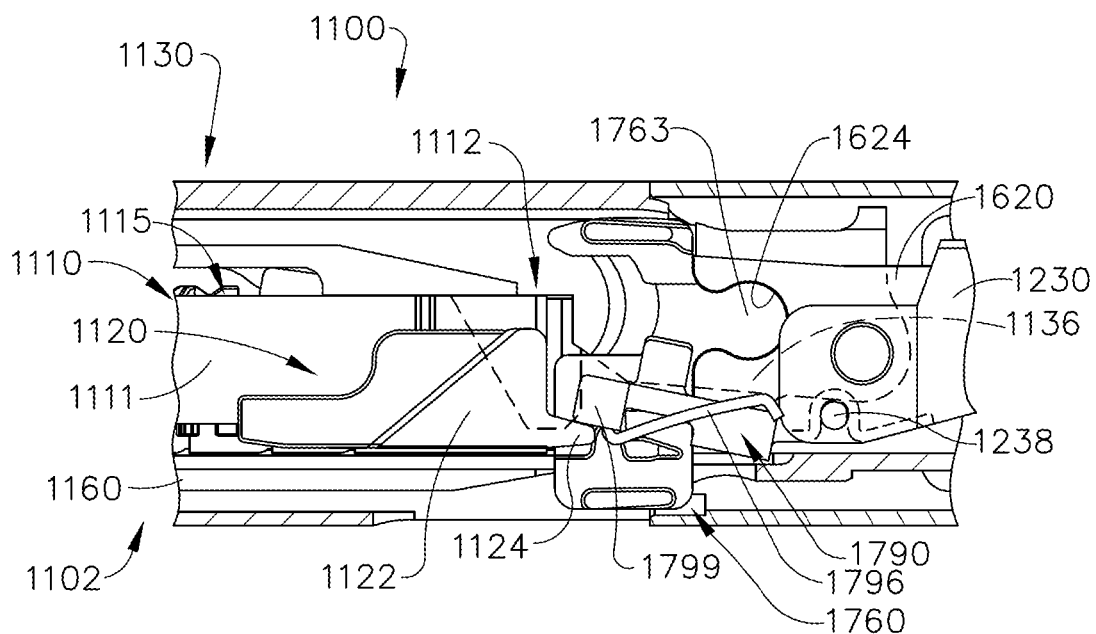
FIG. 36 is another cross-sectional side elevational view of the surgical end effector of FIG. 35 with an unspent surgical staple cartridge supported in one of the jaws and retaining the firing member lock in the unlocked orientation.
Figure 37:
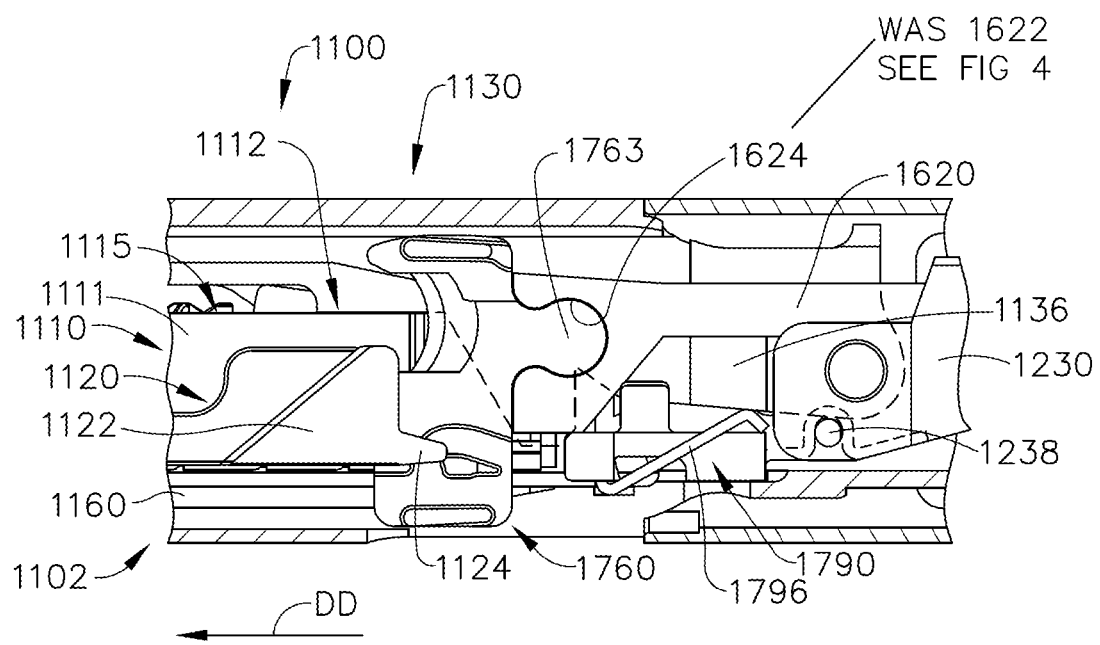
FIG. 37 is another cross-sectional side elevational view of the surgical end effector of FIG. 36 after a firing sequence has been commenced.

Turning next to FIGS. 33, 36 and 37, the firing member 1760 is configured to operably interface with a sled assembly 1120 that is operably supported within the body 1111 of the surgical staple cartridge 1110. The sled assembly 1120 is slidably displaceable within the surgical staple cartridge body 1111 from a proximal starting position adjacent the proximal end 1112 of the cartridge body 1111 to an ending position adjacent the distal end 1113 of the cartridge body 1111. See FIG. 4. The centrally disposed slot 1114 enables the firing member 1760 to pass therethrough and cut the tissue that is clamped between the anvil 1130 and the staple cartridge 1110. The drivers 1170 are associated with corresponding pockets 1116 that open through the upper deck surface 1115 of the cartridge body 1111. The sled assembly 1120 includes a plurality of sloped or wedge-shaped cams 1122 wherein each cam 1122 corresponds to a particular camming surface 1186, 1190 on the corresponding drivers 1170 located on each side of the slot 1114. When the firing member 1760 is fired or driven distally, the firing member 1760 drives the sled assembly 1120 distally as well. As the firing member 1760 moves distally through the cartridge 1110, the tissue cutting feature 1766 cuts the tissue that is clamped between the anvil assembly 1130 and the cartridge 1110 and the sled assembly 1120 drives the drivers 1170 upwardly in the cartridge which drive the corresponding staples or fasteners into forming contact with the anvil assembly 1130. In the illustrated example, the body portion 1762 of the firing member 1760 is configured to engage with the distal end of the sled assembly 1120. In particular, in at least one example, as shown in FIG. 33, the distal end of the body portion 1762 is oriented to simply contact the proximal end of the center portion of the sled 1120. In other firing member arrangements, the firing member body 1762 may be uniquely shaped or configured to operably mesh, mate or operably interface with the corresponding end portion of the sled assembly contained within a corresponding cartridge assembly so that should the user unwittingly load the wrong cartridge into the elongate channel and thereafter attempt to fire the cartridge, the firing member and sled would not properly interface to enable the distal advancement thereof.

In those embodiments wherein the firing member includes a tissue cutting surface, it may be desirable for the elongate shaft assembly to be configured in such a way so as to prevent the inadvertent advancement of the firing member unless an unspent staple cartridge is properly supported in the elongate channel 1102 of the surgical end effector 1100. If, for example, no staple cartridge is present at all and the firing member is distally advanced through the end effector, the tissue would be severed, but not stapled. Similarly, if a spent staple cartridge (i.e., a staple cartridge wherein at least some of the staples have already been fired therefrom) is present in the end effector and the firing member is advanced, the tissue would be severed, but may not be completely stapled, if at all. It will be appreciated that such occurrences could lead to undesirable catastrophic results during the surgical procedure. U.S. Pat. No. 6,988,649 entitled SURGICAL STAPLING INSTRUMENT HAVING A SPENT CARTRIDGE LOCKOUT, U.S. Pat. No. 7,044,352 entitled SURGICAL STAPLING INSTRUMENT HAVING A SINGLE LOCKOUT MECHANISM FOR PREVENTION OF FIRING, and U.S. Pat. No. 7,380,695 entitled SURGICAL STAPLING INSTRUMENT HAVING A SINGLE LOCKOUT MECHANISM FOR PREVENTION OF FIRING, and U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING each disclose various firing member lockout arrangements. Each of those references is hereby incorporated by reference in its entirety herein.

An "unfired", "unspent", "fresh" or "new" cartridge 1110 means herein that the cartridge 1110 has all of its fasteners in their "ready-to-be-fired positions". When in that position, the sled assembly 1120 is located in its starting position. The new cartridge 1110 is seated within the elongate channel 1102 and may be retained therein by snap features on the cartridge body that are configured to retainingly engage corresponding portions of the elongate channel 1102. FIG. 36 illustrates a portion of the surgical end effector 1100 with a new or unfired surgical staple cartridge 1110 seated therein. As can be seen in FIG. 36, the sled assembly 1120 is in the starting position. To prevent the firing system from being activated and, more precisely, to prevent the firing member 1760 from being distally driven through the end effector 1110 unless an unfired or new surgical staple cartridge has been properly seated within the elongate channel 1102, the illustrated interchangeable surgical tool assembly 1000 employs a firing member lockout system generally designated as 1790.

Figure 35:
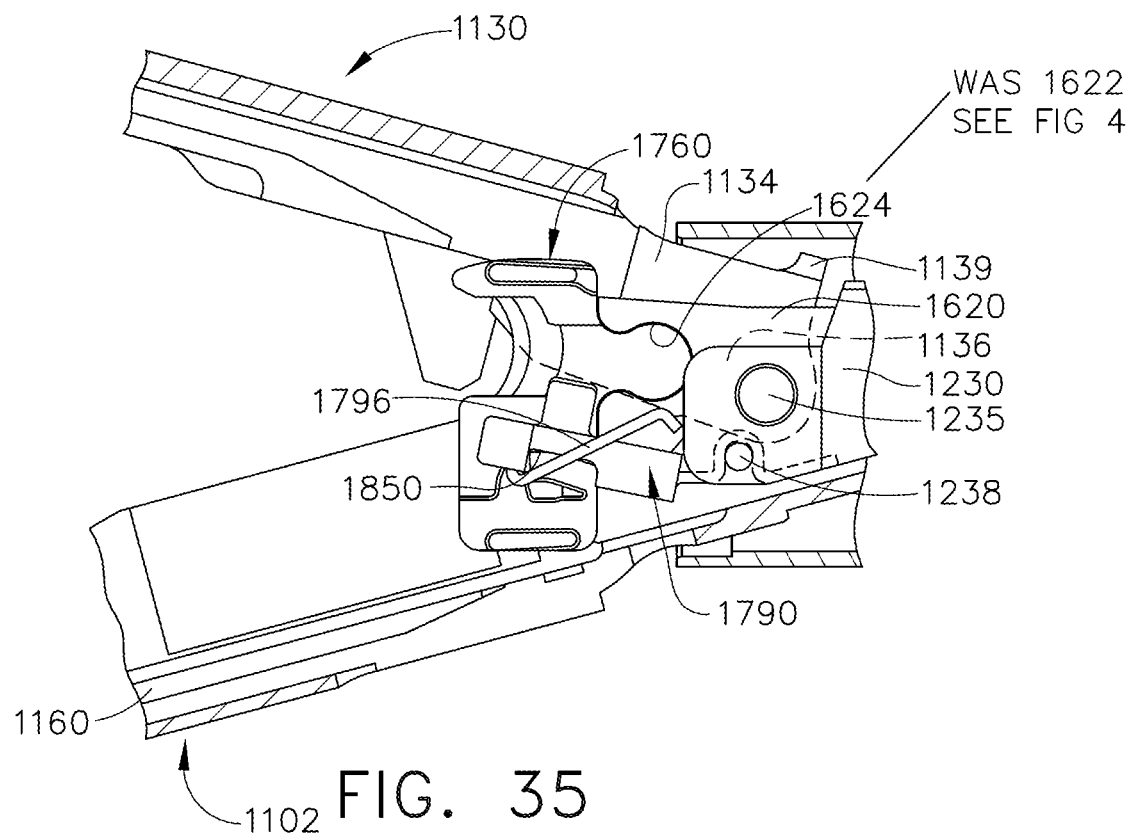
FIG. 35 is a cross-sectional side elevational view of a portion of a surgical end effector embodiment with jaws thereof in a fully open orientation and the firing member lock of FIG. 33 in an unlocked orientation.

Referring now to FIGS. 33-37, in one form, the firing member lockout system 1790 includes movable lock member 1792 that is configured to retainingly engage the firing member 1760 when an unspent surgical staple cartridge 1110 is not properly seated within the elongate channel 1102. The lock member 1792 comprises a pair of lateral spring arms 1793 that are interconnected by a central mount tab feature 1794. The central mount tab feature 1794 has a mounting hook 1795 formed therein that is configured to be hooked over a retaining pin 1238 in the anvil mounting assembly 1230 as can be seen in FIGS. 35-37. When installed, the mount tab 1794 is configured to bias the lock member 1792 upward. In addition, the lock member 1792 includes two lateral anvil spring arms 1796 that angle upward to engage the bottom surface of a corresponding anvil mounting wall 1136 on the anvil mounting portion 1134 to bias the lock member 1792 downward when the anvil 1130 is closed. A firing member alignment tab 1797 extends upward from each of the lateral spring arms 1793 to maintain alignment between the firing member 1760 and the lock member 1792. As can be most particularly seen in FIG. 33, the distal portion of each lateral spring arm 1793 includes a laterally extending forward arm 1798 that terminates in a sled tab 1799 that corresponds to a sled boss 1124 that is formed on the outermost wedge-shaped cams 1122 on the sled 1120. Each of the lateral spring arms 1793 includes a lock notch 1850 therein that is configured to lockingly engage a corresponding one of the central lock lugs 1780 therein. Those of ordinary skill in the art will appreciate that different numbers and arrangements of sled bosses may be employed in the sleds of different staple cartridge arrangements. The number of, and arrangement of, the sled boss(es) may be configured to only interact with corresponding sled tabs of the lock member of the proper instrument with which the staple cartridge is intended to be used. Thus, the sled bosses may function as a "key" to only actuate the lock member of the proper device. Such arrangement may therefore prevent the user from actuating the device when the wrong surgical staple cartridge has been loaded into the elongate channel.

FIG. 35 illustrates the end effector 1100 with the anvil 1130 and the elongate channel 1102 in their fully opened position without a surgical staple cartridge installed therein. As can be seen in FIG. 35, the anvil spring arms 1796 are in contact with the underside of the mounting walls 1136, but they are not "loaded". Such position enables the surgical staple cartridge 1110 to be seated into the elongate channel 1102. If one were to close the anvil 1130 when in that position, the anvil spring arms 1796 will bias the spring arms 1793 downwardly to cause the central lugs 1780 to be lockingly received within the corresponding lock notch 1850 in the spring arm 1793. When in that position, the firing member 1760 cannot be distally advanced. FIG. 36 illustrates a fresh surgical staple cartridge 1110 properly seated within the elongate channel 1102 when the anvil 1130 is in the fully closed position. As can be seen in FIG. 36, the sled 1120 is in its starting position. When in that position, the sled bosses 1124 engage the sled tabs 1799 and bias the spring arms 1793 upward to positions wherein the lock notches 1850 do not engage the central tabs 1780. Thus, the firing member 1760 is free to be distally advanced. FIG. 37 illustrates the position of the firing member 1760 after it has been advanced distally from its starting position. As can be seen in FIG. 37, the firing member 1760 is distal to the lock spring and out of engagement therewith. The anvil spring arms 1796 have biased the lock member downwardly to an unlocked position.

Figure 38:
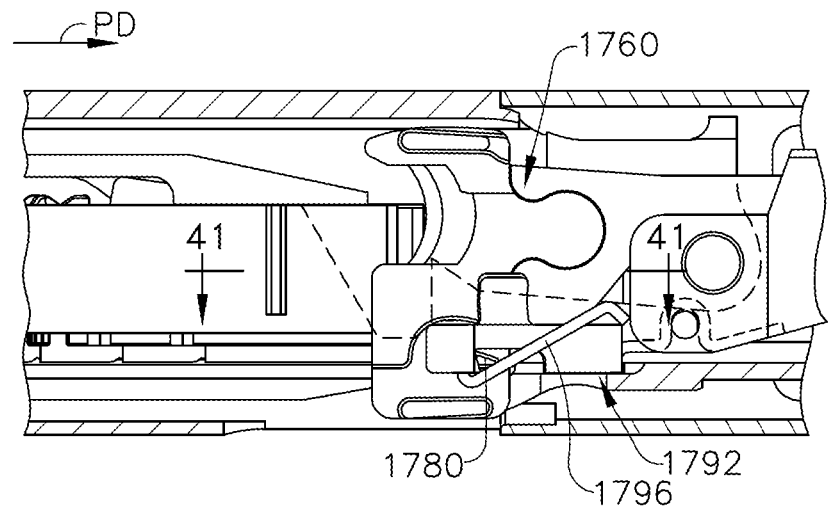
FIG. 38 is another cross-sectional side elevational view of the surgical end effector of FIG. 36 as the firing member is being retracted back to a starting position.
Figure 39:
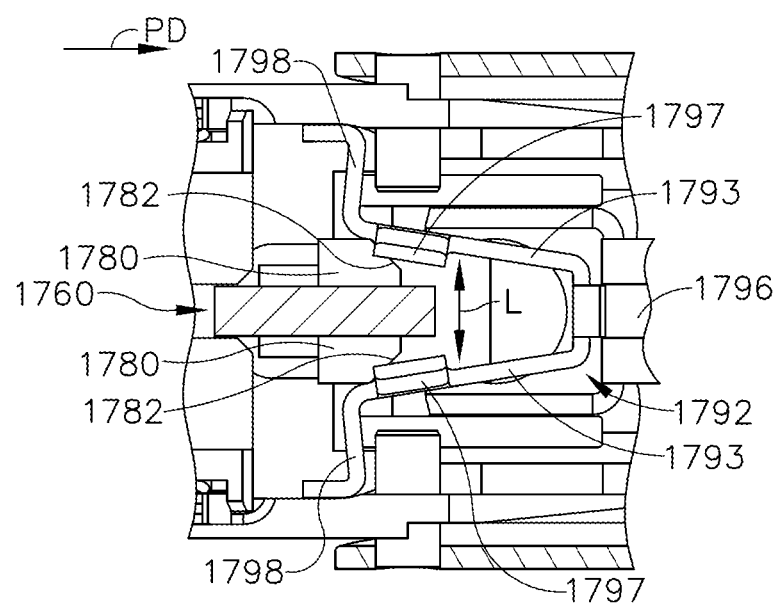
FIG. 39 is a top cross-sectional view of the firing member and firing member lock in the position shown in FIG. 38.
Figure 40:
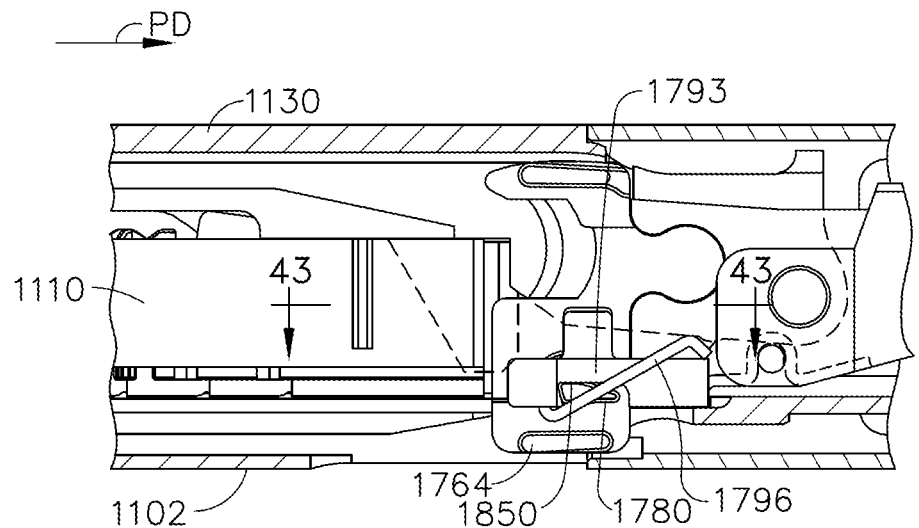
FIG. 40 is another cross-sectional side elevational view of the surgical end effector of FIG. 36 after the firing member has been retracted back to the starting position.
Figure 41:
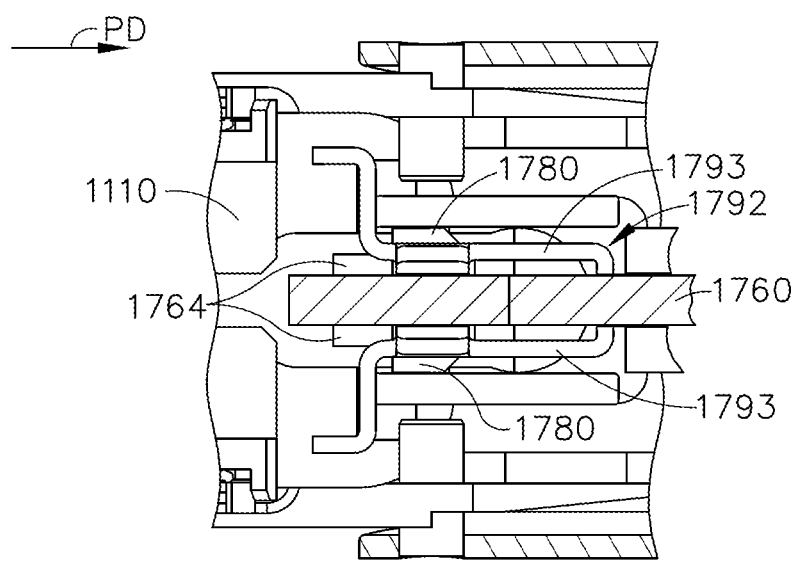
FIG. 41 a top cross-sectional view of the firing member and firing member lock in the position shown in FIG. 40.

FIGS. 38 and 39 illustrate the position of the firing member 1760 and the lock member 1792 after the firing member 1760 has been initially retracted in the proximal direction. In the illustrated arrangement, each of the central lock lugs 1780 includes a chamfered proximal end portion 1782. See FIGS. 30 and 31. As the firing member 1760 is retracted to the position shown in FIGS. 38 and 39, the chamfered proximal ends 1782 of the central lock lugs 1780 contact the corresponding forward arms 1798 of the lock member 1792 and bias the spring arms laterally outwardly (arrow L in FIG. 39). FIGS. 40 and 41 illustrate the position of the firing member 1760 and the lock member 1792 after the firing member 1760 has been fully retracted back into its starting position. When in that position, each of the central lock lugs 1780 is lockingly received within the lock notches 1850 in the corresponding spring arm 1793. When in that position, the firing member 1760 cannot be distally advanced.

Figure 42:
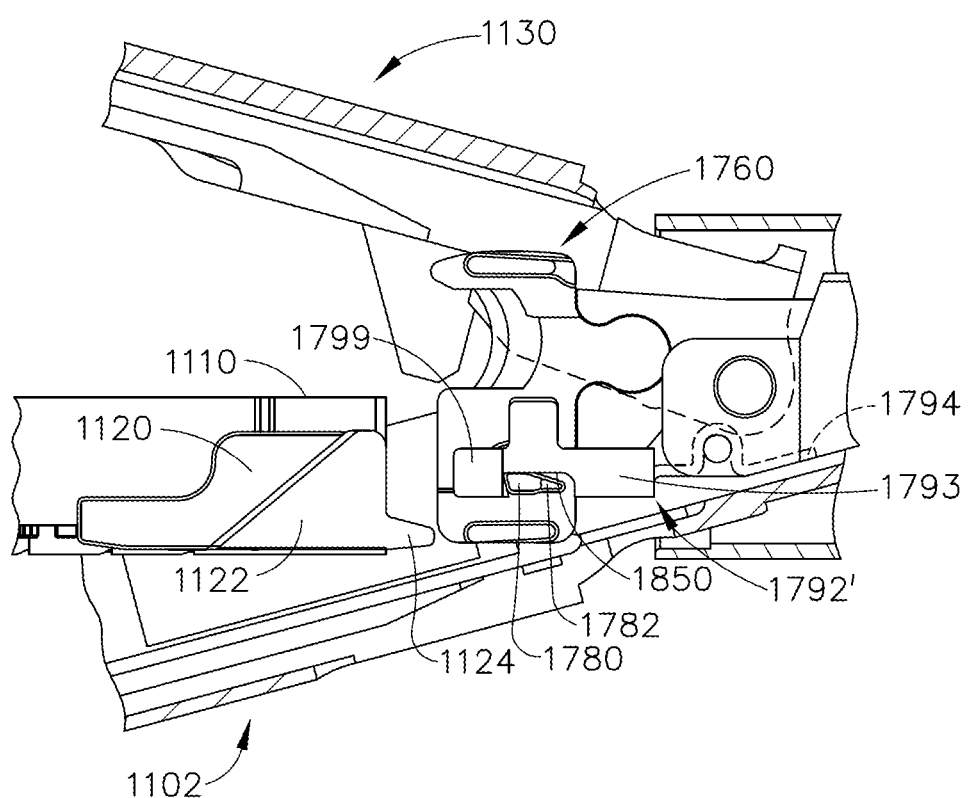
FIG. 42 is a cross-sectional side elevational view of a portion of another surgical end effector embodiment with jaws thereof in a fully open orientation and another firing member lock embodiment of FIG. 33 in a locked orientation.

FIG. 42 illustrates an alternative lock member 1792'. In this embodiment, the mount tab 1794 biases the lock member 1792' downwardly without the use of anvil spring arms. Thus, the central lock lugs 1780 remain in locking engagement with the spring arms 1793 during opening of the anvil 1130 and elongate jaw 1102 and loading of the surgical staple cartridge 1110 therein.

As discussed above, the cartridge body 1111 has a plurality of anvil pockets 1116 that are serially arranged in lines on both sides of the central slot 1114. Housed within these pockets 1116 are staple drivers that operably support one or more surgical staples or fasteners thereon. When the target tissue is clamped between the anvil 1130 and the staple cartridge deck surface 1115, the target tissue must be so positioned so that the tissue that is severed is stapled on each side of the cut line. To avoid the target tissue from being positioned proximal of the proximal most staples or fasteners, the anvil typically contains downwardly extending walls commonly referred to as "tissue stops" which serve to block the target tissue from getting too far proximal between the anvil and cartridge. As the anvil is closed toward the cartridge, the tissue stops extend downward past the cartridge deck surface to prevent the tissue from being positioned too far proximal between the anvil and cartridge. In at least one of the end effector embodiments described herein, the anvil 1130 and the elongate channel 1102 both can move about the pivot jaw axis JA. Such arrangement may permit the anvil 1130 and the elongate channel 1102 to be opened further than other end effector arrangements wherein only one of the anvil or elongate channel can move or pivot. Stated another way, the distance between the undersurface of the anvil body 1132 and the cartridge deck surface 1115 of a staple cartridge 1110 that is seated in the elongate channel 1102 of the end effector 1110 described herein when both the anvil 1130 and elongate channel 1102 are in their respective fully open positions is generally larger than the distance between the underside of the anvil and the deck surface of a cartridge that is seated in an elongate channel of an end effector wherein only one of the anvil and channel move relative to the other. Thus, at least one form of the end effector 1100 is configured to employ a staple cartridge arrangement with at least one "active" tissue stop or "expandable" tissue stop. In the illustrated arrangement, two active tissue stops generally designated as 1250 are employed.

Figure 45:
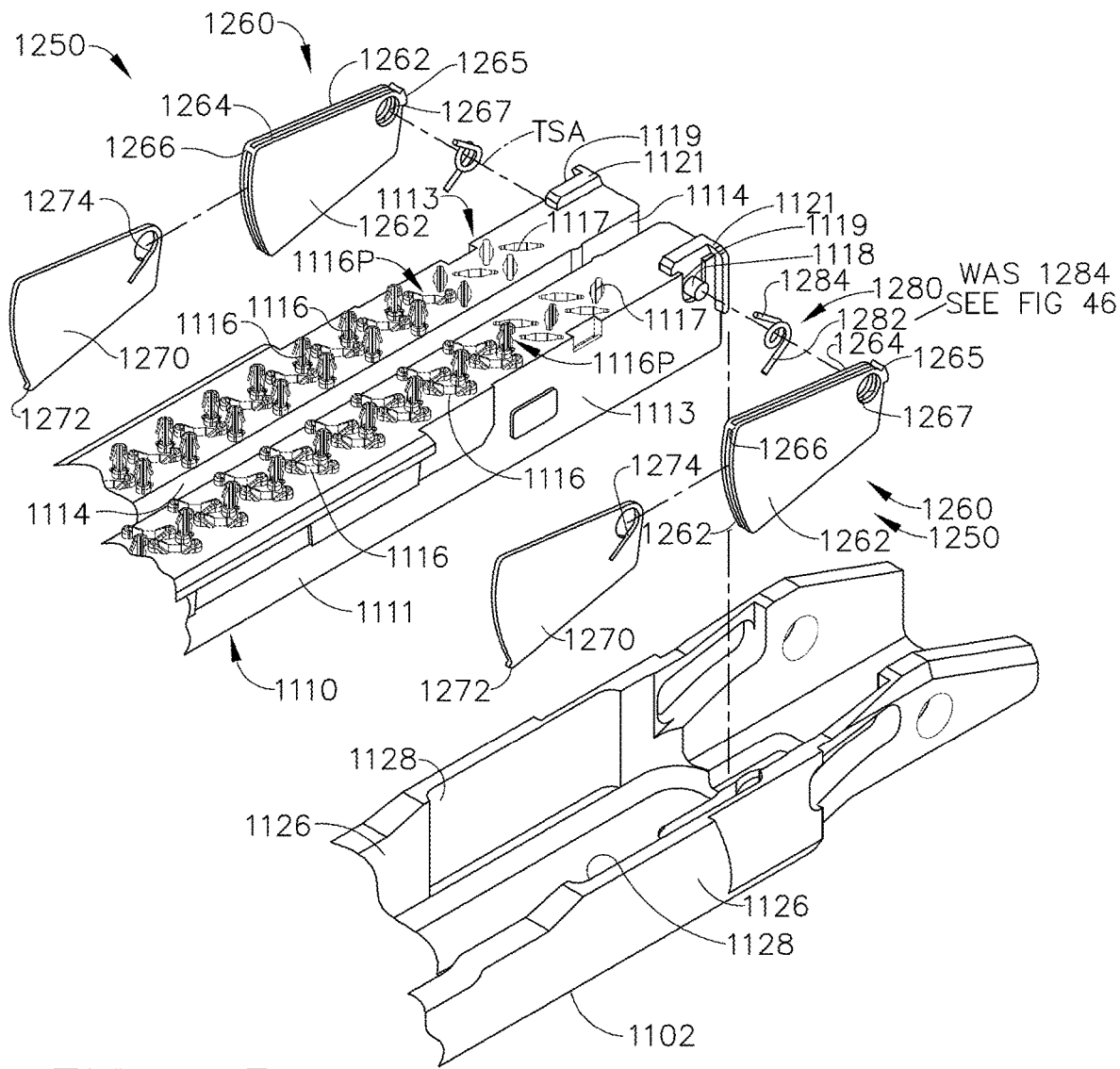
FIG. 45 is an exploded perspective view of one of the jaws and the surgical staple cartridge of FIGS. 43 and 44.
Figure 47:
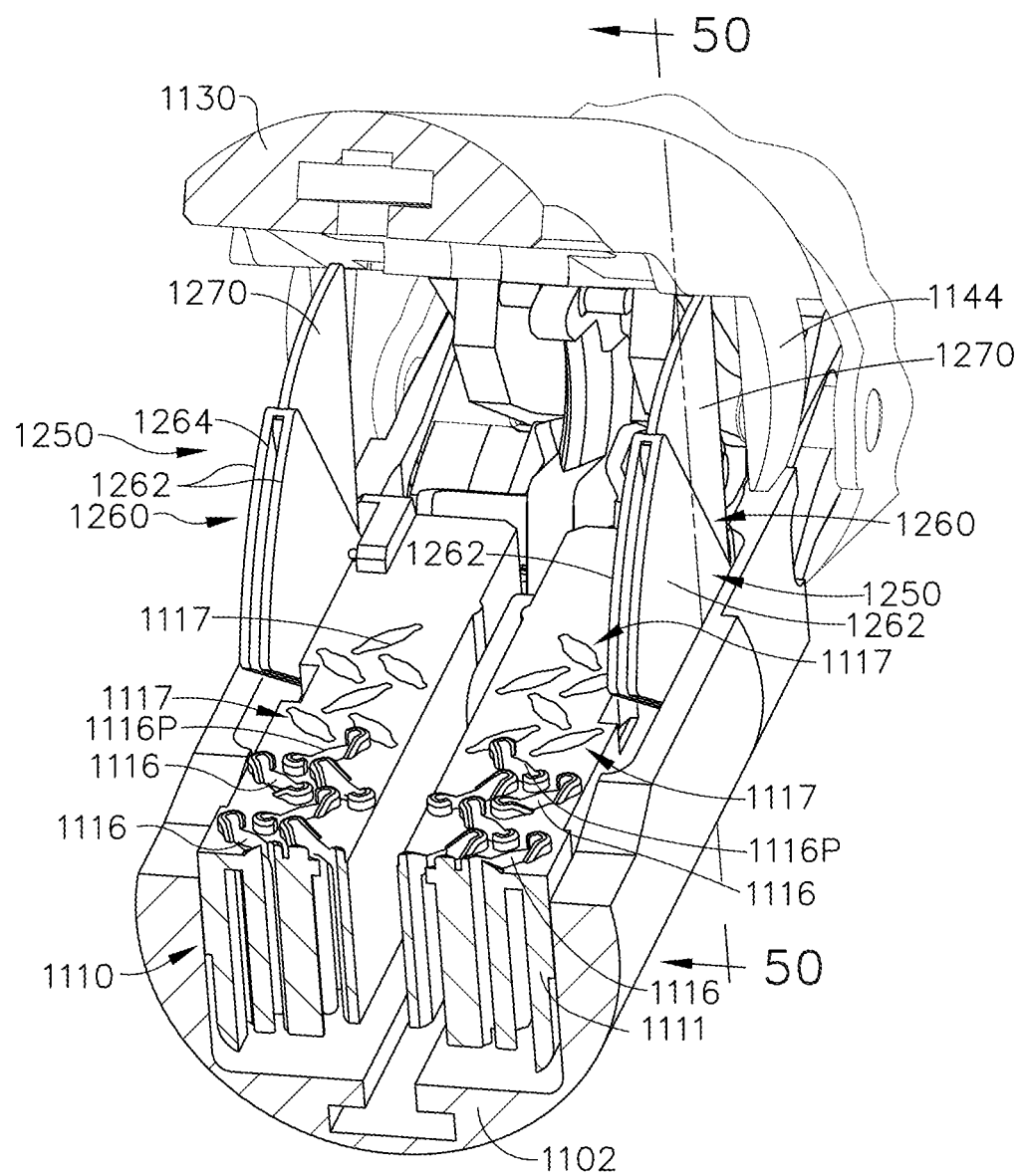
FIG. 47 is a partial cross-sectional end view of the surgical end effector of FIGS. 42 and 43 with the jaws thereof in the fully open orientation and the expandable tissue stops thereof in their fully expanded orientations.
Figure 48:
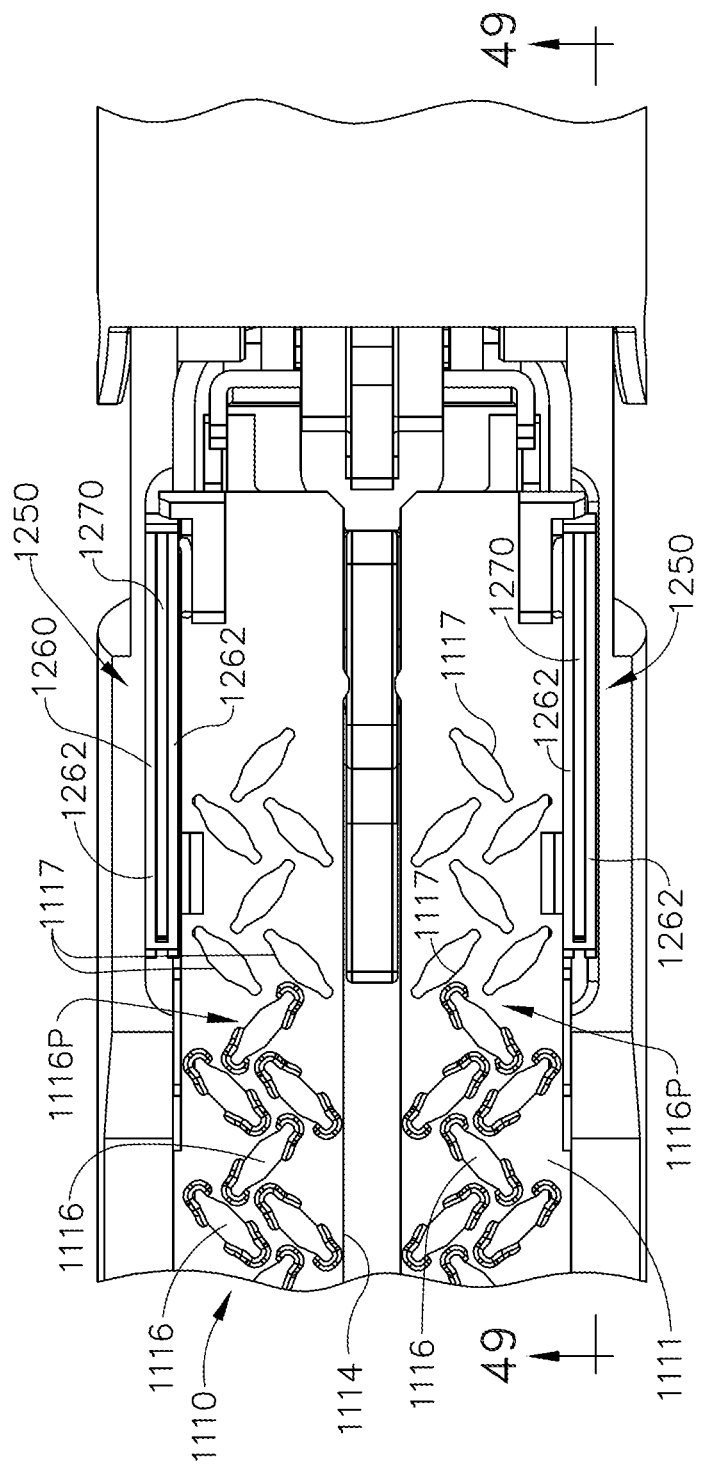
FIG. 48 is a top view of a portion of the surgical staple cartridge of FIGS. 42 and 43.

Turning now to FIGS. 45, 47 and 48, as discussed above, the staple cartridge body 1111 includes a plurality of staple pockets 1116 located on each side of the elongate slot 1114 that is configured to accommodate the firing member 1760 as it is distally advanced through the cartridge. Depending upon the configuration number and arrangement of the staple pockets 1116, one or more staple driver configurations may be operably supported therein that each supports one or more surgical staples thereon. Some pockets located at the proximal end of the cartridge body may not contain drivers and staples. For example, in the illustrated arrangement, the staple pockets 1116 contain drivers (not shown) and staples (not shown). The proximal most pockets that support a driver and a staple are labeled 1116P. Although additional "unused" pockets (labeled 1117), none of those pockets contain drivers and staples. In the illustrated arrangement, all of the staple pockets 1116 on both sides of the elongate slot 1114 that are to the proximal most pockets 1116P contain drivers and surgical staples. The active tissue stops 1250 are therefore configured to prevent tissue from being clamped between the anvil 1130 and the cartridge 1110 in a position that is proximal to the proximal staple pockets 1116P to prevent the tissue from being cut without first being stapled.

In one arrangement, the surgical staple cartridge 1110 alone and/or in combination with the elongate channel 1102 may be referred to herein as the "first jaw" and the anvil 1130 may be referred to as the "second jaw". The proximal end 1112 of the staple cartridge 1110 may be referred to as the "first proximal end" or the proximal end of the first jaw. The deck surface 1115 may be referred to as the 'first jaw surface". In the illustrated arrangement, the anvil body 1132 includes a staple forming undersurface 1135 that faces the cartridge deck and serves to form the staples as they are driven into contact therewith. The staple forming undersurface 1135 (FIG. 3) may also be referred to herein as the "second jaw surface".

In the illustrated arrangement, the active tissue stops 1250 are operably attached to the cartridge body 1111. However, other arrangements are contemplated wherein the active tissue stops are attached to portions of the elongate channel 1102.

Figure 46:
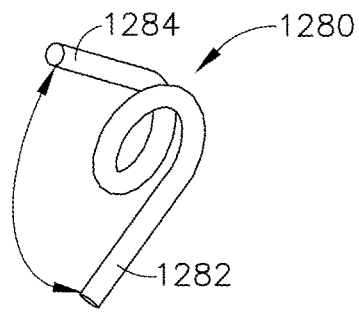
FIG. 46 is a perspective view of a stop spring of one of the expandable tissue stops of FIG. 43.

Turning to FIG. 45, in at least one arrangement, two active or expandable tissue stops 1250 are employed—one tissue stop on each side of the elongate slot 1114. As can be seen in FIG. 47, an active tissue stop 1250 comprises a bifurcated lower tissue stop portion 1260 that comprises two cam walls 1262 that are separated by a space 1264 and are interconnected by a connector 1265. Movably supported within the space 1264 is an upper tissue stop portion 1270. As can be seen in FIG. 45, a stop bridge 1266 is provided between the walls 1260 at the upper portion of their distal ends. The stop bridge 1266 cooperates with a stop tab 1272 formed on the upper tissue stop portion 1270 to prevent the upper tissue stop portion 1270 from extending completely out of the space 1264. Mounting holes 1267 are provided through the walls 1260 to enable the lower tissue stop portion 1260 to be pivotally journaled on a corresponding stop pin 1118 that protrudes laterally out of the sides 1113 of the cartridge body 1111. As can also be seen in FIG. 45, each of the upper stops 1270 includes a spring mounting hole 1274 that is configured to receive a leg portion 1282 of a biasing member or stop spring 1280 therein. See FIG. 46.

The upper tissue stop portion 1270 is slidably received within the space 1264 of the corresponding lower tissue stop portion 1260 to create the active or expandable tissue stop 1250. The upper and lower tissue stop portions 1260, 1270, along with the corresponding biasing member or stop spring 1280, are pivotally journaled on the corresponding stop pin 1118. Each active tissue stop assembly 1250 is free to pivot about a tissue stop axis TSA that is defined by the stop pins 1118. As can be seen in FIG. 45, the tissue stop axis TSA is transverse to the elongate slot 1114 in the cartridge body 1111. A second leg 1284 of the stop spring 1280 bears upon a corresponding ledge or portion 1119 of the cartridge body 1111 such that when journaled on the stop pin 1118, the stop spring 1280 serve to bias the upper tissue stop portion 1270 upward within the space 1264 until the stop tab 1272 contains the stop bridge 1266. At that point, the biasing member or stop spring 1280 serves to bias the entire active tissue stop assembly 1250 upward about the tissue stop axis TSA until the upper tissue stop portion 1270 contacts a corresponding stop ledge 1121 formed on the cartridge body 1111.

Figure 43:
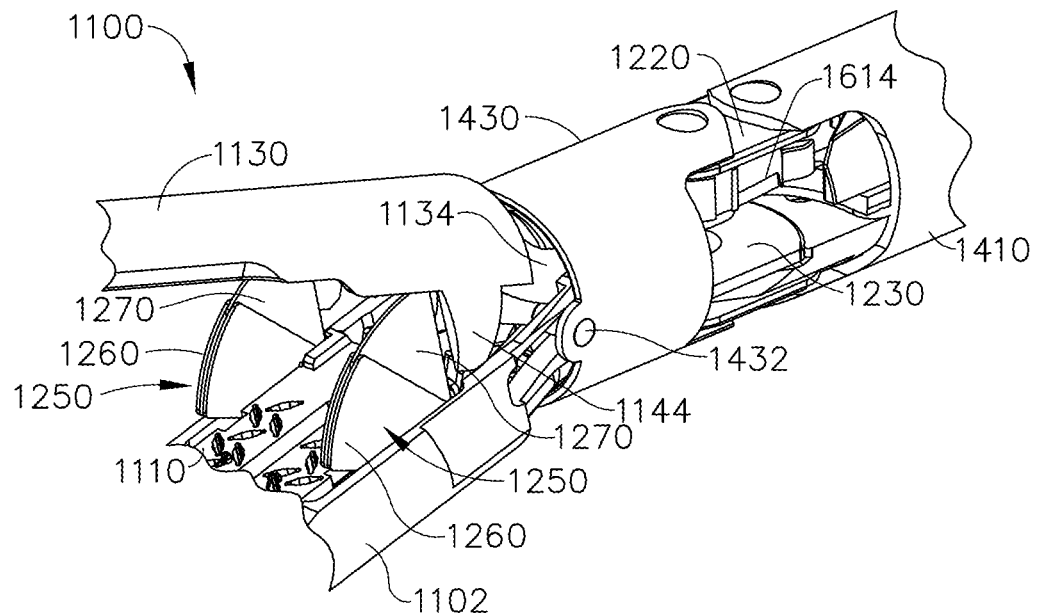
FIG. 43 is a left side perspective view of portions of another surgical end effector embodiment and distal closure member embodiment with jaws of the surgical end effector in a fully open position and supporting a surgical staple cartridge therein with expandable tissue stops in a fully expanded orientation.
Figure 44:
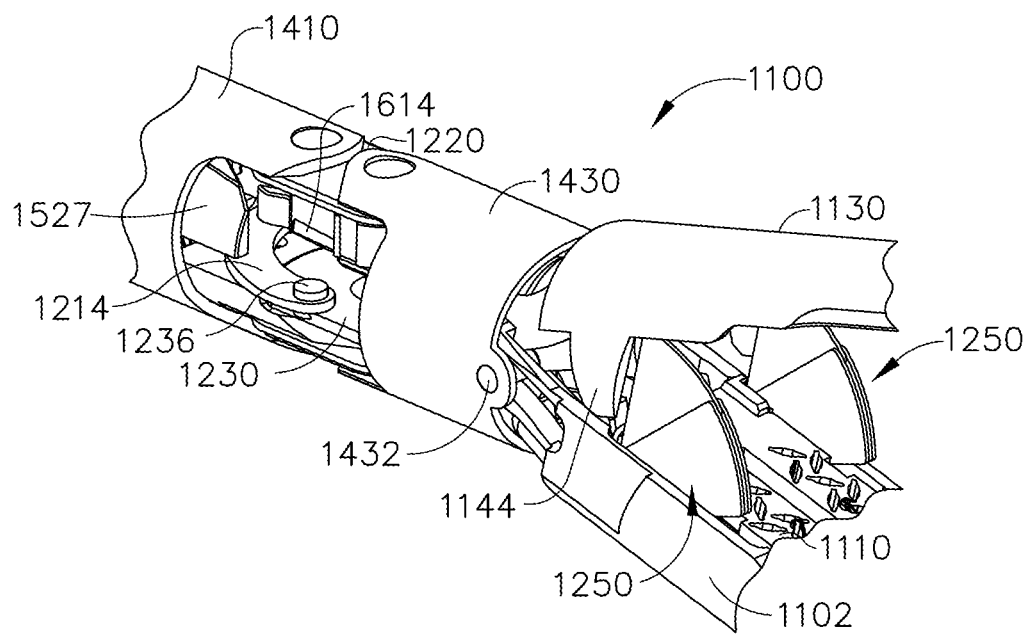
FIG. 44 is a right side perspective view of the surgical end effector of FIG. 43.
Figure 49:
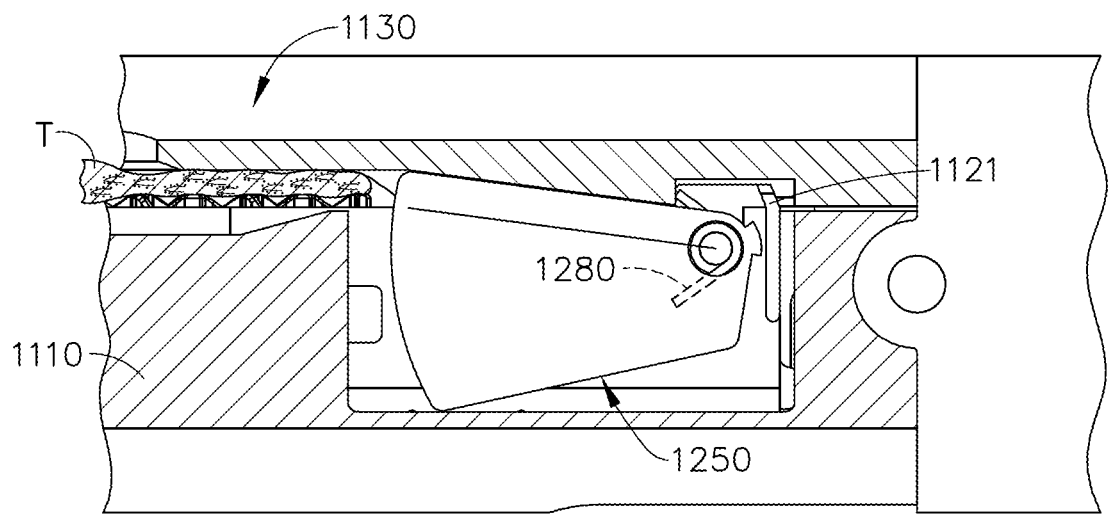
FIG. 49 is a cross-sectional side view of the surgical end effector of FIG. 48, taken along line 49-49 of FIG. 48, with the jaws thereof in the fully closed position.
Figure 50:
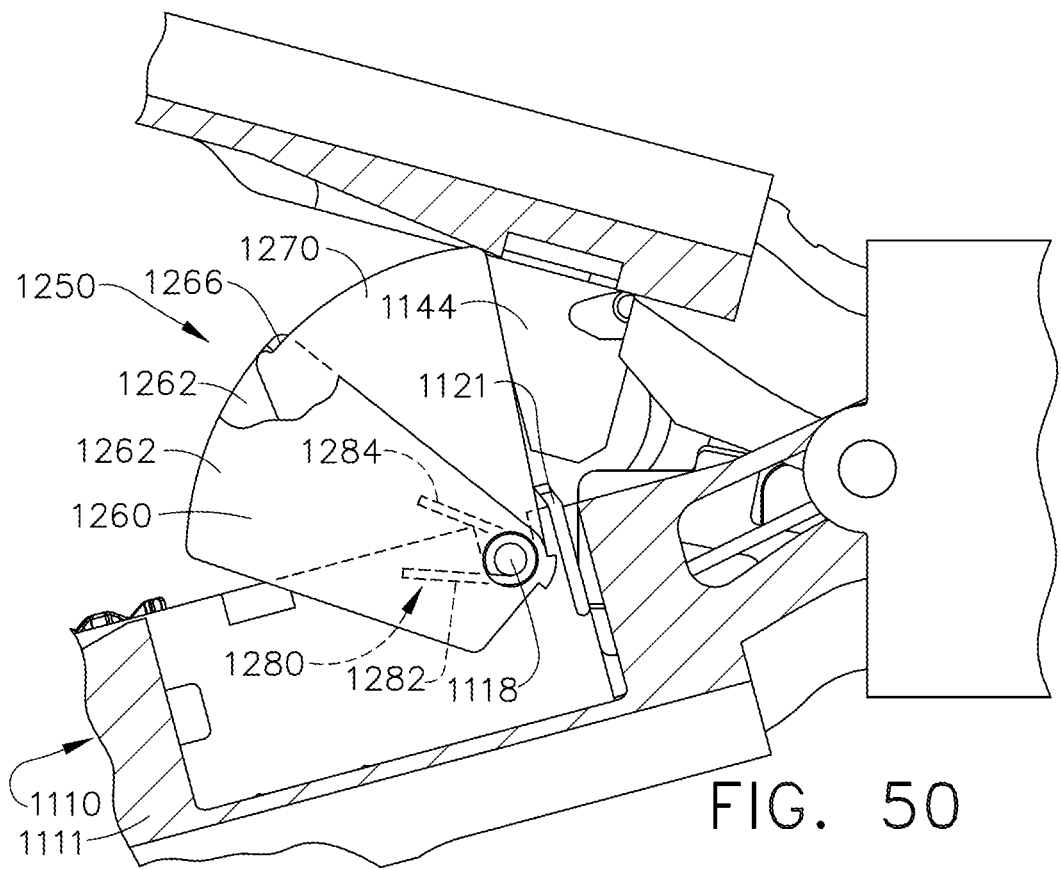
FIG. 50 is another cross-sectional side view of the surgical end effector of FIG. 47, taken along line 50-50 of FIG. 47, with the jaws thereof in the fully open position.

Thus, in the illustrated arrangement, each of the active tissue stop assemblies 1250 are attached to a corresponding lateral side 1113 of the cartridge body 1110. As can be seen in FIG. 45, each side wall 1126 of the elongate channel 1102 has a tissue stop notch 1128 formed therein to receive an active tissue stop assembly 1250 therein when the jaws 1130, 1110 are in their fully closed positions. FIG. 49 illustrates the anvil 1130 and elongate channel 1102 and cartridge 1110 in their "fully closed" positions. The orientations of the active tissue stop assemblies 1250 when the anvil 1130 and elongate channel 1102 or surgical cartridge 1110 are in their fully closed positions may be referred to as their "fully compressed" orientations. In certain embodiments the anvil assembly 1130 may also have fixed tissue stops 1144 formed thereon which are proximal to the active tissue stop assemblies 1250. See FIGS. 43 and 44. FIGS. 47 and 50 illustrate the orientation of an active tissue stop assembly 1250 when the anvil 1130 and the elongate channel 1102 are in their respective fully opened positions. The orientations of the active tissue stop assemblies 1250 when the anvil 1130 and elongate channel 1102 or surgical cartridge 1110 are in their fully open positions may be referred to as their "fully deployed" or "fully expanded" orientations. When in their fully deployed position, the active tissue stops 1250 serve to prevent tissue from significantly advancing proximally past the proximal most staple pockets 1116P. FIG. 49 illustrates the anvil 1130 and elongate channel 1102 clamping tissue therebetween in their respective fully closed positions. Prior to being installed within the elongate channel 1102, the tissue stop assemblies may be retained in the collapsed orientation shown in FIG. 49 by a removably staple cover that is removably attached to the cartridge deck. Once the cartridge is installed in the elongate channel, the staple cover maybe removed from the cartridge deck.

Figure 51:
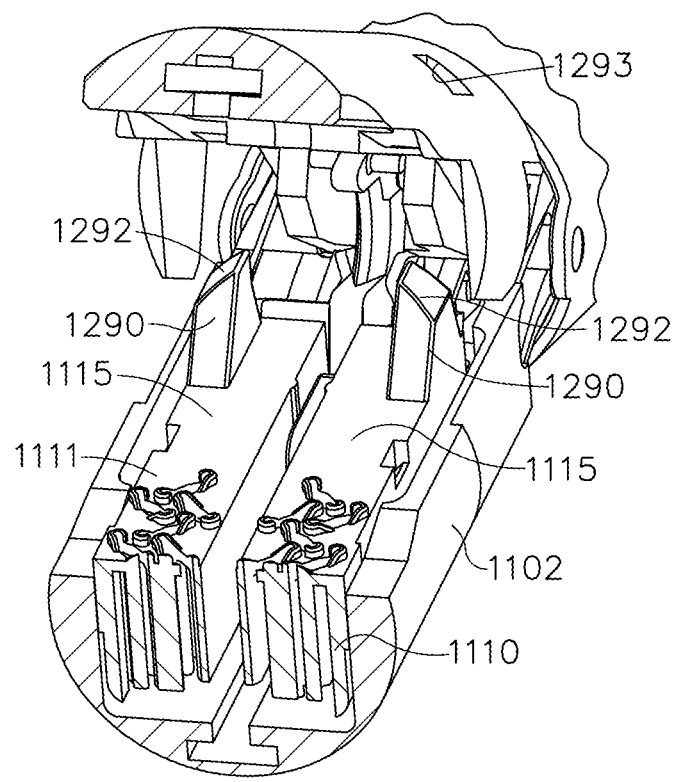
FIG. 51 is a partial cross-sectional end view of another surgical end effector embodiment with the jaws thereof in a fully open orientation.
Figure 52:
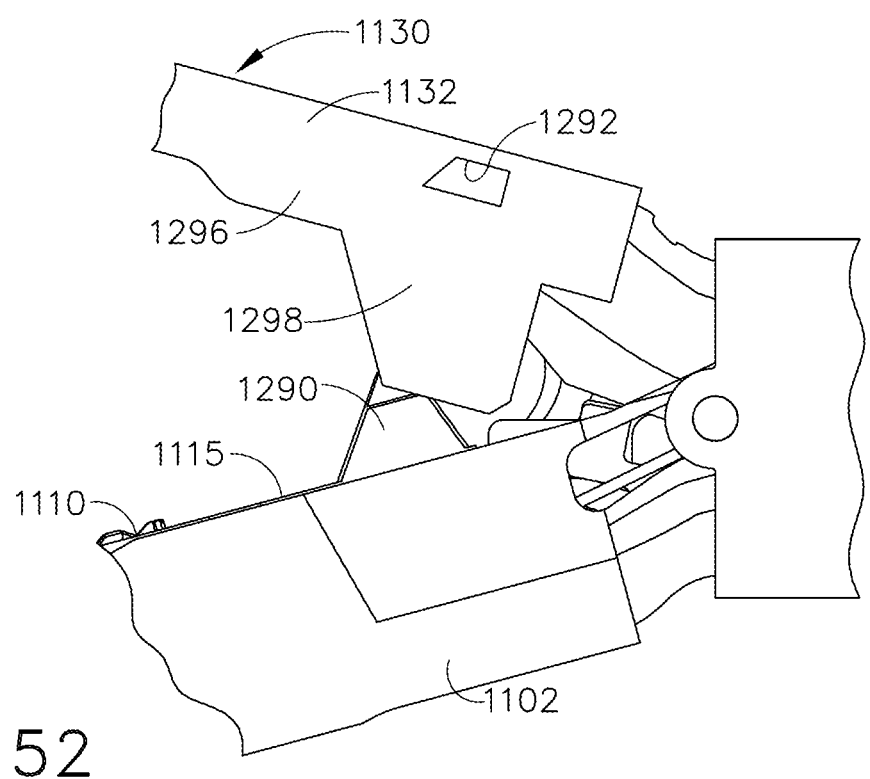
FIG. 52 is a side elevational view of a portion of the surgical end effector of FIG. 51 with the jaws thereof in a fully open orientation.
Figure 53:
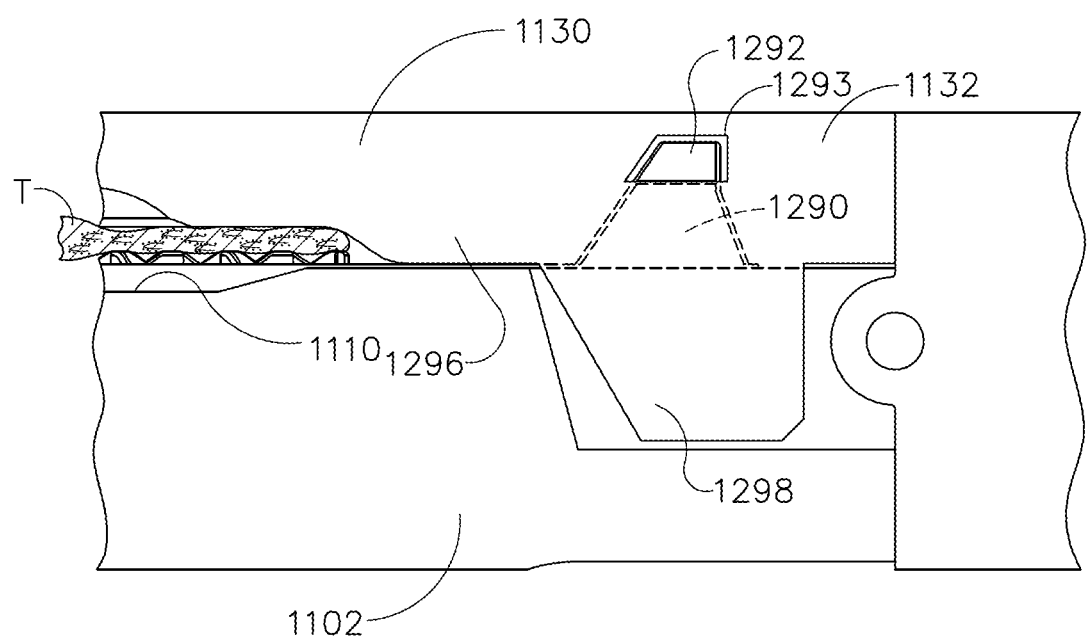
FIG. 53 is another side elevational view of a portion of the surgical end effector of FIG. 51 with the jaws thereof in a fully closed orientation.

FIGS. 51-53 illustrate another tissue stop arrangement that comprises cooperating tissue stops on the anvil as well as the cartridge. For example, in the embodiment shown in FIGS. 51-53, a pair of upstanding cartridge tissue stops 1290 that extend upward from the cartridge deck surface 1115. When the anvil 1130 and the elongate channel 1102 are in their fully closed positions, the upper ends 1292 of the cartridge tissue stops 1290 extend into holes or cavities 1293 provided in the anvil body 1132. The upper ends 1292 of the cartridge tissue stops 1290 are angled so that when the anvil 1130 and elongate channel 1102 are fully closed, the upper ends 1292 do not protrude beyond the outer surface of the anvil body 1132. See FIG. 53. In addition, the anvil 1130 includes downwardly extending distal tissue stops 1296 that do not extend below the cartridge deck surface 1115 when the anvil 1130 and the elongate channel 1102 are in their fully closed positions and a pair of proximal tissue stops 1298 that extend downwardly below the deck surface 1115 of the cartridge 1110 when the anvil 1130 and elongate channel 1102 are in their fully closed position. See FIG. 53. In an alternative arrangement, an elastic band may be placed around the exterior of the jaws such that the distal edge of the band is at the desired location for the tissue stops. As the jaws are opened, the band stretches but serves as a tissue stop. The band can rest in recesses in the anvil and elongate channel that circumscribe the anvil/channel so that the end effector can pass through standard trocar arrangements.

In the illustrated example, the cartridge body 1111 operably supports therein a plurality of staple drivers that are aligned in rows on each side of a centrally disposed slot 1114. FIGS. 33A-33C illustrate one example of a staple driver 1170 that may be employed to support staples on one side of a surgical staple cartridge. The drivers located on the opposite side of the centrally disposed slot 1114 may comprise mirror images of drivers 1170. Other staple driver configurations may also be effectively employed as well. As can be seen in FIGS. 33A-33C, one form of a staple driver 1700 comprises a staple driver body 1172. The driver body 1172 includes a first or innermost staple support portion 1174 that is configured to support a staple (not shown) thereon. A second or central staple support portion 1176 is configured to support another staple (not shown) thereon and a third support portion 1870 that is configured to support a third staple (not shown) thereon. The first staple support portion 1174, the second staple support portion 1176 and the third staple support portion 1178 are all coupled together by a connector portion 1180. In at least one arrangement, the connector portion 1180 is formed with a centrally disposed opening or aperture 1182 that is configured to slidably receive a corresponding first driver guide (not shown) that is formed in the cartridge body. The connector portion 1180 includes a first cam portion 1184 that has a first camming surface or ramp 1186 formed thereon. The connector portion 1180 also includes a second cam portion 1188 that has a second a second camming surface 1190 formed thereon. The camming surfaces 1186, 1190 have the same slope or angle or they may have different slopes/angles. In at least one embodiment, each staple driver 1170 is integrally formed from or molded from, for example, Ultem®, with no fill. However, other materials such as, for example, Ultem® with a glass or mineral fill or Nylon or Nylon with a glass file could be used. In other arrangements, the various portions of the staple drivers 1170 may be separately fabricated from other materials and be attached together by adhesive, solder, etc. Further details concerning the staple drivers 1170 as well as other driver embodiments that may be effectively employed with the various embodiments disclosed herein may be found in U.S. patent application Ser. No. 14/843,243, filed Sep. 2, 2015, entitled SURGICAL STAPLE CONFIGURATIONS WITH CAMMING SURFACES LOCATED BETWEEN PORTIONS SUPPORTING SURGICAL STAPLES, the entire disclosure of which is hereby incorporated by reference herein.

The staple cavities 1116 are angularly oriented relative to the shaft axis SA. More specifically, the staple cavities 1116 are oriented at oblique angles relative to the shaft axis SA and form a herringbone pattern in the deck surface 1115.

Various alternative patterns for staple cavities in a staple cartridge body are described herein.

Variations to the arrangement and/or geometry of staples in a staple line can affect the flexibility and sealing properties of the staple line. For example, a staple line comprised of linear staples can provide a limited amount of flexibility or stretch because the staple line can flex or stretch between the linear staples. Consequently, a limited portion of the staple line (e.g., the portion between staples) is flexible. A staple line comprised of angularly-oriented staples can also flex or stretch between the staples. However, the angularly-oriented staples are also able to rotate, which provides an additional degree of stretch within the staple line. A staple line comprised of angularly-oriented staples can stretch in excess of 60%, for example. In certain instances, a staple line comprised of angularly-oriented staples can stretch at least 25% or at least 50%, for example. The arrangement of staples includes the relative orientation of the staples and the spacing between the staples, for example. The geometry of the staples includes the size and shape of the staples, for example. The flexibility and sealing properties of a staple line can change at longitudinal and/or lateral positions based on the arrangement and/or geometry of the staples. In certain instances, it is desirable to alter the flexibility and/or sealing properties of a staple line at one or more locations along the staple line. For example, it can be desirable to maximize the flexibility of the staple line or a portion thereof. Additionally or alternatively, it can be desirable to minimize the flexibility of the staple line or a portion thereof. It can also be desirable to maximize the sealing properties of the staple line or a portion thereof. Additionally or alternatively, it can be desirable to minimize the sealing properties of the staple line or a portion thereof.

The arrangement of staple cavities in a staple cartridge corresponds to the arrangement of staples in a staple line generated by the staple cartridge. For example, the spacing and relative orientation of staple cavities in a staple cartridge corresponds to the spacing and relative orientation of staples in a staple line generated by the staple cartridge. In various instances, a staple cartridge can include an arrangement of staples cavities that is selected and/or designed to optimize the flexibility and/or sealing properties of the resultant staple line. A surgeon may select a staple cartridge having a particular arrangement of staple cavities based on the surgical procedure to be performed and/or the properties of the tissue to be treated during the surgical procedure, for example.

In certain instances, it can be desirable to generate a staple line with different staple patterns. A staple line can include a first pattern of staples for a first portion thereof and a second pattern of staples for a second portion thereof. The first pattern and the second pattern can be longitudinally offset. For example, the first pattern can be positioned at the proximal or distal end of the staple line. In other instances, the first pattern and the second pattern can be laterally offset and, in still other instances, the first pattern and the second pattern can be laterally offset and longitudinally offset. A staple line can include at least two different patterns of staples.

In certain instances, the majority of staples in a staple line can form a major pattern and other staples in the staple line can form one or more minor patterns. The major pattern can span a significant portion of the staple line and can include a longitudinally-repetitive sub-pattern. In certain instances, the minor pattern, or irregularity, can deviate from the major pattern. The minor pattern can be an anomaly at one or more locations along the length of the staple line, for example.

The different patterns in a staple line can be configured to produce different properties at predefined locations. For example, the major pattern can be a highly flexible or elastic pattern, which can permit extensive stretching of the stapled tissue, and the minor pattern can be less flexible or less elastic. It can be desirable for the majority of the staple line to be highly flexible and for one or more limited portions to be less flexible, for example. In other instances, the minor pattern can be more flexible than the major pattern. In certain instances, because the minor pattern extends along a shorter portion of the staple line, the flexibility of the minor pattern may not impact, or may not significantly impact, the overall flexibility of the entire staple line.

Referring now to FIGS. 54-57, a staple cartridge body 3000 for use with a surgical end effector is depicted. The staple cartridge body 3000 includes a deck 3002 and a slot 3004, which extends through the deck 3002 from a proximal end 3006 toward a distal end 3008 of the cartridge body 3000. The slot 3004 extends along the longitudinal axis LA (FIG. 56) of the cartridge body 3000. Staple cavities 3010 are defined in the cartridge body 3000 and each staple cavity 3010 defines an opening 3012 in the deck 3002.

The majority of the staple cavities 3010 are arranged in a first pattern, or major pattern, 3020. The first pattern 3020 is a longitudinally-repetitive pattern of angularly-oriented staple cavities 3010. Longitudinally-repetitive patterns are patterns in which a sub-pattern or arrangement is longitudinally repeated. For example, an arrangement of three staple cavities on each side of the slot 3004 (an inner staple cavity, an intermediate staple cavity, and an outer staple cavity) can be repeated along at least a portion of the length of the staple cartridge body 3000. Various longitudinally-repetitive patterns of angularly-oriented staples cavities are described in U.S. patent application Ser. No. 14/498,145, filed Sep. 26, 2014, now U.S. Patent Application Publication No. 2016/0089142, entitled METHOD FOR CREATING A FLEXIBLE STAPLE LINE, which is incorporated by reference herein in its entirety. The openings 3012 of the staple cavities 3010 in the first pattern 3020 form a herringbone pattern having six rows of angularly-oriented staple cavity openings 3012 in the cartridge deck 3002. An inner row 3014a, an intermediate row 3014b, and an outer row 3014c of staple cavities 3010 are positioned on each side of the slot 3004.

Each staple cavity opening 3012 has a proximal end 3016 and a distal end 3018. The proximal end 3016 and the distal end 3018 of the staple cavities 3010 in the first pattern 3020 are laterally offset. Stated differently, each staple cavity 3010 in the first pattern 3020 is angularly oriented relative to the longitudinal axis LA (FIG. 56). A cavity axis CA (FIG. 56) extends between the proximal end 3016 and the distal end 3018 of each opening 3012. The cavity axes CA are obliquely oriented relative to the slot 3004. More specifically, the openings 3012 in the inner rows 3014a of staple cavities 3010 and the outer rows 3014c of staple cavities 3010 are oriented at 45 degrees, or about 45 degrees, relative to the longitudinal axis LA, and the openings 3012 in the intermediate rows 3014b of staple cavities 3010 are oriented at 90 degrees, or about 90 degrees, relative to the openings 3012 of the inner rows 3014a and the outer rows 3014a.

Certain staple cavities 3010 in the cartridge body 3000 are oriented at an angle that is anomalous or irregular with respect to the staple cavities 3010 in the first pattern 3020. More specifically, the angular orientation of proximal staple cavities 3010a, 3010b, 3010c, and 3010d and distal staples cavities 3010e, 3010f, 3010g, and 3010h does not conform to the herringbone arrangement of the staple cavities 3010 in the first pattern 3020. Rather, the proximal staple cavities 3010*a*-3010*d* and the distal staple cavities 3010*e*-3010*h* are angularly offset from the staple cavities 3010 in the first pattern 3020. The proximal staple cavities 3010*a*, 3010*b*, 3010*c*, and 3010*d* are obliquely oriented relative to the staples cavities 3010 in the first pattern 3020, and the distal staple cavities 3010*e*, 3010*f*, 3010*g*, and 3010*h* are also obliquely oriented relative to the staples cavities 3010 in the first pattern 3020. The proximal and distal staple cavities 3010*a*-3010*h* are oriented parallel to the slot 3004 and to the longitudinal axis LA.

The proximal staple cavities 3010*a*-3010*d* form a proximal pattern 3022 that is distinct from the first pattern 3020, and the distal staple cavities 3010*e*-3010*h* form a distal pattern 3024 that is also distinct from the first pattern 3020. In the depicted arrangement, the proximal pattern 3022 includes a first pair of parallel, longitudinally-aligned staple cavities 3010*a*, 3010*b* on a first side of the slot 3004 and a second pair of parallel, longitudinally-aligned staple cavities 3010*c*, 3010*d* on a second side of the longitudinal slot 3004. The distal pattern 3024 also includes a first pair of parallel, longitudinally-aligned staple cavities 3010*e*, 3010*f* on the first side of the longitudinal slot 3004 and a second pair of parallel, longitudinally-aligned staple cavities 3010*g*, 3010*h* on the second side of the longitudinal slot 3004. In other instances, the distal pattern 3024 can be different from the proximal pattern 3022.

The proximal pattern 3022 and the distal pattern 3024 are symmetric relative to the longitudinal axis LA. In other instances, the proximal pattern 3022 and/or the distal pattern 3024 can be asymmetric relative to the longitudinal axis LA. For example, the staple cavities 3010*e* and 3010*f* can be longitudinally offset from the staple cavities 3010*g* and 3010*h* and/or the staple cavities 3010*a* and 3010*b* can be longitudinally offset from the staple cavities 3010*c* and 3010*d*. Additionally or alternatively, in certain instances, the staple cartridge body 3000 can include either the proximal pattern 3022 or the distal pattern 3024. In other instances, the staple cavities 3010 defined in the staple cartridge body 3000 can include additional and/or different patterns of staple cavities 3010.

Figure 54:
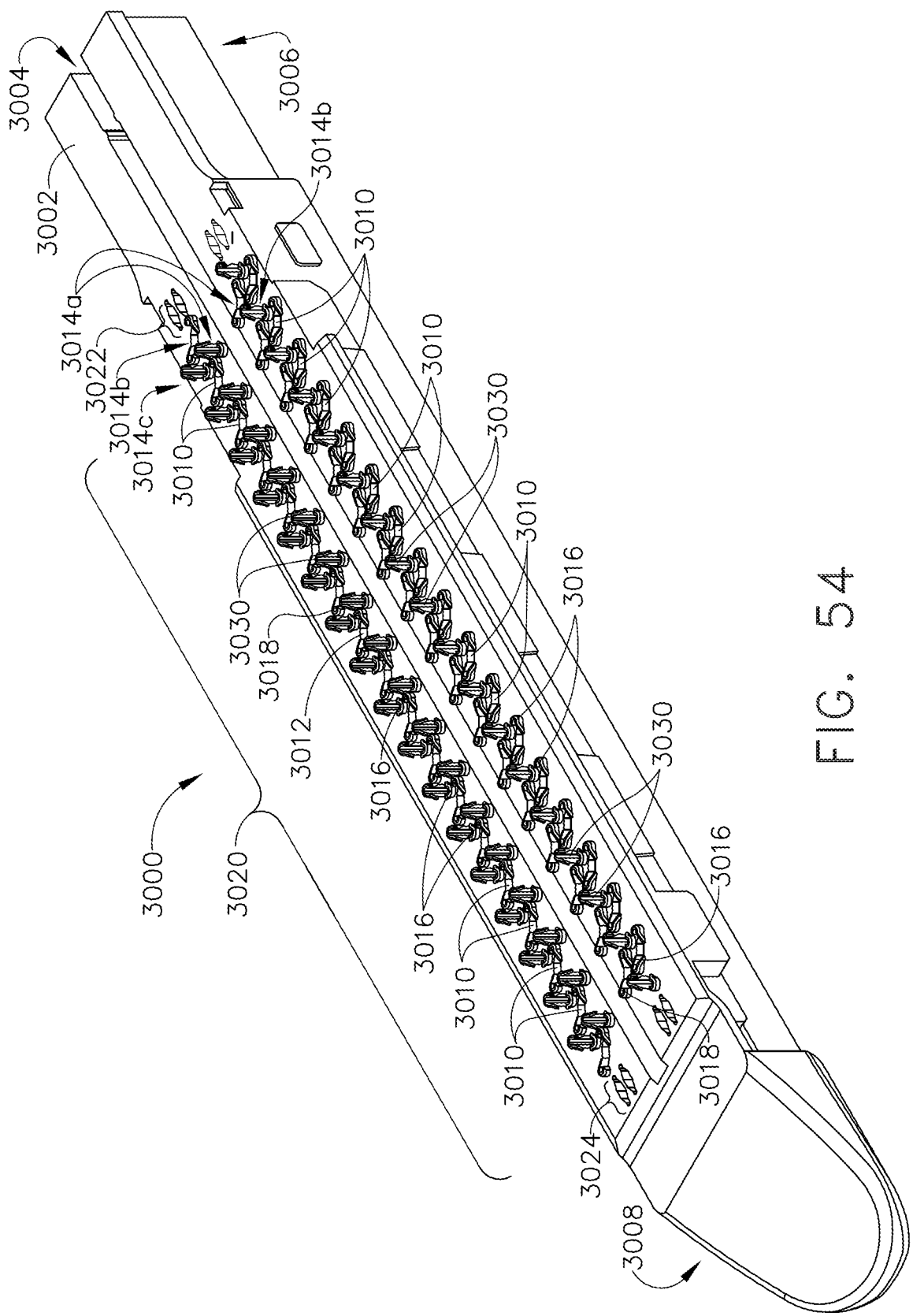
FIG. 54 is a perspective view of a staple cartridge body having a plurality of staple cavities defined therein.

Referring primarily to FIG. 54, atraumatic extenders 3030 extend or protrude from the deck 3002 around a portion of the staple cavities 3010 in the first pattern 3020. The atraumatic extenders 3030 surround the proximal and distal ends 3016 and 3018, respectively, of the openings 3012 of the staple cavities 3010 in the first pattern 3020. The atraumatic extenders 3030 may be configured to grip tissue that is clamped by the end effector. Additionally or alternatively, in certain instances, the tips of the staple legs can protrude from the cartridge body 3000. In such instances, the atraumatic extenders 3030 may be configured to extend flush with and/or beyond the tips of the staple legs to prevent the tips from prematurely penetrating tissue. Consequently, larger staples, e.g., staples having longer legs, can be positioned in the staple cavities 3010 having atraumatic extenders 3030 positioned therearound. For example, referring again to FIG. 54, larger staples can be positioned in the staple cavities 3010 in the first pattern 3020 than the staples in the staple cavities in the proximal pattern 3022 and the distal pattern 3024 without risking premature piercing of tissue by the longer staple legs. In certain instances, atraumatic extenders 3030 can be positioned around staples cavities 3010 in the proximal pattern 3022 and/or the distal pattern 3024, and larger staples can be positioned in one of more of those staple cavities 3010*a*-3010*h*, as well.

The staple cartridge body 3000 can be configured to generate a staple line having different properties along the length thereof. A staple line 3040 generated by the staple cartridge body 3000 and embedded in tissue T is depicted in FIG. 58. The staple line 3040 is comprised of staples 3042, and an exemplary staple 3042 for use with various staple cartridges described herein is depicted in FIG. 59. The staple 3042 can be comprised of a bent wire, for example. The wire can have a diameter of 0.0079 inches, or approximately 0.0079 inches. In other instances, the wire can have a diameter of 0.0089 inches, or approximately 0.0089 inches. In still other instances, the wire can have a diameter of 0.0094, or approximately 0.0094 inches. In certain instances, the wire can have a diameter of less than 0.0079 inches or more than 0.0094 inches. The reader will appreciate that the diameter of the wire can dictate the diameter of the staple. The staple 3042 is a substantially U-shaped staple having a base 3050, a first leg 3052 extending from a first end of the base 3050, and a second leg 3054 extending from a second end of the base 3050. The first leg 3052 is substantially parallel to the second leg 3054 and substantially perpendicular to the base 3050. When implanted in tissue T, the angular orientation of the base 3050 corresponds to the angular orientation of the staple cavity opening 3012 from which the staple 3042 was fired.

Another exemplary staple 3142 for use with various staple cartridges described herein is depicted in FIG. 60. The staple 3142 is a substantially V-shaped staple having a base 3150, a first leg 3152 extending from a first end of the base 3050, and a second leg 3154 extending from a second end of the base 3150. The first leg 3152 is obliquely oriented relative to the second leg 3154 and the base 3150. When implanted in tissue T, the orientation of the base 3150 corresponds to the orientation of the staple cavity opening 3012 from which the staple 3142 was fired. The reader will appreciate that staples having different geometries can also be fired from the staple cartridges described herein.

Referring again to FIG. 58, the staple line 3040 includes a first portion 3044, a proximal portion 3046, and a distal portion 3048. The first portion 3044 is generated from the first pattern, or major pattern, 3020 and extends along a substantial portion of the staple line 3040. Owing to the angular orientation of the staples 3042 in the first portion 3044, the first portion 3044 is substantially flexible or compliant. For example, because the angularly-oriented staples 3042 can rotate within the stapled tissue T while minimizing trauma to the tissue T, the first portion 3044 is configured to stretch or extend longitudinally and/or laterally as the stapled tissue stretches.

The proximal portion 3046 is generated from the proximal pattern 3022 and forms the proximal end of the staple line 3040. The distal portion 3048 is generated from the distal pattern 3024 and forms the distal end of the staple 3040. Owing to the parallel orientation of the staples 3042 in the proximal portion 3046 and the distal portion 3048 of the staple line 3040, the proximal portion 3046 and the distal portion 3046 of the staple line 3040 can be less flexible than the first portion 3044. However, the reduced flexibility of the proximal portion 3046 and the distal portion 3048 may not impact, or not substantially impact, the overall flexibility of the staple line 3040. Moreover, as described herein, the proximal portion 3046 and the distal portion 3048 may not extend adjacent to the cutline and, in certain instances, the proximal portion 3046 may be absent or missing from the staple line 3040.

Figure 55:
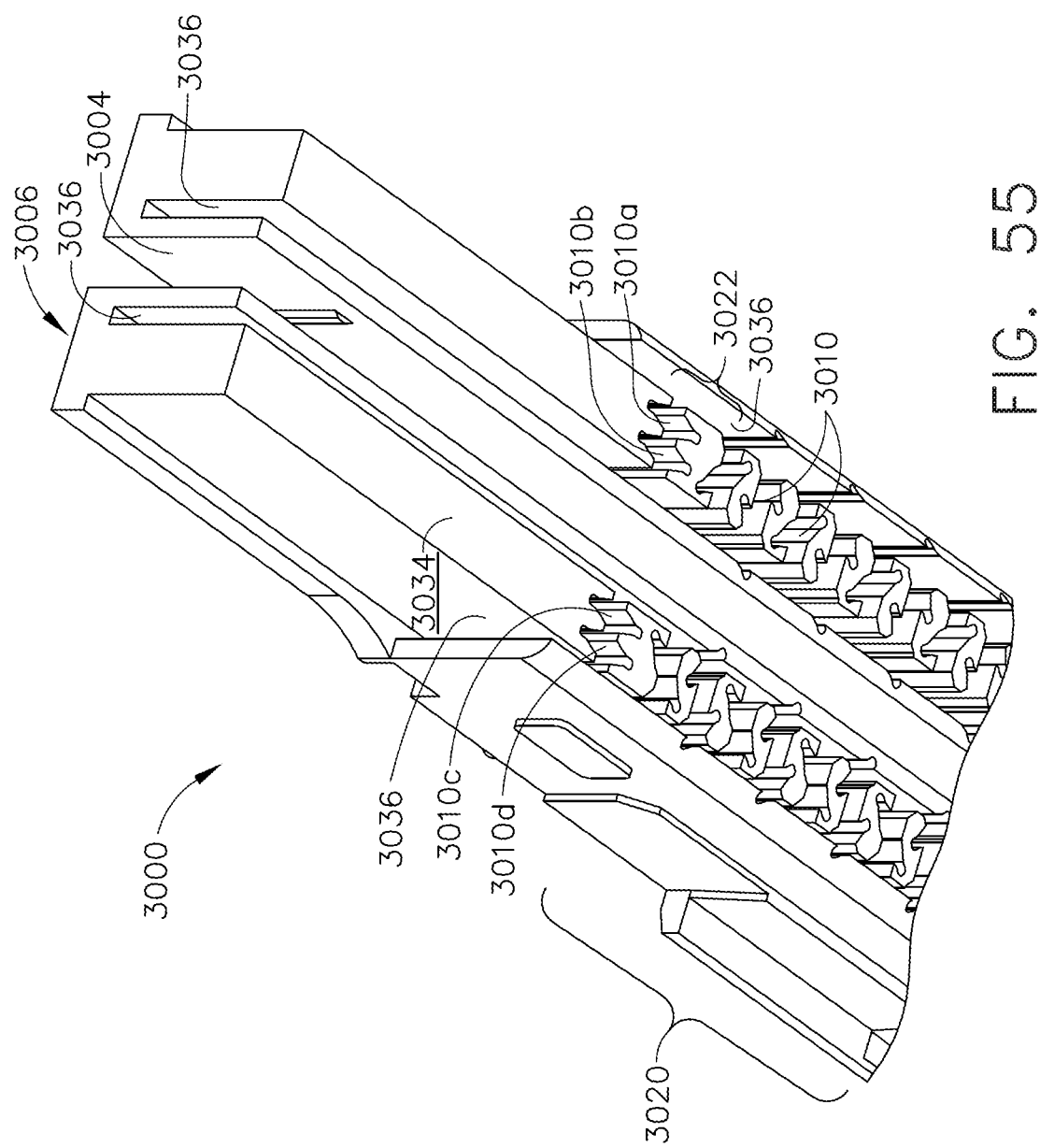
FIG. 55 is a partial perspective bottom view of the staple cartridge body of FIG. 54.

A firing element, such as the firing member 1760 (FIG. 4), is configured to move along at least a portion of the slot 3004 to fire the staples 3042 from the staple cavities 3010. The firing element can include and/or engage one of more wedge sleds and/or camming surfaces, such as the sled assembly 1120 having wedge-shaped cams 1122 (FIG. 4). The cams of the sled are configured to drive the staples upward toward a staple-forming surface, such as into forming pockets in the anvil 1130 (FIGS. 1, 3 and 4), for example. Referring to FIG. 55, the staple cartridge body 3000 includes a plurality of channels 3036 along a bottom surface 3034 through which the wedge-shaped cams can move during a firing stroke.

In use, target tissue is clamped between the staple cartridge body 3000 and an anvil, such as the anvil 1130 (FIGS. 1, 3 and 4). The tissue overlapping the staple cavities 3010 is stapled. If tissue is not positioned over certain staple cavities 3010, staples fired from those staple cavities 3010 may not engage the tissue. An anvil typically contains downwardly extending sidewalls commonly referred to as "tissue stops". The tissue stops are configured to block the target tissue from getting too far proximal between the anvil and cartridge. For example, referring to the end effector 1100 in FIG. 4, the anvil 1130 includes tissue stops 1131, which extend toward the staple cartridge 1110. When the anvil 1130 is closed toward the cartridge 1110, the tissue stops 1131 on either side of the anvil 1130 extend downward past the cartridge deck surface 1115 and form a wall or barrier, which prevents tissue from being positioned too far proximal between the anvil 1130 and cartridge 1110. The distal ends of the tissue stops 1131 define a proximal starting point for the cutline. A proximal axis PA corresponding to the distal ends of the tissue stops 1131 is depicted in FIG. 56. Because target tissue is not positioned proximal to the proximal axis PA, the staples that are fired from the staple cavities located proximal to the proximal axis PA, i.e., the proximal staple cavities 3010a-3010d, are not fired into the target tissue. In such instances, staples fired from the proximal pattern 3022 do not form a part of the staple line.

A cutting element 3028 (FIG. 56) is also configured to move along the longitudinal slot 3004. In various instances, the cutting element 3028 can be an integral part of the firing element, such as the tissue cutting feature 1766 on the firing member 1760 (FIG. 4), for example. The cutting element 3028 has a distal cutting edge 3029 that is configured to incise tissue clamped by the end effector and stapled by the staples 3042. Referring primarily to FIG. 56, the cutting edge 3029 of the cutting element 3028 is configured to move between a proximal position near the proximal end portion 3006 of the cartridge body 3000 and a distal position near the distal end portion 3008 of the cartridge body 3000. The distal-most position of the cutting edge 3029 is defined by a distal termination point for the cutline. A distal axis DA corresponding to the distal termination point of the cutting edge 3029 is depicted in FIG. 56. Tissue positioned distal to the distal axis DA is not incised by the cutting element 3028 during the firing stroke.

The first pattern 3020 of staple cavities 3010 extends between the proximal axis PA and the distal axis DA. Moreover, at least one staple cavity 3010 in the first pattern 3020 overlaps the proximal axis PA and the distal axis DA. In other instances, more than one longitudinally-repetitive pattern of staple cavities 3010 can be positioned between the proximal axis PA and the distal axis DA. The proximal pattern 3022 is positioned proximal to the proximal axis PA, and the distal pattern 3024 is positioned distal to the distal axis DA. In such instances, staples fired from the distal staple cavities 3010e-3010h are not configured to staple incised tissue. Moreover, staples fired from the proximal staple cavities 3010a-3010d are not configured to staple the target tissue. Accordingly, such staples may not impact the flexibility and/or sealing quality of the resultant staple line.

In certain instances, it can be desirable to generate a staple line having a first flexibility adjacent to the cutline and a different flexibility proximal to and/or distal to the cutline. For example, a staple line that includes at least two parallel staples on each side of the cutline and positioned distal to the distal end of the cutline, may provide certain advantages. In certain instances, a staple arrangement that provides less flexibility may prevent and/or limit the propagation of the cutline and/or tearing of the tissue. Additionally, the tissue adjacent to an uncut portion may experience less stress and/or strain than the tissue adjacent to the cutline and, thus, may require less flexibility to prevent and/or limit tissue trauma. More specifically, tissue adjacent to the cutline may experience more forces during the cutting stroke and, thus, increased flexibility may prevent trauma to the tissue. Additionally, the tissue adjacent to the cutline may stretch as it heals and thus, increased flexibility may facilitate the healing process. For tissue that experiences fewer forces, such as the tissue distal to the cutline, for example, the reduced flexibility may reinforce or strengthen the staple line and prevent distal propagation of the cutline.

In the depicted arrangement, the proximal pattern 3022 includes two irregular staple cavities on each side of the knife slot 3004 adjacent to the proximal end of the first pattern 3020 and the distal pattern 3024 includes two irregular staple cavities on each side of the knife slot 3004 adjacent to the distal end of the first pattern 3020. In other instances, the proximal pattern 3022 and/or the distal pattern 3024 can consist of a single irregular staple cavity on one or both sides of the knife slot 3004. In still other instances, the proximal pattern 3022 and/or the distal pattern 3024 can include three or more irregular staple cavities on one or both sides of the knife slot 3004. The proximal pattern 3022 and/or the distal pattern 3024 can include longitudinally repetitive sub-patterns. For example, the proximal pattern 3022 and/or the distal pattern 3024 can include multiple columns of parallel staple cavity openings 3012. In certain instances, the staple cartridge body 3000 can have a single irregular pattern, which can be positioned at either the proximal end or distal end of the first pattern 3020.

In certain instances, one or more staple cavities in the proximal pattern 3022 and/or the distal pattern 3024 can be non-parallel to the knife slot 3004. For example, such staple cavities can be oriented perpendicular to the knife slot 3004 or at an oblique angle relative to the knife slot 3004. Additionally or alternatively, certain staple cavities in the proximal pattern 3022 and/or the distal pattern 3024 can be non-parallel to each other Referring primarily to FIG. 57, staple drivers 3060 are positioned in the staple cavities 3010 of the cartridge body 3000. The staple drivers 3060 are positioned to support the staples 3042 (FIGS. 58 and 59) therein and to drive the staples 3042 from the staple cavities 3010 during a firing stroke. Owing to the different patterns of staple cavities 3010 in the cartridge body 3000, e.g., the patterns 3020, 3022 and 3024, the staple drivers 3060 can have different geometries and/or orientations. For example, the staple drivers 3060 positioned in the staple cavities 3010 of the first pattern 3020 may include connected drivers as described in U.S. patent application Ser. No. 14/498,145, filed Sep. 26, 2014, now U.S. Patent Application Publication No. 2016/0089142, entitled METHOD FOR CREATING A FLEXIBLE STAPLE LINE, which is incorporated by reference herein in its entirety. Each connected driver can include an inner driver positioned in a staple cavity 3010 in the inner row 3014a, an intermediate driver positioned in a staple cavity 3010 in the intermediate row 3014b, and an outer driver positioned in a staple cavity 3010 in the outer row 3014c. A connecting flange can connect the intermediate driver to at least one inner driver and at least one outer driver. In other instances, the staple drivers positioned in the staple cavities in the first pattern 3020 may include individual drivers, wherein each driver drives a single staple. In still other instances, the staples can be direct-drive staples, which can be driven by direct contact with a wedge sled and/or camming surfaces, as described in U.S. patent application Ser. No. 14/138,475, filed on Dec. 23, 2013, now U.S. Patent Application Publication No. 2015/0173749, entitled SURGICAL STAPLES AND STAPLE CARTRIDGES and U.S. patent application Ser. No. 14/498,145, which are incorporated by reference herein in their respective entireties.

The drivers 3060 positioned in the staple cavities 3010 are dimensioned and positioned for driving engagement by the sled and camming surfaces thereof. For example, the drivers 3060 are positioned in the staple cavities 3010 of the first pattern 3020. Proximal drivers 3060a, 3060b, 3060c, and 3060d are positioned in the staple cavities 3010a, 3010b, 3010c, and 3010d, respectively, of the proximal pattern 3022, and distal drivers 3060e, 3060f, 3060g, and 3060h are positioned in the staple cavities 3010e, 3010f, 3010g, and 3010h, respectively, of the distal pattern 3024. Referring again to FIG. 4, the sled assembly 1120 and the wedge-shaped cams 1122 thereof can be configured to lift the drivers 3060 in the staple cavities 3010. In such instances, the cams 1122 are configured to drivingly engage the drivers 3060 along the length of the cartridge body 3000. More specifically, the cams 1122 initially engage and drive the proximal drivers 3060a, 3060b, 3060c, and 3060d to fire the staples in the proximal pattern 3022, then engage and drive the drivers 3060 to fire the staples in the first pattern 3022, and finally engage and drive the distal drivers 3060e, 3060f, 3060g, and 3060h to fire the staples in the distal pattern 3024. Although the proximal drivers 3060a, 3060b, 3060c, and 3060d and/or the distal drivers 3060e, 3060f, 3060g, and 3060h have a different geometry than the drivers 3060 in the first pattern 3020 of staple cavities 3010, the sled and camming surfaces thereof are compatible with the different drivers in the cartridge body 3000.

Referring again to FIG. 4, the sled assembly 1120 includes four camming surfaces 1122. A first pair of camming surfaces 1122 are positioned for driving engagement with the staple drivers on the first side of the longitudinal axis LA, and a second pair of camming surfaces 1122 are positioned for driving engagement with the staple drivers on the second side of the longitudinal axis LA. The camming surfaces 1122 in each pair are longitudinally offset. In other instances, the camming surfaces 1122 can be longitudinally aligned. Each pair of camming surfaces 1122 is configured to lift a triple driver (see, e.g., the driver 1170 in FIGS. 33A-33C), i.e., a connected driver supporting a staple in the inner row 3014a of staple cavities 3010, a staple in the intermediate row 3014b of staple cavities 3010, and a staple in the outer row 3014c of staple cavities 3010. The camming surfaces 1122 are also configured to lift the proximal drivers 3060a, 3060b, 3060c, and 3060d and the distal drivers 3060e, 3060f, 3060g, and 3060h. In other instances, the sled assembly 1120 can include more than or less than four camming surfaces.

Figure 63:
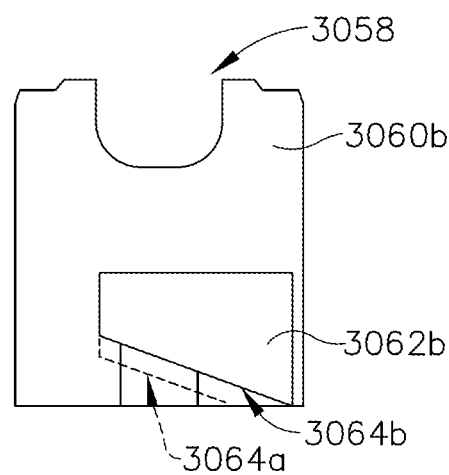
FIG. 63 is a side elevation view of the drivers of FIG. 62 depicting an offset ramped surface with a phantom line.
Figure 64:
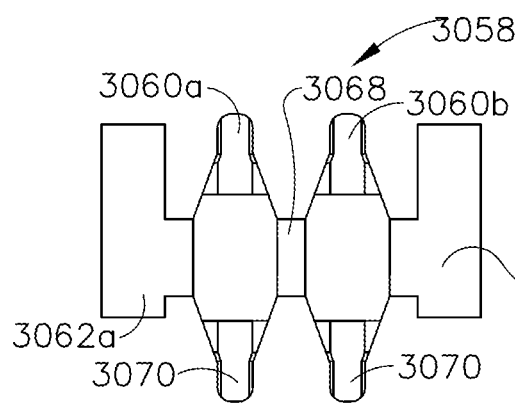
FIG. 64 is a plan view of the drivers of FIG. 62.
Figure 65:
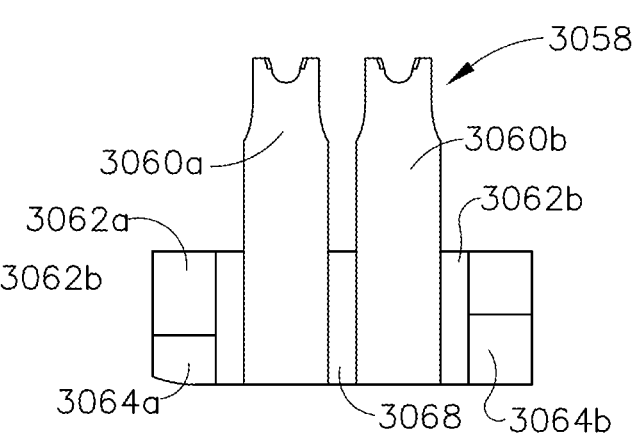
FIG. 65 is a front elevation view of the drivers of FIG. 62.

The proximal drivers 3060a-3060d and the distal drivers 3060e-3060h are connected drivers 3058. An exemplary connected driver 3058 is depicted in FIGS. 62-65. The connected driver 3058 includes the first driver 3060a and the second driver 3060b. A connecting flange 3068 extends between the two drivers 3060a and 3060b. Because the first and second drivers 3060a and 3060b are connected, the staples supported by the first and second drivers 3060a, 3060b are fired simultaneously by the sled assembly. Each driver 3060a and 3060b also includes a cradle 3070 for supporting the base of the staple. A guide 3062a and 3062b extends laterally from each driver 3060a and 3060b, respectively. The first guide 3062a extends in a first direction and forms an outside portion of the connected driver 3058 and the second guide 3062b extends in a second, opposite direction and forms an inside portion of the connected driver 3058. Ramped surfaces 3064a and 3064b on the guides 3062a and 3062b, respectively, are positioned for driving contact with the camming surfaces of the sled assembly. The guides 3062a and 3062b are driven upward in the channels 3036 (FIG. 55) of the cartridge body 3000 when moved to a fired position by the sled assembly. The channels 3036 form a vertical support structure through which the guides 3062a, 3062b are driven by the camming surfaces. As described herein, the camming surfaces can be longitudinally offset. In such instances, the ramped surfaces 3064a, 3064b are correspondingly offset, as depicted in FIGS. 63 and 65. In other instances, the ramped surfaces 3064a and 3064b can be aligned.

Figure 61:
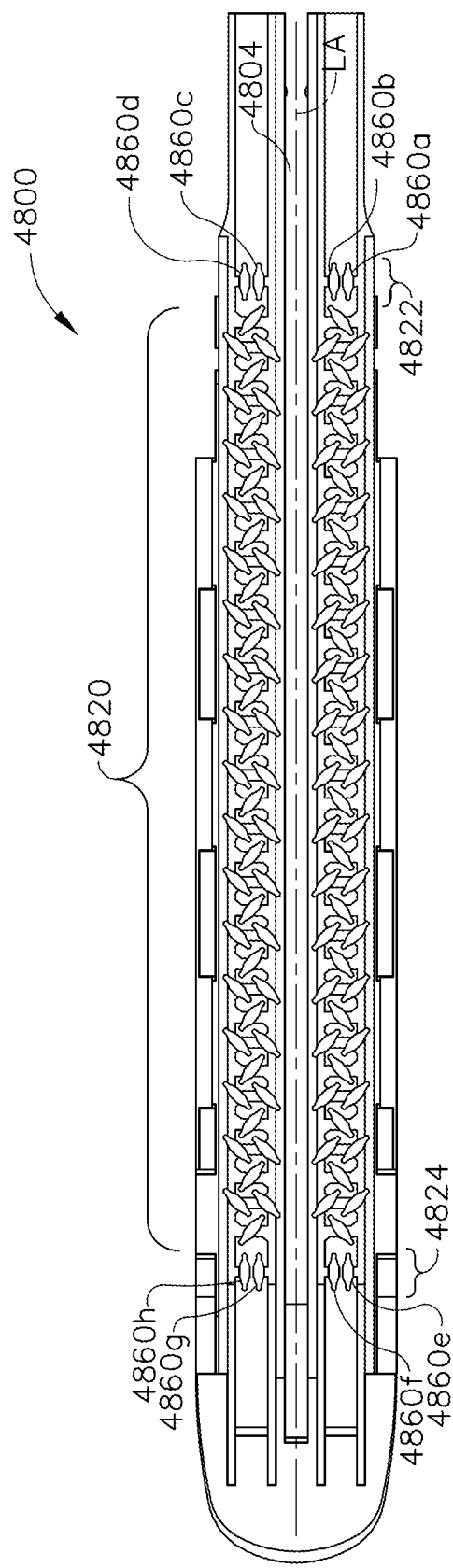
FIG. 61 is a bottom plan view of a staple cartridge body having a plurality of staple cavities defined therein and depicting drivers positioned in the staple cavities.
Figure 62:
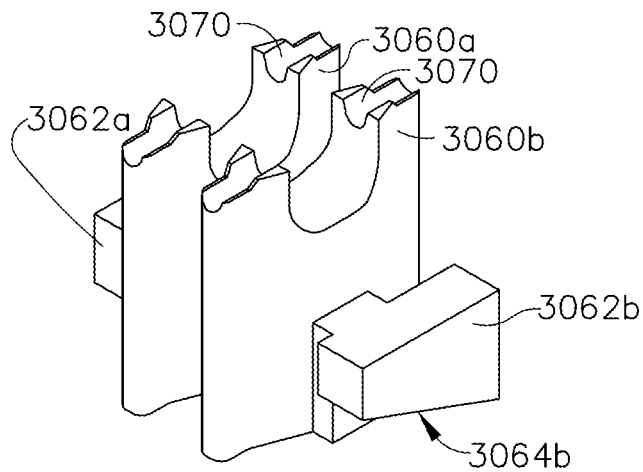
FIG. 62 is a perspective view of the drivers in the proximal staple cavities of FIG. 57.

In other instances, the proximal drivers and/or the distal drivers in a staple cartridge may not be connected. For example, referring to FIG. 61, a staple cartridge 4800 is depicted. The staple cartridge body 4800 is similar in many aspects to the staple cartridge body 3000. For example, the staple cartridge body 4800 includes a first pattern 4820 of angularly-oriented staple cavities, which are arranged in a herringbone pattern. A slot 4804 extends along the longitudinal axis LA of the cartridge body 4800. The staple cartridge body 4800 also includes proximal staple cavities arranged in a proximal pattern 4822 and distal staple cavities arranged in a distal pattern 4824. The proximal pattern 4822 includes a first pair of parallel, longitudinally-aligned staple cavities on a first side of the slot 4804 and a second pair of parallel, longitudinally-aligned staple cavities on a second side of the longitudinal slot 4804. The distal pattern 4824 also includes a first pair of parallel, longitudinally-aligned staple cavities on the first side of the slot 4804 and a second pair of parallel, longitudinally-offset staple cavities on the second side of the longitudinal slot 4804. The proximal pattern 4822 and the distal pattern 4824 are symmetric relative to the longitudinal axis LA. In other instances, the proximal pattern 4822 and/or the distal pattern 4824 can be asymmetric relative to the longitudinal axis LA.

Figure 66:
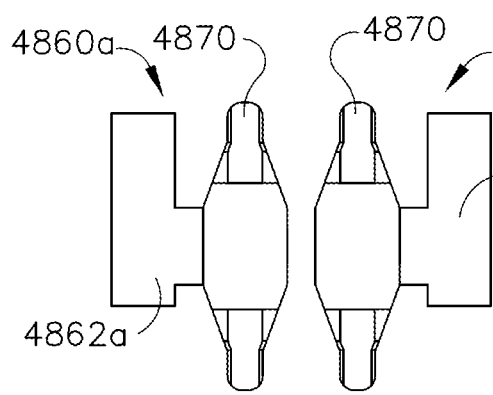
FIG. 66 is a plan view of the drivers in the proximal staple cavities of the staple cartridge body of FIG. 61.
Figure 67:
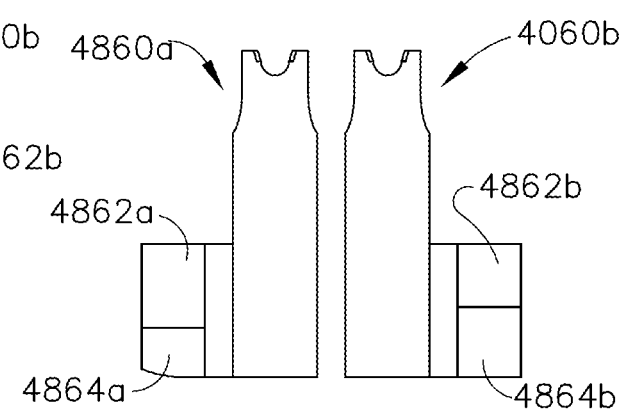
FIG. 67 is a front elevation view of the drivers of FIG. 66.

Drivers 4860 are positioned in the staple cavities 4810 of the first pattern 4820. The drivers 4860 in the staple cavities 4810 of the first pattern 4820 are triple drivers, as described herein. Proximal drivers 4860a, 4860b, 4860c, and 4860d are positioned in the staple cavities of the proximal pattern 4822, and distal drivers 4860e, 4860f, 4860g, and 4860h are positioned in the staple cavities of the distal pattern 4824. The proximal drivers 4860a-4860d and the distal drivers 4860e-4860h are single drivers. Exemplary single drivers 4860a and 4860b are depicted in FIGS. 66 and 67.

Each driver 4860a and 4860b includes a cradle 4870 for supporting the base of the staple. A guide 4862a and 4862b extends laterally from each driver 4860a and 4860b, respectively. The first guide 4862a extends in a first direction and forms an outside portion of the first driver 4860a and the second guide 4862b extends in a second, opposite direction and forms an outside portion of the second driver 4860b. Ramped surfaces 4864a and 4864b on the guides 4862a and

4862b, respectively, are positioned for driving contact with the camming surfaces of a sled assembly. The guides 4862a and 4862b are driven upward in channels in the cartridge body 4800, such as the channels 3036 in the cartridge 3000 (FIG. 55), when the drivers 4860a and 4860b are moved to a fired position by the sled assembly. The channels form a vertical support structure through which the guides 4862a and 4862b are driven by the camming surfaces. Such channels can stabilize the guides 4862a and 4862b and, thus, stabilize the individual drivers 4860a and 4860b, respectively, during deployment. As described herein, the camming surfaces can be longitudinally offset. In such instances, the ramped surfaces 4864a, 4864b are correspondingly offset, as depicted in FIG. 67. In other instances, the ramped surfaces 4864a and 4864b can be aligned.

Because the first and second drivers 4860a, 4860b are separate, the staples supported by the first and second drivers 4860a, 4860b can be fired independently. In certain instances, the first driver 4860a and the second driver 4860b can be fired sequentially. It can be advantageous to fire an inner staple before an outer staple, for example, which can be accomplished with the separate drivers 4860a and 4860b. In other instances, an outer staple can be fired before an inner staple with the separate drivers 4860a and 4860b. The firing order can be modified by adjusting the relationship between the camming surfaces and the ramped surfaces 3864a and 4864b, for example.

In various instances, the staple cavities in a distal pattern and/or a proximal pattern may not be longitudinally-aligned and/or may not be parallel. For example, referring now to FIGS. 68 and 69, a staple cartridge body 4600 is depicted. The staple cartridge body 4600 is similar in many aspects to the staple cartridge body 3000. For example, the staple cartridge body 4600 includes a first pattern 4620 of angularly-oriented staple cavities 4610, which are arranged in a herringbone pattern. A slot 4604 extends through a deck 4602 of the staple cartridge body 4600 along the longitudinal axis LA of the cartridge body 4600. The staple cartridge body 4600 also includes proximal staple cavities 4610a-4610d arranged in a proximal pattern 4622 and distal staple cavities 4610e-4610h arranged in a distal pattern 4624. The proximal pattern 4622 includes a first pair of parallel, longitudinally-offset staple cavities 4610a, 4610b on a first side of the slot 4604 and a second pair of parallel, longitudinally-offset staple cavities 4610c, 4610d on a second side of the longitudinal slot 4604. The distal pattern 4624 also includes a first pair of parallel, longitudinally-offset staple cavities 4610e, 4610f on the first side of the slot 4604 and a second pair of parallel, longitudinally-offset staple cavities 4610g, 4610h on the second side of the longitudinal slot 4604. The proximal pattern 4622 and the distal pattern 4624 are symmetric relative to the longitudinal axis LA. In other instances, the proximal pattern 4622 and the distal pattern 4624 can be asymmetric relative to the longitudinal axis LA.

Figures 70, 71:
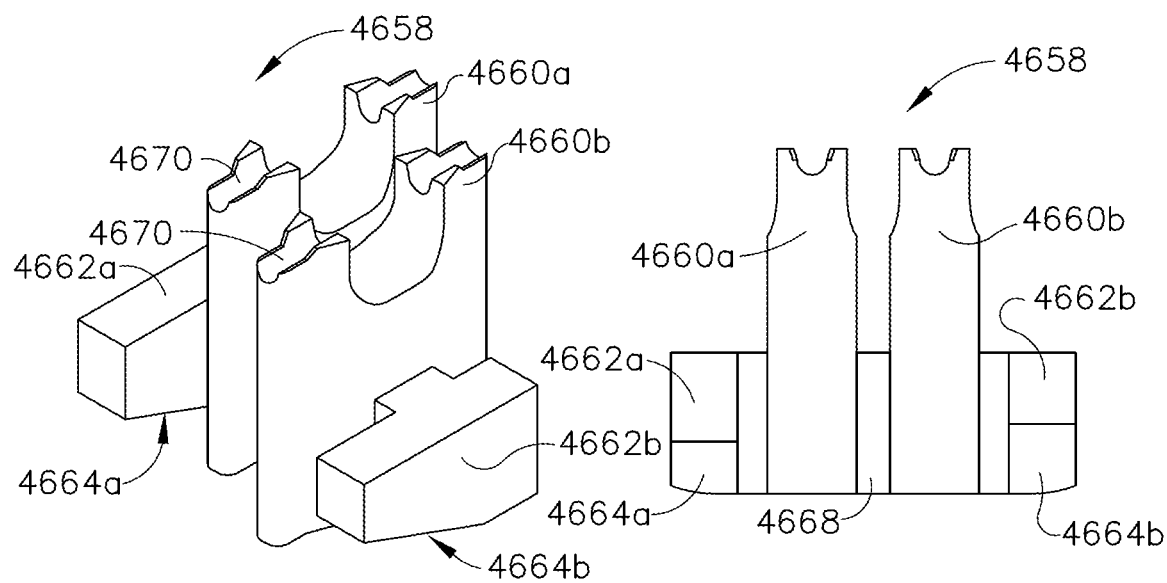
FIG. 70 is a perspective view of the drivers in the proximal staple cavities of FIG. 69.
FIG. 71 is a front elevation view of the drivers of FIG. 70.
Figures 72, 73:
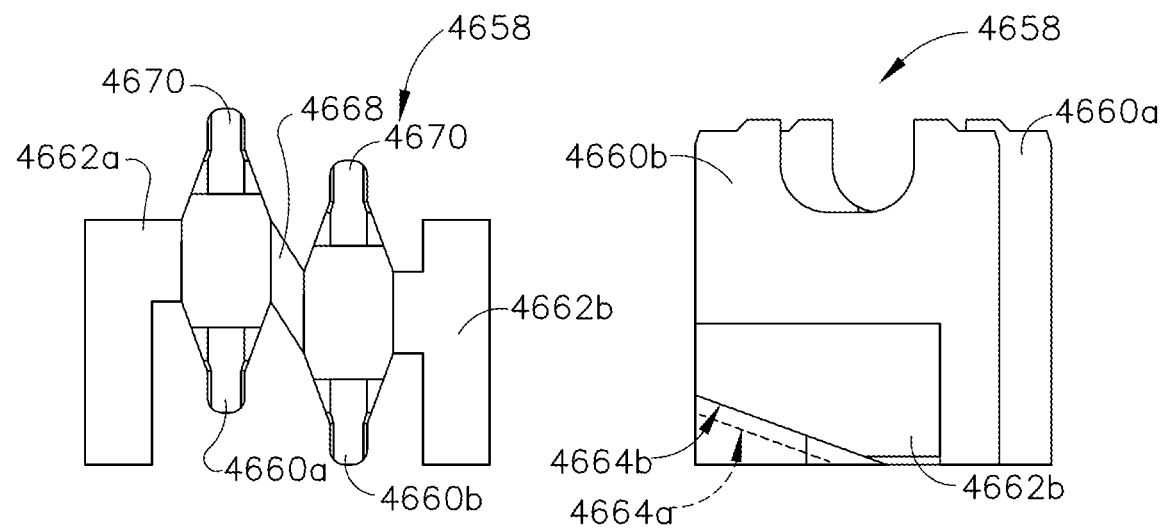
FIG. 72 is a plan view of the drivers of FIG. 70.
FIG. 73 is a side elevation view of the drivers of FIG. 70 depicting an offset ramped surface with a phantom line.

Connected drivers 4658 are positioned in the proximal and distal staple cavities 4610a-4610h. An exemplary connected driver 4658 is depicted in FIGS. 70-73. The connected driver 4658 includes the first driver 4660a and the second driver 4660b. A connecting flange 4668 extends between the two offset drivers 4660a and 4660b. Because the drivers 4660a and 4660b are connected, the staples supported by the drivers 4660a, 4660b are fired simultaneously by the sled assembly. Each driver 4660a and 4660b includes a cradle 4670 for supporting the base of the staple. A guide 4662a and 4662b extends laterally from each driver 4660a and 4660b, respectively. The first guide 4662a extends in a first direction and forms an outside portion of the connected driver 4658 and the second guide 4662b extends in a second, opposite direction and forms an inside portion of the connected driver 4658. Ramped surfaces 4664a and 4664b on the guides 4662a and 4662b, respectively, are positioned for driving contact with the camming surfaces of a sled assembly. The guides 4662a and 4662b are driven upward in channels in the cartridge body 4800, such as the channels 3036 in the staple cartridge 3000 (FIG. 55), for example, when the drivers 4660a, 4660b are moved to a fired position by the sled assembly. The channels form a vertical support structure through which the guides 4662a, 4662b are supported as they are driven by the camming surfaces. As described herein, the camming surfaces can be longitudinally offset. In such instances, the ramped surfaces 4664a, 4664b are correspondingly offset, as depicted in FIGS. 71 and 73. In other instances, the ramped surfaces 4664a and 4664b can be aligned.

Figure 74:
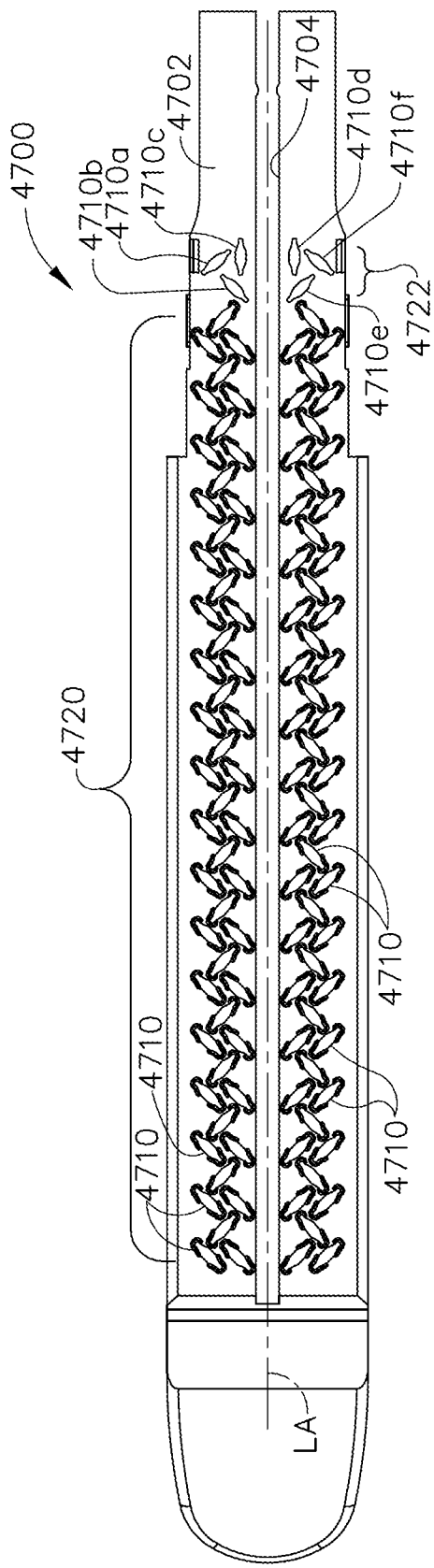
FIG. 74 is a top plan view of a staple cartridge body having a plurality of staple cavities defined therein.
Figure 75:
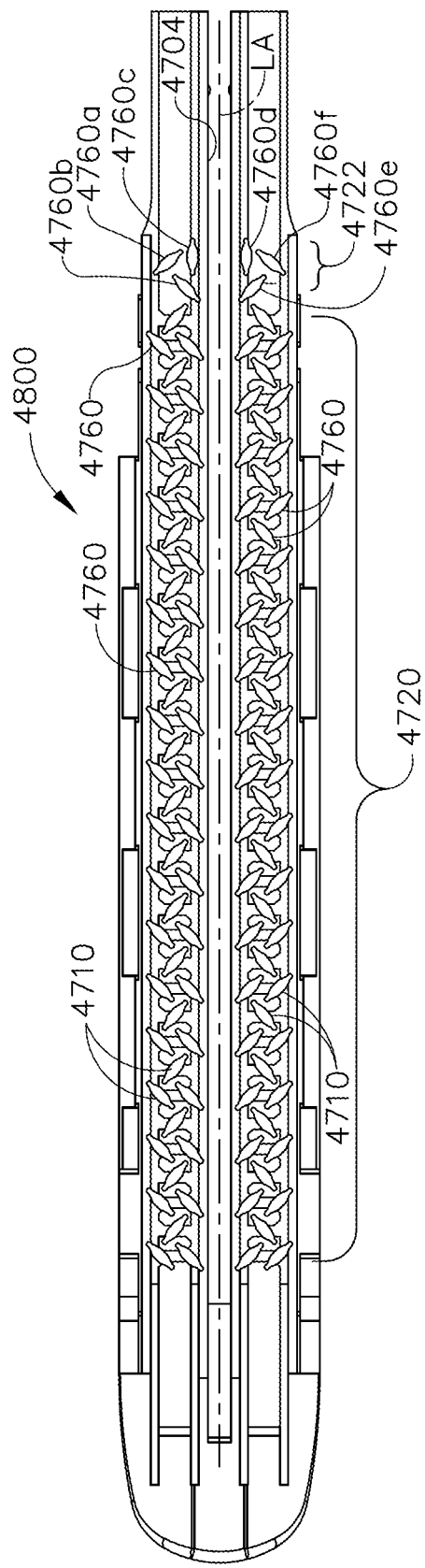
FIG. 75 is a bottom plan view of the staple cartridge body of FIG. 74 and depicting drivers positioned in the staple cavities.

Referring now to FIGS. 74 and 75, a staple cartridge body 4700 is depicted. The staple cartridge body 4700 is similar in many aspects to the staple cartridge body 3000. For example, the staple cartridge body 4700 includes a first pattern 4720 of angularly-oriented staple cavities 4710, which are arranged in a herringbone pattern. A slot 4704 extends through a deck 4702 of the staple cartridge body 4700 along the longitudinal axis LA of the cartridge body 4700. The staple cartridge body 4700 also includes proximal staple cavities 4710a-4710f arranged in a proximal pattern 4722. The proximal pattern 4722 includes inner staple cavities 4710c and 4710d, which are oriented parallel to the longitudinal axis LA. The proximal pattern 4722 also includes angularly-oriented outer staple cavities 4710a and 4710f, and angularly-oriented intermediate cavities 4710b and 4710e. The outer staple cavities 4710a and 4710f and the intermediate staple cavities 4710b and 4710e are oriented at oblique angles relative to the longitudinal axis LA. The angularly-oriented outer staple cavities 4710a and 4710f are also oriented at oblique angles relative to the cavity axes of the staple cavities 4710 in the first pattern 4720. The outer staple cavities 4710a and 4710f are less angled than the staple cavities 4710 in the first pattern 4720. In other words, the outer staple cavities 4710a and 4710f are oriented at an angle that is closer to parallel with the longitudinal axis LA than the staple cavities 4710 in the first pattern 4720. In such instances, the proximal pattern 4722 can be less flexible than the first pattern 4720.

The intermediate staple cavities 4710b and 4710e are oriented parallel to certain staple cavities 4710 in the first pattern 4020. For example, the intermediate staple cavities 4710b and 4710e are oriented parallel to the staple cavities 4710 in an inner row in the first pattern 4720. Though certain staple cavities in the proximal pattern 4722 are not angularly offset from the staple cavities in the first pattern 4020, the proximal pattern 4722, when considered as a whole, is different than the first pattern 4020 and is different than the longitudinally-repetitive sub-patterns within the first pattern 4020.

The proximal pattern 4722 includes three staple cavities positioned on each side of the slot 4704. In other instances, less than three staple cavities or more than three staple cavities can be arranged in the proximal pattern 4722 on one or both sides of the slot 4704. The proximal pattern 4722 does not include a longitudinally-repetitive sub-pattern. In other instances, the proximal pattern 4722 can be longitudinally repetitive. Additionally, the proximal pattern 4722 is symmetric relative to the longitudinal axis LA. In other instances, the proximal pattern 4722 can be asymmetric relative to the longitudinal axis LA.

Drivers 4760 are positioned in the staple cavities 4710 in the cartridge body 4700. The drivers 4760 in the staple cavities 4710 of the first pattern 4720 are triple drivers, as described herein. Proximal drivers 4760a, 4760b, 4760c, 4760d, 4710e, and 4710f are positioned in the proximal staple cavities 4710a, 4710b, 4710c, 4710d, 4710e, and 4710f respectively, of the proximal pattern 4722. The proximal drivers 4760a-4760f are single drivers. In certain instances, the proximal drivers 4760c and 4760d in the inner cavities 4710c and 4710d, respectively, can be single drivers, the proximal drivers 4760a and 4760b can be connected drivers, and the proximal drivers 4760e and 4760f can be connected drivers. In still other instances, the proximal drivers 4760a, 4760b, and 4760c can comprise a first connected driver, and the distal drivers 4760d, 4760e, and 4760f can comprise a second connected driver.

The reader will appreciate that the various patterns of staple cavities described herein can be combined and/or interchanged. In certain instances, one or more irregular patterns of staple cavities can be defined at the proximal and/or distal end of a staple cartridge body. Additionally or alternatively, one or more irregular patterns, or minor patterns, can be sandwiched or inserted within a major pattern.

The angular orientation of staples in a staple line can influence the flexibility or compliance of the stapled tissue along the staple line. For example, the flexibility of a staple line can increase when staples are oriented at an oblique angle relative to the longitudinal axis and/or cutline. Such an angular orientation can provide flexibility or extendibility, within certain limits, in response to forces, such as tension and/or torsion, along and/or adjacent to the cutline. More specifically, the flexibility in the staple line can permit stretching, buckling, folding, and/or twisting of the stapled tissue. Generally, as the angular orientation of a staple approaches 45 degrees or 135 degrees relative to the longitudinal axis of the staple line and/or the cutline, the flexibility of the stapled tissue increases. A staple line comprised of angularly-oriented staples can be considered a compliant or elastic staple line, for example.

In certain instances, the flexibility of a staple line can vary laterally relative to the cutline. For example, one or more staples in a first portion of the staple line can be oriented at a first angle relative to the cutline and one or more staples in a second portion of the staple line can be oriented at a different angle relative to the cutline. The first portion of the staple line can have a first flexibility and the second portion of the staple line can have a different flexibility. In certain instances, the first portion can be laterally offset from the second portion. For example, the first portion of the staple line can include a first row of staples or portion of the first row, and the second portion of the staple line can include a second row of staples or portion of the second row. In such instances, the flexibility of the staple line along the first row of staples can be different than the flexibility of the staple line along the second row of staples.

Figure 76:
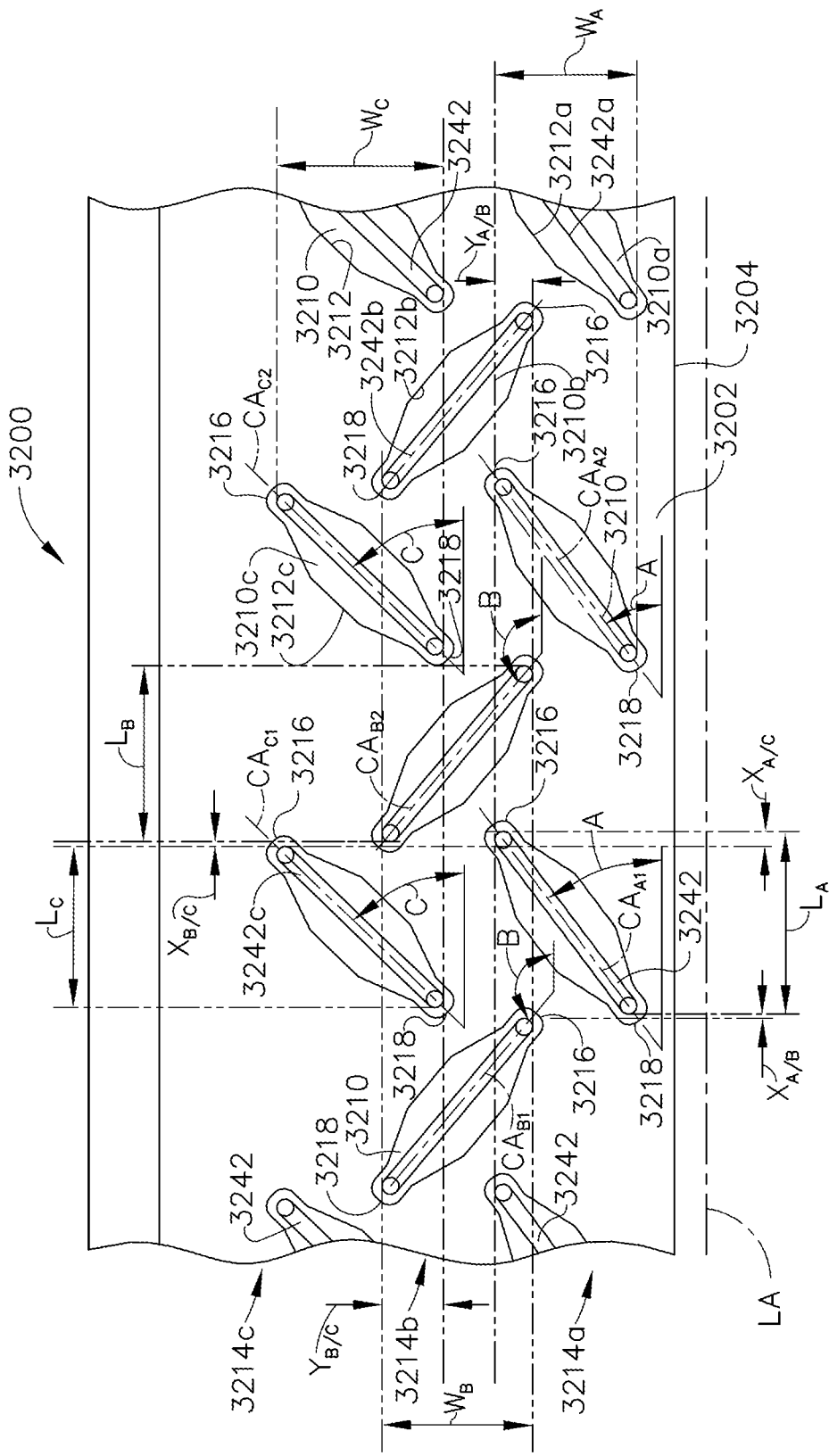
FIG. 76 is a plan view of a portion of a staple cartridge body having a plurality of angularly-oriented staple cavities defined therein and depicting staples in the staple cavities.

Referring now to FIG. 76, a portion of a staple cartridge body 3200 is depicted. The staple cartridge body 3200 includes a deck 3202 and a longitudinal slot 3204. The longitudinal slot 3204 extends along the longitudinal axis LA. Staple cavities 3210 are defined in the staple cartridge body 3200, and each staple cavity 3210 defines an opening 3212 in the deck 3202. A staple 3242 is positioned in each staple cavity 3210. The staple 3242 can be similar in many aspects to the staple 3042 (FIG. 59) or the staple 3142 (FIG. 60). In certain instances, the legs of each staple 3242 can be biased against the inside wall of the staple cavity 3210. The reader will appreciate that the arrangement of staples 3242 in the staple cavities 3210 corresponds to the arrangement of staples 3242 in a staple line when the staples 3242 are fired from the staple cartridge body 3200 and into tissue. More specifically, the bases of each staple 3242 in a resultant staple line are collinear, or substantially collinear, with the cavities axes CA.

The staple cavity openings 3212 are arranged in three rows 3214a, 3214b, and 3214c on a first side of the longitudinal slot 3204. Inner openings 3212a define the perimeter of inner cavities 3210a in the inner row 3214a, intermediate openings 3212b define the perimeter of intermediate cavities 3210b in the intermediate row 3214b, and outer openings 3212c define the perimeter of outer cavities 3210c in the outer row 3214c. Inner staples 3242a are positioned in the inner cavities 3210a, intermediate staples 3242b are positioned in the intermediate cavities 3210b, and outer staples 3242c are positioned in the outer cavities 3210c. Although not shown in FIG. 76, in at least one instance, the staple cavities 3210 on the opposing side of the slot 3204 form a mirror image reflection of the staple cavities 3210 on the first side of the longitudinal slot 3204. Consequently, the arrangement of staples 3242 in a resultant staple line is symmetric relative to the cutline. In other instances, the staple line can be asymmetric relative to the cutline.

Each staple cavity opening 3212 has a first end, or proximal end, 3216 and a second end, or distal end, 3218. A cavity axis CA extends between the proximal end 3216 and the distal end 3218 of each opening 3212. The staple cavity openings 3212 in each respective row are parallel. For example, the inner cavities 3210a are oriented at an angle A relative to the longitudinal axis LA. Stated differently, the cavity axes (e.g., $CA_{A1}$ and $CA_{A2}$) of the inner openings 3212a are oriented at the angle A relative to the longitudinal axis LA. The intermediate cavities 3210b are oriented at an angle B relative to the longitudinal axis LA. Stated differently, the cavity axes (e.g., $CA_{B1}$ and $CA_{B2}$) of the intermediate openings 3212b are oriented at the angle B relative to the longitudinal axis LA. The outer cavities 3210c are oriented at an angle C relative to the longitudinal axis LA. Stated differently, the cavity axes (e.g., $CA_{C1}$ and $CA_{C2}$) defined by the outer openings 3212 are oriented at the angle C relative to the longitudinal axis LA.

The angles A, B, and C are different. Consequently, the inner openings 3212a are obliquely oriented relative to the outer openings 3212c. Because the cavity axes CA of the outer openings 3212c (e.g., axes $CA_{C1}$ and $CA_{C2}$) are not parallel to the cavity axes of the inner openings 3212a (e.g., axes $CA_{A1}$ and $CA_{A2}$), the openings 3212 in the staple cartridge body 3200 form a modified or skewed herringbone pattern. The cavity axes $CA_{B1}$ and $CA_{B2}$ of the intermediate openings 3212b can be oriented perpendicular, or substantially perpendicular, to either the inner openings 3212a or the outer openings 3212c. For example, the angle B can be a supplementary angle to either angle A or angle C. In other instances, the angle B may not be a supplementary angle to either angle A or angle C.

Owing to the different angles A, B, and C, the widths $W_A$, $W_B$, $W_C$ of the staple rows in the staple line can be different. For example, the inner staples 3242a form a row of staples having a width $W_A$, the intermediate staples 3242b form a row of staples having a width $W_B$, and the outer staples 3242c form a row of staples having a width $W_C$. The widths $W_A$ and $W_C$ are different because the angle A is different than the angle C. In certain instances, the width $W_B$ is different than the widths $W_A$ and $W_C$. In other instances, the width $W_B$ can match one of the widths $W_A$ or $W_C$. For example, if the angle B is a supplementary angle to angle A, the width $W_B$ matches the width $W_A$. Similarly, if the angle B is a supplementary angle to angle C, the width $W_B$ matches the width $W_C$.

Furthermore, owing to the different angles A, B, and C, the longitudinal lengths $L_A$, $L_B$, and $L_C$ of the staples 3242a, 3242b, and 3242c, respectively, are different. For example, the inner staples 3242a have a longitudinal length $L_A$, the intermediate staples 3242b have a longitudinal length $L_B$, and the outer staples 3242c have a longitudinal length $L_C$. The longitudinal lengths $L_A$ and $L_C$ are different because the angle A is different than the angle C. Because the longitudinal lengths $L_A$ and $L_C$ are different, the inner staples 3242a are at least partially longitudinally staggered or offset relative to the outer staples 3242c. Stated differently, at least one end of each inner staple 3242a is not aligned with a corresponding end of an outer staple 3242b. Because the ends are not aligned, the longitudinal overlap and/or gap with respect to the intermediate staples 3242b differs between the inner staples 3242a and the outer staples 3242c. In certain instances, the longitudinal length $L_B$ is different than the lengths $L_A$ and $L_C$. In other instances, the longitudinal length $L_B$ can match one of the longitudinal lengths $L_A$ or $L_C$. For example, if the angle B is a supplementary angle to angle A, the longitudinal length $L_B$ matches the longitudinal length $L_A$. Similarly, if the angle B is a supplementary angle to angle C, the longitudinal length $L_B$ matches the longitudinal length $L_C$.

The length of the staple bases may also impact the widths $W_A$, $W_B$, and $W_C$ and the longitudinal lengths $L_A$, $L_B$, and $L_C$. In the staple cartridge body 3200, the inner staples 3242a, the intermediate staples 3242b, and the outer staples 3242c have the same length base. For example, identical staples can be positioned in each staple cavity 3210. In other instances, as further described herein, staples having different geometries and/or sizes, such as bases of different lengths, for example, can be positioned in certain staple cavities in a cartridge body.

Referring still to FIG. 76, the angular orientation of the staple cavities 3210a, 3210b, and 3210c, and the corresponding widths $W_A$, $W_B$, and $W_C$ and longitudinal lengths $L_A$, $L_B$, and $L_C$, respectively, can impact the amount of lateral and longitudinal overlap in the staple line. The longitudinal and lateral overlap between the staples 3242 also depends on the spacing of the staple cavities 3210. Generally, a greater overlap between adjacent staples corresponds to less direct fluid pathways, which can correspond to greater tissue sealing properties. A greater overlap can also decrease the flexibility of the staple line because the tissue may be more constrained in the overlapped region. Moreover, a greater overlap can correspond to less spacing between the staples. In certain instances, it can be desirable to modify the degree of lateral and/or longitudinal overlap in a staple line. As the overlap varies, the flexibility and sealing properties of the staple line can also vary.

The overlap or degree of overlap described herein can refer to a positive overlap or a negative overlap, for example. When staples and/or rows of staples define a negative overlap, the staples and/or rows of staples may be spaced apart such that they do not overlap and a gap is defined therebetween. In still other instances, the staples or rows of staples can be aligned such that the overlap is equal to the diameter of the staples.

The reader will further appreciate that the degree of overlap with respect to the staples or rows of staples in a staple cartridge corresponds to the degree of overlap with respect to the staple cavities or rows of staple cavities in the staple cartridge. For example, relative differences in the lateral and/or longitudinal overlaps between staples or rows of staples correspond to the relative differences in the lateral and/or longitudinal overlaps in the staple cavities or rows of staple cavities in the staple cartridge. In certain instances, at least a portion of the staple legs can be positioned against and/or biased into the inside walls of the staple cavities at the proximal and distal ends of the staple cavity. In such instances, a distance measured with respect to the outside edges of the staples equal the distance measured with respect to the inside edges of the corresponding staple cavities. In other instances, the difference between such distances can be minimal or insignificant.

In certain instances, the degree of overlap can be minimized, such as when ends of the staples are aligned. When the ends of the staples are aligned, the overlap is equal, or substantially equal, to the diameter of the staples. For example, if the staples are comprised of a wire having a diameter of about 0.0079 inches, the overlap can be about 0.0079 inches. In other instances, the overlap can be less than the diameter of staples. For example, the overlap can be less than about 0.0079 inches. In still other instances, the degree of overlap can be a non-overlap or negative overlap, i.e., a space or gap between the ends of the staples. In still other instances, a minimized overlap can be equal to or less than one-third of the staple length. For example, the overlap can be less 33% of the staple length. In other instances, the overlap can be less than 25% or less than 10% of the staple length. In still other instances, the overlap can be more than 33% of the staple length, for example.

In certain instances, a staple line can include a first degree of overlap between the inner and intermediate rows of staples and a second degree of overlap between the intermediate and outer rows of staples. The second degree of overlap can be different from the first degree of overlap in a lateral and/or longitudinal direction. Consequently, an inner portion of the staple line can comprise a different flexibility than an outer portion of the staple line. Moreover, the tissue sealing properties of the inner portion can be different than the tissue sealing properties of the outer portion.

Referring again to FIG. 76, the angle A is less than the angle C. Consequently, the width $W_A$ is less than the width $W_C$ and the length $L_A$ is greater than the length $L_C$. The angle A can be 35 degrees to 40 degrees, for example, and the angle C can be 43 degrees to 47 degrees, for example. In other instances, the angle A can be less than 35 degrees or more than 40 degrees and/or the angle C can be less than 43 degrees or more than 47 degrees. The difference between the angle A and the angle C can be between three degrees and twelve degrees. For example, the difference can be about eight degrees. In still other instances, the difference between the angle A and the angle C can be less than three degrees or more than twelve degrees.

Referring still to FIG. 76, the staples 3242 in each respective row are aligned. More specifically, the proximal ends of the inner staples 3242a are longitudinally aligned, the distal ends of the inner staples 3242a are longitudinally aligned, the proximal ends of the intermediate staples 3242b are longitudinally aligned, the distal ends of the intermediate staples 3242b are longitudinally aligned, the proximal ends of the outer staples 3242c are longitudinally aligned, and the distal ends of the outer staples 3242c are longitudinally aligned. The aligned staples 3242 in each row 3214a, 3214b, and 3214c of staple cavities 3310 are configured to form rows of aligned staples 3242 in a staple line. Owing to the angular orientation of the staples 3242 and the spacing therebetween, the rows of staples 3242 laterally overlap. The inner staples 3242a laterally overlap the intermediate staples 3242b by a lateral overlap $Y_{A/B}$ and the outer staples 3242c laterally overlap the intermediate staples 3242b by a lateral overlap $Y_{B/C}$. The lateral overlap $Y_{A/B}$ between the inner staples 3242a and the intermediate staples 3242b is greater than the lateral overlap $Y_{B/C}$ between the outer staples 3242c and the intermediate staples 3242b. In such instances, the outer staples are positioned closer to the intermediate staples than the inner staples are positioned to the intermediate staples. In other instances, the lateral overlap $Y_{A/B}$ can be less than or equal to the lateral overlap $Y_{B/C}$.

The intermediate staples 3242b are longitudinally staggered with respect to the inner staples 3242a and the outer staples 3242c. In particular, each intermediate staple 3242b is positioned longitudinally equidistant between adjacent inner staples 3242a and longitudinally equidistant between adjacent outer staples 3242c. Owing to the angular orientation of the staples 3242 and the spacing therebetween, the staples 3242 do not longitudinally overlap. The inner staples 3242a are spaced apart from the intermediate staples 3242b by a longitudinal gap $X_{A/B}$ and the outer staples 3242c are spaced apart from the intermediate staples 3242b by a longitudinal gap $X_{B/C}$. The longitudinal gap $X_{A/B}$ between the inner staples 3242a and the intermediate staples 3242b is less than the longitudinal gap $X_{B/C}$ between the outer staples 3242c and the intermediate staples 3242b. In other instances, the longitudinal gap $X_{A/B}$ can be greater than or equal to the longitudinal gap $X_{B/C}$. In certain instances, the intermediate staples 3242b can longitudinally overlap the inner staples 3242a and/or the outer staples 3242c.

The lateral overlaps and longitudinal gaps generated by the arrangement of staple cavities in FIG. 76 can be sufficient to sufficiently obstruct the fluid pathways across the staple line to seal the tissue. In various instances, the lateral and/or longitudinal overlaps and/or gaps can be configured to selectively optimize the sealing properties of the staple line. Additionally or alternatively, the lateral and/or longitudinal overlaps and/or gaps can be configured to selectively optimize the flexibility of the staple line. Moreover, the overlaps can be minimized. In certain instances, the lateral overlaps can be less than one-third of the staple length and, in at least one instance, can equal approximately the diameter of the staple.

Figure 77:
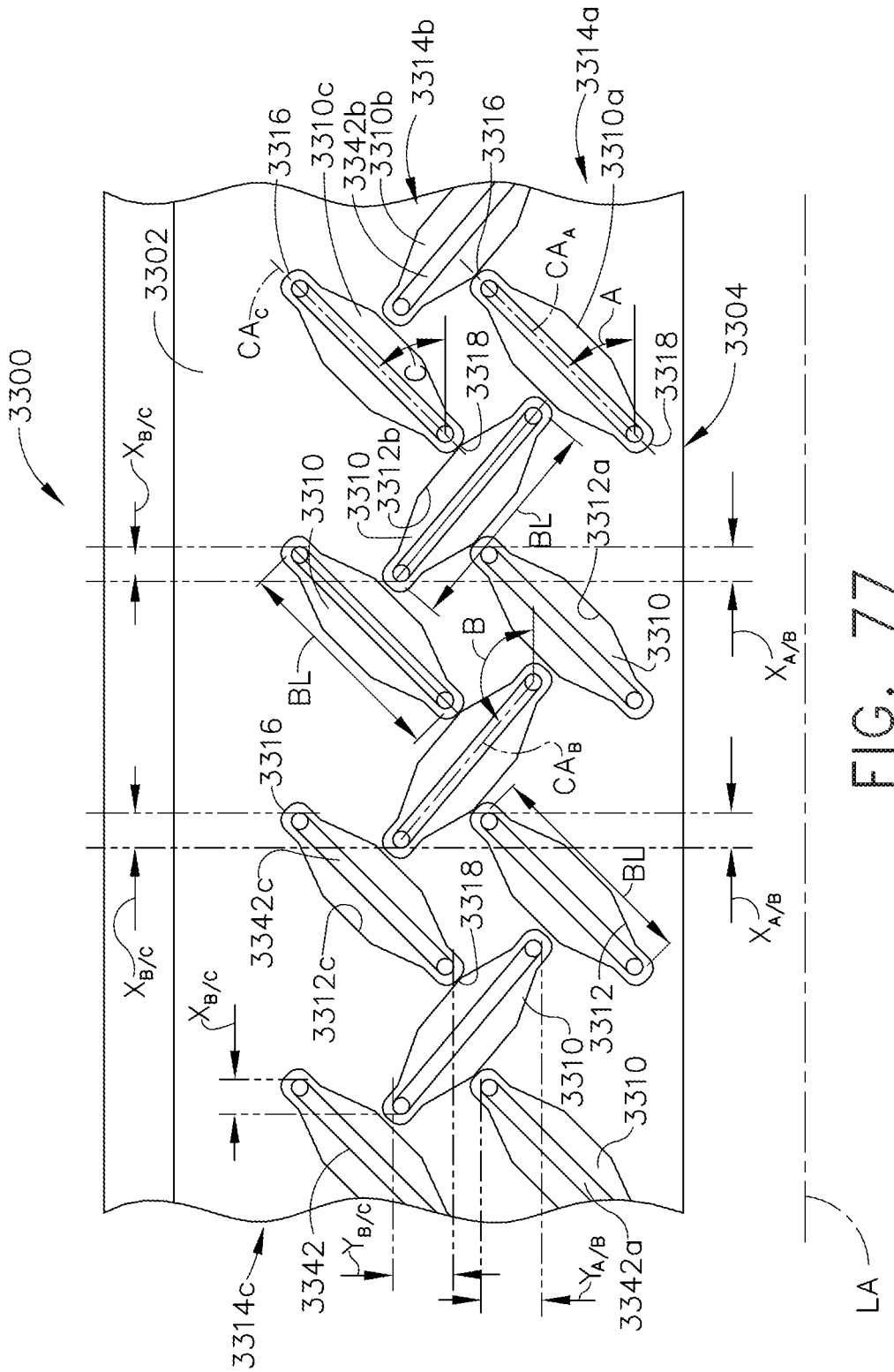
FIG. 77 is a plan view of a portion of a staple cartridge body having a plurality of angularly-oriented staple cavities defined therein and depicting staples in the staple cavities.

Referring now to FIG. 77, a portion of a staple cartridge body 3300 is depicted. The staple cartridge body 3300 includes a deck 3302 and a longitudinal slot 3304. The longitudinal slot 3304 extends along the longitudinal axis LA. Staple cavities 3310 are defined in the staple cartridge body 3300, and each staple cavity 3310 includes an opening 3312 in the deck 3302. A staple 3342 is positioned in each staple cavity 3310. The staple 3342 can be similar in many aspects to the staple 3042 (FIG. 59) or the staple 3142 (FIG. 60). In certain instances, the legs of each staple 3342 can be biased against the inside wall of the staple cavity 3310. The reader will appreciate that the arrangement of staples 3342 in the staple cavities 3310 corresponds to the arrangement of staples 3342 in a staple line when the staples 3342 are fired from the staple cartridge body 3300 and into tissue. More specifically, the bases of each staple 3342 in a resultant staple line are collinear, or substantially collinear, with the cavities axes CA.

The staple cavity openings 3312 are arranged in three rows 3314a, 3314b, and 3314c on a first side of the longitudinal slot 3304. Inner openings 3312a define the perimeter of inner cavities 3310a in the inner row 3314a, intermediate openings 3312b define the perimeter of intermediate cavities 3310b in the intermediate row 3314b, and outer openings 3312c define the perimeter of outer cavities 3310c in the outer row 3314c. Inner staples 3342a are positioned in the inner cavities 3310a, intermediate staples 3342b are positioned in the intermediate cavities 3310b, and outer staples 3342c are positioned in the outer cavities 3310c. Although not shown in FIG. 77, in at least one instance, the staple cavities 3310 on the opposing side of the slot 3304 form a mirror image reflection of the staple cavities 3310 on the first side of the longitudinal slot 3304. Consequently, the arrangement of staples 3342 in a resultant staple line is symmetric relative to the cutline. In other instances, the staple line can be asymmetric relative to the cutline.

Each staple cavity opening 3312 has a first end, or proximal end, 3316 and a second end, or distal end, 3318. A cavity axis CA extends between the proximal end 3316 and the distal end 3318 of each opening 3312. The staple cavity openings 3312 in each respective row are parallel. For example, the inner cavities 3310a are oriented at an angle A relative to the longitudinal axis LA. Stated differently, the cavity axes (e.g., $CA_A$) of the inner openings 3312a are oriented at the angle A relative to the longitudinal axis LA. The intermediate cavities 3310b are oriented at an angle B relative to the longitudinal axis LA. Stated differently, the cavity axes (e.g., $CA_B$) of the intermediate openings 3312b are oriented at the angle B relative to the longitudinal axis LA. The outer cavities 3310c are oriented at an angle C relative to the longitudinal axis LA. Stated differently, the cavity axes (e.g., $CA_C$) defined by the outer openings 3312c are oriented at the angle C relative to the longitudinal axis LA.

In the staple cartridge body 3300, the angle A is equal to the angle C, and the angle B is a supplementary angle to the angles A and C. Consequently, the inner openings 3312a are parallel to outer openings 3312c and the intermediate openings 3312b are perpendicular to the inner and outer openings 3312a and 3312c, respectively. The staple cavity openings 3312 in the staple cartridge body 3300 form a herringbone pattern. Moreover, referring still to FIG. 77, the staples 3342 in each row 3314a, 3314b, 3314c have the same length base BL. The widths of the staple rows are equal, and the longitudinal lengths of the staples 3342 are also equal.

Referring still to FIG. 77, the longitudinal overlap $X_{A/B}$ between the inner staples 3342a and the intermediate staples 3342b is equal to the longitudinal overlap $X_{B/C}$ between the outer staples 3342c and the intermediate staples 3342b. Moreover, the lateral overlap $Y_{A/B}$ between the inner staples 3342a and the intermediate staples 3342b is equal to the lateral overlap $Y_{B/C}$ between the outer staples 3342c and the intermediate staples 3342b. In such instances, the intermediate staples 3342b are positioned equidistantly close to the inner staples 3342a and the outer staples 3342c.

Referring still to FIG. 77, the spacing between the staple cavities 3310 in the cartridge body 3300 is minimized. For example, the proximal and distal ends 3316, 3318 of the staple cavity openings 3312 are positioned adjacent to other staple cavities 3312. In certain instances, adjacent staple cavities can be in abutting contact. By minimizing the spacing between the staple cavities 3310, the density of the staple cavities 3310 and the degree of overlap between the staple cavities 3310 in the arrangement of FIG. 77 is maximized. Although the degree of overlap is maximized, because of the close proximity of the staple cavities, the lateral overlap is still less than one-third of the staple length.

In other instances, the angular orientation of the staple cavities in at least one row of staple cavities can differ from the angular orientation of the staple cavities in other rows. Additionally or alternatively, the length of the staple bases in at least one row of staple cavities can differ from the length of the staple bases in at least one other row. Additionally or alternatively, the staple cavities may not be equidistantly staggered or offset from adjacent staple cavities in each adjacent row. Such variations to the staple cartridge and staples therein can generate staple lines with varying properties laterally with respect to the cutline.

In certain instances, the staples in an inner portion of the staple line, such as the staples fired from the inner rows of staple cavities, for example, can have a different base length than the staples in an outer portion of the staple line. For example, the staples in the inner row of staple cavities on each side of a knife slot can have a longer base than the staples in the other rows of staple cavities. The longer bases can provide greater sealing capabilities because more tissue can be captured by the staples, for example. Additionally or alternatively, the longer bases can reinforce the staple line and reduce the flexibility thereof.

Figure 78:
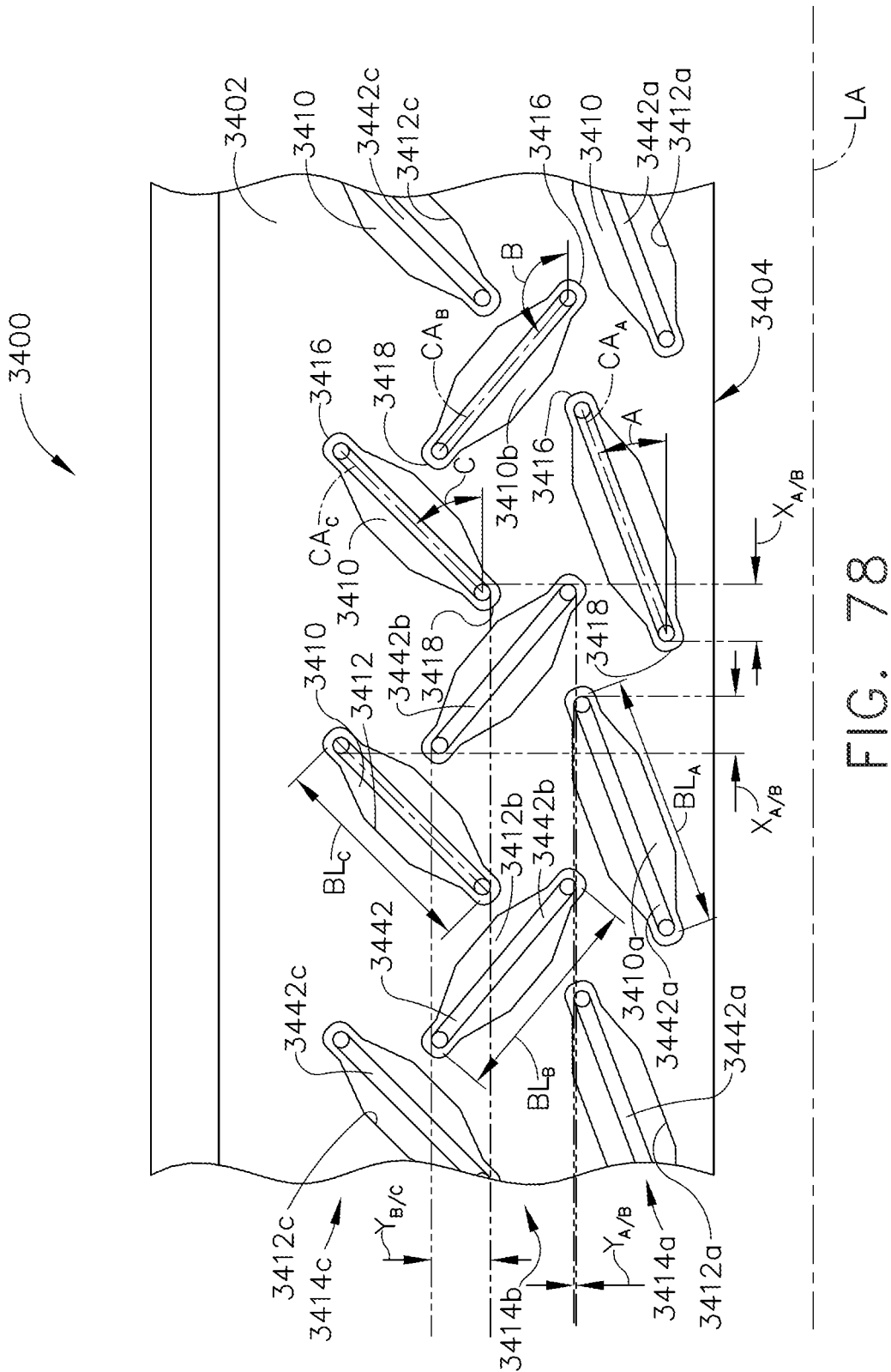
FIG. 78 is a plan view of a portion of a staple cartridge body having a plurality of angularly-oriented staple cavities defined therein and depicting staples in the staple cavities.

Referring now to FIG. 78, a portion of a staple cartridge body 3400 is depicted. The staple cartridge body 3400 includes a deck 3402 and a longitudinal slot 3404. The longitudinal slot 3404 extends along the longitudinal axis LA. Staple cavities 3410 are defined in the staple cartridge body 3400, and each staple cavity 3410 defines an opening 3412 in the deck 3402. A staple 3442 is positioned in each staple cavity 3410. The staple 3442 can be similar in many aspects to the staple 3042 (FIG. 59) or the staple 3142 (FIG. 60). In certain instances, the legs of each staple 3442 can be biased against the inside wall of the staple cavity 3410. The reader will appreciate that the arrangement of staples 3442 in the staple cavities 3410 corresponds to the arrangement of staples 3442 in a staple line when the staples 3442 are fired from the cartridge body 3400 and into tissue. More specifically, the bases of each staple 3442 in a resultant staple line are collinear, or substantially collinear, with the cavities axes CA.

The staple cavity openings 3412 are arranged in three rows 3414a, 3414b, and 3414c on a first side of the longitudinal slot 3404. Inner openings 3412a define the perimeter of inner cavities 3410a in the inner row 3414a, intermediate openings 3412b define the perimeter of intermediate cavities 3410b in the intermediate row 3414b, and outer openings 3412c define the perimeter of outer cavities 3410c in the outer row 3414c. Inner staples 3442a are positioned in the inner cavities 3410a, intermediate staples 3442b are positioned in the intermediate cavities 3410b, and outer staples 3442c are positioned in the outer cavities 3410c. Although not shown in FIG. 78, in at least one instance, the staple cavities 3410 on the opposing side of the slot 3404 form a mirror image reflection of the staple cavities 3410 on the first side of the longitudinal slot 3404. Consequently, the arrangement of staples 3442 in a resultant staple line is symmetric relative to the cutline. In other instances, the staple line can be asymmetric relative to the cutline.

Each staple cavity opening 3412 has a first end, or proximal end, 3416 and a second end, or distal end, 3418. A cavity axis CA extends between the proximal end 3416 and the distal end 3418 of each opening 3412. The staple cavity openings 3412 in each row are parallel. For example, the inner cavities 3410a are oriented at an angle A relative to the longitudinal axis LA. Stated differently, the cavity axes (e.g., $CA_A$) of the inner openings 3412a are oriented at the angle A relative to the longitudinal axis LA. The intermediate cavities 3410b are oriented at an angle B relative to the longitudinal axis LA. Stated differently, the cavity axes (e.g., $CA_B$) of the intermediate openings 3412b are oriented at the angle B relative to the longitudinal axis LA. The outer cavities 3410c are oriented at an angle C relative to the longitudinal axis LA. Stated differently, the cavity axes (e.g., $CA_C$) defined by the outer openings 3412c are oriented at the angle C relative to the longitudinal axis LA.

The angles A, B, and C are different. The inner openings 3412a are obliquely oriented relative to the outer openings 3412c. The angle A is less than the angle C. Because the axes of outer openings 3412c (e.g., axis $CA_C$) are not parallel to the axes of inner openings 3412a (e.g., axis $CA_A$), the staple cavity openings 3412 in the staple cartridge body 3400 form a modified or skewed herringbone pattern. The cavity axes $CA_B$ of the intermediate openings 3412b can be oriented perpendicular, or substantially perpendicular, to either the inner openings 3412a or the outer openings 3412c. For example, the angle B can be a supplementary angle to either angle A or C. In other instances, the angle B may not be a supplementary angle to either angle A or C.

Referring still to FIG. 78, the inner staples 3442a have a base length $BL_A$, the intermediate staples 3442b have a base length $BL_B$, and the outer staples 3442c have a base length $BL_C$. The base length $BL_A$ is greater than the base length $BL_B$ and the base length $BL_C$. In other words, the inner staples 3442a are longer than the intermediate staples 3442b and the outer staples 3442c. Moreover, the staple cavities 3410 housing the inner staples 3442a are correspondingly larger to accommodate the longer length base $BL_A$.

The arrangement of staple cavities 3410 in the cartridge body 3400 provides a longitudinal overlap $X_{A/B}$ between inner staples 3442a and the intermediate staples 3442b at both the proximal and distal ends of the intermediate staples 3442b. The intermediate staples 3442b are equidistantly spaced and longitudinally staggered between two adjacent inner staples 3442a. The intermediate staples 3442b are also equidistantly spaced and longitudinally staggered between two adjacent outer staples 3442c. The proximal end of each outer staple 3442c is longitudinally aligned with the distal end of an intermediate staple 3442b and the distal end of each outer staple 3442c is longitudinally aligned with the proximal end of another intermediate staple 3442b. In other words, such staples are longitudinally aligned and the longitudinal overlap is equal to the diameter of the staples 3442. The arrangement of staples cavities 3410 in the cartridge body 3400 also provides a lateral gap $Y_{A/B}$ between the inner row 3414a and the intermediate row 3414b and a lateral overlap $Y_{B/C}$ between the outer row 3414c and the intermediate row 3414b. In such instances, the intermediate staples 3442b are positioned closer to the outer staples 3442c than to the inner staples 3442a.

Referring still to FIG. 78, a staple line generated by the staple cartridge body 3400 can have different properties laterally with respect to the cutline. In particular, the staple line may have a greater sealing effectiveness along the cutline than laterally outward from the cutline. Furthermore, the staple line may have a greater flexibility laterally away from the cutline than inward toward the cutline. For example, because the bases $BL_A$ of the inner staples 3442a are longer than the bases $BL_B$ and $BL_C$ of the intermediate staples 3442b and the outer staples 3442c, respectively, an inner portion of the staple line may have greater sealing effectiveness and/or less flexibility than an outer portion of the staple line. Additionally or alternatively, because the inner staples 3442a are oriented at an angle that is less than the outer staples 3442c and is closer to a parallel orientation than the outer staples 3442c, an inner portion of the staple line may have greater sealing effectiveness and/or less flexibility than an outer portion of the staple line. Additionally or alternatively, because the intermediate staples 3442b longitudinally overlap the inner staples 3442a but do not longitudinally overlap the outer staples 3442c, an inner portion of the staple line may have greater sealing effectiveness and/or less flexibility than an outer portion of the staple line. The amount of overlap can be minimized. For example, the overlap can be less than one-third of the staple length and, in at least one instance, can equal approximately the diameter of the staple.

In certain instances, the staples in an outer portion of the staple line, such as the staples fired from the outer rows of staple cavities, for example, can have a different base length than the staples in an inner portion of the staple line. For example, the staples in the outer row of staple cavities on each side of a knife slot can have a shorter base than the staples in the other rows of staple cavities. The shorter bases can provide increased flexibility of the staple line, for example.

Figure 79:
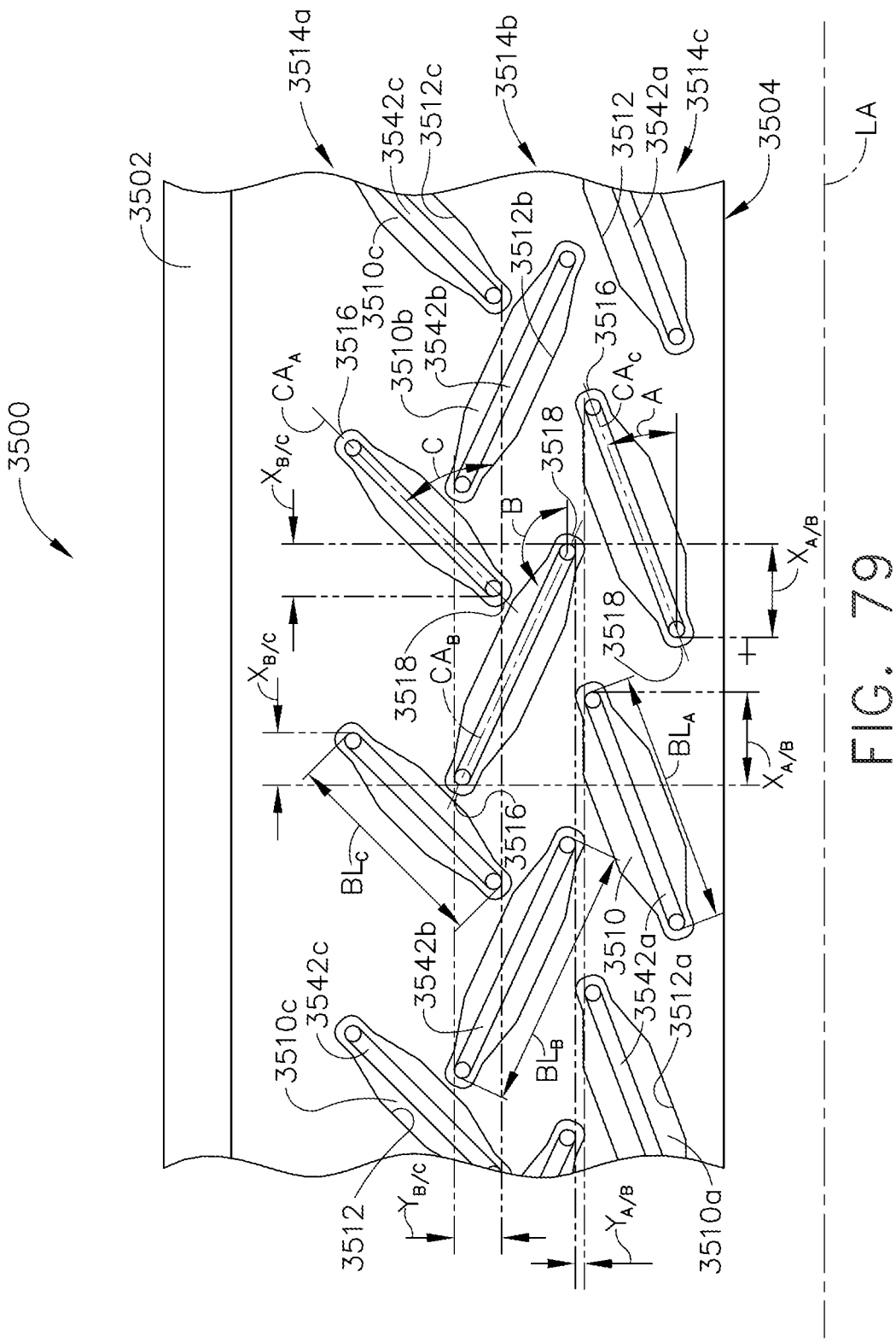
FIG. 79 is a plan view of a portion of a staple cartridge body having a plurality of angularly-oriented staple cavities defined therein and depicting staples in the staple cavities.

Referring now to FIG. 79, a portion of a staple cartridge body 3500 is depicted. The staple cartridge body 3500 includes a deck 3502 and a longitudinal slot 3504. The longitudinal slot 3504 extends along the longitudinal axis LA. Staple cavities 3510 are defined in the staple cartridge body 3500, and each staple cavity 3510 defines an opening 3512 in the deck 3502. A staple 3542 is positioned in each staple cavity 3510. The staple 3542 can be similar in many aspects to the staple 3042 (FIG. 59) or the staple 3142 (FIG. 60). In certain instances, the legs of each staple 3542 can be biased against the inside wall of the staple cavity 3510. The reader will appreciate that the arrangement of staples 3542 in the staple cavities 3510 corresponds to the arrangement of staples 3542 in a staple line when the staples 3542 are fired from the cartridge body 3500 and into tissue. More specifically, the bases of each staple 3542 in a resultant staple line are collinear, or substantially collinear, with the cavities axes CA.

The staple cavity openings 3512 are arranged in three rows 3514a, 3514b, and 3514c on a first side of the longitudinal slot 3504. Inner openings 3512a define the perimeter of inner cavities 3510a in the inner row 3514a, intermediate openings 3512b define the perimeter of intermediate cavities 3510b in the intermediate row 3514b, and outer openings 3512c define the perimeter of outer cavities 3510c in the outer row 3514c. Inner staples 3542a are positioned in the inner cavities 3510a, intermediate staples 3542b are positioned in the intermediate cavities 3510b, and outer staples 3542c are positioned in the outer cavities 3510c. Although not shown in FIG. 79, in at least one instance, the staple cavities 3510 on the opposing side of the slot 3504 form a mirror image reflection of the staple cavities 3510 on the first side of the longitudinal slot 3504. Consequently, the arrangement of staples 3542 in a resultant staple line is symmetric relative to the cutline. In other instances, the staple line can be asymmetric relative to the cutline.

Each staple cavity opening 3512 has a first end, or proximal end, 3516 and a second end, or distal end, 3518. A cavity axis CA extends between the proximal end 3516 and the distal end 3518 of each opening 3512. The staple cavity openings 3512 in each row are parallel. For example, the inner cavities 3510a are oriented at an angle A relative to the longitudinal axis LA. Stated differently, the cavity axes (e.g., $CA_A$) of the inner openings 3512a are oriented at the angle A relative to the longitudinal axis LA. The intermediate cavities 3510b are oriented at an angle B relative to the longitudinal axis LA. Stated differently, the cavity axes (e.g., $CA_B$) of the intermediate openings 3512b are oriented at the angle B relative to the longitudinal axis LA. The outer cavities 3510c are oriented at an angle C relative to the longitudinal axis LA. Stated differently, the cavity axes (e.g., $CA_C$) defined by the outer openings 3512c are oriented at the angle C relative to the longitudinal axis LA.

The angles A, B, and C may be different. The inner openings 3512a are obliquely oriented relative to the outer openings 3512c. The angle A is less than the angle C. Because the axes of the outer openings 3512c (e.g., axis $CA_C$) are not parallel to the axes of the inner openings 3512a (e.g., axis $CA_A$), the staple cavity openings 3512 in the staple cartridge body 3500 form a modified or skewed herringbone pattern. The cavity axes $CA_B$ of the intermediate openings 3512b can be oriented perpendicular, or substantially perpendicular, to either the inner openings 3512a or the outer openings 3512c. For example, the angle B can be a supplementary angle to either angle A or C. In other instances, the angle B may not be a supplementary angle to either angle A or C.

The inner staples 3542a have a base length $BL_A$, the intermediate staples 3542b have a base length $BL_B$, and the outer staples 3542c have a base length $BL_C$. The base length $BL_C$ is less than the base length $BL_B$ and the base length $BL_A$. In other words, the outer staples 3542c are shorter than the intermediate staples 3542b and the inner staples 3542a. Moreover, the staple cavities 3510 housing the outer staples 3542c are correspondingly shorter to accommodate the shorter length base $BL_C$.

The arrangement of staple cavities 3510 in the cartridge body 3500 provides a longitudinal overlap $X_{A/B}$ between the inner staples 3542a and the intermediate staples 3542b at both the proximal and distal ends of the intermediate staples 3542b. The intermediate staples 3542b are equidistantly spaced and longitudinally staggered between two adjacent inner staples 3542a. The arrangement of staple cavities 3510 in the cartridge body 3500 also provides a longitudinal overlap $X_{B/C}$ between the intermediate staples 3542b and the outer staples 3542c at both the proximal and distal ends of the intermediate staples 3542b. The intermediate staples 3542b are also equidistantly spaced and longitudinally staggered between two adjacent outer staples 3542c. Owing to the angular orientation and spacing of the staples 3542, the longitudinal overlap $X_{A/B}$ is greater than the longitudinal overlap $X_{B/C}$. The arrangement of staples cavities 3510 in the cartridge body 3500 also provides a lateral gap $Y_{A/B}$ between the inner staples 3542a and the intermediate staples 3542b and a lateral overlap $Y_{B/C}$ between the outer staples 3542c and the intermediate staples 3542b. In such instances, the intermediate staples 3542b are positioned closer to the outer staples 3542c than to the inner staples 3542a.

Referring still to FIG. 79, a staple line generated by the staple cartridge body 3500 can have different properties laterally with respect to the cutline. In particular, the staple line may have a greater sealing effectiveness along the cutline than laterally outward from the cutline. Furthermore, the staple line may have a greater flexibility laterally away from the cutline than inward toward the cutline. For example, because the bases $BL_C$ of the outer staples 3542c are shorter than the bases $BL_A$ and $BL_B$ of the intermediate staples 3542b and the outer staples 3542c, respectively, an inner portion of the staple line may have greater sealing effectiveness and/or less flexibility than an outer portion of the staple line. Additionally or alternatively, because the inner staples 3542a are oriented at an angle that is less than the outer staples 3542c and is closer to a parallel orientation than the outer staples 3542c, an inner portion of the staple line may have greater sealing effectiveness and/or less flexibility than an outer portion of the staple line. Additionally or alternatively, because the intermediate staples 3542b longitudinally overlap the inner staples 3542a more than the intermediate staples 3542b longitudinally overlap the outer staples 3542c, an inner portion of the staple line may have greater sealing effectiveness and/or less flexibility than an outer portion of the staple line.

In various instances, the properties of the staple line can be customized in each row of staples. The staples in each row of staple cavities on one side of a knife slot can have different base lengths. Additionally, the staples in each row of staple cavities on one side of a knife slot can be oriented at different angles relative to the knife slot. Moreover, the spacing between the cavities can be varied row-to-row. For example, the size and orientation of the staples in each row can be selected to optimize the flexibility of the staple line and sealing properties in each row based on the row's position laterally from the cutline toward the outer boundary of the staple line. In certain instances, the sealing effectiveness can be maximized or emphasized along the cutline, for example, and the flexibility of the staple line can be maximized or emphasized along the outer boundary of the staple line, for example. Alternatively, in certain instances, the sealing effectiveness can be maximized or emphasized along the outer boundary of the staple line and/or the flexibility of the staple line can be maximized or emphasized along the cutline.

Figure 80:
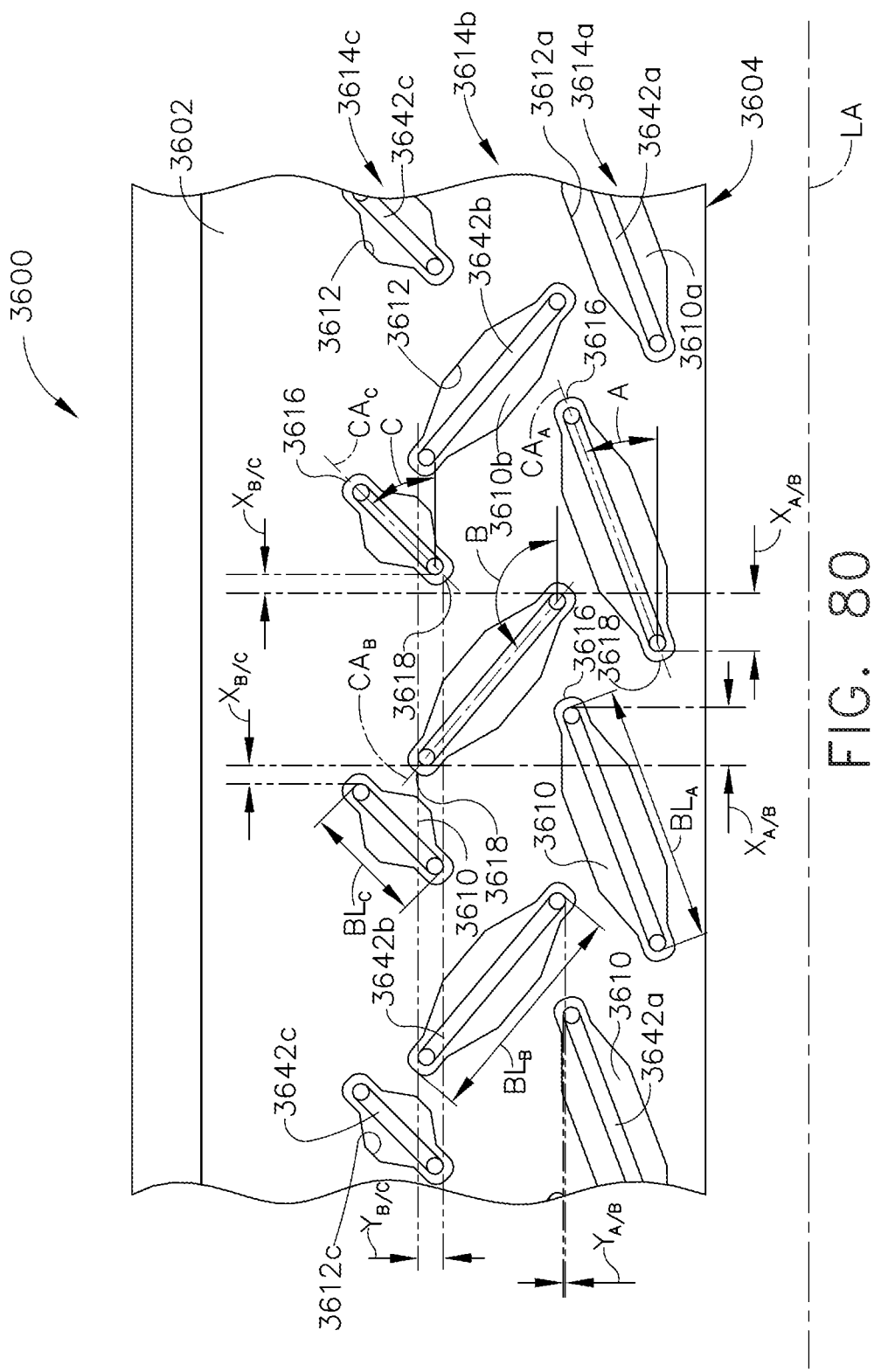
FIG. 80 is a plan view of a portion of a staple cartridge body having a plurality of angularly-oriented staple cavities defined therein and depicting staples in the staple cavities.

Referring now to FIG. 80, a portion of a staple cartridge body 3600 is depicted. The staple cartridge body 3600 includes a deck 3602 and a longitudinal slot 3604. The longitudinal slot 3604 extends along the longitudinal axis LA. Staple cavities 3610 are defined in the staple cartridge body 3600, and each staple cavity 3610 defines an opening 3612 in the deck 3602. A staple 3642 is positioned in each staple cavity 3610. The staple 3642 can be similar in many aspects to the staple 3042 (FIG. 59) or the staple 3142 (FIG. 60). In certain instances, the legs of each staple 3642 can be biased against the inside wall of the staple cavity 3610. The reader will appreciate that the arrangement of staples 3642 in the staple cavities 3610 corresponds to the arrangement of staples 3642 in a staple line when the staples 3642 are fired from the cartridge body 3600 and into tissue. More specifically, the bases of each staple 3642 in a resultant staple line are collinear, or substantially collinear, with the cavities axes CA.

The staple cavity openings 3612 are arranged in three rows 3614a, 3614b, 3614c on a first side of the longitudinal slot 3604. Inner openings 3612a define the perimeter of inner cavities 3610a in the inner row 3614a, intermediate openings 3612b define the perimeter of intermediate cavities 3610b in the intermediate row 3614b, and outer openings 3612c define the perimeter of outer cavities 3610c in the outer row 3614c. Inner staples 3642a are positioned in the inner cavities 3610a, intermediate staples 3642b are positioned in the intermediate cavities 3610b, and outer staples 3642c are positioned in the outer cavities 3610c. Although not shown in FIG. 80, in at least one instance, the staple cavities 3610 on the opposing side of the slot 3604 form a mirror image reflection of the staple cavities 3610 on the first side of the longitudinal slot 3604. Consequently, the arrangement of staples 3642 in a resultant staple line is symmetric relative to the cutline. In other instances, the staple line can be asymmetric relative to the cutline.

Each staple cavity opening 3612 has a first end, or proximal end, 3616 and a second end, or distal end, 3618. A cavity axis CA extends between the proximal end 3616 and the distal end 3618 of each opening 3612. The staple cavity openings 3612 in each row are parallel. For example, the inner cavities 3610a are oriented at an angle A relative to the longitudinal axis LA. Stated differently, the cavity axes (e.g., $CA_A$) of the inner openings 3612a are oriented at the angle A relative to the longitudinal axis LA. The intermediate cavities 3610b are oriented at an angle B relative to the longitudinal axis LA. Stated differently, the cavity axes (e.g., $CA_B$) of the intermediate openings 3612b are oriented at the angle B relative to the longitudinal axis LA. The outer cavities 3610c are oriented at an angle C relative to the longitudinal axis LA. Stated differently, the cavity axes (e.g., $CA_C$) defined by the outer openings 3612c are oriented at the angle C relative to the longitudinal axis LA.

The angles A, B, and C may be different. The inner openings 3612a are obliquely oriented relative to the outer openings 3612c. The angle A is less than the angle C. Because the axes of the outer openings 3612c (e.g., axis $CA_C$) are not parallel to the axes of the inner openings 3612a (e.g., axis $CA_A$), the staple cavity openings 3612 in the staple cartridge body 3600 form a modified or skewed herringbone pattern. The cavity axes $CA_B$ of the intermediate openings 3612b can be oriented perpendicular, or substantially perpendicular, to either the inner openings 3612a or the outer openings 3612c. For example, the angle B can be a supplementary angle to either angle A or C. In other instances, the angle B may not be a supplementary angle to either angle A or C.

The inner staples 3642a have a base length $BL_A$, the intermediate staples 3642b have a base length $BL_B$, and the outer staples 3642c have a base length $BL_C$. The base length $BL_C$ is less than the base length $BL_B$, and the base length $BL_B$ is less than the base length $BL_A$. In other words, the length of the staples 3642 increases laterally toward the longitudinal slot 3604. Moreover, the staple cavities 3610 correspondingly increase in length laterally toward the longitudinal slot 3604 to accommodate the larger staples.

The arrangement of staple cavities 3610 in the cartridge body 3600 provides a longitudinal overlap $X_{A/B}$ between the inner staples 3642a and the intermediate staples 3642b at both the proximal and distal ends of the intermediate staples 3642b. The intermediate staples 3642b are equidistantly spaced and longitudinally staggered between two adjacent inner staples 3642a. The arrangement of staple cavities 3610 in the cartridge body 3600 also provides a longitudinal gap $X_{B/C}$ between the intermediate staples 3642b and the outer staples 3642c at both the proximal and distal ends of the intermediate staples 3642b. The intermediate staples 3642b are also equidistantly spaced and longitudinally staggered between two adjacent outer staples 3642c. Owing to the variations in the angular orientation of the staples, the spacing of the staples, and the length of the staples, the longitudinal overlap $X_{A/B}$ is greater than the longitudinal gap $X_{B/C}$. In other instances, the longitudinal overlap $X_{A/B}$ can be equal to or less than the longitudinal overlap $X_{B/C}$. The arrangement of staples cavities 3610 in the cartridge body 3600 also provides a lateral gap $Y_{A/B}$ between the inner row 3614a and the intermediate row 3614b and a lateral overlap $Y_{B/C}$ between the outer row 3614c and the intermediate row 3614b.

Referring still to FIG. 80, a staple line generated by the staple cartridge body 3600 can have different properties laterally with respect to the cutline. In particular, the staple line may have a greater sealing effectiveness adjacent to the cutline than laterally outward from the cutline. Furthermore, the staple line may have a greater flexibility laterally away from the cutline than inward toward the cutline. For example, because the length of the bases $BL_A$, $BL_B$, and $BL_C$ of the staples 3642a, 3642b, and 3642c, respectively, increases laterally inward toward the cutline, an inner portion of the staple line may have greater sealing effectiveness than an outer portion of the staple line. Additionally or alternatively, because the angular orientation of the staples 3642a, 3642b, and 3642c increases laterally outward away from the cutline, an outer portion of the staple line may have greater flexibility than an inner portion of the staple line.

As described herein, staples are removably positioned in a staple cartridge and fired from the staple cartridge during use. In various instances, the staples can be driven out of staple cavities in the staple cartridge and into forming contact with an anvil. For example, a firing element can translate through the staple cartridge during a firing stroke to drive the staples from the staple cartridge toward an anvil. In certain instances, the staples can be supported by staple drivers and the firing element can lift the staple drivers to eject or remove the staples from the staple cartridge.

An anvil can include a staple-forming surface having staple-forming pockets defined therein. In certain instances, the staple-forming pockets can be stamped in the anvil. For example, the staple-forming pockets can be coined in a flat surface of the anvil. The reader will appreciate that certain features of the staple-forming pockets can be a deliberate consequence of a coining process. For example, a certain degree of rounding at corners and/or edges of the staple-forming produce can be an intentional result of the coining process. Such features can also be designed to better form the staples to their formed configurations, including staples that become skewed and/or otherwise misaligned during deployment.

Each staple in the staple cartridge can be aligned with a staple-forming pocket of the anvil. In other words, the arrangement of staple cavities and staples in a staple cartridge for an end effector can correspond or match the arrangement of staple-forming pockets in an anvil of the end effector. More specifically, the angular orientation of each staple cavity can match the angular orientation of the respective staple-forming pocket. For example, when the staple cavities are arranged in a herringbone pattern, the staple-forming pockets can also be arranged in a herringbone pattern.

When staples are driven from the staple cartridge and into forming contact with the anvil, the staples can be formed into a fired configuration. In various instances, the fired configuration can be a B-form configuration, in which the tips of the staple legs are bent toward the staple base or crown to form a capital letter B having symmetrical upper and lower loops. In other instances, the fired configuration can be a modified B-form, such as a skewed B-form configuration, in which at least a portion of a staple leg torques out of plane with the staple base, or an asymmetrical B-form configuration, in which the upper and lower loops of the capital letter B are asymmetric. Tissue can be captured or clamped within the formed staple.

The arrangement of staples and/or staple cavities in a staple cartridge can be configured to optimize the corresponding arrangement of staple-forming pockets in the forming surface of a complementary anvil. For example, the angular orientation and spacing of staples in a staple cartridge can be designed to optimize the forming surface of an anvil. In certain instances, the footprint of the staple-forming pockets in an anvil can be limited by the geometry of the anvil. In instances in which the staple-forming pockets are obliquely-oriented relative to a longitudinal axis, the width of the anvil can limit the size and spacing of the obliquely-oriented staple-forming pockets. For example, the width of an intermediate row of staple-forming pockets can define a minimum distance between a first row (e.g. an outer row) on one side of the intermediate row and a second row (e.g. an inner row) on the other side of the intermediate row. Moreover, the rows of staple-forming pockets are confined between an inside edge on the anvil, such as a knife slot, and an outside edge of the anvil.

In various instances, the pockets can be adjacently nested along a staple-forming surface of the anvil. For example, an intermediate pocket can be nested between an inner pocket and an outer pocket. The angular orientation of the pockets can vary row-to-row to facilitate the nesting thereof. For example, the staple-forming pockets in an inner row can be oriented at a first angle, the staple-forming pockets in an intermediate row can be oriented at a second angle, and the staple-forming pockets in an outer row can be oriented at a third angle. The first angle, the second angle, and the third angle can be different, which can facilitate the close arrangement of the staple-forming pockets.

Referring again to the staple cartridges depicted in FIGS. 76-80, the varying angles of the staples and the staple cavities in each row can be selected to optimize the nesting of the staple-forming pockets in a complementary anvil. For each staple cartridge depicted in FIGS. 76-80, a complementary anvil can be configured to have a corresponding arrangement of staple-forming pockets. Moreover, the staple-forming pockets in the complementary anvils can be larger than the staple cavities depicted in FIGS. 76-80 to ensure that the staple legs land or fall within the staple-forming pockets. For example, the staple legs may be biased outward, such as in the case of V-shaped staples (see FIG. 60) and the larger footprint of the staple-forming pockets can catch the outwardly-biased staple legs during firing. In various instances, the staple-forming pockets can be 0.005 inches to 0.015 inches longer than the corresponding staple cavities and/or staples. Additionally or alternatively, the staple-receiving cups of each staple-forming pocket can be 0.005 inches to 0.015 inches wider than the corresponding staple cavities. In other instances, the difference in length and/or width can be less than 0.005 inches or more than 0.015 inches.

In instances in which the size of the staples varies within a staple cartridge (see, e.g., FIGS. 78-80), the size of the staple-forming pockets can correspondingly vary within a complementary anvil. Varying the size of the staple-forming pockets can further facilitate the nesting thereof. For example, in instances in which staple-forming pockets in an intermediate row are shorter than the staple-forming pockets in an inner row or an outer row, the width of the intermediate row of staple-forming pockets can be reduced, which can minimize the requisite spacing between the inner row and the outer row.

The spacing of the staple-forming pockets can also be configured to optimize the nesting thereof. For example, the pockets arranged in an inner row can be longitudinally staggered relative to the pockets arranged in an outer row. Moreover, the pockets in the inner row can partially longitudinally overlap the pockets in the outer row. The pockets in an intermediate row can be longitudinally staggered relative to the pockets in the inner row and the pockets in the outer row. For example, the pockets in the intermediate row can be equidistantly longitudinally offset from the pockets in the outer row and the pockets in the inner row.

Figure 129:
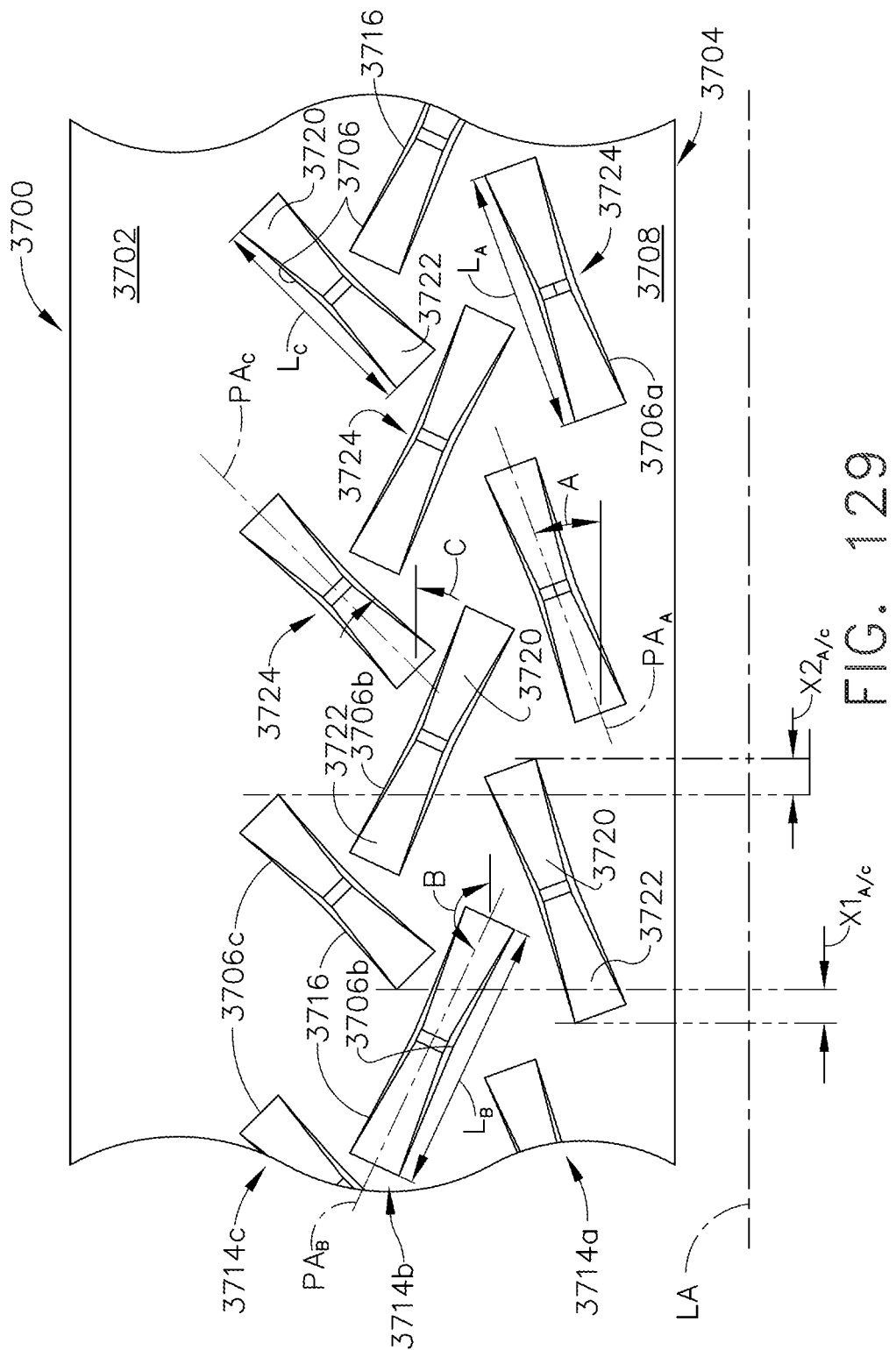

Referring now to FIG. 129, an anvil 3700 is depicted. The anvil 3700 can be complementary to the staple cartridge 3500 (FIG. 79). For example, the arrangement of staple-forming pockets 3706 in the anvil 3700 can correspond to the arrangement of staples 3542 and staple cavities 3510 (FIG. 79) in the staple cartridge 3500. The anvil 3700 includes a staple-forming surface 3702 and a longitudinal slot 3704. The longitudinal slot 3704 extends along the longitudinal axis LA of the anvil 3700. In certain instances, a firing element and/or cutting element can translate through the longitudinal slot 3704 during at least a portion of a firing stroke. Staple-forming pockets 3706 are defined in the staple-forming surface 3702. The staple-forming surface 3702 also includes a non-forming portion 3708 that extends around the pockets 3706. The non-forming portion 3708 extends entirely around each pocket 3706 in FIG. 129. In other words, the non-forming portion 3708 surrounds the staple-forming pockets 3706. In other instances, at least a portion of two or more adjacent pockets 3706 can be in abutting contact such that a non-forming portion 3708 is not positioned therebetween.

The forming ratio of the staple-forming surface 3702 can be optimized. By optimizing the forming ratio, more staples can be formed and/or formed to their desired configurations. In certain instances, the surface area of the non-forming portion 3708 of the anvil 3700 can be minimized with respect to the staple-forming pockets 3706. Additionally or alternatively, the footprint of the staple-forming pockets 3706 can be extended or enlarged to maximize the portion of the staple-forming surface 3702 that is designed to catch and form the staples.

The pockets 3706 depicted in FIG. 129 are arranged in three rows 3714a, 3714b, 3714c on a first side of the longitudinal slot 3704. The first row 3714a is an inner row, the second row 3714b is an intermediate row, and the third row 3714c is an outer row. Inner pockets 3706a are positioned in the inner row 3714a, intermediate pockets 3706b are positioned in the intermediate row 3714b, and outer pockets 3706c are positioned in the outer row 3714c. The pockets 3706 are arranged in a herringbone arrangement along the staple-forming surface 3702 of the anvil 3700. Although not shown in FIG. 129, in at least one instance, the pockets 3706 on the opposing side of the slot 3704 can form a mirror image reflection of the pockets 3706 on the first side of the longitudinal slot 3704. In other instances, the arrangement of pockets 3706 in the staple-forming surface 3702 can be asymmetrical relative to the slot 3704 and, in certain instances, the anvil 3700 may not include the longitudinal slot 3704. In various instances, the pockets 3706 can be arranged in less than or more than three rows on each side of the slot 3704.

Each pocket 3706 includes a perimeter 3716, which defines the boundary of the pocket 3706b. Each pocket 3706 also includes a proximal cup 3720, a distal cup 3722, and a neck portion 3724 connecting the proximal cup 3720 and the distal cup 3722. When a staple is driven into forming contact with the staple-forming surface 3702, the proximal cup 3720 is aligned with a proximal staple leg, and the distal cup 3722 is aligned with a distal staple leg. The tips of the staple legs are positioned and configured to land in the respective cups 3720, 3722. Stated differently, the proximal cup 3720 is configured to receive a proximal staple leg and the distal cup 3722 is configured to receive a distal staple leg. The cups 3720 and 3722 are also configured to direct or funnel the staple legs toward the pocket axis PA and a central portion of the pocket 3806, such as the neck portion 3724, and to deform the staple legs into the formed configuration.

The geometry, spacing, and/or orientation of the pockets 3706 can vary row-to-row. A pocket axis PA extends from the proximal cup 3720, through the neck portion 3724, and to the distal cup 3722 of each pocket 3706. The pockets 3706 in each row are parallel. For example, the inner pockets 3706a are oriented at an angle A relative to the longitudinal axis LA. Stated differently, the pocket axes (e.g., $PA_A$) of the inner pockets 3706a are oriented at the angle A relative to the longitudinal axis LA. The intermediate pockets 3706b are oriented at an angle B relative to the longitudinal axis LA. Stated differently, the pocket axes (e.g., $PA_B$) of the inner pockets 3706b are oriented at the angle B relative to the longitudinal axis LA. The outer pockets 3706c are oriented at an angle C relative to the longitudinal axis LA. Stated differently, the pocket axes (e.g., $PA_C$) of the inner pockets 3706a are oriented at the angle C relative to the longitudinal axis LA.

The angles A, B, and C may be different. The inner pockets 3706a are obliquely oriented relative to the outer pockets 3706c. The angle A is less than the angle C. Because the axes of the outer pockets 3706c (e.g., axis $PA_C$) are not parallel to the axes of the inner pockets 3706a (e.g., axis $PA_A$), the staple-forming pockets 3706 in the anvil 3700 form a modified or skewed herringbone pattern. The pocket axes $PA_B$ of the intermediate pockets 3706b are obliquely oriented relative to the inner pockets 3706a and outer pockets 3706c. In other instances, the pocket axes $PA_B$ of the intermediate pockets 3706b can be oriented perpendicular, or substantially perpendicular, to either the inner pocket 3706a or the outer pocket 3706c. For example, the angle B can be a supplementary angle to either angle A or C.

The inner pockets 3706a have a length $L_A$, the intermediate pockets 3706b have a length $L_B$, and the outer pockets 3706c have a length $L_C$. The length $L_C$ is less than the length $L_B$ and the length $L_A$. In other words, the outer pockets 3706c are shorter than the intermediate pockets 3706b and the inner pockets 3706a. In certain instances, the lengths $L_A$, $L_B$, and $L_C$ can be different. In other instances, the lengths $L_A$, $L_B$, and $L_C$ can be the same. In still other instances, the length $L_B$ can be less than the length $L_A$ and/or $L_B$, and/or the length $L_A$ can be less than the length $L_A$ and/or $L_C$. The lengths $L_A$, $L_B$, and $L_C$ can be selected to optimize the nesting of the pockets 3706.

The spacing of the staple-forming pockets 3706 can also be configured to optimize the nesting thereof. For example, the inner pockets 3706a can be longitudinally staggered relative to the outer pockets 3706c. Moreover, the inner pockets 3706a can partially longitudinally overlap the outer pockets 3706c. Referring to FIG. 129, a first end of the inner pocket 3706a is longitudinally offset from the corresponding end of the outer pocket 3706c by a distance $X1_{A/C}$. Moreover, a second end of the inner pocket 3706a is longitudinally offset from the corresponding end of the outer pocket 3706c by a distance $X2_{A/C}$. The distance $X2_{A/C}$ is less than the distance $X1_{A/C}$. In other instances, the distance $X2_{A/C}$ can be equal to or greater than the distance $X1_{A/C}$. The intermediate pockets 3706b are longitudinally staggered relative to the inner pockets 3706a and the outer pockets 3706c. More specifically, the intermediate pockets 3706b are equidistantly longitudinally offset between adjacent inner pockets 3706a and between adjacent outer pockets 3706c. In other instances, the intermediate pockets 3706b may be non-equidistantly offset between adjacent inner pockets 3706a and between adjacent outer pockets 3706c.

The arrangement of pockets 3706 is configured to nest the pockets 3706 such that the pockets 3706 fit within a pre-defined space. For example, in certain instances, the width of the anvil can be minimized or otherwise restrained to fit within a surgical trocar and/or within a narrow surgical field, and the arrangement of staple-forming pockets 3706 (and the corresponding arrangement of staples and/or staple cavities) can fit within a narrow anvil.

Referring now to FIGS. 81-84C, staple-forming pockets 3806 in a portion of an anvil 3800 are shown. The anvil 3800 includes a staple-forming surface 3802 and a longitudinal slot 3804. The longitudinal slot 3804 extends along the longitudinal axis LA of the anvil 3800. In certain instances, a firing element and/or cutting element can translate through the longitudinal slot 3804 during at least a portion of a firing stroke. The staple-forming pockets 3806 are defined in the staple-forming surface 3802, which also includes a non-forming portion 3808 that extends around the pockets 3806. The non-forming portion 3808 extends entirely around each pocket 3806. In other words, the non-forming portion 3808 surrounds the staple-forming pockets 3806. In other instances, at least a portion of two or more adjacent pockets can be in abutting contact such that a non-forming portion is not positioned therebetween. In certain instances, the non-forming portion 3808 can extend across one or more of the pockets 3806.

The "forming ratio" of the staple-forming surface 3802 (the ratio of the non-forming portion 3808 to the forming portion, i.e., the pockets 3806) can be optimized. By optimizing the forming ratio, more staples can be formed and/or formed to their desired configurations. In certain instances, the surface area of the non-forming portion 3808 of the anvil 3800 can be minimized with respect to the staple-forming pockets 3806. Additionally or alternatively, the footprint of the staple-forming pockets 3806 can be extended or enlarged to maximize the portion of the staple-forming surface 3802 that is designed to catch and form the staples. Such arrangement, for example, may prevent inadvertent malformed staples that, for whatever reason, miss or fall outside of their corresponding forming pocket during the firing process.

Figure 81:
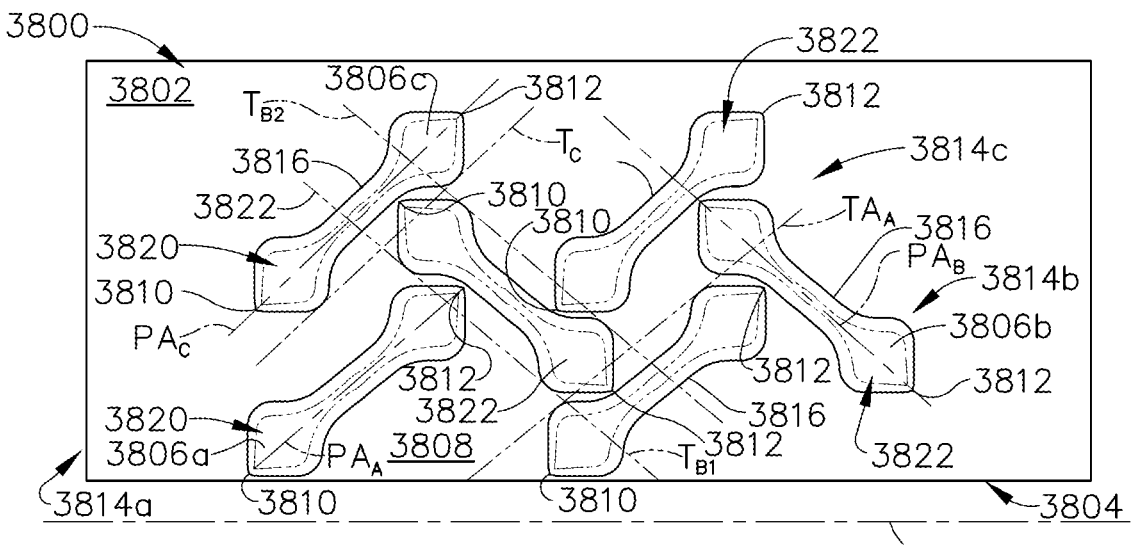
FIG. 81 is a plan view of a portion of an anvil having a plurality of staple-forming pockets defined therein.

The pockets 3806 depicted in FIG. 81 are arranged in three rows 3814a, 3814b, and 3814c on a first side of the longitudinal slot 3804. The first row 3814a is an inner row, the second row 3814b is an intermediate row, and the third row 3814c is an outer row. Inner pockets 3806a are positioned in the inner row 3814a, intermediate pockets 3806b are positioned in the intermediate row 3814b, and outer pockets 3806c are positioned in the outer row 3814c. Although not shown in FIG. 81, in at least one instance, the pockets 3806 on the opposing side of the slot 3804 can form a mirror image reflection of the pockets 3806 on the first side of the longitudinal slot 3804. In other instances, the arrangement of pockets 3806 in the staple-forming surface 3802 can be asymmetrical relative to the slot 3804 and, in certain instances, the anvil 3800 may not include the longitudinal slot 3804. In various instances, the pockets 3806 can be arranged in less than or more than three rows on each side of the slot 3804.

The pockets 3806 depicted in FIG. 81 are identical. Each pocket 3806 defined in the staple-forming surface 3802 has the same geometry. In other instances, the geometry of the pockets 3806 can vary row-to-row and/or longitudinally along the length of the anvil 3800. For example, in certain instances, the depth of the pockets 3806 or portions thereof can vary along the length of the anvil 3800 to accommodate for variations in gap distance between the anvil and the staple cartridge along the length of an end effector and/or tissue flow, as described herein.

An exemplary pocket 3806b is shown in FIGS. 82-84C. The pocket 3806b has a first end, or proximal end, 3810 and a second end, or distal end, 3812. A pocket axis PA extends between the proximal end 3810 and the distal end 3814 of the pocket 3806b. Referring again to FIG. 81, the pockets 3806 in each respective row are parallel. For example, the pocket axes (e.g., $PA_A$) of the inner pockets 3806a are parallel to each other, the pocket axes (e.g., $PA_B$) of the intermediate pockets 3806b are parallel to each other, and the pocket axes (e.g., $PA_C$) of the outer pockets 3806c are parallel to each other. The pocket axes PA are obliquely oriented relative to the slot 3804. Moreover, the axes $PA_B$ of the intermediate pockets 3806b are oriented perpendicular to the axes $PA_A$ and $PA_C$ of the inner pockets 3806a and the outer pockets 3806c, respectively. As such, the pockets 3806 are arranged in a herringbone arrangement along the staple-forming surface 3802.

The pocket 3806b includes a perimeter 3816, which defines the boundary of the pocket 3806b. The pocket 3806b also includes a proximal cup 3820, a distal cup 3822, and a neck portion 3824 connecting the proximal cup 3820 and the distal cup 3822. When a staple is driven into forming contact with the staple-forming surface 3802, the proximal cup 3820 is aligned with a proximal staple leg, and the distal cup 3822 is aligned with a distal staple leg. The tips of the staple legs are positioned and configured to land in the respective cups 3820, 3822. Stated differently, the proximal cup 3820 is configured to receive a proximal staple leg and the distal cup 3822 is configured to receive a distal staple leg. The cups 3820 and 3822 are also configured to direct or funnel the staple legs toward the pocket axis PA and a central portion of the pocket 3806, such as the neck portion 3824, and to deform the staple legs into the formed configuration.

The pockets 3806 include extended landing zones for the staple legs. Referring to the pocket 3806b depicted in FIG. 82, the pocket 3806b includes a proximal extended landing zone 3830 and a distal extended landing zone 3832. The proximal extended landing zone 3830 is positioned in a proximal portion of the proximal cup 3820, and the distal extended landing zone 3832 is positioned in a distal portion of the distal cup 3822. The extended landing zones 3830 and 3832 define a substantially triangular perimeter. Moreover, the extended landing zones 3830 and 3832 terminate along the pocket axis PA at a point to form corners of the pocket 3806b.

In other instances, the extended landing zones 3830 and 3832 can define straight and/or contoured perimeters, for example, and may extend laterally and/or longitudinally relative to the pocket axis PA. In instances where a staple or portion thereof is skewed during firing, the extended landing zones 3830, 3832 can salvage, or at least attempt to salvage, the formation of the skewed staple.

Figure 83:
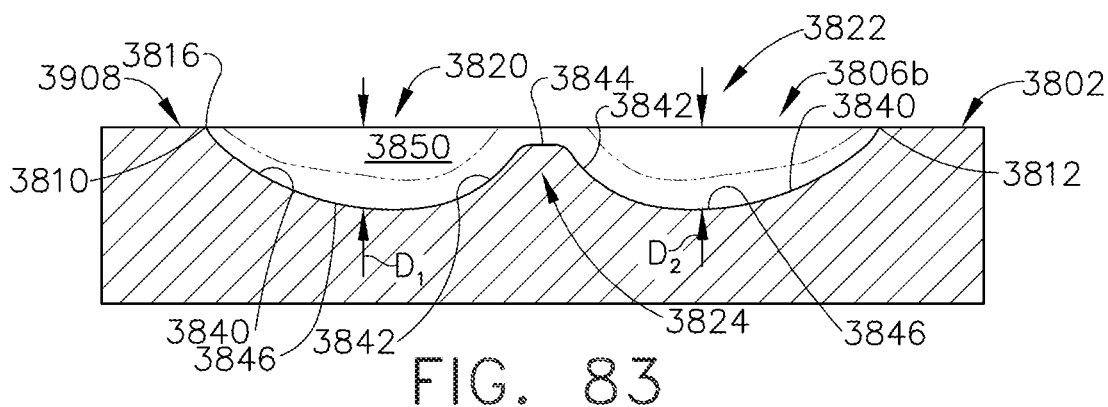
FIGS. 83, 84A, 84B, and 84C are cross-sectional views of the pocket of FIG. 82, taken along lines 83-83, 84A-84A, 84B-84B and 84C-84C respectively.

Referring primarily to FIG. 83, each cup 3820, 3822 of the pocket 3806b defines an entrance ramp 3840 and an exit ramp 3842. The exit ramp 3842 is steeper than the entrance ramp 3840. When forming a staple, the tip of a staple leg can enter the respective cup 3820, 3822 along the entrance ramp 3840 and exit the respective cup 3820, 3822 along the exit ramp 3842. At an apex 3846 between the entrance ramp 3840 and the exit ramp 3842, the tips of the staple legs are deformed toward the staple base to assume the formed configuration, such as a B-form or modified B-form, for example. The proximal cup 3820 defines a proximal depth $D_1$ at the apex 3846 thereof measured relative to the non-forming portion 3808 of the staple-forming surface 3802, and the distal cup 3822 defines a distal depth $D_2$ at the apex 3846 thereof measured relative to the non-forming portion 3808 of the staple-forming surface 3802. In the pocket 3806b, the proximal depth $D_1$ and the distal depth $D_2$ are equal. In other instances, the proximal depth $D_1$ and the distal depth $D_2$ can be different.

The pocket 3806b also defines a bridge 3844 in the neck portion 3824 between the proximal cup 3820 and the distal cup 3822. The bridge 3844 is offset from the non-forming portion 3808 of the staple-forming surface 3802. More specifically, the bridge 3844 is positioned below or recessed relative to the non-forming portion 3808. In other instances, the bridge 3844 can be aligned with the non-forming portion 3808 and/or can protrude away from the non-forming portion 3808 toward the opposing jaw of the end effector.

Figure 84C:
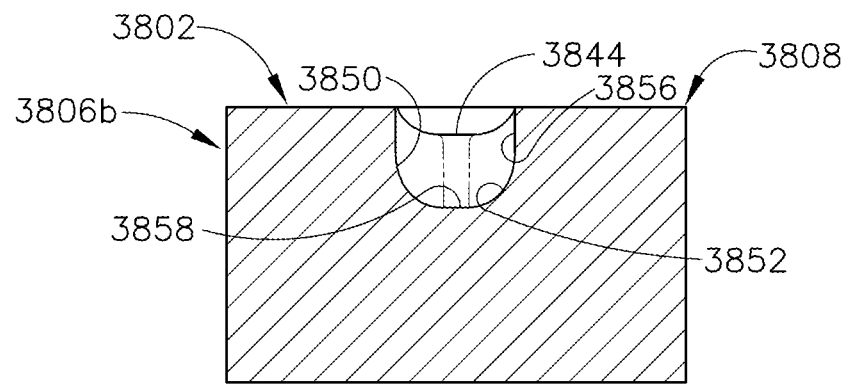
Figure 84B:
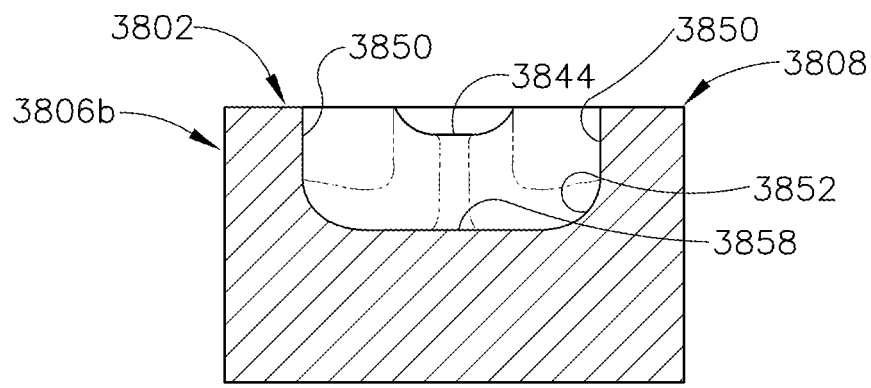
Figure 84A:
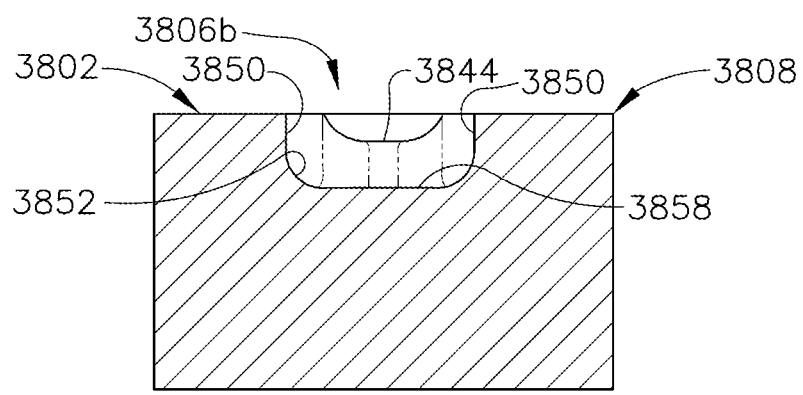

Referring primarily to FIGS. 84A-84C, the pocket 3806$b$ includes sidewalls 3850. The sidewalls 3850 are oriented perpendicular to the non-forming portion 3808 of the staple-forming surface 3802. The sidewalls 3850 widen toward a central region 3821 of each cup 3820, 3822, and narrow from the central region 3821 of each cup 3820, 3822 toward the neck portion 3824. The widened central region 3821 provides an enlarged footprint for receiving the tip of a staple leg. The extended landing zones 3830, 3832 also enlarge the footprint of the respective cups 3820, 3822 for receiving the staple tips. As the cups 3820, 3822 narrow toward the neck portion 3824, the cups 3820, 3822 are configured to funnel and/or guide the tips of the staple legs toward and/or along the pocket axis PA and into a formed configuration. As the cups 3820 and 3822 widen and then narrow toward the neck portion 3824, the perimeter 3816 of the pocket 3806$b$ defines a contour or arced profile. In other instances, the perimeter 3816 of the pocket 3806$b$ can extend along linear, non-contoured profiles having non-rounded corners, for example.

The pocket 3806$b$ defines fillets 3852 (FIGS. 84A-84C) between the sidewalls 3850 and the bottom surface of the pocket 3806$b$. The fillets 3852 are configured to guide the staple legs along the desired path in the pocket 3806$b$. For example, if a staple leg lands along the fillet 3852 or is diverted to the fillet 3852, the fillet 3852 can smoothly guide the staple leg toward the pocket axis PA.

Referring again to FIG. 82, the pocket 3806$b$ is symmetric about the pocket axis PA. For example, the perimeter 3816 of the pocket 3806$b$ is symmetric about the pocket axis PA. Moreover, the pocket 3806$b$ is symmetric about a central axis CA through the neck portion 3824 and perpendicular to the pocket axis PA. For example, the perimeter 3816 of each pocket 3806 is symmetric about the central axis CA, and the proximal cup 3820 has the same geometry as the distal cup 3822.

In other instances, the proximal cup 3820 can be different than the distal cup 3822. For example, referring again to FIG. 83, the distal depth $D_2$ can be less than the proximal depth $D_1$. In various instances, the variation in the depth of a staple-forming pocket can accommodate for variations in gap distance between the anvil and the staple cartridge along the length of an end effector when tissue is clamped therebetween. For example, an anvil may bow or bend away from the staple cartridge as the anvil approaches the distal end of the end effector. Variations to the depth of the staple-forming pockets 3806 can be configured to ensure that an appropriate forming height is maintained in view of the anticipated or expected bowing or bending of the anvil 3800.

Additionally or alternatively, the variation in the depth of a staple-forming pocket can accommodate for tissue movement or flow relative to the end effector. More specifically, when tissue is clamped between the jaws of the end effector, fluid in the clamped tissue can flow or move toward adjacent, unclamped tissue. The tissue can flow laterally toward the longitudinal sides of the anvil 3800, distally toward the distal end of the anvil 3800, and/or proximally toward the proximal end of the anvil 3800. In certain instances, tissue can flow relative to the anvil 3800 when the cutting edge is advanced distally through the tissue. In such instances, tissue may flow laterally, distally, and/or proximally, but it primarily flows distally due to the distal movement of the cutting edge. In instances where the cutting edge moves proximally to incise tissue, the movement or flow of the tissue would be generally proximal during the cutting stroke. Different depths $D_1$ and $D_1$ in the pocket 3806 can accommodate for the distal flow of the tissue, which can shift or skew the staple legs embedded therein distally.

In various instances, tissue movement or flow at the distal end of an end effector can be larger than the tissue movement or flow at the proximal end of the end effector. Such instances can arise as a result of the distal movement of the firing member within the end effector. Although the firing member is configured to progressively staple and incise the tissue as it is moved distally, the firing member can also plow or push the tissue distally. This pushing or plowing effect may begin at the proximal end of the end effector and may compound as the firing member is moved distally such that the largest pushing or plowing effect is realized at the distal end of the end effector. Consequently, the tissue flow can be increased toward the distal end of the end effector. To accommodate for such an increase in tissue flow, the geometries of the staple pockets can vary longitudinally along the length of a row. In instances where the proximal and distal cups of the staple pockets are different to accommodate for tissue flow, a gradient in pocket asymmetries may be utilized within a row of pockets to compensate for the gradient in tissue movement and staple shifting.

In certain instances, different staple geometries can be utilized with the different pocket geometries. The use of different staples to accommodate for tissue flow along the length of an end effector is described in U.S. patent application Ser. No. 14/318,996, entitled FASTENER CARTRIDGES INCLUDING EXTENSIONS HAVING DIFFERENT CONFIGURATIONS, filed Jun. 30, 2014, which is hereby incorporated by reference herein in its entirety. In other instances, identical staples can be utilized with different pocket geometries along the length of an anvil.

Figure 82:
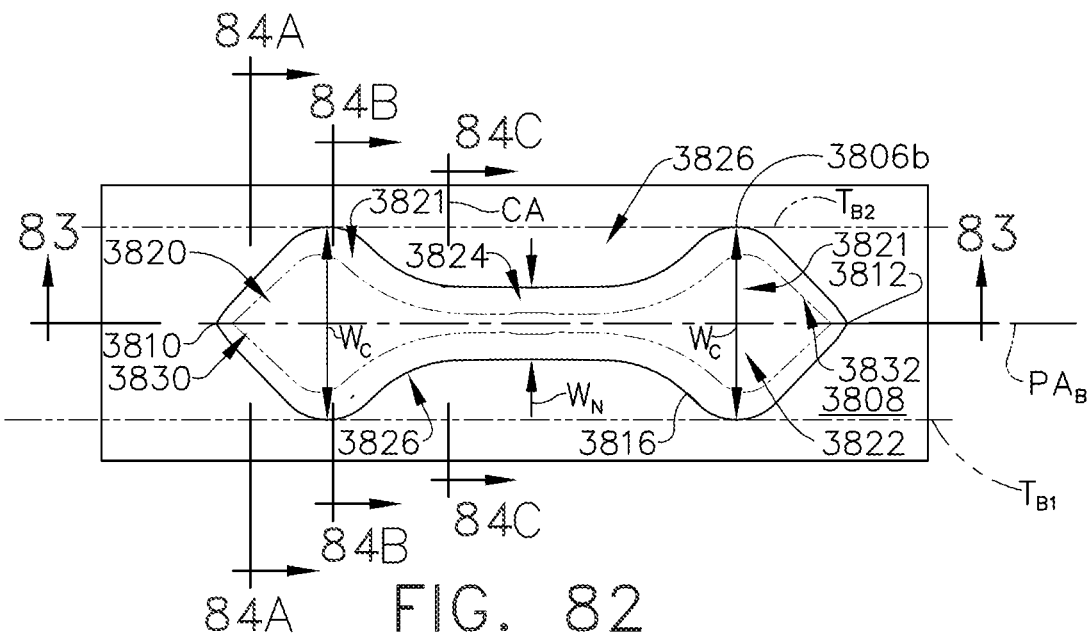
FIG. 82 is a detail view of a pocket of FIG. 81.

Referring again to FIG. 82, the neck portion 3824 defines a width $W_N$ and the proximal and distal cups 3820 and 3822 define a width $W_C$. The width $W_N$ is less than the width $W_C$. Consequently, the central portion of the pocket 3806$b$ is narrower than the proximal and distal cups 3820 and 3822. The narrowed perimeter 3816 of the pocket 3806$b$ at the neck portion 3824 defines a receiving peninsula 3826 between a portion of the proximal cup 3820 and a portion of the distal cup 3822. Owing to the symmetry of the pocket 3806$b$, symmetrical receiving peninsulas 3826 are positioned on each side of the pocket 3806$b$. The receiving peninsulas 3826 are bounded by the perimeter 3816 of the pocket 3806$b$ and a tangent axis (e.g., $T_A$, $T_{B1}$, $T_{B2}$, and $T_C$), which is tangential to the widest portion of the proximal and distal cups 3820 and 3822 on a side of the pocket 3806. A first tangent axis $T_{B1}$ is positioned on a first side of the pocket 3806$b$ and a second tangent axis $T_{B2}$ is positioned on the opposite side of the pocket 3806$b$. The first and second tangent axes $T_{B1}$ and $T_{B2}$ depicted in FIG. 82 are parallel to the pocket axis $PA_B$.

Referring again to FIG. 81, the perimeters 3816 of the pockets 3806 are nested or interlocked along the staple-forming surface 3802. In particular, each pocket 3806 extends into the receiving peninsula 3826 of an adjacent pocket 3806. For example, the intermediate pockets 3806$b$ are nested between the inner pockets 3806$a$ and the outer pockets 3806$c$. Stated differently, the intermediate pockets 3806$b$ extend into the receiving peninsula 3826 of an adjacent inner pocket 3806$a$ and into the receiving peninsula 3826 of an adjacent outer pocket 3806c. Moreover, the inner pockets 3806a and the outer pockets 3806b are nested with the intermediate pockets 3806b. More specifically, the inner pockets 3806a extend into the receiving peninsula 3826 of an adjacent intermediate pocket 3806b, and the outer pockets 3806c extend into the receiving peninsula 3826 of an adjacent intermediate pocket 3806b.

The distal cup 3822 of the intermediate pocket 3806b extend across the tangent axis $T_A$ and into the receiving peninsula 3826 of the adjacent inner pocket 3806a. Moreover, the proximal cup 3820 of the intermediate pocket 3806b extends across the tangent axis $T_C$ and into the receiving peninsula 3826 of the adjacent outer pocket 3806c. Additionally, the distal cup 3822 of the inner pockets 3806a extends across the tangent axis $T_{B1}$ and into the receiving peninsula 3826 of the adjacent intermediate pocket 3806b. Furthermore, the proximal cup 3820 of the outer pockets 3806c extends across the tangent axis $T_{B2}$ and into the receiving peninsula 3826 of the adjacent intermediate pocket 3806b. In various instances, the distal extended landing zone 3832 of the intermediate pocket 3806b is positioned in the receiving peninsula 3826 of an inner pocket 3806a, the proximal extended landing zone 3830 of the intermediate pocket 3806b is positioned in the receiving peninsula 3826 of an outer pocket 3806c, the distal extended landing zone 3832 of an inner pocket 3806a is positioned in the receiving peninsula 3826 of an intermediate pocket 3806b, and the proximal extended landing zone 3830 of the outer pocket 3806c is positioned in the receiving peninsula 3826 of an intermediate pocket 3806b.

The geometry of the pockets 3806 facilitates the nesting of the pockets 3806 in the staple-forming surface 3802. For example, because the pockets 3806 include a narrowed neck portion 3824 between two enlarged cups 3820 and 3822, one of the enlarged cups 3820, 3822 of another pocket 3806 can be positioned adjacent to the narrowed neck portion 3824. For example, one of the enlarged cups 3820, 3822 can be aligned with and/or received by a portion of an adjacent pocket 3806. In such instances, the surface area of the staple-forming surface 3802 that is covered by the pockets 3806 can be optimized. For example, the surface area of the staple-forming surface 3802 that is covered by the pockets 3806 is maximized. The "forming ratio" of the staple-forming surface 3802 is the ratio of the non-forming portion 3808 to the forming portion, i.e., the pockets 3806. The forming ratio is about 1.7:1. In other instances, the forming ratio can be less than 1.7:1 or more than 1.7:1. For example, in at least one instance, more than 50% of the staple-forming surface 3802 can be covered with staple-forming pockets 3806.

The nesting of staple-forming pockets discussed herein can refer to the nesting of adjacent pocket perimeters. For example, where a first pocket defines an inward contour, i.e., a contour extending inward toward the pocket axis, an adjacent second pocket can protrude toward and/or into the region adjacent to the inward contour. Additionally or alternatively, a portion of the second pocket, such as an end of the second pocket, can be aligned with the narrowed region of the first pocket. Consequently, the second pocket can be positioned nearer to the pocket axis of the first pocket than if the end of the second pocket was aligned with a wider region of the first pocket.

Referring now to FIGS. 85-88C, staple-forming pockets 3906 in a portion of an anvil 3900 are depicted. The anvil 3900 includes a staple-forming surface 3902 and a longitudinal slot 3904. The longitudinal slot 3904 extends along the longitudinal axis LA of the anvil 3900. In certain instances, a firing element and/or cutting element can translate through the longitudinal slot 3904 during at least a portion of a firing stroke. The staple-forming pockets 3906 are defined in the staple-forming surface 3902. The staple-forming surface 3902 also includes a non-forming portion 3908 that extends around the pockets 3906. The non-forming portion 3908 extends entirely around each pocket 3906 in FIG. 85. In other words, the non-forming portion 3908 surrounds the staple-forming pockets 3906. In other instances, at least a portion of two or more adjacent pockets 3906 can be in abutting contact such that a non-forming portion 3908 is not positioned therebetween.

The forming ratio of the staple-forming surface 3902 can be optimized. By optimizing the forming ratio, more staples can be formed and/or formed to their desired configurations. In certain instances, the surface area of the non-forming portion 3908 of the anvil 3900 can be minimized with respect to the staple-forming pockets 3906. Additionally or alternatively, the footprint of the staple-forming pockets 3906 can be extended or enlarged to maximize the portion of the staple-forming surface 3902 that is designed to catch and form the staples.

Figure 85:
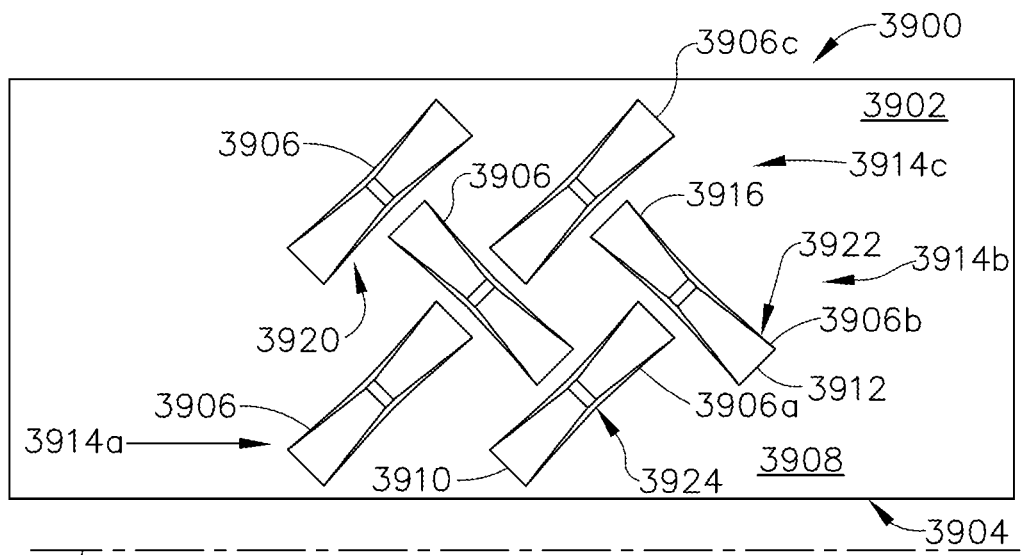
FIG. 85 is a plan view of a portion of an anvil having a plurality of staple-forming pockets defined therein.
Figure 86:
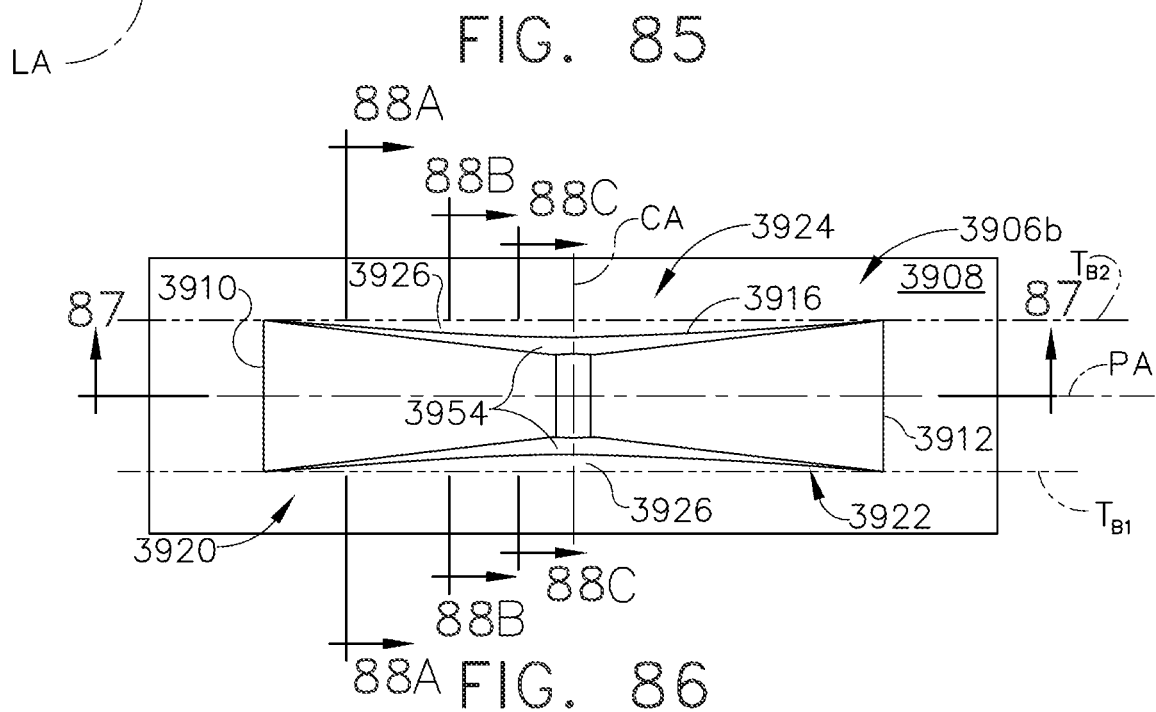
FIG. 86 is a detail view of a pocket of FIG. 85.

The pockets 3906 depicted in FIG. 85 are arranged in three rows 3914a, 3914b, 3914c on a first side of the longitudinal slot 3904. The first row 3914a is an inner row, the second row 3914b is an intermediate row, and the third row 3914c is an outer row. Inner pockets 3906a are positioned in the inner row 3914a, intermediate pockets 3906b are positioned in the intermediate row 3914b, and outer pockets 3906c are positioned in the outer row 3914c. Similar to the anvil 3800, the pockets 3906 are arranged in a herringbone arrangement along the staple-forming surface 3902 of the anvil 3900. Although not shown in FIG. 85, in at least one instance, the pockets 3906 on the opposing side of the slot 3904 can form a mirror image reflection of the pockets 3906 on the first side of the longitudinal slot 3904. In other instances, the arrangement of pockets 3906 in the staple-forming surface 3902 can be asymmetrical relative to the slot 3904 and, in certain instances, the anvil 3900 may not include the longitudinal slot 3904. In various instances, the pockets 3906 can be arranged in less than or more than three rows on each side of the slot 3904.

The pockets 3906 depicted in FIG. 85 are identical. Each pocket 3906 defined in the staple-forming surface 3802 has the same geometry. In other instances, the geometry of the pockets 3906 can vary row-to-row and/or longitudinally along the length of the anvil 3900. For example, in certain instances, the depth of the pockets 3906 or portions thereof can vary along the length of the anvil 3900 to accommodate for variations in gap distance between the anvil and the staple cartridge along the length of an end effector and/or tissue flow, as described herein.

An exemplary pocket 3906b is shown in FIGS. 86-88C. The pocket 3906b has a first end, or proximal end, 3910 and a second end, or distal end, 3912. A pocket axis PA (FIG. 86) extends between the proximal end 3910 and the distal end 3912 of the pocket 3906b. The pocket 3906b includes a perimeter 3916, which defines the boundary of the pocket 3906. The pocket 3906b also includes a proximal cup 3920, a distal cup 3922, and a neck portion 3924 connecting the proximal cup 3920 and the distal cup 3922. When a staple is driven into forming contact with the staple-forming surface 3902, the proximal cup 3920 is aligned with a proximal staple leg, and the distal cup 3922 is aligned with a distal staple leg. The cups 3920 and 3922 are configured to direct or funnel the staple legs toward the pocket axis PA and a central portion of the pocket 3906, such as the neck portion 3924, and to deform the staple legs into the formed configuration.

Figure 87:
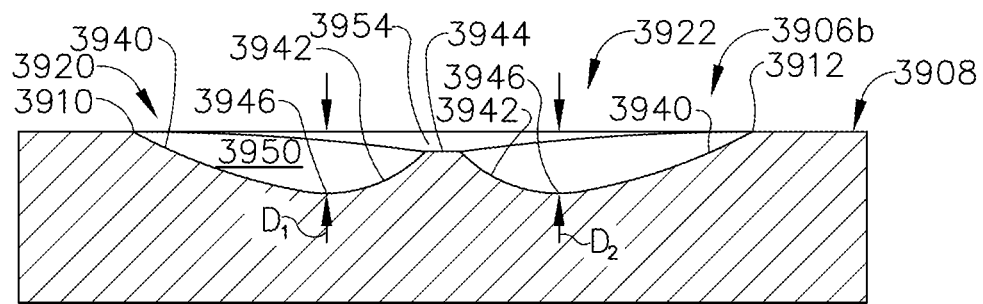
FIGS. 87, 88A, 88B, and 88C are cross-sectional views of the pocket of FIG. 86, taken along lines 87-87, 88A-88A, 88B-88B, and 88C-88C respectively.

Referring primarily to FIG. 87, each cup 3920, 3922 of the pocket 3906*b* defines an entrance ramp 3940 and an exit ramp 3942. The exit ramp 3942 is steeper than the entrance ramp 3940. When forming a staple, the tip of a staple leg can enter the respective cup 3920, 3922 along the entrance ramp 3940 and exit the respective cup 3920, 3922 along the exit ramp 3942. At an apex 3946 between the entrance ramp 3940 and the exit ramp 3942, the tips of the staple legs are deformed toward the staple base to assume the formed configuration, such as a B-form or modified B-form, for example. The proximal cup 3920 defines a proximal depth $D_1$ at the apex 3946 thereof measured relative to the non-forming portion 3908 of the staple-forming surface 3902, and the distal cup 3922 defines a distal depth $D_2$ at the apex 3946 thereof measured relative to the non-forming portion 3908 of the staple-forming surface 3902. In the pocket 3906, the proximal depth $D_1$ and the distal depth $D_2$ are equal. In other instances, the proximal depth $D_1$ and the distal depth $D_2$ can be different. The pocket 3906*b* also defines a bridge 3944 in the neck portion 3924 between the proximal cup 3920 and the distal cup 3922. The bridge 3944 is offset from the non-forming portion 3908 of the staple-forming surface 3902. More specifically, the bridge 3944 is positioned below or recessed relative to the non-forming portion 3908.

Figure 88C:
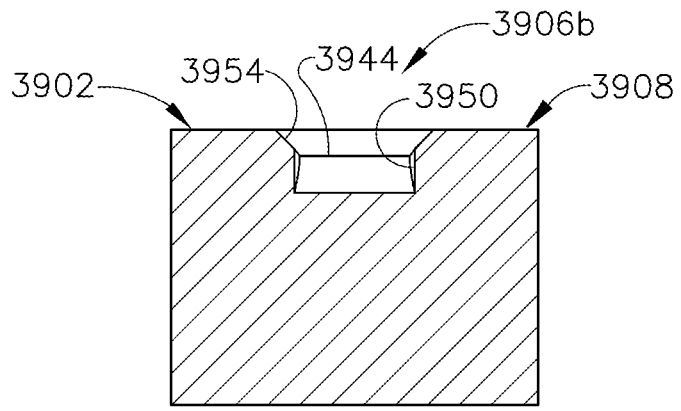
Figure 88B:
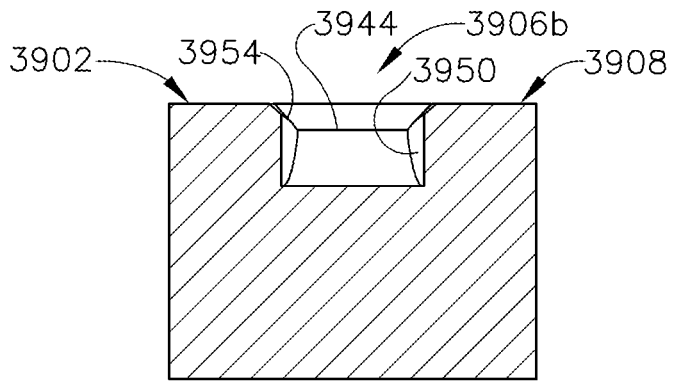
Figure 88A:
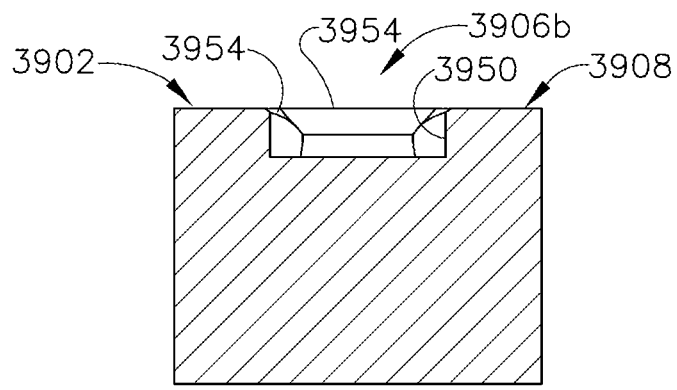

Referring primarily to FIGS. 88A-88C, the pocket 3906*b* includes sidewalls 3950. The sidewalls 3950 are oriented perpendicular to the non-forming portion 3908 of the staple-forming surface 3902. The sidewalls 3950 narrow linearly from the outer ends of each cup 3920, 3922 toward the neck portion 3924. Consequently, the widest portion of the cups 3920, 3922 is at the proximal and distal ends 3910, 3912 of the pocket 3906*b*, respectively. The profile 3916 of the pocket 3906*b* defines a bow-tie shape perimeter. The widened region at the proximal and distal ends 3910, 3912 provides an enlarged footprint for receiving the tip of a staple leg. In various instances, the widened portions of the cups 3920 and 3922 define extended landing zones for receiving the staple tips. As the cups 3920, 3922 narrow toward the neck portion 3924, the cups 3920, 3922 are configured to funnel and/or guide the tips of the staple legs toward and/or along the pocket axis PA into a formed configuration. The pocket 3906*b* defines a chamfered edge 3954 along the sides of the pocket 3906*b*. The chamfered edge 3954 serves to enlarge the footprint of the pocket 3906*b* and guide the tips of the staple legs toward the pocket axis PA.

Referring again to FIG. 86, the pocket 3906*b* is symmetric about the pocket axis PA. For example, the perimeter 3916 of the pocket 3906*b* is symmetric about the pocket axis PA. Moreover, the pocket 3906*b* is symmetric about a central axis CA through the neck portion 3924 and perpendicular to the pocket axis PA. For example, the perimeter 3916 of the pocket 3906*b* is symmetric about the central axis CA, and the proximal cup 3920 has the same geometry as the distal cup 3922. In other instances, the proximal cup 3920 can be different than the distal cup 3922. For example, referring again to FIG. 87, the distal depth $D_2$ can be less than the proximal depth $D_1$ to accommodate for variations in gap distance between the anvil and the staple cartridge and/or tissue flow, as described herein.

Referring again to FIG. 86, the width of the neck portion 3924 is less than the width of the cups 3920 and 3922. Consequently, the central portion of the pocket 3906*b* is narrower than the proximal and distal cups 3920 and 3922. The narrowed perimeter 3916 of the pocket 3906*b* at the neck portion 3924 defines a receiving peninsula 3926 between a portion of the proximal cup 3920 and a portion of the distal cup 3922. Owing to the symmetry of the pocket 3906*b*, symmetrical receiving peninsulas 3926 are positioned on each side of the pocket 3906*b*. The receiving peninsulas 3926 are bounded by the perimeter 3916 of the pocket 3906*b* and a tangent axis (e.g., $T_{B1}$ and $T_{B2}$), which is tangential to the widest portion of the proximal and distal cups 3920 and 3922 on a side of the pocket 3906*b*. A first tangent axis $T_{B1}$ is positioned on a first side of the pocket 3906*b* and a second tangent axis $T_{B2}$ is positioned on the opposite side of the pocket 3906*b*. The first and second tangent axes $T_{B1}$ and $T_{B2}$ are parallel to the pocket axis PA.

Referring again to FIG. 85, each pocket 3906 extends toward the receiving peninsula 3926 of an adjacent pocket 3906. For example, the intermediate pockets 3906*b* are aligned with the neck portions 3924 of the inner pockets 3906*a* and the outer pockets 3906*c*. Moreover, the inner pockets 3906*a* and the outer pockets 3906*b* extend toward the receiving peninsula 3926 of one of the intermediate pockets 3906*b*. More specifically, the pocket axes PA of the intermediate pockets 3906*b* are aligned with the neck portions 3924 of adjacent inner and outer pockets 3906*a* and 3906*c*, respectively, the pocket axes PA of the inner pockets 3906*a* are aligned with the neck portion 3924 of an adjacent intermediate pocket 3906*b*, and the pocket axes PA of the outer pockets 3906*c* are aligned with the neck portion 3924 of an adjacent intermediate pocket 3906*b*. In certain instances, a portion of one or more of the pockets 3906 can extend into the receiving peninsula of an adjacent pocket 3906.

The geometry of the pockets 3906 facilitates the close arrangement of the pockets 3906 in the staple-forming surface 3902. For example, because the pockets 3906 include a narrowed neck portion 3924 between two enlarged cups 3920 and 3922, the enlarged cup 3920, 3922 of another pocket 3906 can be positioned adjacent to the narrowed neck portion 3924. For example, an enlarged cup 3920, 3922 can be aligned with and/or received by a portion of the adjacent pocket 3906. Consequently, the surface area of the staple-forming surface 3902 that is covered by the pockets 3906 can be optimized. For example, the surface area of the staple-forming surface 3902 that is covered by pockets 3906 is maximized. The "forming ratio" is the ratio of the non-forming portion 3908 to the forming portion, i.e., the pockets 3906. In various instances, the forming ratio can be at least 1:1, for example.

In certain instances, though the pockets 3906 are positioned in close proximity to each other, because the neck portion 3924 narrows, there is space for the non-forming portion 3908 between adjacent pockets 3906. For example, the non-forming portion 3908 can extend between the neck portion 3924 of an inner pocket 3906*a* and the distal cup 3922 of an adjacent intermediate pocket 3906*b*. The non-forming portion 3908 between adjacent pockets 3906 can provide sufficient spacing between pockets 3906 to strengthen and/or reinforce the anvil 3900.

Referring now to FIGS. 89-92C, staple-forming pockets 4006 in a portion of an anvil 4000 are depicted. The pockets 4006 and arrangement thereof in the anvil 4000 are similar in many aspects to the pockets 3906 and arrangement thereof in the anvil 3900. For example, the anvil 4000 includes a staple-forming surface 4002 and a longitudinal slot 4004. The longitudinal slot 4004 extends along the longitudinal axis LA of the anvil 4000. In certain instances, a firing element and/or cutting element can translate through the longitudinal slot 4004 during at least a portion of a firing stroke. The staple-forming pockets 4006 are defined in the staple-forming surface 4002. The staple-forming surface 4002 also includes a non-forming portion 4008 that extends around the pockets 4006. The non-forming portion 4008 extends entirely around each pocket 4006 in FIG. 89. In other words, the non-forming portion 4008 surrounds the staple-forming pockets 4006. In other instances, at least a portion of two or more adjacent pockets 4006 can be in abutting contact such that a non-forming portion 4008 is not positioned therebetween.

The forming ratio of the staple-forming surface 4002 can be optimized. By optimizing the forming ratio, more staples can be formed and/or formed to their desired configurations. In certain instances, the surface area of the non-forming portion 4008 of the anvil 4000 can be minimized with respect to the staple-forming pockets 4006. Additionally or alternatively, the footprint of the staple-forming pockets 4006 can be extended or enlarged to maximize the portion of the staple-forming surface 4002 that is designed to catch and form the staples.

The pockets 4006 are arranged in an inner row 4014a, an intermediate row 4014b, and an outer row 4014c on a first side of the longitudinal slot 4004. Inner pockets 4006a are positioned in the inner row 4014a, intermediate pockets 4006b are positioned in the intermediate row 4014b, and outer pockets 4006c are positioned in the outer row 4014c. Similar to the anvil 3800, the pockets 4006 are arranged in a herringbone arrangement along the staple-forming surface 4002 of the anvil 4000. Although not shown in FIG. 89, in at least one instance, the pockets 4006 on the opposing side of the slot 4004 can form a mirror image reflection of the pockets 4006 on the first side of the longitudinal slot 4004. In other instances, the arrangement of pockets 4006 in the staple-forming surface 4002 can be asymmetrical relative to the slot 4004 and, in certain instances, the anvil 4000 may not include the longitudinal slot 4004. In various instances, the pockets 4006 can be arranged in less than or more than three rows on each side of the slot 4004.

Figure 89:
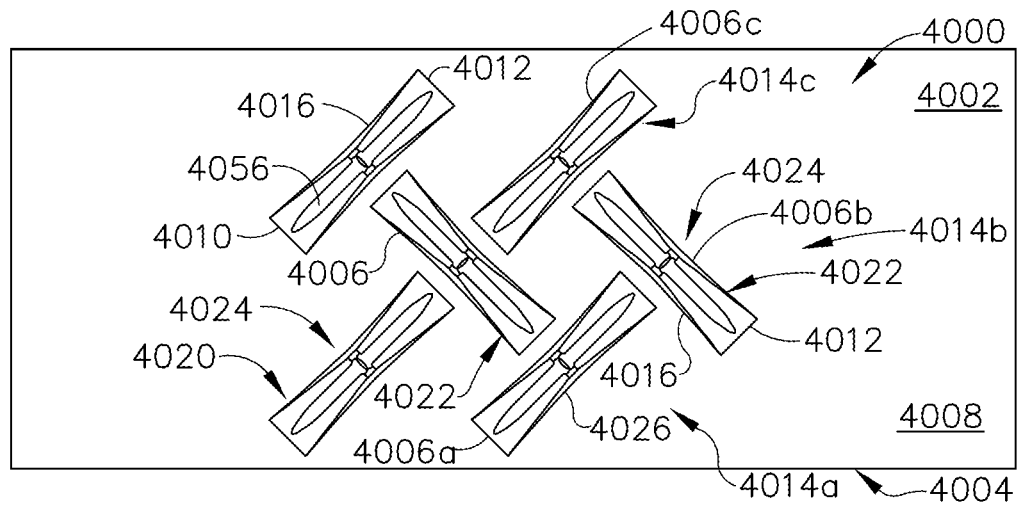
FIG. 89 is a plan view of a portion of an anvil having a plurality of staple-forming pockets defined therein.

The pockets 4006 depicted in FIG. 89 are identical. Each pocket 4006 defined in the staple-forming surface 4002 has the same geometry. In other instances, the geometry of the pockets 4006 can vary row-to-row and/or longitudinally along the length of the anvil 4000. For example, in certain instances, the depth of the pockets 4006 or portions thereof can vary along the length of the anvil 4000 to accommodate for variations in gap distance between the anvil and the staple cartridge along the length of an end effector and/or tissue flow, as described herein.

An exemplary pocket 4006b is shown in FIGS. 90-92C. The pocket 4006b has a first end, or proximal end, 4010 and a second end, or distal end, 4012. A pocket axis PA (FIG. 90) extends between the proximal end 4010 and the distal end 4012 of the pocket 4006b. The pocket 4006b includes a perimeter 4016, which defines the boundary of the pocket 4006b. The pocket 4006b also includes a proximal cup 4020, a distal cup 4022, and a neck portion 4024 connecting the proximal cup 4020 and the distal cup 4022. When a staple is driven into forming contact with the staple-forming surface 4002, the proximal cup 4020 is aligned with a proximal staple leg, and the distal cup 4022 is aligned with a distal staple leg. The cups 4020 and 4022 are configured to direct or funnel the staple legs toward the pocket axis PA and a central portion of the pocket 4006, such as the neck portion 4024, and to deform the staple legs into the formed configuration.

Figure 91:
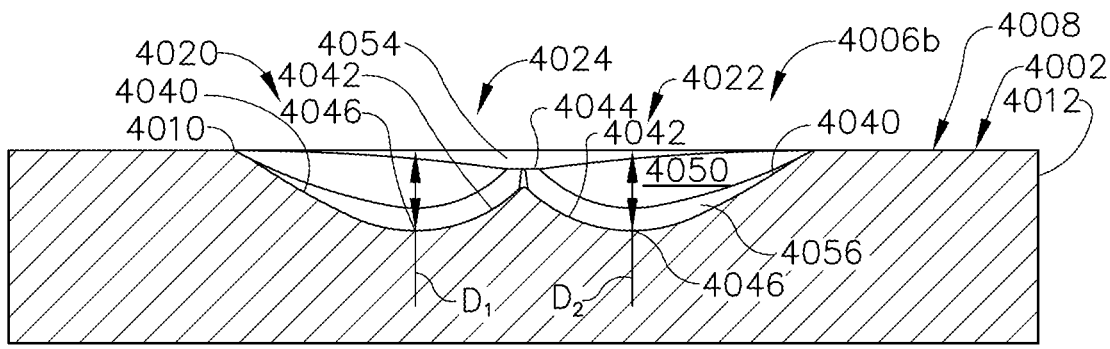
FIGS. 91, 92A, 92B, and 92C are cross-sectional views of the pocket of FIG. 90, taken along lines 91-91, 92A-92A, 92B-92B, and 92C-92C respectively.

Referring primarily to FIG. 91, each cup 4020, 4022 of the pocket 4006b defines an entrance ramp 4040 and an exit ramp 4042. When forming a staple, the tip of a staple leg can enter the respective cup 4020, 4022 along the entrance ramp 4040 and exit the respective cup 4020, 4022 along the exit ramp 4042. At an apex 4046 between the entrance ramp 4040 and the exit ramp 4042, the tips of the staple legs are deformed toward the staple base to assume the formed configuration, such as a B-form or modified B-form, for example. The pocket 4006b also defines a bridge 4044 between the proximal cup 4020 and the distal cup 4022. The bridge 4044 is offset from the non-forming portion 4008. More specifically, the bridge 4044 is positioned below or recessed relative to the non-forming portion 4008.

Figure 92C:
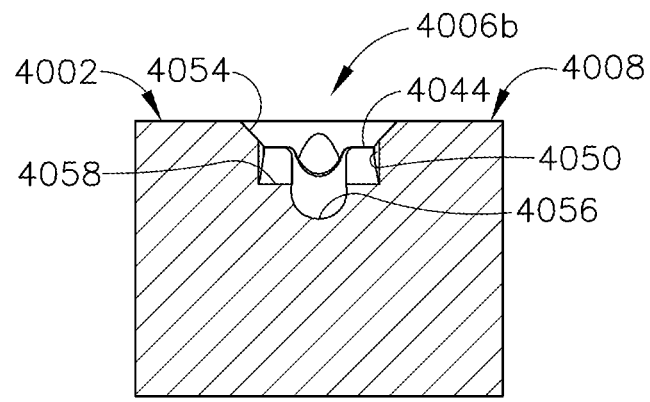
Figure 92B:
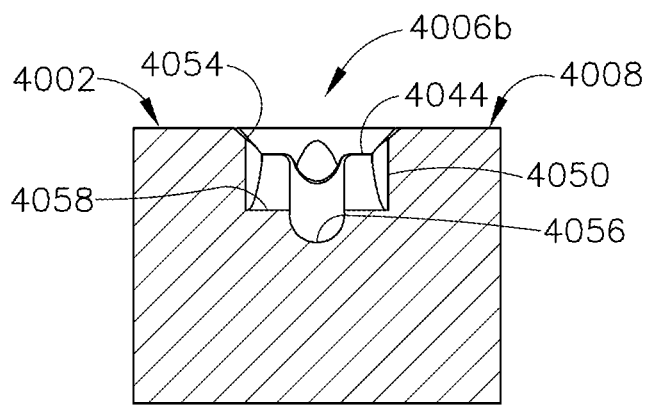
Figure 92A:
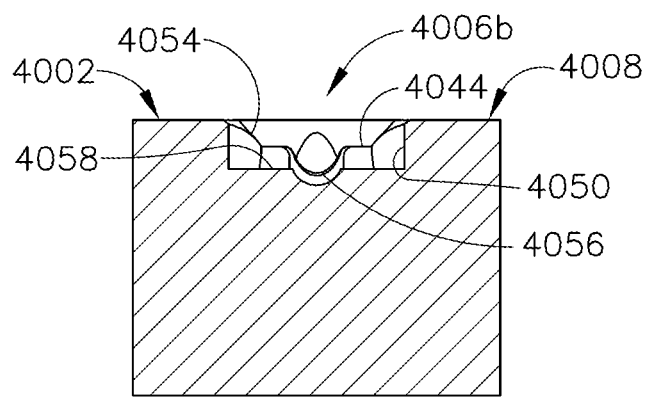

Referring primarily to FIGS. 92A-92C, the pocket 4006b includes sidewalls 4050, which are oriented perpendicular to the non-forming portion 4008 of the staple-forming surface 4002. The sidewalls 4050 narrow from the outer ends of each cup 4020, 4022 toward the neck portion 4024. Consequently, the widest portion of the cups 4020, 4022 is at the proximal and distal ends 4010, 4012 of the pocket 4006b, respectively. The profile 4016 of the pocket 4006b defines a bow-tie shape perimeter. The widened region at the proximal and distal ends 4010, 4012 provides an enlarged footprint for receiving the tip of a staple leg. In various instances, the widened portions of the cups 4020, 4022 define extended landing zones for receiving the staple tips. As the cups 4020, 4022 narrow toward the neck portion 4024, the cups 4020, 4022 are configured to funnel and/or guide the tips of the staple legs toward and/or along the pocket axis PA and into a formed configuration.

The pocket 4006b defines a chamfered edge 4054 along the sides of the pocket 4006b. Additionally, the pocket 4006b includes a groove 4056 in the bottom surface 4058 thereof. The groove 4056 extends from the proximal cup 4020 over the bridge 4024 and into the distal cup 4022. The groove 4056 is configured to constrain and guide the staple legs as they move to the deformed configuration.

In various instances, the diameter of the groove 4056 can be less than the diameter of the staple engaged with the groove 4056. For example, a staple can have a diameter of at least 0.0079 inches, and the diameter of the groove 4056 can be less than 0.0079 inches. The diameter of the groove 4056 can be about 0.007 inches, about 0.005 inches, or less than 0.005 inches. In certain instances, the staple can have a diameter of more than 0.0079 inches, such as about 0.0089 inches or about 0.0094 inches, for example. In various instances, the diameter of the staple can be less than 0.0079 inches or more than 0.0094 inches. In end effectors in which different staple geometries are utilized with the same staple-forming pocket geometry, the width of the groove in the pocket can be less than the smallest diameter staple. In still other instances, the width of the groove 4056 can vary staple-to-staple within a row and/or row-to-row.

Referring again to FIG. 90, the pocket 4006b is symmetric about the pocket axis PA. For example, the perimeter 4016 of the pocket 4006b is symmetric about the pocket axis PA. Moreover, the pocket 4006b is symmetric about a central axis CA through the neck portion 4024 and perpendicular to the pocket axis PA. For example, the perimeter 4016 of the pocket 4006b is symmetric about the central axis CA, and the proximal cup 4020 has the same geometry as the distal cup 4022. In other instances, the proximal cup 4020 can be different than the distal cup 4022. For example, referring again to FIG. 91, the distal depth $D_2$ can be less than the proximal depth $D_1$ to accommodate for variations in gap distance between the anvil and the staple cartridge and/or tissue flow, as described herein.

Figure 90:
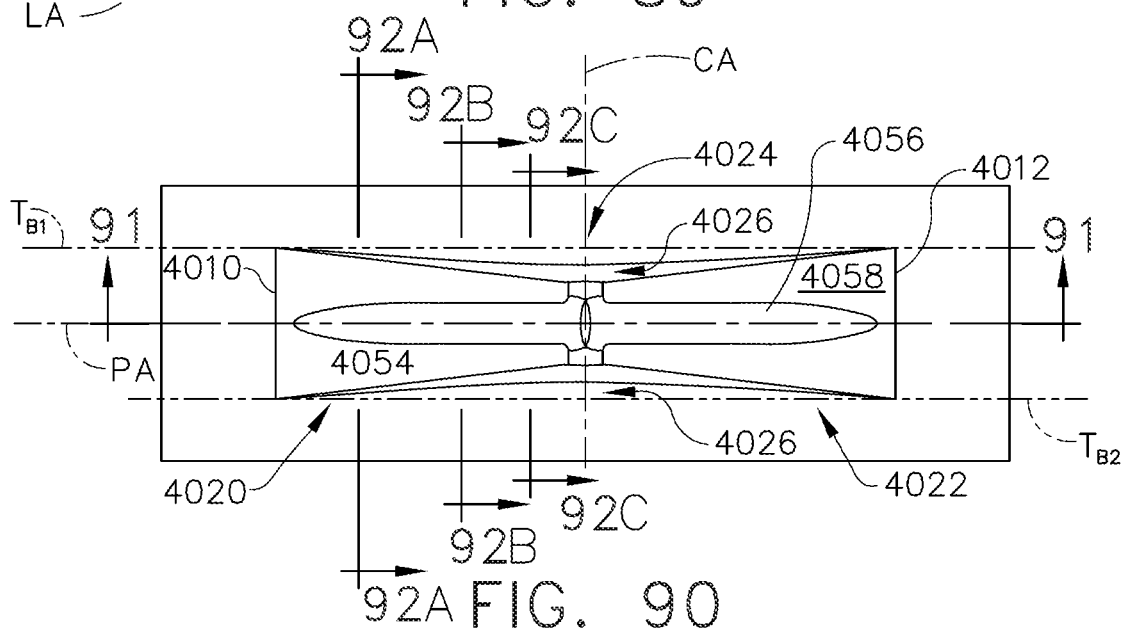
FIG. 90 is a detail view of a pocket of FIG. 89.

Referring again to FIG. 90, the neck portion 4024 of the pocket 4006b is narrower than the proximal and distal cups 4020 and 4022. The narrowed perimeter 4016 of the pocket 4006b defines a receiving peninsula 4026 between a portion of the proximal cup 4020 and a portion of the distal cup 4022. Owing to the symmetry of the pocket 4006b, symmetrical receiving peninsulas 4026 are positioned on each side of the pocket 4006b. The receiving peninsulas 4026 are bounded by the perimeter 4016 of the pocket 4006b and a tangent axis (e.g., $T_{B1}$ and $T_{B2}$), which is tangential to the widest portion of the proximal and distal cups 4020 and 4022 on a side of the pocket 4006b. A first tangent axis $T_{B1}$ is positioned on a first side of the pocket 4006b and a second tangent axis $T_{B2}$ is positioned on the opposite side of the pocket 4006b. The first and second tangent axes $T_{B1}$ and $T_{B2}$ depicted in FIG. 90 are parallel to the pocket axis PA.

Referring again to FIG. 89, each pocket 4006 extends toward the receiving peninsula 4026 of an adjacent pocket 4006. For example, the intermediate pockets 4006b are aligned with the neck portions 4024 of the inner pockets 4006a and the outer pockets 4006c. Moreover, the inner pockets 4006a and the outer pockets 4006b extend toward the receiving peninsula 4026 of one of the intermediate pockets 4006b. More specifically, the inner pockets 4006a are aligned with the neck portion 4024 of an adjacent intermediate pocket 4006b, and the outer pockets 4006c are aligned with the neck portion 4024 of an adjacent intermediate pocket 4006b. In certain instances, a portion of the pockets 4006 can extend into the receiving peninsula 4026 of an adjacent pocket 4006. Similar to the pockets 3906 in the anvil 3900, the geometry of the pockets 4006 facilitates the close arrangement of the pockets 4006 in the staple-forming surface 4002. The "forming ratio" is the ratio of the non-forming portion 4008 to the forming portion, i.e., the pockets 4006. In various instances, the forming ratio can be at least 1:1, for example Referring now to FIGS. 93-96C, staple-forming pockets 4106 in a portion of an anvil 4100 are depicted. The pockets 4106 and arrangement thereof in the anvil 4100 are similar in many aspects to the pockets 4006 and arrangement thereof in the anvil 4000. For example, the anvil 4100 includes a staple-forming surface 4102 and a longitudinal slot 4104. The longitudinal slot 4104 extends along the longitudinal axis LA of the anvil 4100. In certain instances, a firing element and/or cutting element can translate through the longitudinal slot 4104 during at least a portion of a firing stroke. Staple-forming pockets 4106 are defined in the staple-forming surface 4102. The staple-forming surface 4102 also includes a non-forming portion 4108 that extends around the pockets 4106. The non-forming portion 4108 extends entirely around each pocket 4106 in FIG. 90. In other words, the non-forming portion 4108 surrounds the staple-forming pockets 4106. In other instances, at least a portion of two or more adjacent pockets 4106 can be in abutting contact such that a non-forming portion 4108 is not positioned therebetween.

The forming ratio of the staple-forming surface 4102 can be optimized. By optimizing the forming ratio, more staples can be formed and/or formed to their desired configurations. In certain instances, the surface area of the non-forming portion 4108 of the anvil 4100 can be minimized with respect to the staple-forming pockets 4106. Additionally or alternatively, the footprint of the staple-forming pockets 4106 can be extended or enlarged to maximize the portion of the staple-forming surface 4102 that is designed to catch and form the staples.

Figure 93:
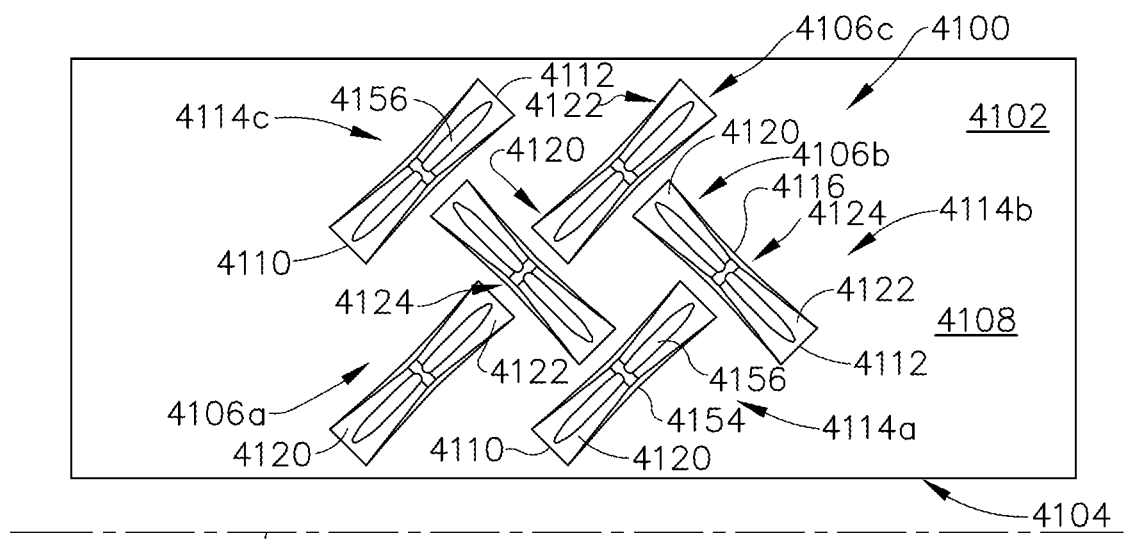
FIG. 93 is a plan view of a portion of an anvil having a plurality of staple-forming pockets defined therein.

The pockets 4106 depicted in FIG. 93 are arranged in an inner row 4114a, an intermediate row 4114b, and an outer row 4114c on a first side of the longitudinal slot 4104. Inner pockets 4106a are positioned in the inner row 4114a, intermediate pockets 4106b are positioned in the intermediate row 4114b, and outer pockets 4106c are positioned in the outer row 4114c. Similar to the anvil 3800, the pockets 4106 are arranged in a herringbone arrangement along the staple-forming surface 4102 of the anvil 4100. Although not shown in FIG. 93, in at least one instance, the pockets 4106 on the opposing side of the slot 4104 can form a mirror image reflection of the pockets 4106 on the first side of the longitudinal slot 4104. In other instances, the arrangement of pockets 4106 in the staple-forming surface 4102 can be asymmetrical relative to the slot 4104 and, in certain instances, the anvil 4100 may not include the longitudinal slot 4104. In various instances, the pockets 4106 can be arranged in less than or more than three rows on each side of the slot 4104.

The pockets 4106 depicted in FIG. 93 are identical. Each pocket 4106 defined in the staple-forming surface 4102 has the same geometry. In other instances, the geometry of the pockets 4106 can vary row-to-row and/or longitudinally along the length of the anvil 4100. For example, in certain instances, the depth of the pockets 4106 or portions thereof can vary along the length of the anvil 4100 to accommodate for variations in gap distance between the anvil and the staple cartridge along the length of an end effector and/or tissue flow, as described herein.

An exemplary pocket 4106b is shown in FIGS. 94-96C. The pocket 4106b has a first end, or proximal end, 4110 and a second end, or distal end, 4112. A pocket axis PA (FIG. 94) extends between the proximal end 4110 and the distal end 4112 of the pocket 4106b. The pocket 4106b includes a perimeter 4116, which defines the boundary of the pocket 4106b. The pocket 4106 also includes a proximal cup 4120, a distal cup 4122, and a neck portion 4124 connecting the proximal cup 4120 and the distal cup 4122. When a staple is driven into forming contact with the staple-forming surface 4102, the proximal cup 4120 is aligned with a proximal staple leg, and the distal cup 4122 is aligned with a distal staple leg. The cups 4120, 4122 are configured to direct or funnel the staple legs toward the pocket axis PA and a central portion of the pocket 4106, such as the neck portion 4124, and to deform the staple legs into the formed configuration.

Figure 95:
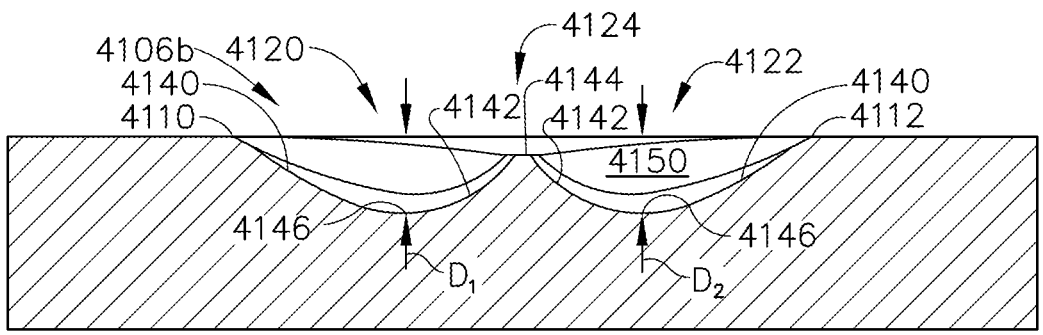
FIGS. 95, 96A, 96B, and 96C are cross-sectional views of the pocket of FIG. 94, taken along lines 95-95, 96A-96A, 96B-96B, and 96C-96C respectively.

Referring primarily to FIG. 95, each cup 4120, 4122 of the pocket 4106b defines an entrance ramp 4140 and an exit ramp 4142. The exit ramp 4142 is steeper than the entrance ramp 4140. When forming a staple, the tip of a staple leg can enter the respective cup 4120, 4122 along the entrance ramp 4140 and exit the respective cup 4120, 4122 along the exit ramp 4142. At an apex 4146 between the entrance ramp 4140 and the exit ramp 4142, the tips of the staple legs are deformed toward the staple base to assume the formed configuration, such as a B-form or modified B-form, for example. The pocket 4106b also defines a bridge 4144 in the neck portion 4124 between the proximal cup 4120 and the distal cup 4122. The bridge 4144 is offset from the non-forming portion 4108. More specifically, the bridge 4144 is positioned below or recessed relative to the non-forming portion 4108.

Figure 96C:
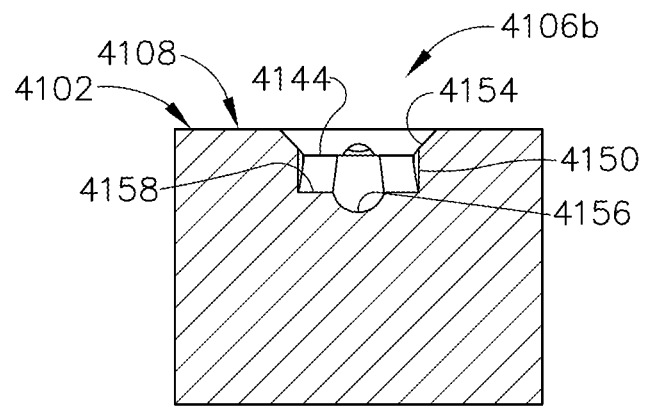
Figure 96B:
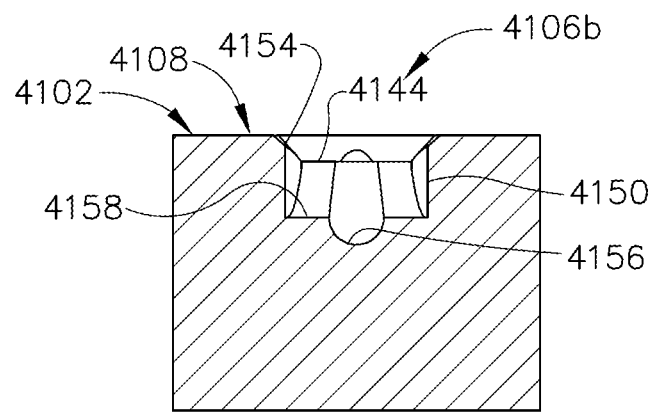
Figure 96A:
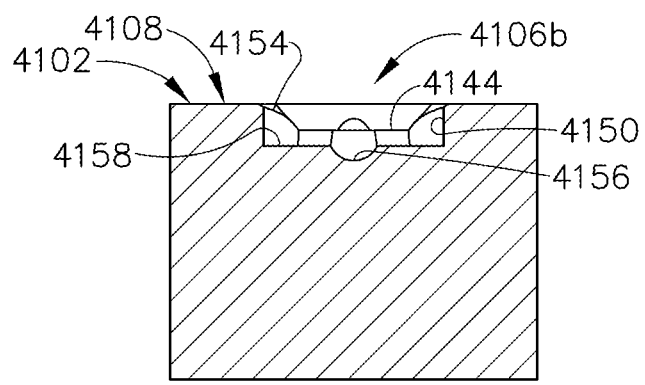

Referring primarily to FIGS. 96-96C, the pocket 4106b includes sidewalls 4150, which are oriented perpendicular to the non-forming portion 4108 of the staple-forming surface 4102. The sidewalls 4150 narrow from the outer ends of each cup 4120, 4122 toward the neck portion 4124. Consequently, the widest portion of the cups 4120 and 4122 is at the proximal and distal ends 4110 and 4112, respectively, of the pocket 4106b. The profile 4116 of the pocket 4106b defines a bow-tie shape perimeter. The widened region at the proximal and distal ends 4110, 4112 provides an enlarged footprint for receiving the tip of a staple leg. In various instances, the widened portions of the cups 4120, 4122 define extended landing zones for receiving the staple tips. As the cups 4120, 4122 narrow toward the neck portion 4124, the cups 4120, 4122 are configured to funnel and/or guide the tips of the staple legs toward and/or along the pocket axis PA and into a formed configuration.

Referring again to FIG. 96A-96C, the pocket 4106b defines a chamfered edge 4154 along the sides of the pocket 4106b. Additionally, the pocket 4106b includes a groove 4156 in the bottom surface 4158 thereof. The groove 4156 is defined in the proximal cup 4120 and the distal cup 4122. In the depicted embodiment, the groove 4156 does not extend across the bridge 4144 of the pocket 4106b. The groove 4156 is configured to constrain and guide the staple legs as they move to the deformed configuration. For example, the staple legs can slide through the groove 4156 as the staples move along at least a portion of the entrance ramp 4140 and the exit ramp 4142. In various instances, the diameter of the groove 4156 can be less than the diameter of the staple engaged with the groove 4156. In end effectors in which different staple geometries are utilized with the same staple-forming pocket geometry, the width of the groove in the pocket can be less than the smallest diameter staple. In various instances, the staple legs are deformed toward the staple base before reaching the bridge 4144 and, thus, do not engage the bridge 4144 of the pocket 4106b.

Referring again to FIG. 94, the pocket 4106b is symmetric about the pocket axis PA. For example, the perimeter 4116 of the pocket 4106b is symmetric about the pocket axis PA. Moreover, the pocket 4106b is symmetric about a central axis CA through the neck portion 4124 and perpendicular to the pocket axis PA. For example, the perimeter 4116 of the pocket 4106b is symmetric about the central axis CA, and the proximal cup 4120 has the same geometry as the distal cup 4122. In other instances, the proximal cup 4120 can be different than the distal cup 4122. For example, referring again to FIG. 91, the distal depth $D_2$ can be less than the proximal depth $D_1$ to accommodate for variations in gap distance between the anvil and the staple cartridge and/or tissue flow, as described herein.

Figure 94:
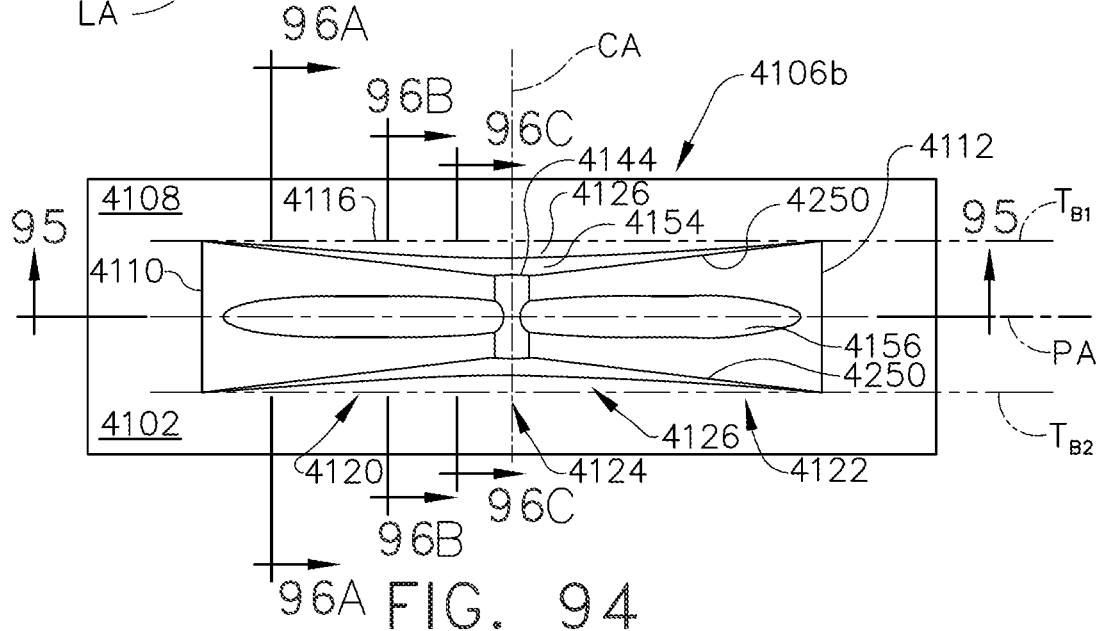
FIG. 94 is a detail view of a pocket of FIG. 93.

Referring again to FIG. 94, the neck portion 4124 of the pocket 4106b is narrower than the proximal and distal cups 4120 and 4122. The narrowed perimeter 4116 of the pocket 4106b defines a receiving peninsula 4126 between a portion of the proximal cup 4120 and a portion of the distal cup 4122. Owing to the symmetry of the pocket 4106b, symmetrical receiving peninsulas 4126 are positioned on each side of the pocket 4106b. The receiving peninsulas 4126 are bounded by the perimeter 4116 of the pocket 4106b and a tangent axis (e.g., $T_{B1}$ and $T_{B2}$), which is tangential to the widest portion of the proximal and distal cups 4120 and 4122 on a side of the pocket 4106b. A first tangent axis $T_{B1}$ is positioned on a first side of the pocket 4106b and a second tangent axis $T_{B2}$ is positioned on the opposite side of the pocket 4106b. The first and second tangent axes $T_{B1}$ and $T_{B2}$ depicted in FIG. 94 are parallel to the pocket axis PA.

Referring again to FIG. 93, each pocket 4106 extends toward the receiving peninsula 4126 of an adjacent pocket 4106. For example, the intermediate pockets 4106b are aligned with the neck portion 4124 of the inner pockets 4106a and the outer pockets 4106c. Moreover, the inner pockets 4106a and the outer pockets 4106b extend toward the receiving peninsula 4126 of one of the intermediate pockets 4106b. More specifically, the inner pockets 4106a are aligned with the neck portion 4124 of an adjacent intermediate pocket 4106b, and the outer pockets 4106c are aligned with the neck portion 4124 of an adjacent intermediate pocket 4106b. In certain instances, a portion of the pockets 4106 can extend into the receiving peninsula 4126 of an adjacent pocket 4106. Similar to the pockets 3906 in the anvil 3900, the geometry of the pockets 4106 facilitates the close arrangement of the pockets 4106 in the staple-forming surface 4102. The "forming ratio" is the ratio of the non-forming portion 4108 to the forming portion, i.e., the pockets 4106. In various instances, the forming ratio can be at least 1:1, for example.

Referring now to FIGS. 97-100C, staple-forming pockets 4206 in a portion of an anvil 4200 are depicted. The pockets 4206 and arrangement thereof in the anvil 4200 are similar in many aspects to the pockets 4106 and arrangement thereof in the anvil 4100. For example, the anvil 4200 includes a staple-forming surface 4202 and a longitudinal slot 4204. The longitudinal slot 4204 extends along the longitudinal axis LA of the anvil 4200. In certain instances, a firing element and/or cutting element can translate through the longitudinal slot 4204 during at least a portion of a firing stroke. The staple-forming pockets 4206 are defined in the staple-forming surface 4202. The staple-forming surface 4202 also includes a non-forming portion 4208 that extends around the pockets 4206. The non-forming portion 4208 extends entirely around each pocket 4206 in FIG. 97. In other words, the non-forming portion 4208 surrounds the staple-forming pockets 4206. In other instances, at least a portion of two or more adjacent pockets 4206 can be in abutting contact such that a non-forming portion 4208 is not positioned therebetween.

The forming ratio of the staple-forming surface 4202 can be optimized. By optimizing the forming ratio, more staples can be formed and/or formed to their desired configurations. In certain instances, the surface area of the non-forming portion 4208 of the anvil 4200 can be minimized with respect to the staple-forming pockets 4206. Additionally or alternatively, the footprint of the staple-forming pockets 4206 can be extended or enlarged to maximize the portion of the staple-forming surface 4202 that is designed to catch and form the staples.

Figure 97:
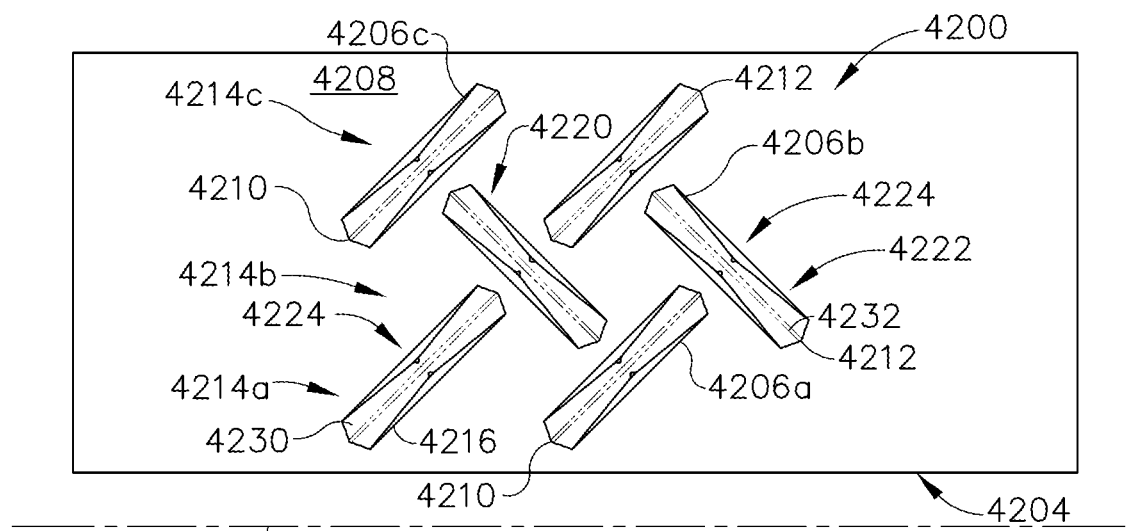
FIG. 97 is a plan view of a portion of an anvil having a plurality of staple-forming pockets defined therein.

The pockets 4206 depicted in FIG. 97 are arranged in an inner row 4214a, an intermediate row 4214b, and an outer row 4214c on a first side of the longitudinal slot 4204. Inner pockets 4206a are positioned in the inner row 4214a, intermediate pockets 4206b are positioned in the intermediate row 4214b, and outer pockets 4206c are positioned in the outer row 4214c. Similar to the anvil 3800, the pockets 4206 are arranged in a herringbone arrangement along the staple-forming surface 4202 of the anvil 4200. Although not shown in FIG. 97, in at least one instance, the pockets 4206 on the opposing side of the slot 4204 can form a mirror image reflection of the pockets 4206 on the first side of the longitudinal slot 4204. In other instances, the arrangement of pockets 4206 in the staple-forming surface 4202 can be asymmetrical relative to the slot 4204 and, in certain instances, the anvil 4200 may not include the longitudinal slot 4204. In various instances, the pockets 4206 can be arranged in less than or more than three rows on each side of the slot 4204.

The pockets 4206 depicted in FIG. 97 are identical. Each pocket 4206 defined in the staple-forming surface 4202 has the same geometry. In other instances, the geometry of the pockets 4206 can vary row-to-row and/or longitudinally along the length of the anvil 4200. For example, in certain instances, the depth of the pockets 4206 or portions thereof can vary along the length of the anvil 4200 to accommodate for variations in gap distance between the anvil and the staple cartridge along the length of an end effector and/or tissue flow, as described herein.

An exemplary pocket 4206b is shown in FIGS. 98-100C. The pocket 4206b has a first end, or proximal end, 4210 and a second end, or distal end, 4212. A pocket axis PA (FIG. 98) extends between the proximal end 4210 and the distal end 4212 of each pocket 4206. The pocket 4206b includes a perimeter 4216, which defines the boundary of the pocket 4206b. The pocket 4206b also includes a proximal cup 4220, a distal cup 4222, and a neck portion 4224 connecting the proximal cup 4220 and the distal cup 4222. When a staple is driven into forming contact with the staple-forming surface 4202, the proximal cup 4220 is aligned with a proximal staple leg, and the distal cup 4222 is aligned with a distal staple leg. The cups 4220, 4222 are configured to direct or funnel the staple legs toward the pocket axis PA and a central portion of the pocket 4206, such as the neck portion 4224, and to deform the staple legs into the formed configuration.

Figure 99:
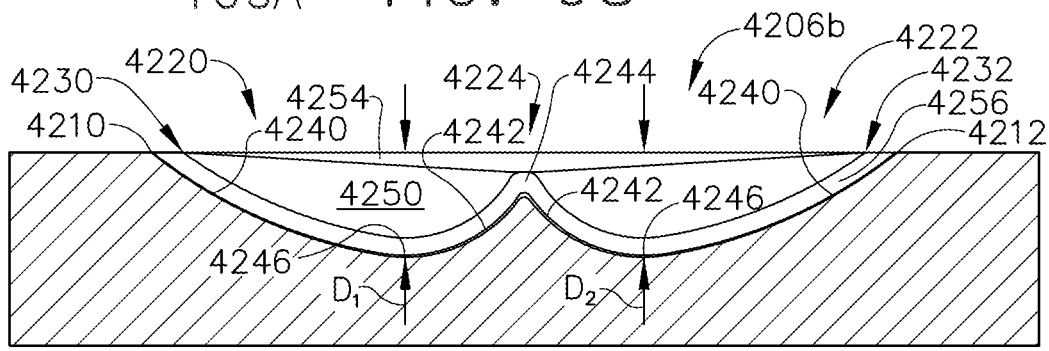
FIGS. 99, 100A, 100B, and 100C are cross-sectional views of the pocket of FIG. 98, taken along lines 99-99, 100A-100A, 100B-100B, and 100C-100C respectively.

Referring primarily to FIG. 99, each cup 4220, 4222 of the pocket 4206b defines an entrance ramp 4240 and an exit ramp 4242. The exit ramp 4242 is steeper than the entrance ramp 4240. When forming a staple, the tip of a staple leg can enter the respective cup 4220, 4222 along the entrance ramp 4240 and exit the respective cup 4220, 4222 along the exit ramp 4242. At an apex 4246 between the entrance ramp 4240 and the exit ramp 4242, the tips of the staple legs are deformed toward the staple base to assume the formed configuration, such as a B-form or modified B-form, for example. The pocket 4206b also defines a bridge 4244 between the proximal cup 4220 and the distal cup 4222. The bridge 4244 is offset from the non-forming portion 4208. More specifically, the bridge 4244 is positioned below or recessed relative to the non-forming portion 4208.

Figure 100C:
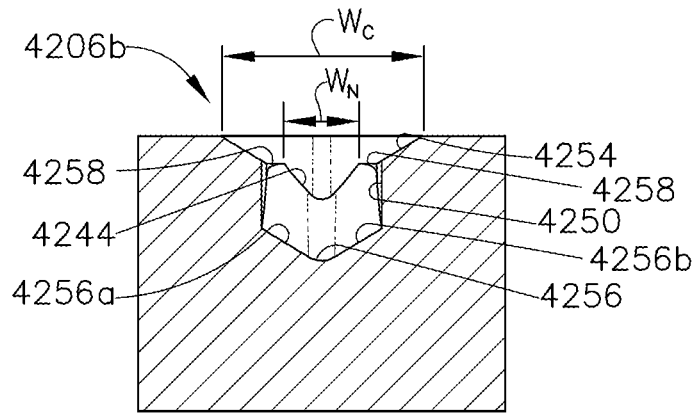
Figure 100B:
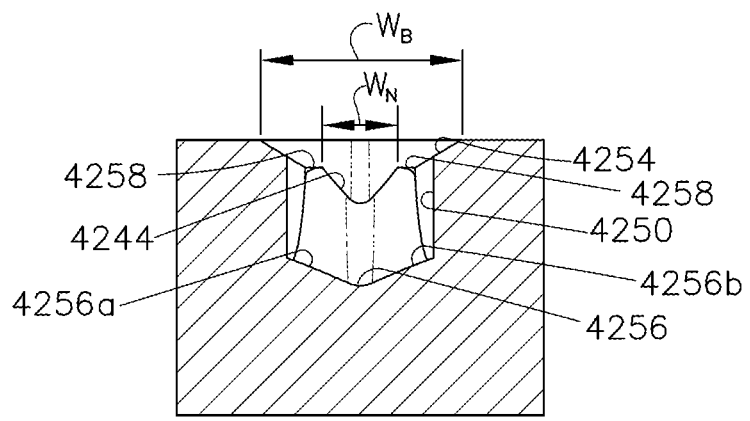
Figure 100A:
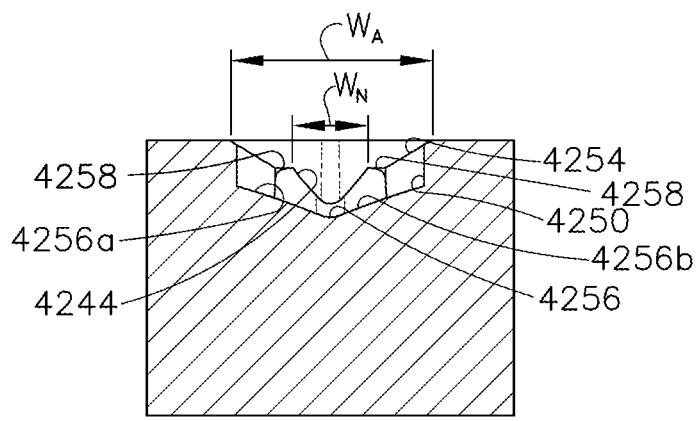

Referring primarily to FIGS. 100A-100C, the pocket 4206b includes sidewalls 4250, which are oriented perpendicular to the non-forming portion 4208 of the staple-forming surface 4202. The sidewalls 4250 narrow toward the neck portion 4224. Consequently, the widest portion of the cups 4220, 4222 is at the proximal and distal ends of the sidewalls 4250. The widened region provides an enlarged footprint for receiving the tip of a staple leg. As the cups 4220, 4222 narrow toward the neck portion 4224, the cups 4220, 4222 are configured to funnel and/or guide the tips of the staple legs toward and/or along the pocket axis PA and into a formed configuration.

The cups 4220, 4222 also include extended landing zones 4230, 4232, respectively, which further enlarge the footprint of the cups 4220, 4222. The proximal extended landing zone 4230 extends proximally along the pocket axis PA, and the distal extended landing zone 4232 extends distally along the pocket axis PA. In the pocket 4206b, the extended landing zones 4230 and 4232 define a substantially triangular perimeter. Moreover, the extended landing zones 4230 and 4232 terminate along the respective pocket axis PA at a corner. In other instances, the extended landing zones 4230 and 4232 can define straight or contoured perimeters, for example, and can extend laterally and/or longitudinally from the cups 4220 and 4222, for example.

Figure 98:
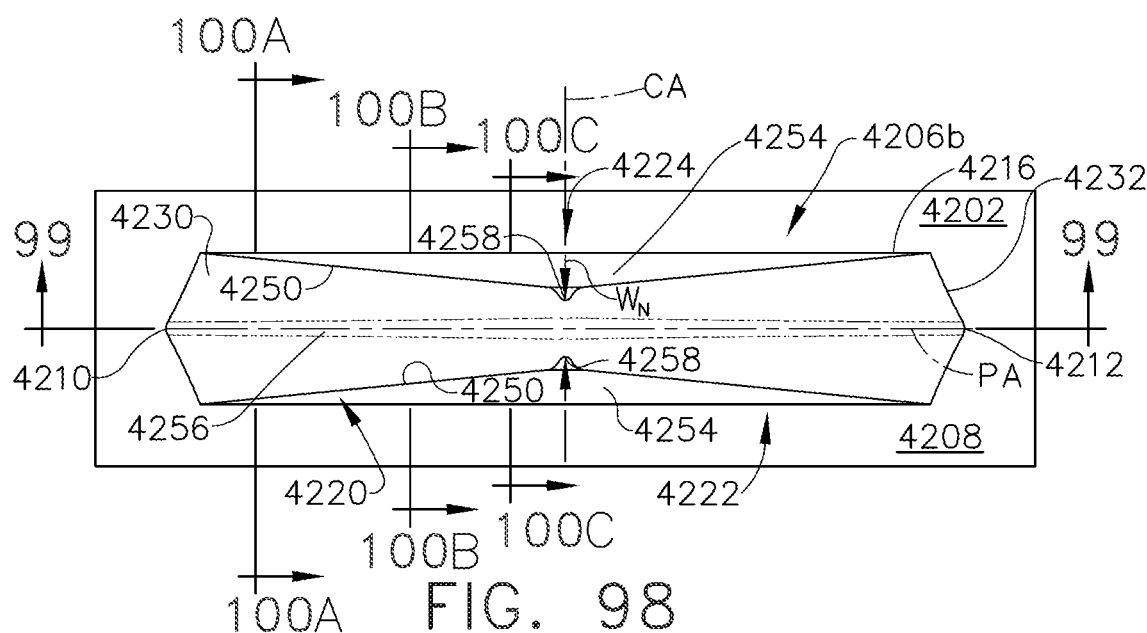
FIG. 98 is a detail view of a pocket of FIG. 97.

Additionally, the pocket 4206b includes a trough 4256 in the bottom surface thereof. The trough 4256 is configured to constrain and guide the staple legs as they move to the deformed configuration. In the depicted embodiment, the trough 4256 spans between the sidewalls 4250 and defines the entire bottom surface of the pocket 4206b. The trough 4256 extends from the proximal cup 4220 over the bridge 4224 and into the distal cup 4222. In other instances, the trough 4256 may not extend across the bridge 4244 of the pocket 4206b. The trough 4256 includes two ramped surfaces 4256a and 4256b that extend downward away from the non-forming portion 4208 and meet along the pocket axis PA (FIG. 98). As depicted in FIGS. 100A-100C, the trough 4256 defines a steeper gradient along the bridge 4244 than in the cups 4220, 4222. In other instances, the gradient can be uniform along the length of the trough 4256 and/or can be steeper in the cups 4220, 4222 than along the bridge 4244, for example.

Still referring to FIGS. 100A-100C, the pocket 4206b also defines a chamfered edge 4254 along the sides of the pocket 4206b. In the pocket 4206b, the chamfered edge 4254 defines the overall width of the pocket 4206b. The overall width of the pocket 4206b is uniform. For example, the width $W_A$ (FIG. 100A) is equal to the width $W_B$ (FIG. 100B) and the width $W_C$ (FIG. 100C). In other instances, the widths $W_A$, $W_B$, and/or $W_C$ may not be equal. Because the sidewalls 4250 narrow toward the neck portion 4224, the width of the chamfered edge 4254 correspondingly expands toward the neck portion 4224 to maintain the same overall pocket width. The pocket 4206b also includes projections or knobs 4258 which extend toward the pocket axis PA at the neck portion 4224 of the pocket 4206b. The knobs 4258 further narrow the neck portion 4224 to a width $W_N$. The trough 4256 spans the bottom surface of the neck portion 4224 across the width $W_N$.

Referring again to FIG. 98, the pocket 4206b is symmetric about the pocket axis PA. For example, the perimeter 4216 of the pocket 4206b is symmetric about the pocket axis PA. Moreover, the pocket 4206b is symmetric about a central axis CA through the neck portion 4224 and perpendicular to the pocket axis PA. For example, the perimeter 4216 of the pocket 4206b is symmetric about the central axis CA, and the proximal cup 4220 has the same geometry as the distal cup 4222. In other instances, the proximal cup 4220 can be different than the distal cup 4222. For example, referring again to FIG. 99, the distal depth $D_2$ can be less than the proximal depth $D_1$ to accommodate for variations in gap distance between the anvil and the staple cartridge and/or tissue flow, as described herein.

Referring again to FIG. 97, each pocket 4206 extends toward the neck portion 4224 of an adjacent pocket 4206. For example, the intermediate pockets 4206b are aligned with the neck portions 4224 of the inner pockets 4206a and the outer pockets 4206c. More specifically, the proximal landing zones 4230 of the intermediate pockets 4206b are aligned with the neck portion 4224 of an adjacent outer staple 4206c, and the distal landing zones 4232 of the intermediate pockets 4206b are aligned with the neck portion 4224 of an adjacent inner staple 4206a. Moreover, the inner pockets 4206a and the outer pockets 4206b extend toward the neck portion 4224 of one of the intermediate pockets 4206b. More specifically, the distal landing zones 4232 of the inner pockets 4206a are aligned with the neck portion 4224 of an adjacent intermediate pocket 4206b, and the proximal landing zones 4230 of the outer pockets 4206c are aligned with the neck portion 4224 of an adjacent intermediate pocket 4206b.

Referring now to FIGS. 101-104C, staple-forming pockets 4306 in a portion of an anvil 4300 are depicted. The pockets 4306 and arrangement thereof in the anvil 4300 are similar in many aspects to the pockets 3906 and arrangement thereof in the anvil 3900. For example, the anvil 4300 includes a staple-forming surface 4302 and a longitudinal slot 4304. The longitudinal slot 4304 extends along the longitudinal axis LA of the anvil 4300. In certain instances, a firing element and/or cutting element can translate through the longitudinal slot 4304 during at least a portion of a firing stroke. The staple-forming pockets 4306 are defined in the staple-forming surface 4302. The staple-forming surface 4302 also includes a non-forming portion 4308 that extends around the pockets 4306. The non-forming portion 4308 extends entirely around each pocket 4306 in FIG. 101. In other words, the non-forming portion 4308 surrounds the staple-forming pockets 4306. In other instances, at least a portion of two or more adjacent pockets 4306 can be in abutting contact such that a non-forming portion 4308 is not positioned therebetween.

The forming ratio of the staple-forming surface 4302 can be optimized. By optimizing the forming ratio, more staples can be formed and/or formed to their desired configurations. In certain instances, the surface area of the non-forming portion 4308 of the anvil 4300 can be minimized with respect to the staple-forming pockets 4306. Additionally or alternatively, the footprint of the staple-forming pockets 4306 can be extended or enlarged to maximize the portion of the staple-forming surface 4302 that is designed to catch and form the staples.

Figure 101:
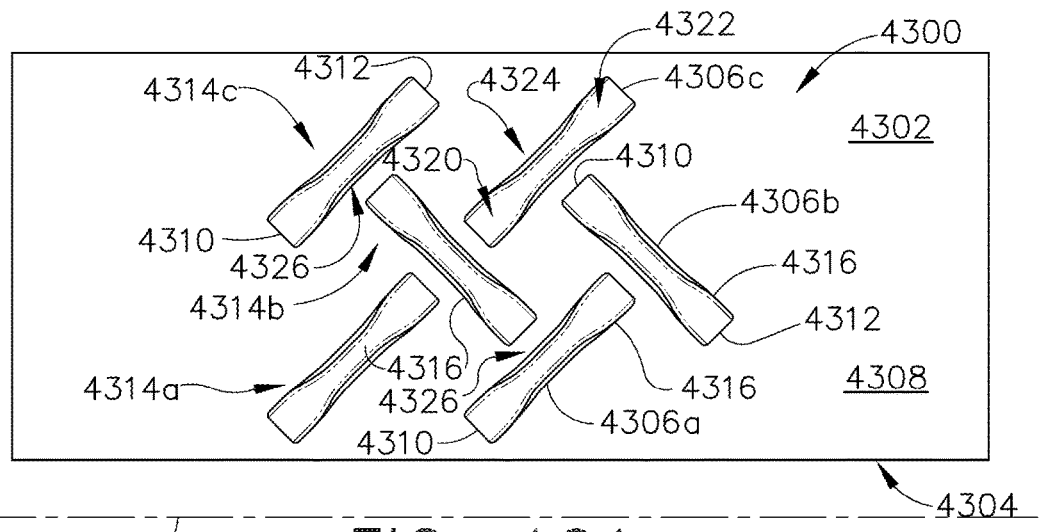
FIG. 101 is a plan view of a portion of an anvil having a plurality of staple-forming pockets defined therein.

The pockets 4306 depicted in FIG. 101 are arranged in an inner row 4314*a*, an intermediate row 4314*b*, and an outer row 4314*c* on a first side of the longitudinal slot 4304. Inner pockets 4306*a* are positioned in the inner row 4314*a*, intermediate pockets 4306*b* are positioned in the intermediate row 4314*b*, and outer pockets 4306*c* are positioned in the outer row 4314*c*. Similar to the anvil 3800, the pockets 4306 are arranged in a herringbone arrangement along the staple-forming surface 4302 of the anvil 4300. Although not shown in FIG. 101, in at least one instance, the pockets 4306 on the opposing side of the slot 4304 can form a mirror image reflection of the pockets 4306 on the first side of the longitudinal slot 4304. In other instances, the arrangement of pockets 4306 in the staple-forming surface 4302 can be asymmetrical relative to the slot 4304 and, in certain instances, the anvil 4300 may not include the longitudinal slot 4304. In various instances, the pockets 4306 can be arranged in less than or more than three rows on each side of the slot 4304.

The pockets 4306 depicted in FIG. 101 are identical. Each pocket 4306 defined in the staple-forming surface 4302 has the same geometry. In other instances, the geometry of the pockets 4306 can vary row-to-row and/or longitudinally along the length of the anvil 4300. For example, in certain instances, the depth of the pockets 4306 or portions thereof can vary along the length of the anvil 4300 to accommodate for variations in gap distance between the anvil and the staple cartridge along the length of an end effector and/or tissue flow, as described herein.

An exemplary pocket 4306*b* is shown in FIGS. 102-104C. The pocket 4306*b* has a first end, or proximal end, 4310 and a second end, or distal end, 4312. A pocket axis PA (FIG. 102) extends between the proximal end 4310 and the distal end 4312 of the pocket 4306*b*. The pocket 4306*b* includes a perimeter 4316, which defines the boundary of the pocket 4306*b*. The perimeter 4316 includes rounded corners at the proximal and distal ends of the pockets 4306. The pocket 4306*b* also includes a proximal cup 4320, a distal cup 4322, and a neck portion 4324 connecting the proximal cup 4320 and the distal cup 4322. When a staple is driven into forming contact with the staple-forming surface 4302, the proximal cup 4320 is aligned with a proximal staple leg, and the distal cup 4322 is aligned with a distal staple leg. The cups 4320, 4322 are configured to direct or funnel the staple legs toward the pocket axis PA and a central portion of the pocket 4306, such as the neck portion 4324, and to deform the staple legs into the formed configuration.

Figure 103:
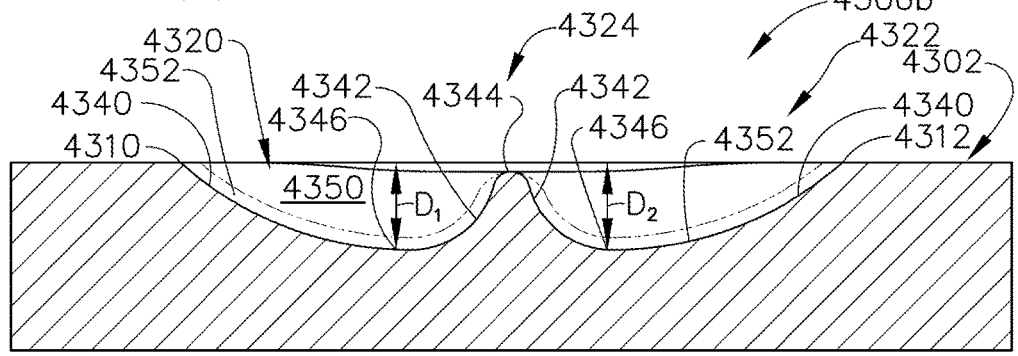
FIGS. 103, 104A, 104B, and 104C are cross-sectional views of the pocket of FIG. 102, taken along lines 103-103, 104A-104A, 104B-104B, and 104C-104C respectively.

Referring primarily to FIG. 103, each cup 4320, 4322 of the pocket 4306*b* defines an entrance ramp 4340 and an exit ramp 4342. The exit ramp 4342 is steeper than the entrance ramp 4340. When forming a staple, the tip of a staple leg can enter the respective cup 4320, 4322 along the entrance ramp 4340 and exit the respective cup 4320, 4322 along the exit ramp 4342. At an apex 4346 between the entrance ramp 4340 and the exit ramp 4342, the tips of the staple legs are deformed toward the staple base to assume the formed configuration, such as a B-form or modified B-form, for example. The pocket 4306*b* also defines a bridge 4344 between the proximal cup 4320 and the distal cup 4322. The bridge 4344 is offset from the non-forming portion 4308. More specifically, the bridge 4344 is positioned below or recessed relative to the non-forming portion 4308.

Figure 104C:
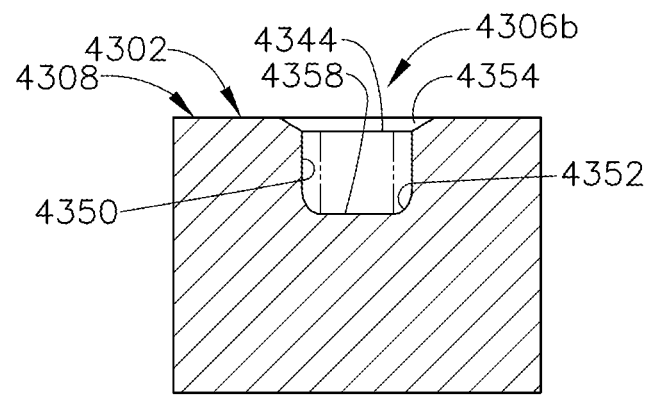
Figure 104B:
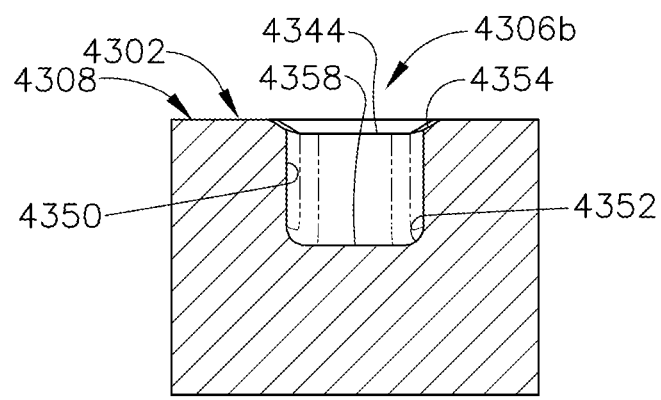
Figure 104A:
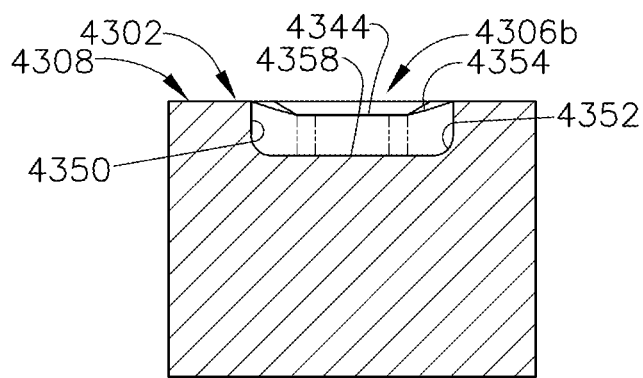

Referring primarily to FIGS. 104A-104C, the pocket 4306*b* includes sidewalls 4350, which are oriented perpendicular to the non-forming portion 4308 of the staple-forming surface 4302. The sidewalls 4350 narrow between the outer ends of each cup 4320, 4322 and the neck portion 4324. More specifically, the sidewalls 4350 extend along an inward contour to define a contour in the perimeter 4316 of the pocket 4306*b*. The widest portion of the cups 4320, 4322 is at the proximal and distal ends of the sidewalls 4350. The widened region provides an enlarged footprint for receiving the tip of a staple leg. As the cups 4320, 4322 narrow toward the neck portion 4324, the cups 4320, 4322 are configured to funnel and/or guide the tips of the staple legs toward and/or along the pocket axis PA and into a formed configuration.

The pocket 4306*b* defines a chamfered edge 4354 along the sides of the pocket 4306*b*. In the pocket 4306*b*, the chamfered edge 4354 defines the overall width of the pocket 4306*b*, which narrows toward the neck portion 4324. The pocket 4306*b* also defines a fillet 4352 (FIGS. 104A-104C) between the sidewalls 4350 and the bottom surface 4358 the pocket 4306*b*. The fillets 4352 are configured to guide the staple legs along the desired path in the pocket 4306*b*. For example, if a staple leg lands along the chamfer 4352, the fillet corner 4352 can smoothly guide the staple leg toward the pocket axis PA.

Referring again to FIG. 102, the pocket 4306*b* is symmetric about the pocket axis PA. For example, the perimeter 4316 of the pocket 4306*b* is symmetric about the pocket axis PA. Moreover, the pocket 4306*b* is symmetric about a central axis CA through the neck portion 4324 and perpendicular to the pocket axis PA. For example, the perimeter 4316 of the pocket 4306*b* is symmetric about the central axis CA, and the proximal cup 4320 has the same geometry as the distal cup 4322. In other instances, the proximal cup 4320 can be different than the distal cup 4322. For example, referring again to FIG. 103, the distal depth $D_2$ can be less than the proximal depth $D_1$ to accommodate for variations in gap distance between the anvil and the staple cartridge and/or tissue flow, as described herein.

Figure 102:
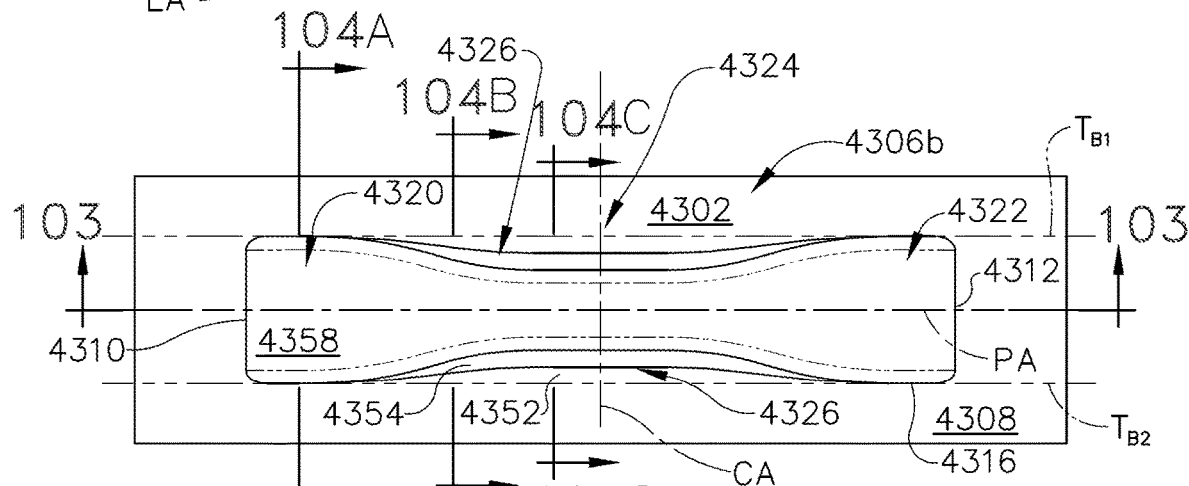
FIG. 102 is a detail view of a pocket of FIG. 101.

Referring again to FIG. 102, the neck portion 4324 of the pocket 4306*b* is narrower than the proximal and distal cups 4320 and 4322. The narrowed perimeter 4316 of the pocket 4306b defines a receiving peninsula 4326 between a portion of the proximal cup 4320 and a portion of the distal cup 4322. Owing to the symmetry of the pocket 4306b, symmetrical receiving peninsulas 4326 are positioned on each side of the pocket 4306b. The receiving peninsulas 4326 are bounded by the perimeter 4316 of the pocket 4306b and a tangent axis (e.g., $T_{B1}$ and $T_{B2}$), which is tangential to the widest portion of the proximal and distal cups 4320 and 4322 on a side of the pocket 4306b. A first tangent axis $T_{B1}$ is positioned on a first side of the pocket 4306b and a second tangent axis $T_{B2}$ is positioned on the opposite side of the pocket 4306b. The first and second tangent axes $T_{B1}$ and $T_{B2}$ depicted in FIG. 102 are parallel to the pocket axis PA.

Referring again to FIG. 101, each pocket 4306 extends toward the receiving peninsula 4326 of an adjacent pocket 4306. For example, the intermediate pockets 4306b are aligned with the neck portions 4324 of the inner pockets 4306a and the outer pockets 4306c. Moreover, the inner pockets 4306a and the outer pockets 4306b extend toward the receiving peninsula 4326 of one of the intermediate pockets 4306b. More specifically, the inner pockets 4306a are aligned with the neck portion 4324 of an adjacent intermediate pocket 4306b, and the outer pockets 4306c are aligned with the neck portion 4324 of an adjacent intermediate pocket 4306b. In certain instances, a portion of the pockets 4306 can extend into the receiving peninsula 4326 of an adjacent pocket 4306. Similar to the pockets 3906 in the anvil 3900, the geometry of the pockets 4306 facilitates the close arrangement of the pockets 4306 in the staple-forming surface 4302. The "forming ratio" is the ratio of the non-forming portion 4308 to the forming portion, i.e., the pockets 4306. In at least one instance, the forming ratio can be at least 1:1, for example.

Referring now to FIGS. 105-108C, staple-forming pockets 4406 in a portion of an anvil 4400 are depicted. The pockets 4406 and arrangement thereof in the anvil 4400 are similar in many aspects to the pockets 4306 and arrangement thereof in the anvil 4300. For example, the anvil 4400 includes a staple-forming surface 4402 and a longitudinal slot 4404. The longitudinal slot 4404 extends along the longitudinal axis LA of the anvil 4400. In certain instances, a firing element and/or cutting element can translate through the longitudinal slot 4404 during at least a portion of a firing stroke. The staple-forming pockets 4406 are defined in the staple-forming surface 4402. The staple-forming surface 4402 also includes a non-forming portion 4408 that extends around the pockets 4406. The non-forming portion 4408 extends entirely around each pocket 4406 in FIG. 105. In other words, the non-forming portion 4408 surrounds the staple-forming pockets 4406. In other instances, at least a portion of two or more adjacent pockets 4406 can be in abutting contact such that a non-forming portion 4408 is not positioned therebetween. Additionally, the non-forming portion 4406 extends through each pocket 4406, as described herein.

The forming ratio of the staple-forming surface 4402 can be optimized. By optimizing the forming ratio, more staples can be formed and/or formed to their desired configurations. In certain instances, the surface area of the non-forming portion 4408 of the anvil 4400 can be minimized with respect to the staple-forming pockets 4406. Additionally or alternatively, the footprint of the staple-forming pockets 4406 can be extended or enlarged to maximize the portion of the staple-forming surface 4402 that is designed to catch and form the staples.

Figure 105:
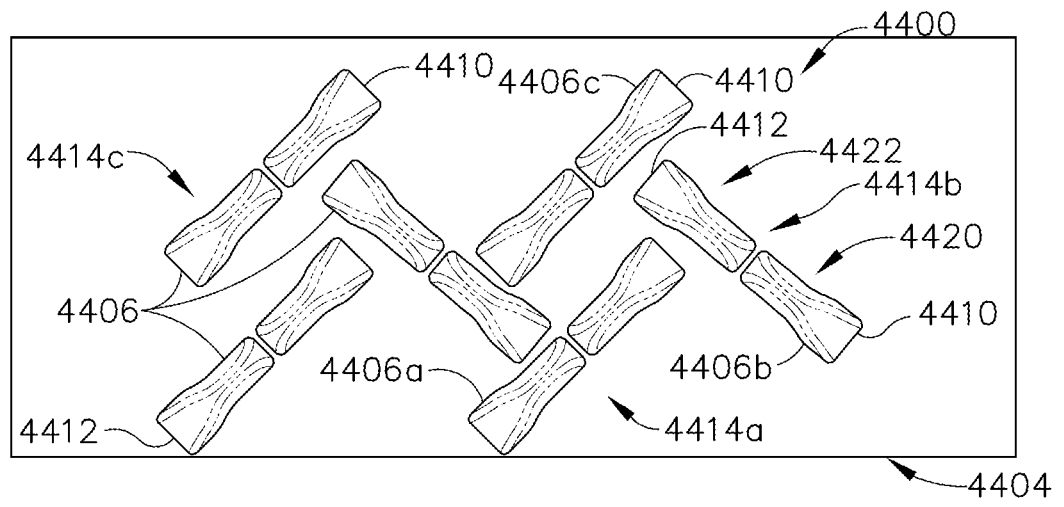
FIG. 105 is a plan view of a portion of an anvil having a plurality of staple-forming pockets defined therein.

The pockets 4406 depicted in FIG. 105 are arranged in an inner row 4414a, an intermediate row 4414b, and an outer row 4414c on a first side of the longitudinal slot 4404. Inner pockets 4406a are positioned in the inner row 4414a, intermediate pockets 4406b are positioned in the intermediate row 4414b, and outer pockets 4406c are positioned in the outer row 4414c. Similar to the anvil 3800, the pockets 4406 are arranged in a herringbone arrangement along the staple-forming surface 4402 of the anvil 4400. Although not shown in FIG. 105, in at least one instance, the pockets 4406 on the opposing side of the slot 4404 can form a mirror image reflection of the pockets 4406 on the first side of the longitudinal slot 4404. In other instances, the arrangement of pockets 4406 in the staple-forming surface 4402 can be asymmetrical relative to the slot 4404 and, in certain instances, the anvil 4400 may not include the longitudinal slot 4404. In various instances, the pockets 4406 can be arranged in less than or more than three rows on each side of the slot 4404.

The pockets 4406 depicted in FIG. 105 are identical. Each pocket 4406 defined in the staple-forming surface 4402 has the same geometry. In other instances, the geometry of the pockets 4406 can vary row-to-row and/or longitudinally along the length of the anvil 4400. For example, in certain instances, the depth of the pockets 4406 or portions thereof can vary along the length of the anvil 4400 to accommodate for variations in gap distance between the anvil and the staple cartridge along the length of an end effector and/or tissue flow, as described herein.

An exemplary pocket 4406b is shown in FIGS. 106-108C. The pocket 4406b has a first end, or proximal end, 4410 and a second end, or distal end, 4412. A pocket axis PA (FIG. 106) extends between the proximal end 4410 and the distal end 4412 of the pocket 4406b. The pocket 4406b includes a perimeter 4416, which defines the boundary of the pocket 4406b. The perimeter 4416 includes rounded corners at the proximal and distal ends 4410 and 4412 of the pocket 4406b. The pocket 4406b also includes a proximal cup 4420 and a distal cup 4422. A portion of the non-forming portion 4408 extends between the proximal cup 4420 and the distal cup 4422. In other words, the pocket 4406b includes two separate and discrete cups 4420 and 4422 in the staple-forming surface 4402. When a staple is driven into forming contact with the staple-forming surface 4402, the proximal cup 4420 is aligned with a proximal staple leg, and the distal cup 4422 is aligned with a distal staple leg. The cups 4420, 4422 are configured to direct or funnel the staple legs toward the pocket axis PA and a central portion of the pocket 4406 and to deform the staple legs into the formed configuration.

Figure 107:
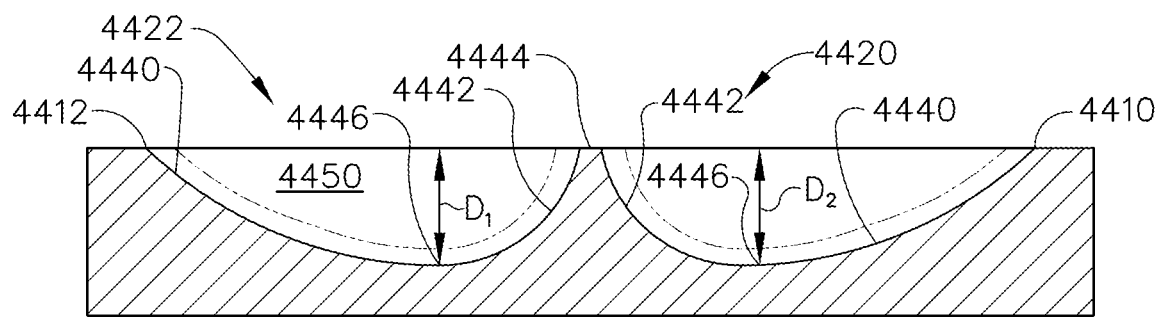
FIGS. 107, 108A, 108B, and 108C are cross-sectional views of the pocket of FIG. 106, taken along lines 107-107, 108A-108A, 108B-108B, and 108C-108C respectively.

Referring primarily to FIG. 107, each cup 4420, 4422 of the pocket 4406b defines an entrance ramp 4440 and an exit ramp 4442. The exit ramp 4442 is steeper than the entrance ramp 4440. When forming a staple, the tip of a staple leg can enter the respective cup 4420, 4422 along the entrance ramp 4440 and exit the respective cup 4420, 4422 along the exit ramp 4442. At an apex 4446 between the entrance ramp 4440 and the exit ramp 4442, the tips of the staple legs are deformed toward the staple base to assume the formed configuration, such as a B-form or modified B-form, for example. The pocket 4406b also defines a bridge 4444 between the proximal cup 4420 and the distal cup 4422. The bridge 4444 is aligned with the non-forming portion 4408. More specifically, the bridge 4444 is a planar extension of the non-forming portion 4408, which extends between the proximal and distal cups 4420, 4422.

Figure 108C:
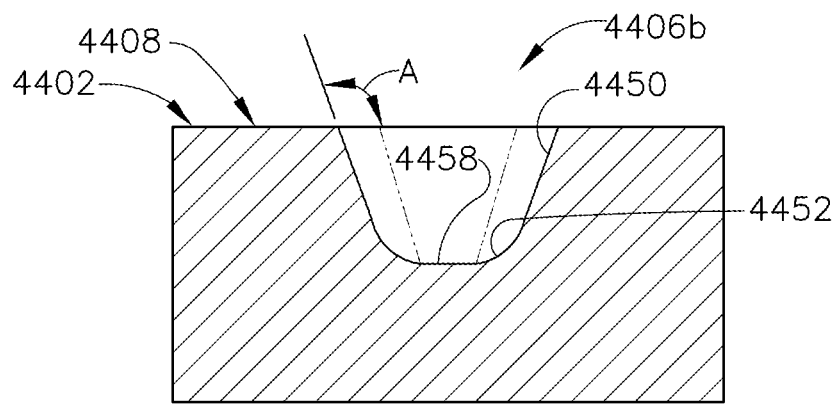
Figure 108B:
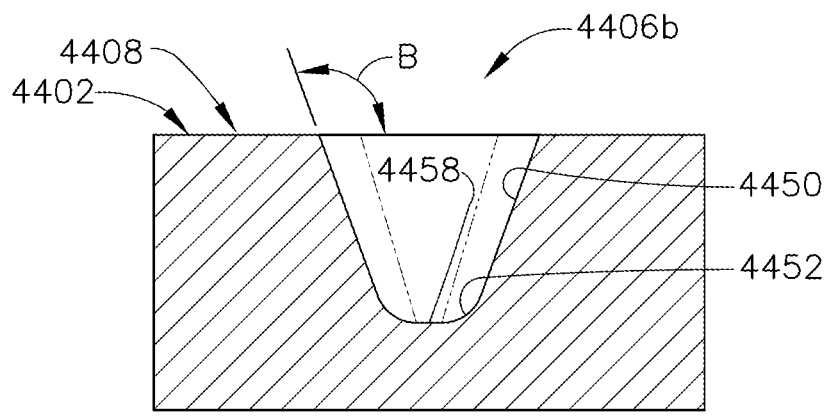
Figure 108A:
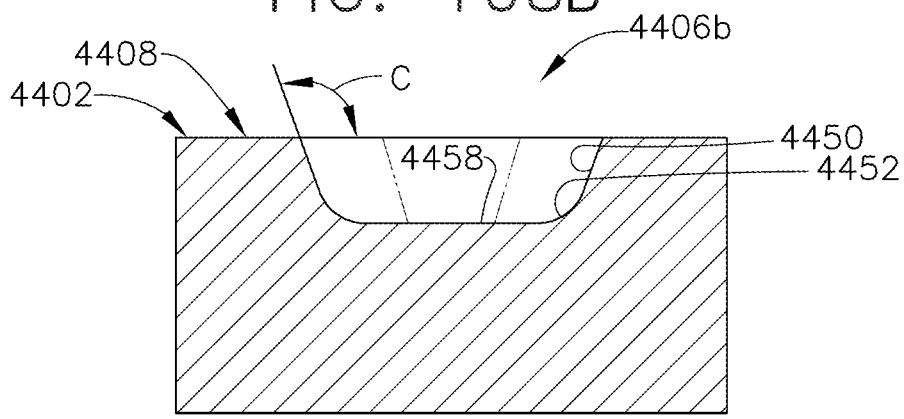

Referring primarily to FIGS. 108A-108C, the pocket 4406b includes sidewalls 4450, which are oriented at an angle relative to the non-forming portion 4408 of the staple-forming surface 4402. More specifically, the sidewalls 4450 are obliquely oriented relative to the non-forming portion 4408. Moreover, the angular orientation of the sidewalls 4450 is constant along the length of the cups. For example, the angles A, B, and C depicted in FIGS. 108A, 108B, and 108C, respectively, are equal. In other instances, one of more of the angles A, B, and C can be different. The sidewalls 4450 narrow between the outer ends of each cup 4420, 4422 and inner ends of the cups 4420, 4422. More specifically, the sidewalls 4450 extend along an inward contour to define a contour in the perimeter 4416 of the pocket 4406b. The widest portion of the cups 4420, 4422 is at the proximal and distal ends of the pocket 4406b. The widened region provides an enlarged footprint for receiving the tip of a staple leg. As the cups 4420, 4422 narrow toward the bridge 4444, the cups 4420, 4422 are configured to funnel and/or guide the tips of the staple legs toward and/or along the pocket axis PA and into a formed configuration.

The pocket 4406b defines a fillet 4452 (FIGS. 108A-108C) between the sidewalls 4450 and the bottom surface 4458 of the pocket 4406b. The fillets 4452 are configured to guide the staple legs along the desired path in the pocket 4406b. For example, if a staple leg lands along the fillet 4452, the fillet 4452 can smoothly guide the staple leg toward the pocket axis PA.

Referring again to FIG. 106, the pocket 4406b is symmetric about the pocket axis PA. For example, the perimeter 4416 of the pocket 4406b is symmetric about the pocket axis PA. Moreover, the pocket 4406b is symmetric about a central axis CA between the proximal and distal cups 4420 and 4422 and perpendicular to the pocket axis PA. For example, the perimeter 4416 of the pocket 4406b is symmetric about the central axis CA, and the proximal cup 4420 has the same geometry as the distal cup 4422. In other instances, the proximal cup 4420 can be different than the distal cup 4422. For example, referring again to FIG. 107, the distal depth $D_2$ can be less than the proximal depth $D_1$ to accommodate for variations in gap distance between the anvil and the staple cartridge and/or tissue flow, as described herein.

Figure 106:
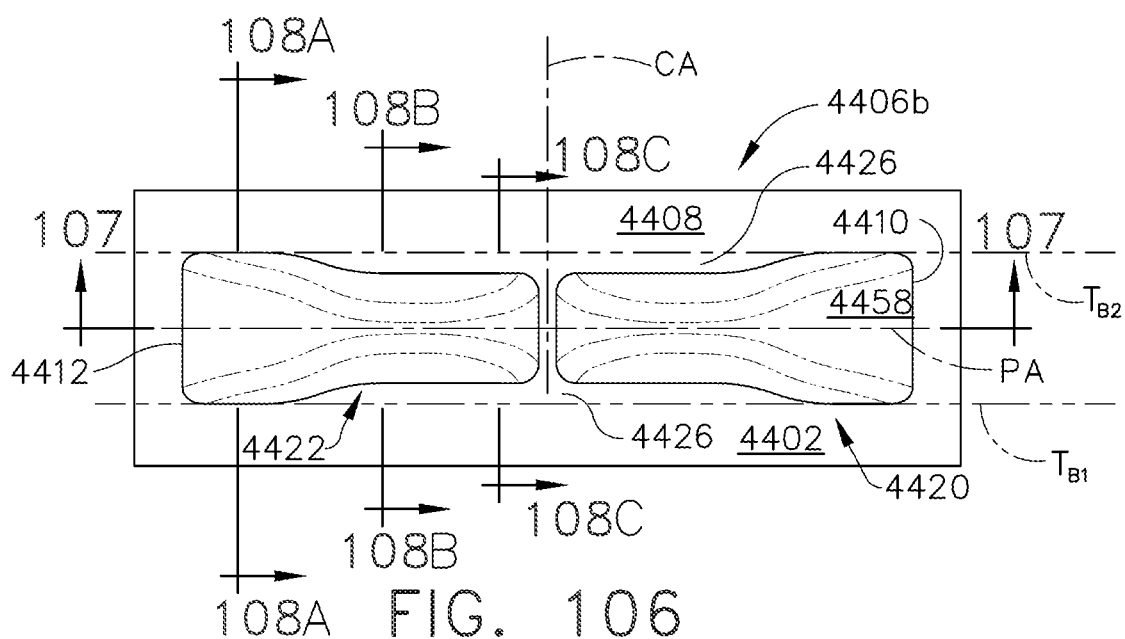
FIG. 106 is a detail view of a pocket of FIG. 105.

Referring again to FIG. 106, the central portion of the pocket 4406b is narrower than the proximal and distal ends 4410 and 4412 of the cups 4420 and 4422, respectively. The narrowed perimeter 4416 of the pocket 4406b defines a receiving peninsula 4426 between a portion of the proximal cup 4420 and a portion of the distal cup 4422. Owing to the symmetry of the pocket 4406b, symmetrical receiving peninsulas 4426 are positioned on each side of the pocket 4406b. The receiving peninsulas 4426 are bounded by the perimeter 4416 of the pocket 4406b and a tangent axis (e.g., $T_{B1}$ and $T_{B2}$), which is tangential to the widest portion of the proximal and distal cups 4420 and 4422 on a side of the pocket 4406b. A first tangent axis $T_{B1}$ is positioned on a first side of the pocket 4406b and a second tangent axis $T_{B2}$ is positioned on the opposite side of the pocket 4406b. The first and second tangent axes $T_{B1}$ and $T_{B2}$ depicted in FIG. 106 are parallel to the pocket axis PA.

Referring again to FIG. 105, each pocket 4406 extends toward the receiving peninsula 4426 of an adjacent pocket 4406. For example, the intermediate pockets 4406b are aligned with the central portion of the inner pockets 4406a and the outer pockets 4406c. Moreover, the inner pockets 4406a and the outer pockets 4406b extend toward the receiving peninsula 4426 of one of the intermediate pockets 4406b. More specifically, the inner pockets 4406a are aligned with the central portion of an adjacent intermediate pocket 4406b, and the outer pockets 4406c are aligned with the central portion of an adjacent intermediate pocket 4406b. In certain instances, a portion of the pockets 4406 can extend into the receiving peninsula 4426 of an adjacent pocket 4406. Similar to the pockets 3906 in the anvil 3900, the geometry of the pockets 4406 facilitates the close arrangement of the pockets 4406 in the staple-forming surface 4402. The "forming ratio" of the staple-forming surface 4402 is the ratio of the non-forming portion 4408 to the forming portion, i.e., the pockets 4406. The forming ratio of the staple-forming surface 4402 is about 2.56:1. In other instances, the forming ratio can be less than 2.56:1 or more than 2.56:1. For example, in at least one instance, more than 50% of the staple-forming surface 4402 can be covered with staple-forming pockets 4406.

Referring now to FIGS. 109-112C, staple-forming pockets 4506 in a portion of an anvil 4500 are depicted. The pockets 4506 and arrangement thereof in the anvil 4500 are similar in many aspects to the pockets 3906 and arrangement thereof in the anvil 3900. For example, the anvil 4500 includes a staple-forming surface 4502 and a longitudinal slot 4504. The longitudinal slot 4504 extends along the longitudinal axis LA of the anvil 4500. In certain instances, a firing element and/or cutting element can translate through the longitudinal slot 4504 during at least a portion of a firing stroke. The staple-forming pockets 4506 are defined in the staple-forming surface 4502. The staple-forming surface 4502 also includes a non-forming portion 4508 that extends around the pockets 4506. The non-forming portion 4508 extends entirely around each pocket 4506 in FIG. 109. In other words, the non-forming portion 4508 surrounds the staple-forming pockets 4506. In other instances, at least a portion of two or more adjacent pockets 4506 can be in abutting contact such that a non-forming portion 4508 is not positioned therebetween.

The forming ratio of the staple-forming surface 4502 can be optimized. By optimizing the forming ratio, more staples can be formed and/or formed to their desired configurations. In certain instances, the surface area of the non-forming portion 4508 of the anvil 4500 can be minimized with respect to the staple-forming pockets 4506. Additionally or alternatively, the footprint of the staple-forming pockets 4506 can be extended or enlarged to maximize the portion of the staple-forming surface 4502 that is designed to catch and form the staples.

Figure 109:
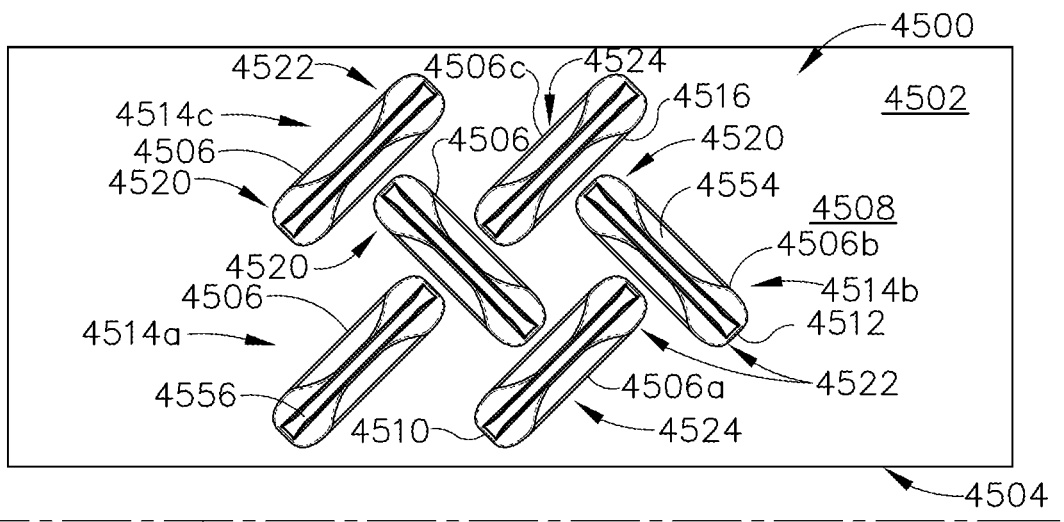
FIG. 109 is a plan view of a portion of an anvil having a plurality of staple-forming pockets defined therein.
Figure 110:
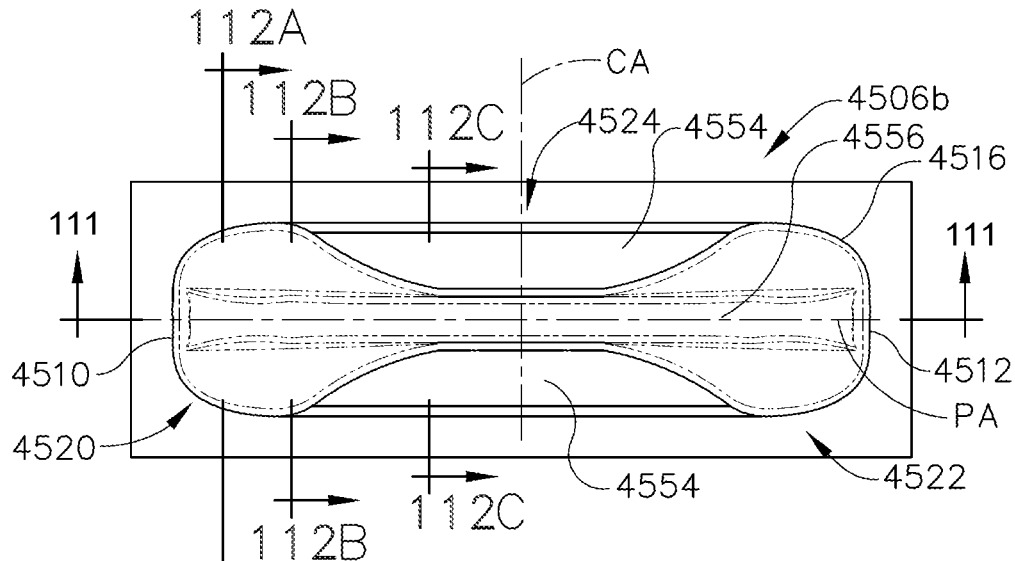
FIG. 110 is a detail view of a pocket of FIG. 109.

The pockets 4506 depicted in FIG. 109 are arranged in an inner row 4514a, an intermediate row 4514b, and an outer row 4514c on a first side of the longitudinal slot 4504. Inner pockets 4506a are positioned in the inner row 4514a, intermediate pockets 4506b are positioned in the intermediate row 4514b, and outer pockets 4506c are positioned in the outer row 4514c. Similar to the anvil 3800, the pockets 4506 are arranged in a herringbone arrangement along the staple-forming surface 4502 of the anvil 4500. Although not shown in FIG. 109, in at least one instance, the pockets 4506 on the opposing side of the slot 4504 can form a mirror image reflection of the pockets 4506 on the first side of the longitudinal slot 4504. In other instances, the arrangement of pockets 4506 in the staple-forming surface 4502 can be asymmetrical relative to the slot 4504 and, in certain instances, the anvil 4500 may not include the longitudinal slot 4504. In various instances, the pockets 4506 can be arranged in less than or more than three rows on each side of the slot 4504.

The pockets 4506 depicted in FIG. 109 are identical. Each pocket 4506 defined in the staple-forming surface 4502 has the same geometry. In other instances, the geometry of the pockets 4506 can vary row-to-row and/or longitudinally along the length of the anvil 4500. For example, in certain instances, the depth of the pockets 4506 or portions thereof can vary along the length of the anvil 4500 to accommodate for variations in gap distance between the anvil and the staple cartridge along the length of an end effector and/or tissue flow, as described herein.

An exemplary pocket 4506b is shown in FIGS. 110-112C. The pocket 4506b has a first end, or proximal end, 4510 and a second end, or distal end, 4512. A pocket axis PA (FIG. 110) extends between the proximal end 4510 and the distal end 4512 of the pocket 4506b. The pocket 4506b includes a perimeter 4516, which defines the boundary of the pocket 4506b. Similar to the pockets 4306, the perimeter 4516 includes rounded corners at the proximal and distal ends 4510 and 4512 of the pocket 4506b. The pocket 4506b also includes a proximal cup 4520, a distal cup 4522, and a neck 4524 extending between the proximal cup 4520 and the distal cup 4522. When a staple is driven into forming contact with the staple-forming surface 4502, the proximal cup 4520 is aligned with a proximal staple leg, and the distal cup 4522 is aligned with a distal staple leg. The cups 4520, 4522 are configured to direct or funnel the staple legs toward the pocket axis PA and a central portion of the pocket 4506, such as the neck 4524, and to deform the staple legs into the formed configuration.

Figure 111:
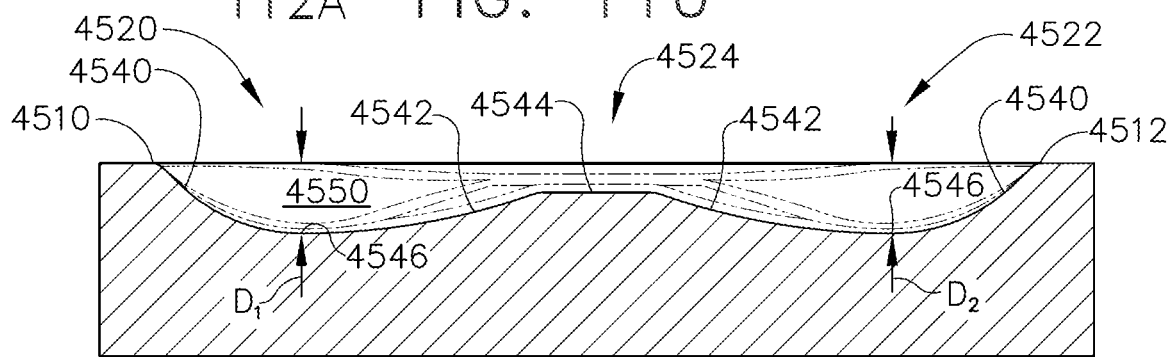
FIGS. 111, 112A, 112B, 112C are cross-sectional views of the pocket of FIG. 110, taken along lines 111-111, 112A-112A, 112B-112B, and 112C-112C respectively.

Referring primarily to FIG. 111, each cup 4520, 4522 of the pocket 4506b defines an entrance ramp 4540 and an exit ramp 4542. The entrance ramp 4540 is steeper than the exit ramp 4542. When forming a staple, the tip of a staple leg can enter the respective cup 4520, 4522 along the entrance ramp 4540 and exit the respective cup 4520, 4522 along the exit ramp 4542. At an apex 4546 between the entrance ramp 4540 and the exit ramp 4542, the tips of the staple legs are deformed toward the staple base to assume the formed configuration, such as a B-form or modified B-form, for example. The pocket 4506b also defines a bridge 4544 between the proximal cup 4520 and the distal cup 4522. The bridge 4544 is offset from the non-forming portion 4508. More specifically, the bridge 4544 is positioned below or recessed relative to the non-forming portion 4508.

Figure 112C:
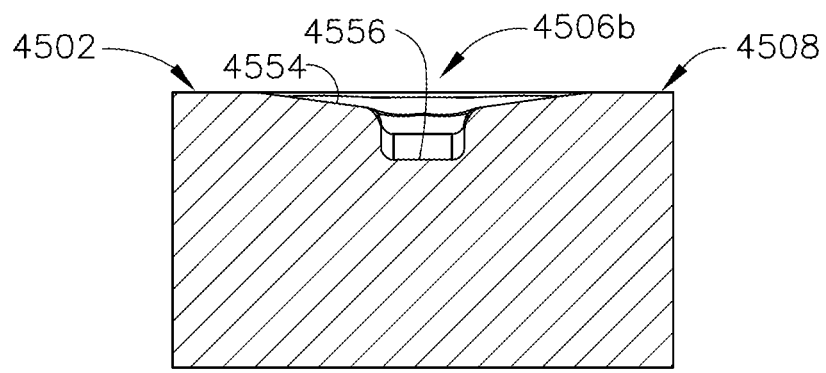
Figure 112B:
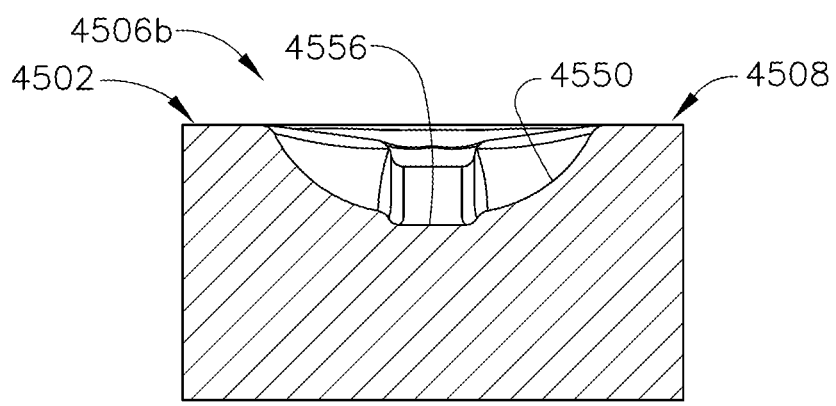
Figure 112A:
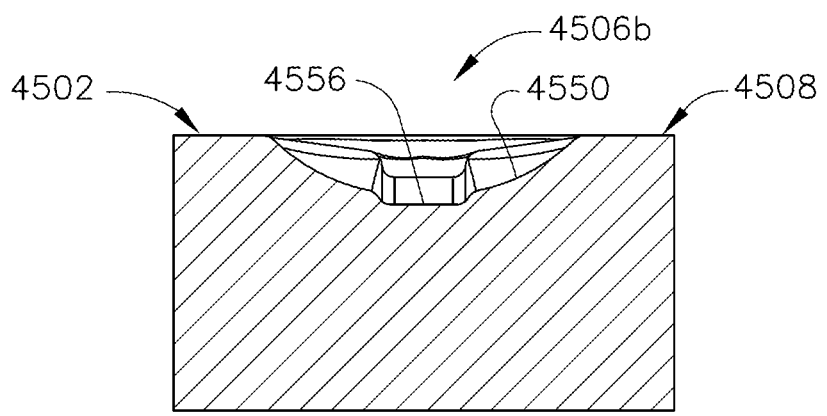

Referring primarily to FIGS. 112A-112C, the pocket 4506b includes contoured or arced walls 4550. The walls 4550 form each cup 4520, 5422 into a wide, rounded basin for receiving and forming the staple legs. Additionally, the pocket 4506b includes a groove 4556 along the bottom surface. The walls 4550 arc downward into the anvil 4500 between the non-forming surface 4508 and the groove 4556. For example, the sidewalls 4550 seamlessly transition to a bottom surface of the pocket 4506b. The groove 4556 extends along the bottom surface from the proximal cup 4520 over the bridge 4524 and into the distal cup 4522. The groove 4556 is configured to constrain and guide the staple legs as they move to the deformed configuration. In various instances, the diameter of the groove 4556 can be less than the diameter of the staple engaged with the groove 4556. In end effectors in which different staple geometries are utilized with the same staple-forming pocket geometry, the width of the groove in the pocket can be less than the smallest diameter staple.

The contoured walls 4550 narrow between the outer ends of each cup 4520, 4522 and the neck 4524. More specifically, the walls 4550 extend along an inward contour to define a contour in the perimeter 4516 of the pocket 4506b. The widened region provides an enlarged footprint for receiving the tip of a staple leg. As the cups 4520, 4522 narrow toward the bridge 4544, the cups 4520, 4522 are configured to funnel and/or guide the tips of the staple legs toward and/or along the pocket axis PA and into a formed configuration.

The pocket 4506b also defines a chamfered edge 4554 along a portion of the sides of the pocket 4506b. As the sidewalls 4550 narrow toward the neck portion 4524, the width of the chamfered edge 4554 correspondingly expands toward the neck portion 4224 to maintain the overall pocket width.

Referring again to FIG. 110, the pocket 4506b is symmetric about the pocket axis PA. For example, the perimeter 4516 of the pocket 4406b is symmetric about the pocket axis PA. Moreover, the pocket 4506b is symmetric about a central axis CA through the neck portion 4524 and perpendicular to the pocket axis PA. For example, the perimeter 4516 of the pocket 4506b is symmetric about the central axis CA, and the proximal cup 4520 has the same geometry as the distal cup 4522. In other instances, the proximal cup 4520 can be different than the distal cup 4522. For example, referring again to FIG. 111, the distal depth $D_2$ can be less than the proximal depth $D_1$ to accommodate for variations in gap distance between the anvil and the staple cartridge and/or tissue flow, as described herein.

Referring again to FIG. 109, each pocket 4506 extends toward the neck portion 4524 of an adjacent pocket 4506. For example, the intermediate pockets 4506b are aligned with the neck portions 4524 of the inner pockets 4506a and the outer pockets 4506c. Moreover, the inner pockets 4506a and the outer pockets 4506b extend toward the neck portion 4524 of one of the intermediate pockets 4506b.

Staple-forming pockets can include extended landing zones for receiving the tips of the staple legs when the staples are fired into forming contact with the anvil. In certain instances, the extended landing zones can extend laterally and/or longitudinally from the cups of the staple-forming pockets, as described herein. The profile, or perimeter, of the staple-forming pockets can nest with the profile, or perimeter, of one or more adjacent staple-forming pockets. For example, at least a portion of the perimeter of a staple-forming pocket can extend along a contour or path that matches, tracks, follows and/or parallels a portion of the perimeter of one or more adjacent staple-forming pockets. Such tracking portions or adjacent perimeters can define concentric profiles.

In various instances, the surface area of a staple-forming pocket having one or more extended landing zones can be greater than the surface area of a staple-forming pocket without the one or more extended landing zones. For example, extended landing zones can increase the surface area of a staple-forming pocket by at least 10%. Extended landing zones can increase the surface area of a staple-forming pocket by 15% or 25%, for example. In other instances, extended landing zones can increase the surface area of a staple-forming pocket by less than 10%, such as 5%, for example. Certain staple-forming pockets described herein can have a greater surface area than the staple-forming pockets in an anvil having six rows of parallel staple-forming pockets but that is otherwise identical to certain anvils described herein having six rows of angularly-oriented staple-forming pockets. In still other instances, a staple-forming pocket having extended landing zones may also include narrowed and/or otherwise reduced portions having a surface area that is equal to or greater than the surface area of the extended landing zones.

In certain instances, the staple-forming pockets can be asymmetrical. For example, the staple-forming pockets can be asymmetrical relative to a pocket axis extending between a proximal end and a distal end of the pocket and/or can be asymmetrical relative to a central axis extending perpendicular to the pocket axis and transecting a central portion of the pocket. The asymmetry of the staple-forming pockets can facilitate nesting of the pockets and/or can maximize the surface area of the pockets in a staple-forming surface, for example.

Referring now to FIGS. 113-116C, staple-forming pockets 5006 in a portion of an anvil 5000 are depicted. Similar to the anvil 3800, the pockets 5006 are arranged in a herringbone arrangement along the staple-forming surface 5002 of the anvil 5000. The anvil 5000 includes a staple-forming surface 5002 and a longitudinal slot 5004. The longitudinal slot 5004 extends along the longitudinal axis LA of the anvil 5000. In certain instances, a firing element and/or a cutting element can translate through the longitudinal slot 5004 during at least a portion of a firing stroke. The staple-forming pockets 5006 are defined in the staple-forming surface 5002. The staple-forming surface 5002 also includes a non-forming portion 5008 that extends around the pockets 5006. The non-forming portion 5008 extends entirely around each pocket 5006. In other words, the non-forming portion 5008 surrounds the staple-forming pockets 5006. In other instances, at least a portion of two or more adjacent pockets 5006 can be in abutting contact such that a non-forming portion 5008 is not positioned therebetween.

The forming ratio of the staple-forming surface 5002 can be optimized. By optimizing the forming ratio, more staples can be formed and/or formed to their desired configurations. In certain instances, the surface area of the non-forming portion 5008 of the anvil 5000 can be minimized with respect to the staple-forming pockets 5006. Additionally or alternatively, the footprint of the staple-forming pockets 5006 can be extended or enlarged to maximize the portion of the staple-forming surface 5002 that is designed to catch and form the staples.

Figure 113:
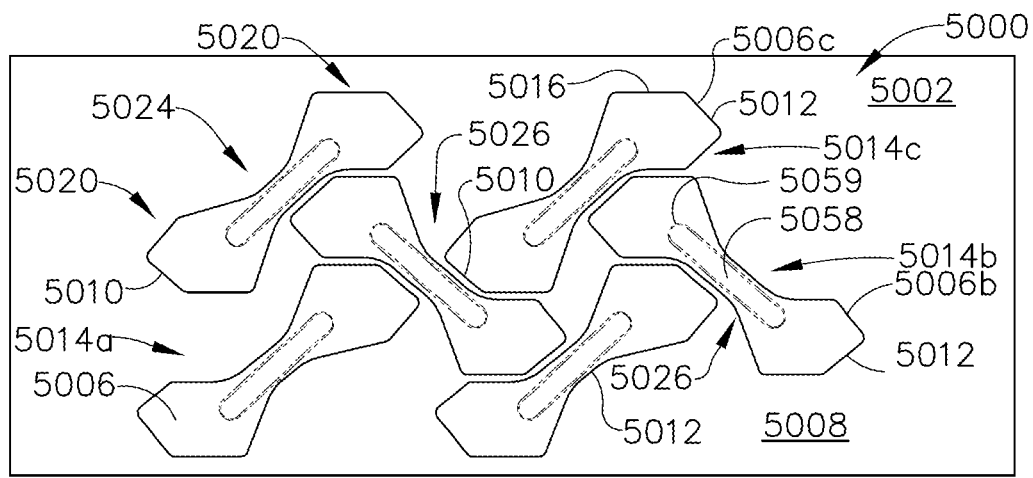
FIG. 113 is a plan view of a portion of an anvil having a plurality of staple-forming pockets defined therein.

The pockets 5006 depicted in FIG. 113 are arranged in an inner row 5014a, an intermediate row 5014b, and an outer row 5014c on a first side of the longitudinal slot 5004. Inner pockets 5006a are positioned in the inner row 5014a, intermediate pockets 5006b are positioned in the intermediate row 5014b, and outer pockets 5006c are positioned in the outer row 5014c. Although not shown in FIG. 113, in at least one instance, the pockets 5006 on the opposing side of the slot 5004 can form a mirror image reflection of the pockets 5006 on the first side of the longitudinal slot 5004. In other instances, the arrangement of pockets 5006 in the staple-forming surface 5002 can be asymmetrical relative to the slot 5004 and, in certain instances, the anvil 5000 may not include the longitudinal slot 5004. In various instances, the pockets 5006 can be arranged in less than or more than three rows on each side of the slot 5004.

The inner pockets 5006a are identical, the intermediate pockets 5006b are identical, and the outer pockets 5006c are identical; however, the inner pockets 5006a are different than the intermediate pockets 5006b and the outer pockets 5006c, and the intermediate pockets 5006b are different than the outer pockets 5006c. In other words, the pockets 5006 in each row 5014a, 5014b, and 5014c are different. Extended landing zones 5030 and 5032 of the pockets 5006a, 5006b, and 5006c, which are described herein, contribute to the different geometries thereof. The shape and size of the extended landing zones 5030 and 5032 are confined by the perimeter 5016 of adjacent, nested pockets 5006.

Although the pockets 5006 in each row 5014a, 5014b, and 5014c are different, the pockets 5006 can be configured to form staples to the same, or substantially the same, formed shape. In other instances, the pockets 5006 can be configured to form staples to different formed shapes, such as to different heights and/or configurations. In certain instances, the pockets 5006 can vary longitudinally within each row 5014a, 5014b, and 5014c. For example, in certain instances, the depth of the pockets 5006 or portions thereof can vary along the length of the anvil 5000 to accommodate for variations in gap distance between the anvil and the staple cartridge along the length of an end effector and/or tissue flow, as described herein.

In certain instances, the pockets 5006 can be configured to engage different geometry staples. For example, staples having different unformed heights and/or different diameters can be formed by the pockets 5006 in the anvil 5000. In certain instances, the geometry of the staples can vary longitudinally, and the pockets 5006 can be configured to form the different geometry staples. For example, the unformed height of the staples and/or the wire diameter can vary along the length of the anvil 5000.

An exemplary intermediate pocket 5006b is shown in FIGS. 113-116C. The pocket 5006b has a first end, or proximal end, 5010 and a second end, or distal end, 5012. A pocket axis PA (FIG. 114) extends between the proximal end 5010 and the distal end 5012 of the pocket 5006b. The pocket 5006b includes a perimeter 5016, which defines the boundary of the pocket 5006b. The perimeter 5016 includes linear portions and contoured portions. More specifically, the perimeter 5016 includes linear portions and contoured corners therebetween at which the linear portions change directions. Referring again to FIG. 113 at least a portion of the perimeter 5016 of each pocket 5006 closely tracks or parallels at least a portion of the perimeter of one or more adjacent pockets 5006.

The pocket 5006b includes a proximal cup 5020, a distal cup 5022, and a neck 5024 extending between the proximal cup 5020 and the distal cup 5022. When a staple is driven into forming contact with the staple-forming surface 5002, the proximal cup 5020 is aligned with a proximal staple leg, and the distal cup 5022 is aligned with a distal staple leg. The cups 5020 and 5022 are configured to direct or funnel the staple legs toward the pocket axis PA and the central portion of the pocket 5006, such as the neck portion 5024, and to deform the staple legs into the formed configuration.

Figure 115:
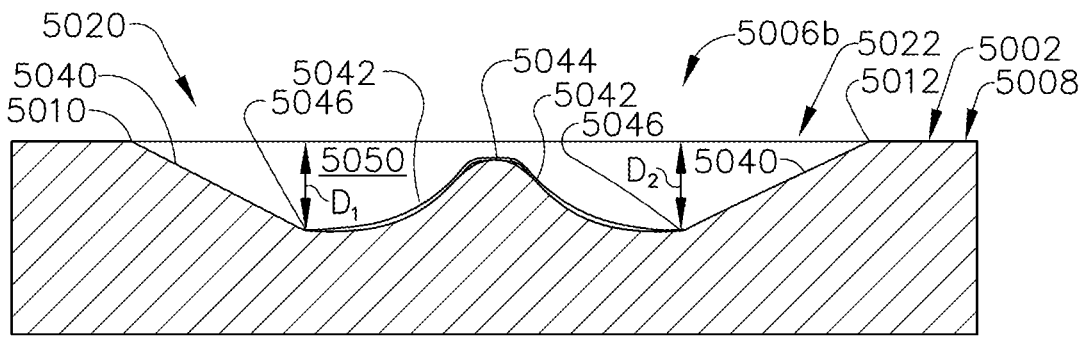
FIGS. 115, 116A, 116B, 116C are cross-sectional views of the pocket of FIG. 114, taken along lines 115-115, 116A-116A, 116B-116B, 116C-116C respectively.

Referring primarily to FIG. 115, each cup 5020, 5022 of the pocket 5006b defines an entrance ramp 5040 and an exit ramp 5042. When forming a staple, the tip of a staple leg can enter the respective pocket 5020, 5022 along the entrance ramp 5040 and exit the respective pocket 5020, 5022 along the exit ramp 5042. At an apex 5046 between the entrance ramp 5040 and the exit ramp 5042, the tips of the staple legs are deformed toward the staple base to assume the formed configuration, such as a B-form or modified B-form, for example. The pocket 5006b also defines a bridge 5044 in the neck portion 5024 between the proximal cup 5020 and the distal cup 5022. The bridge 5044 is offset from the non-forming portion 5008. More specifically, the bridge 5044 is positioned below or recessed relative to the non-forming portion 5008.

Figure 116C:
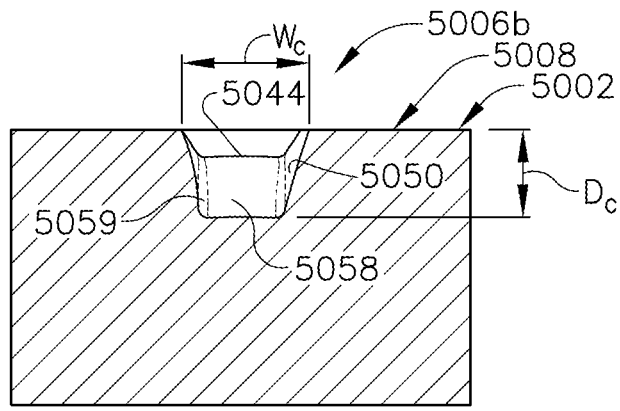
Figure 116B:
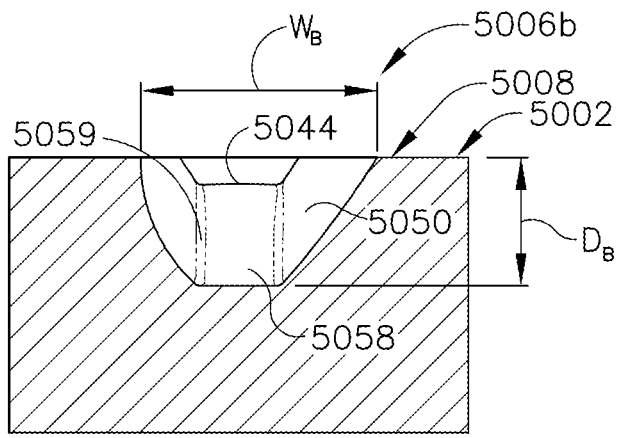
Figure 116A:
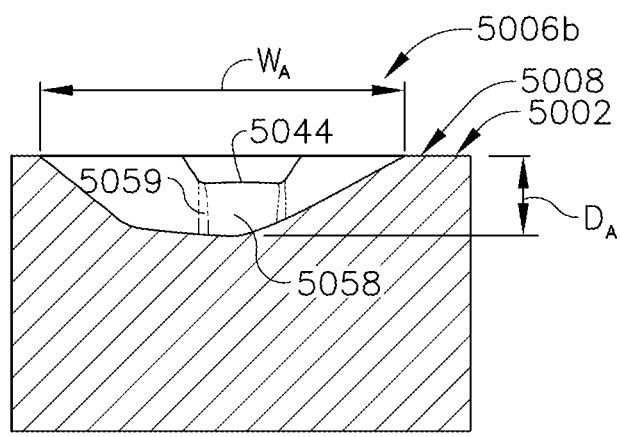

Referring primarily to FIGS. 116A-116C, the pocket 5006b includes sidewalls 5050, which extend from the non-forming portion 5008 to the bottom surface 5058. The sidewalls 5050 include linear portions and contoured portions. The sidewalls 5050 widen toward a central region 5021 (FIG. 114) of each cup 5020, 5022, and narrow from the central region 5021 of each cup 5020, 5022 toward the neck portion 5024. The widened central region 5021 provides an enlarged footprint for receiving the tip of a staple leg. As the cups 5020, 5022 narrow toward the neck 5024, the cups 5020, 5022 are configured to funnel and/or guide the staple legs and tips thereof toward and/or along the pocket axis PA and into a formed configuration.

Figure 114:
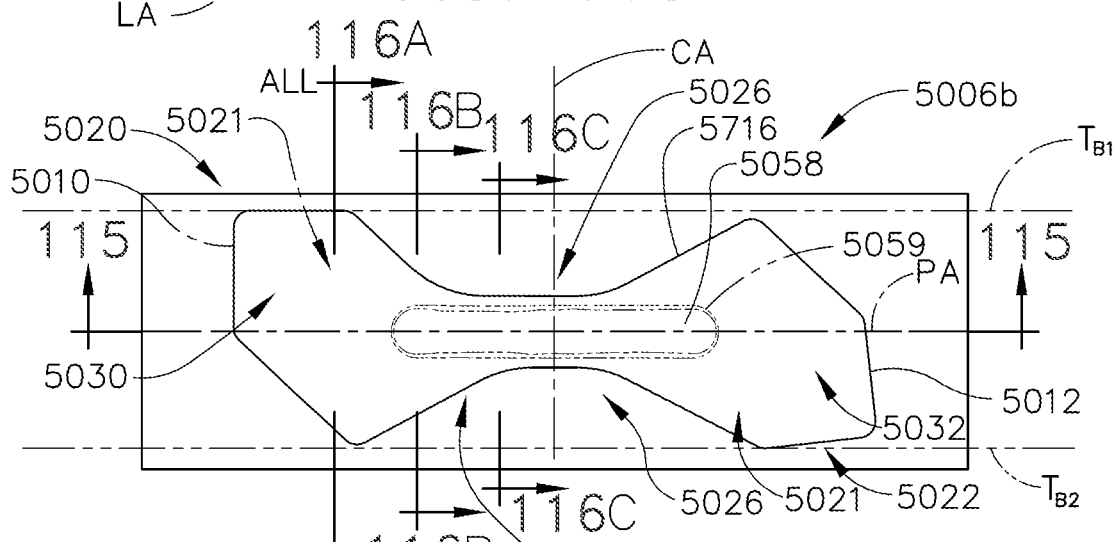
FIG. 114 is a detail view of a pocket of FIG. 113.

FIG. 116A is taken along the plane ALL in FIG. 114, which corresponds to the anticipated landing location (ALL) of a staple leg. For example, the tip of a staple leg can be expected to land in the proximal cup 5020 at and/or near the intersection of the plane ALL and the pocket axis PA. At the plane ALL, the pocket 5006*b* defines a width $W_A$ and a depth $D_A$. The cross-section in FIG. 116B is taken across a transition between the proximal cup 5020 and the neck 5024. FIG. 116B depicts the pocket 5006*b* defining a width $W_B$ and a depth $D_B$. The width $W_B$ is less than the width $W_A$, and the depth $D_B$ is greater than the depth $D_A$. In other words, the pocket 5006*b* narrows and deepens from the plane ALL in the proximal cup 5020 toward the neck 5024. The comparatively large width $W_A$ at the plane ALL is configured to provide a wide receptacle or basin for receiving the staple leg. The cross-section in FIG. 67C is taken across the neck portion 5024. FIG. 116C depicts the pocket 5006*b* defining a width $W_C$ and a depth $D_C$. The width $W_C$ is less than the width $W_B$, and the depth $D_C$ is less than the depth $D_B$. In other words, the pocket 5006*b* continues to narrow, and becomes shallower in the neck 5024 across the bridge 5044.

The bottom surface 5058 of the pocket 5006*b* is a flat surface, which is bounded by an arcuate fillet 5059 therearound. In certain instances, the bottom surface 5058 can have a groove defined along at least a portion thereof. In other instances, the bottom surface 5058 can form a trough. In still other instances, the bottom surface can include hump or ridge along at least a portion thereof, such as across the bridge 5044, for example.

Referring primarily now to FIG. 114, the pocket 5006*b* includes a proximal extended landing zone 5030 and a distal extended landing zone 5032. The proximal extended landing zone 5030 is positioned in a proximal portion of the proximal cup 5020, and the distal extended landing zone 5032 is positioned in a distal portion of the distal cup 5022. More specifically, the extended landing zones 5030 and 5032 are positioned beyond the anticipated landing location of a staple. For example, the proximal extended landing zone 5030 is positioned proximal to the plane ALL and, in instances where the tip of a staple leg lands beyond the plane ALL, the proximal extended landing zones 5030 can catch the staple leg and direct it toward the pocket axis PA and/or toward the neck portion 5024. The landing zones 5030 and 5032 define a generally polygonal shape and, more specifically, a quadrilateral with rounded corners. In other instances, the landing zones 5030 and 5032 can be triangular or substantially triangular and, in still other instances, can define an arcuate or bulbous profile, for example.

The geometry of the extended landing zones 5030 and 5032 is constrained by the perimeter 5016 of the adjacent staple-forming pockets 5006. For example, the extended landing zones 5030 and 5032 can extend toward and/or into nearly abutting contact with one or more adjacent staple-forming pockets. The extended landing zones 5030 and 5032 and/or other portions of the pocket 5006*b* can track and/or extend parallel to adjacent staple-forming pockets 5006. In other instances, the extended landing zones 5030 and 5032 can abut one or more adjacent staple-forming pockets 5006.

Referring again to FIG. 114, the pocket 5006*b* is asymmetric about the pocket axis PA. For example, the perimeter 5016 of the pocket 5006*b* is asymmetric about the pocket axis PA. Moreover, the pocket 5006*b* is asymmetric about a central axis CA through the neck portion 5024 and perpendicular to the pocket axis PA. For example, the perimeter 5016 of the pocket 5006*b* is asymmetric about the central axis CA, and the proximal cup 5020 has a different geometry than the distal cup 5022. Although the proximal cup 5020 and the distal cup 5022 are different, the pocket 5006*b* can be configured to form symmetric staples. For example, referring again to FIG. 115, the distal depth $D_2$ can be less than the proximal depth $D_1$ to accommodate for variations in gap distance between the anvil and the staple cartridge and/or tissue flow, as described herein. The formed height of the proximal and distal legs of a staple can be equal. In other instances, the pocket 5006 can be configured to form asymmetric staples.

Referring again to FIG. 114, the neck portion 5024 is narrower than the proximal and distal cups 5020 and 5022. The narrowed perimeter 5016 of the pocket 5006*b* at the neck portion 5024 defines a receiving peninsula 5026 between a portion of the proximal cup 5020 and a portion of the distal cup 5022. Receiving peninsulas 5026 are positioned on each side of the pocket 5006*b*. The receiving peninsulas 5026 are bounded by the perimeter 5016 of the pocket 5006*b* and a tangent axis (e.g., $T_{B1}$ and $T_{B2}$), which is tangential to the widest portions of the proximal and distal cups 5020 and 5022 on each side of the pocket 5006. A first tangent axis $T_{B1}$ is positioned on a first side of the pocket 5006*b* and a second tangent axis $T_{B2}$ is positioned on the opposite side of the pocket 5006*b*. The first and second tangent axes $T_{B1}$ and $T_{B2}$ depicted in FIG. 116 are parallel to the pocket axis PA. In other instances, one or both of the tangent axes $T_{B1}$ and $T_{B2}$ may not be parallel to the pocket axis PA.

Referring again to FIG. 113, the perimeters 5016 of the pockets 5006 are nested or interlocked along the staple-forming surface 5002. In particular, each pocket 5006 extends into the receiving peninsula 5026 of an adjacent pocket 5006. For example, the intermediate pockets 5006*b* are nested between the inner pockets 5006*a* and the outer pockets 5006*c*. Stated differently, the intermediate pockets 5006*b* extend into the receiving peninsula 5026 of an adjacent inner pocket 5006*a* and into the receiving peninsula 5026 of an adjacent outer pocket 5006*c*. Moreover, the inner pockets 5006*a* and the outer pockets 5006*b* are nested with the intermediate pockets 5006*b*. More specifically, the inner pockets 5006*a* extend into the receiving peninsula 5026 of an adjacent intermediate pocket 5006*b*, and the outer pockets 5006*c* extend into the receiving peninsula 5026 of an adjacent intermediate pocket 5006*b*. In various instances, the distal extended landing zone 5032 of the intermediate pocket 5006*b* is positioned in the receiving peninsula 5026 of an inner pocket 5006*a*, the proximal extended landing zone 5030 of the intermediate pocket 5006*b* is positioned in the receiving peninsula 5026 of an outer pocket 5006*c*, the distal extended landing zone 5032 of an inner pocket 5006*a* is positioned in the receiving peninsula 5026 of an intermediate pocket 5006*b*, and the proximal extended landing zone 5030 of the outer pocket 5006*c* is positioned in the receiving peninsula 5026 of an intermediate pocket 5006*b*.

The geometry of the pockets 5006 facilitates the nesting of the pockets 5006 in the staple-forming surface 5002. For example, because the pockets 5006 include a narrowed neck portion 5024 between two enlarged cups 5020 and 5022, one of the enlarged cups 5020, 5022 of another pocket 5006 can be positioned adjacent to the narrowed neck portion 5024. For example, one of the enlarged cups 5020, 5022 can be aligned with and/or received by a portion of an adjacent pocket 5006. In such instances, the surface area of the staple-forming surface 5002 that is covered by the pockets 5006 can be optimized. The "forming ratio" of the staple-forming surface 5002 is the ratio of the non-forming portion 5008 to the forming portion, i.e., the pockets 5006. The forming ratio of the staple-forming surface 5002 is about 1:1. In other instances, the forming ratio can be less than 1:1 or more than 1:1. For example, in at least one instance, more than 50% of the staple-forming surface 5002 can be covered with staple-forming pockets 5006. In another instances, more than 60% or more than 75% of the stapling-forming surface 5002 can be covered with staple-forming pockets 5006.

Referring now to FIGS. 117-120C, staple-forming pockets 5106 in a portion of an anvil 5100 are depicted. Similar to the anvil 3800, the pockets 5106 are arranged in a herringbone arrangement along the staple-forming surface 5102 of the anvil 5100. The anvil 5100 includes a staple-forming surface 5102 and a longitudinal slot 5104. The longitudinal slot 5104 extends along the longitudinal axis LA of the anvil 5100. In certain instances, a firing element and/or a cutting element can translate through the longitudinal slot 5104 during at least a portion of a firing stroke. The staple-forming pockets 5106 are defined in the staple-forming surface 5102. The staple-forming surface 5102 also includes a non-forming portion 5108 that extends around the pockets 5106. The non-forming portion 5108 extends entirely around each pocket 5106. In other words, the non-forming portion 5108 surrounds the staple-forming pockets 5106. In other instances, at least a portion of two or more adjacent pockets 5106 can be in abutting contact such that a non-forming portion 5108 is not positioned therebetween.

The forming ratio of the staple-forming surface 5102 can be optimized. By optimizing the forming ratio, more staples can be formed and/or formed to their desired configurations. In certain instances, the surface area of the non-forming portion 5108 of the anvil 5100 can be minimized with respect to the staple-forming pockets 5106. Additionally or alternatively, the footprint of the staple-forming pockets 5106 can be extended or enlarged to maximize the portion of the staple-forming surface 5102 that is designed to catch and form the staples.

Figure 117:
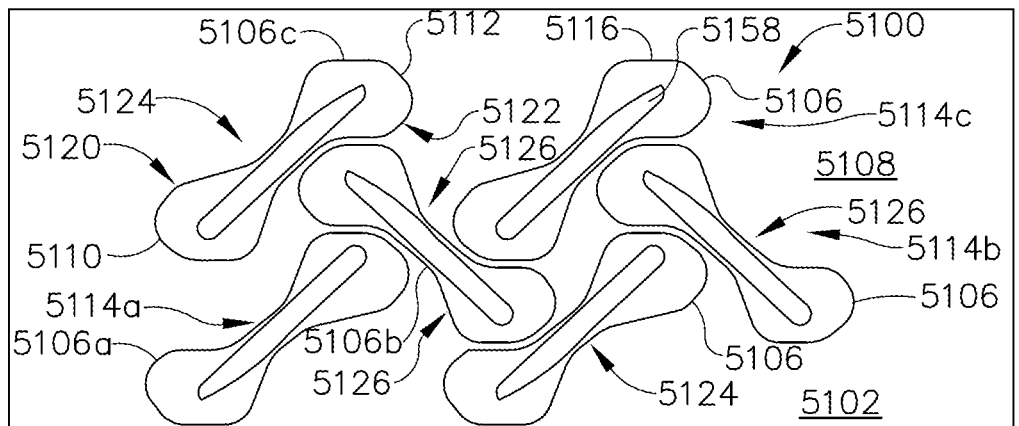
FIG. 117 is a plan view of a portion of an anvil having a plurality of staple-forming pockets defined therein.

The pockets 5106 depicted in FIG. 117 are arranged in an inner row 5114a, an intermediate row 5114b, and an outer row 5114c on a first side of the longitudinal slot 5104. Inner pockets 5106a are positioned in the inner row 5114a, intermediate pockets 5106b are positioned in the intermediate row 5114b, and outer pockets 5106c are positioned in the outer row 5114c. Although not shown in FIG. 117, in at least one instance, the pockets 5106 on the opposing side of the slot 5104 can form a mirror image reflection of the pockets 5106 on the first side of the longitudinal slot 5104. In other instances, the arrangement of pockets 5106 in the staple-forming surface 5102 can be asymmetrical relative to the slot 5104 and, in certain instances, the anvil 5100 may not include the longitudinal slot 5104. In various instances, the pockets 5106 can be arranged in less than or more than three rows on each side of the slot 5104.

The inner pockets 5106a are identical, the intermediate pockets 5106b are identical, and the outer pockets 5106c are identical; however, the inner pockets 5106a are different than the intermediate pockets 5106b and the outer pockets 5106c, and the intermediate pockets 5106b are different than the outer pockets 5106c. In other words, the pockets 5106 in each row 5114a, 5114b, and 5114c are different. In other instances, the pockets 5106 in two or more of the rows can be the same. For example, the inner pockets 5106a can be the same as the outer pockets 5106c. Extended landing zones 5130 and 5132 of the pockets 5106a, 5106b, and 5106c, which are described herein, can contribute to the different geometries thereof. Moreover, the shape and size of the extended landing zones 5130 and 5132 are confined by the perimeter 5116 of the adjacent, nested pockets 5106. The landing zones 5130 and 5132 define an arcuate profile. In other instances, the landing zones 5030 and 5032 can be polygonal and/or include one or more linear and/or contoured portions.

Although the pockets in each row 5114a, 5114b, and 5114c are different, the pockets 5106 can be configured to form staples to the same, or substantially the same, formed shape. In other instances, the pockets 5106 can be configured to form staples to different formed shapes, such as to different heights and/or configurations. In certain instances, the pockets 5106 can vary longitudinally within each row 5114a, 5114b, and 5114c. For example, in certain instances, the depth of the pockets 5106 or portions thereof can vary along the length of the anvil 5100 to accommodate for variations in gap distance between the anvil and the staple cartridge along the length of an end effector and/or tissue flow, as described herein.

An exemplary intermediate pocket 5106b is shown in FIGS. 117-120C. The pocket 5106b has a first end, or proximal end, 5110 and a second end, or distal end, 5112. A pocket axis PA (FIG. 118) extends between the proximal end 5110 and the distal end 5112 of the pocket 5106b. The pocket 5106b includes a perimeter 5116, which defines the boundary of the pocket 5106b. The perimeter 5116 includes linear portions and contoured portions. More specifically, the perimeter 5116 includes linear portions and contoured corners therebetween at which the linear portions change directions. Referring again to FIG. 117, at least a portion of the perimeter 5116 of each pocket 5106 closely tracks or parallels at least a portion of the perimeter of one or more adjacent pockets 5106. The rounded perimeter 5116 of the pocket 5106b can provide a smoother profile, which can be easier to coin and/or stamp in the staple-forming surface 5102 than pockets having sharp corners, for example.

The pocket 5106b includes a proximal cup 5120, a distal cup 5122, and a neck portion 5124 extending between the proximal cup 5120 and the distal cup 5122. When a staple is driven into forming contact with the staple-forming surface 5102, the proximal cup 5120 is aligned with a proximal staple leg, and the distal cup 5122 is aligned with a distal staple leg. The cups 5120 and 5122 are configured to direct or funnel the staple legs toward the pocket axis PA and the central portion of the pocket 5106, such as the neck portion 5124, and to deform the staple legs into the formed configuration.

Figure 119:
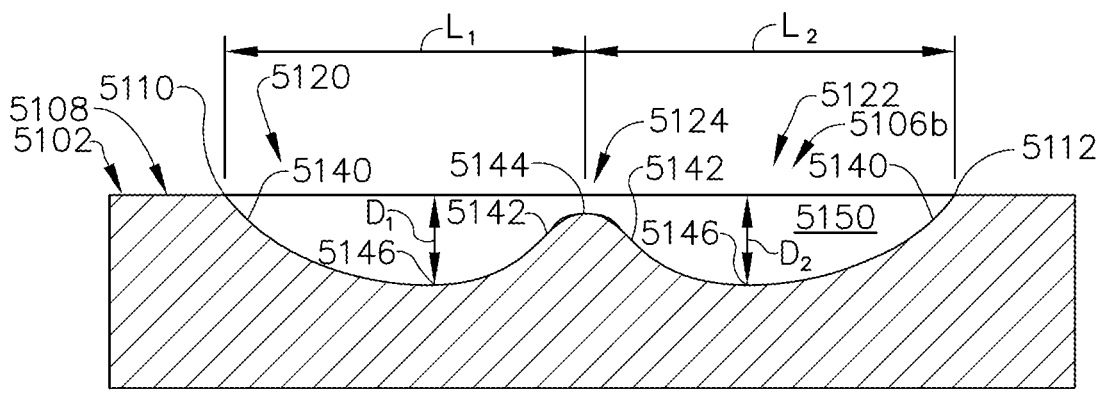
FIGS. 119, 120A, 120B, and 120C are cross-sectional views of the pocket of FIG. 118, taken along lines 119-119, 120A-120A, 120B-120B, and 120C-120C respectively.

Referring primarily to FIG. 119, each cup 5120, 5122 of the pocket 5106b defines an entrance ramp 5140 and an exit ramp 5142. When forming a staple, the tip of a staple leg can enter the respective pocket 5120, 5122 along the entrance ramp 5140 and exit the respective pocket 5120, 5122 along the exit ramp 5142. At an apex 5146 between the entrance ramp 5140 and the exit ramp 5142, the tips of the staple legs are deformed toward the staple base to assume the formed configuration, such as a B-form or modified B-form, for example. The pocket 5106b also defines a bridge 5144 in the neck portion 5124 between the proximal cup 5120 and the distal cup 5122. The bridge 5144 is offset from the non-forming portion 5108. More specifically, the bridge 5144 is positioned below or recessed relative to the non-forming portion 5108.

Figure 120C:
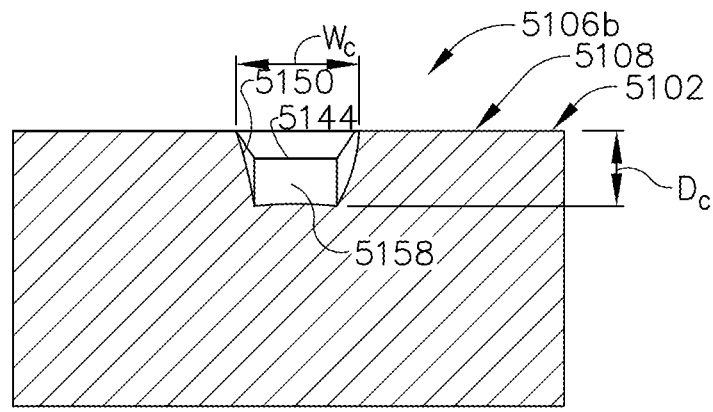
Figure 120B:
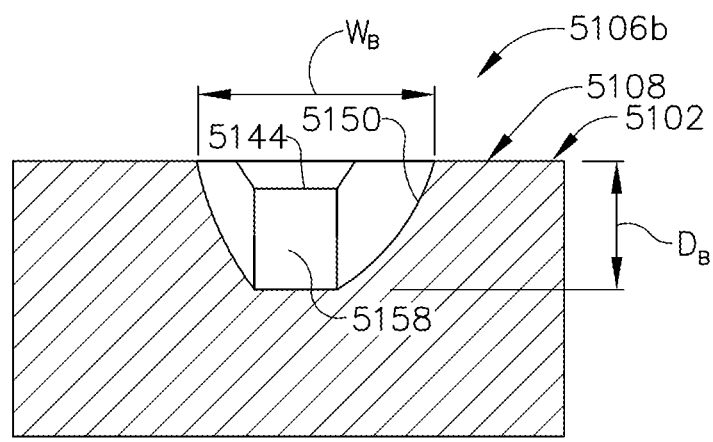
Figure 120A:
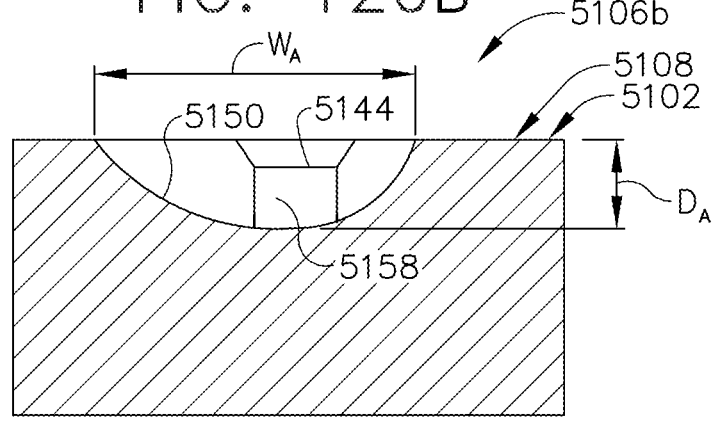

Referring primarily to FIGS. 120A-120C, the pocket 5106*b* includes sidewalls 5150, which extend from the non-forming portion 5108. The sidewalls 5150 include linear portions and contoured portions. The sidewalls 5150 widen toward a central region 5121 (FIG. 118) of each cup 5120, 5122, and narrow from the central region 5121 of each cup 5120, 5122 toward the neck portion 5124. The widened central region 5121 provides an enlarged footprint for receiving the tip of a staple leg. As the cups 5120, 5122 narrow toward the neck 5124, the cups 5120, 5122 are configured to funnel and/or guide the staple legs and tips thereof toward and/or along the pocket axis PA and into a formed configuration.

Figure 118:
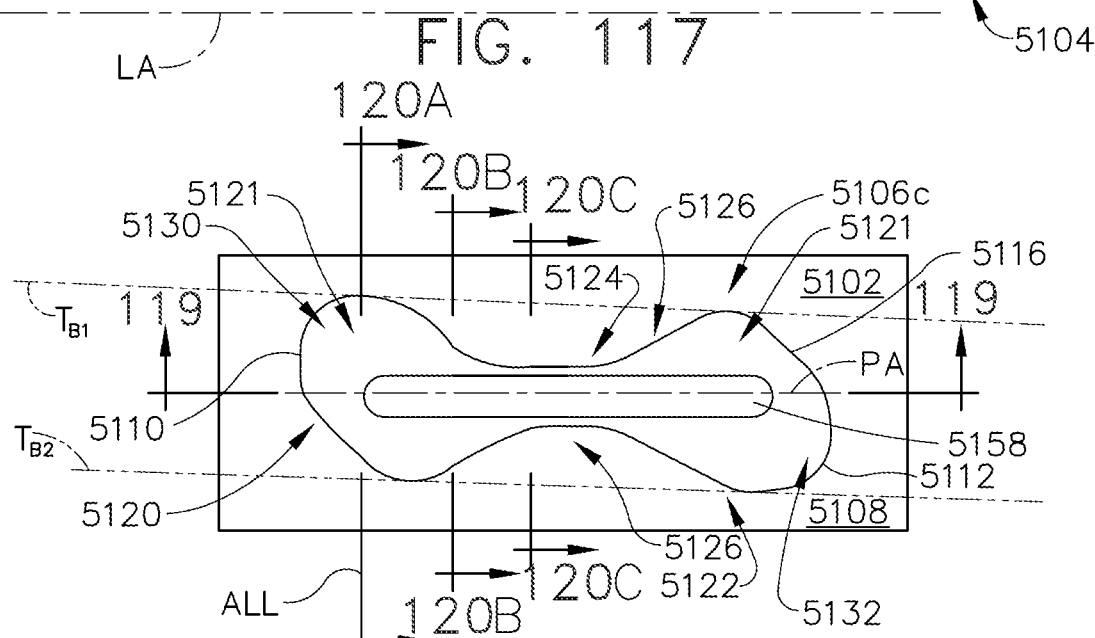
FIG. 118 is a detail view of a pocket of FIG. 117.

FIG. 120A is taken along the plane ALL in FIG. 118, which corresponds to the anticipated landing location of a staple leg. For example, the tip of a staple leg can be expected to land in the proximal cup 5120 at and/or near the intersection of the plane ALL and the pocket axis PA. At the plane ALL, the pocket 5106*b* defines a width $W_A$ and a depth $D_A$. The cross-section in FIG. 120B is taken across a transition between the proximal cup 5120 and the neck 5124. FIG. 120B depicts the pocket 5106*b* defining a width $W_B$ and a depth $D_B$. The width $W_B$ is less than the width $W_A$, and the depth $D_B$ is greater than the depth $D_A$. In other words, the pocket 5106*b* narrows and deepens from the plane ALL in the proximal cup 5120 toward the neck 5124. The comparatively large width $W_A$ at the plane ALL is configured to provide a wide basin or receptacle for receiving the staple leg. The cross-section in FIG. 120C is taken across the neck portion 5124. FIG. 120C depicts the pocket 5106*b* defining a width $W_C$ and a depth $D_C$. The width $W_C$ is less than the width $W_B$, and the depth $D_C$ is less than the depth $D_B$. In other words, the pocket 5106*b* continues to narrow, and becomes shallower in the neck 5124 across the bridge 5144.

The bottom surface 5158 of the pocket 5106*b* is a flat surface. In other instances, the bottom surface 5158 can have a groove defined along at least a portion thereof. In still instances, the bottom surface 5158 can form a trough and/or can include hump or ridge along at least a portion thereof, such as across the bridge 5144, for example.

Referring primarily now to FIG. 118, the pocket 5106*b* includes a proximal extended landing zone 5130 and a distal extended landing zone 5132. The proximal extended landing zone 5130 is positioned in a proximal portion of the proximal cup 5120, and the distal extended landing zone 5132 is positioned in a distal portion of the distal cup 5122. More specifically, the extended landing zones 5130 and 5132 are positioned beyond the anticipated landing location of a staple. For example, the proximal extended landing zone 5130 is positioned proximal to the plane ALL and, in instances where the tip of a staple leg lands beyond the plane ALL, the proximal extended landing zone 5130 can catch the staple leg and direct it toward the pocket axis PA and/or toward the neck portion 5124.

The geometry of the extended landing zones 5130 and 5132 is constrained by the perimeter 5016 of the adjacent staple-forming pockets 5106. For example, the extended landing zones 5130 and 5132 can extend toward and/or into nearly abutting contact with one of more adjacent staple-forming pockets. The extended landing zones 5130 and 5132 and/or other portions of the pocket 5106*b* can extend parallel to adjacent staple-forming pockets 5106. In other instances, the extended landing zones 5130 and 5132 can abut one or more adjacent staple-forming pockets 5106.

Referring again to FIG. 118, the pocket 5106*b* is asymmetric about the pocket axis PA. For example, the perimeter 5116 of the pocket 5106*b* is asymmetric about the pocket axis PA. Moreover, the pocket 5106*b* is asymmetric about a central axis CA through the neck portion 5124 and perpendicular to the pocket axis PA. For example, the perimeter 5116 of the pocket 5106*b* is asymmetric about the central axis CA, and the proximal cup 5120 has a different geometry than the distal cup 5122. Although the proximal cup 5120 and the distal cup 5122 are different, the pocket 5106*b* can be configured to form symmetric staples. For example, referring again to FIG. 119, the distal depth $D_2$ can be less than the proximal depth $D_1$ to accommodate for variations in gap distance between the anvil and the staple cartridge and/or tissue flow, as described herein. Accordingly, the formed height of the proximal and distal legs of a staple can be equal. In other instances, the pocket 5106 can be configured to form asymmetric staples.

Referring again to FIG. 118, the neck portion 5124 is narrower than the proximal and distal cups 5120 and 5122. The narrowed perimeter 5116 of the pocket 5106*b* at the neck portion 5124 defines a receiving peninsula 5126 between a portion of the proximal cup 5120 and a portion of the distal cup 5122. Receiving peninsulas 5126 are positioned on each side of the pocket 5106*b*. The receiving peninsulas 5126 are bounded by the perimeter 5116 of the pocket 5106*b* and a tangent axis (e.g., $T_{B1}$ or $T_{B2}$), which is tangential to the widest portions of the proximal and distal cups 5120 and 5122 on each side of the pocket 5106. A first tangent axis $T_{B1}$ is positioned on a first side of the pocket 5106*b* and a second tangent axis $T_{B2}$ is positioned on the opposite side of the pocket 5106*b*. The first and second tangent axes $T_{B1}$ and $T_{B2}$ depicted in FIG. 118 are skewed relative to the pocket axis PA. In other instances, one or both of the tangent axes $T_{B1}$ and $T_{B2}$ can be parallel to the pocket axis PA.

Referring again to FIG. 117, the perimeters 5116 of the pockets 5106 are nested or interlocked along the staple-forming surface 5102. In particular, each pocket 5106 extends into the receiving peninsula 5126 of an adjacent pocket 5106. For example, the intermediate pockets 5106*b* are nested between the inner pockets 5106*a* and the outer pockets 5106*c*. Stated differently, the intermediate pockets 5106*b* extend into the receiving peninsula 5126 of an adjacent inner pocket 5106*a* and into the receiving peninsula 5126 of an adjacent outer pocket 5106*c*. Moreover, the inner pockets 5106*a* and the outer pockets 5106*b* are nested with the intermediate pockets 5106*b*. More specifically, the inner pockets 5106*a* extend into the receiving peninsula 5126 of an adjacent intermediate pocket 5106*b*, and the outer pockets 5106*c* extend into the receiving peninsula 5126 of an adjacent intermediate pocket 5106*b*. In various instances, the distal extended landing zone 5132 of the intermediate pocket 5106*b* is positioned in the receiving peninsula 5126 of an inner pocket 5106*a*, the proximal extended landing zone 5130 of the intermediate pocket 5106*b* is positioned in the receiving peninsula 5126 of an outer pocket 5106*c*, the distal extended landing zone 5132 of an inner pocket 5106*a* is positioned in the receiving peninsula 5126 of an intermediate pocket 5106*b*, and the proximal extended landing zone 5130 of the outer pocket 5106*c* is positioned in the receiving peninsula 5126 of an intermediate pocket 5106*b*.

The geometry of the pockets 5106 facilitates the nesting of the pockets 5106 in the staple-forming surface 5102. For example, because the pockets 5106 include a narrowed neck portion 5124 between two enlarged cups 5120 and 5122, one of the enlarged cups 5120, 5122 of another pocket 5106 can be positioned adjacent to the narrowed neck portion 5124. For example, one of the enlarged cups 5120, 5122 can be aligned with and/or received by a portion of an adjacent pocket 5106. In such instances, the surface area of the staple-forming surface 5102 that is covered by the pockets 5106 can be optimized. For example, the surface area of the staple-forming surface 5102 that is covered by the pockets 5106 is maximized. The "forming ratio" of the staple-forming surface 5102 is the ratio of the non-forming portion 5108 to the forming portion, i.e., the pockets 5106. In at least one instance, the forming ratio can be at least 1:1, for example. In certain instances, more than 60% or more than 75% of the staple-forming surface 5102 can be covered by staple-forming pockets 5106.

Referring now to FIGS. 121-125C, staple-forming pockets 5206 in a portion of an anvil 5200 are depicted. Similar to the anvil 3800, the pockets 5206 are arranged in a herringbone arrangement along the staple-forming surface 5202 of the anvil 5200. The anvil 5200 includes a staple-forming surface 5202 and a longitudinal slot 5204. The longitudinal slot 5204 extends along the longitudinal axis LA of the anvil 5200. In certain instances, a firing element and/or a cutting element can translate through the longitudinal slot 5204 during at least a portion of a firing stroke. The staple-forming pockets 5206 are defined in the staple-forming surface 5202. The staple-forming surface 5202 also includes a non-forming portion 5208 that extends around the pockets 5206. The non-forming portion 5208 extends entirely around each pocket 5206. In other words, the non-forming portion 5208 surrounds the staple-forming pockets 5206. In other instances, at least a portion of two or more adjacent pockets 5206 can be in abutting contact such that a non-forming portion 5208 is not positioned therebetween.

The forming ratio of the staple-forming surface 5202 can be optimized. By optimizing the forming ratio, more staples can be formed and/or formed to their desired configurations. In certain instances, the surface area of the non-forming portion 5208 of the anvil 5200 can be minimized with respect to the staple-forming pockets 5206. Additionally or alternatively, the footprint of the staple-forming pockets 5206 can be extended or enlarged to maximize the portion of the staple-forming surface 5202 that is designed to catch and form the staples.

Figure 121:
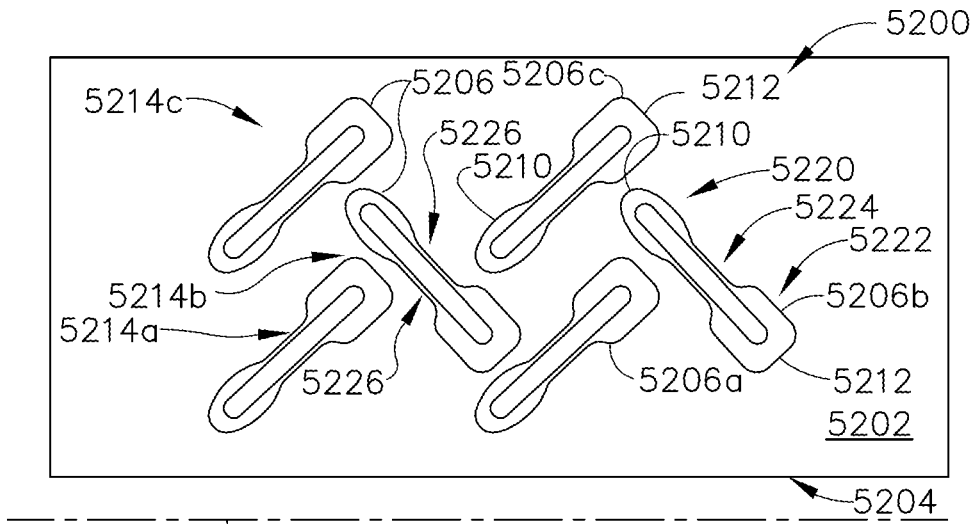
FIG. 121 is a plan view of a portion of an anvil having a plurality of staple-forming pockets defined therein.

The pockets 5206 depicted in FIG. 121 are arranged in an inner row 5214a, an intermediate row 5214b, and an outer row 5214c on a first side of the longitudinal slot 5204. Inner pockets 5206a are positioned in the inner row 5214a, intermediate pockets 5206b are positioned in the intermediate row 5214b, and outer pockets 5206c are positioned in the outer row 5214c. Although not shown in FIG. 121, in at least one instance, the pockets 5206 on the opposing side of the slot 5204 can form a mirror image reflection of the pockets 5206 on the first side of the longitudinal slot 5204. In other instances, the arrangement of pockets 5206 in the staple-forming surface 5202 can be asymmetrical relative to the slot 5204 and, in certain instances, the anvil 5200 may not include the longitudinal slot 5204. In various instances, the pockets 5206 can be arranged in less than or more than three rows on each side of the slot 5204.

The pockets 5206 depicted in FIG. 121 are identical. Each pocket 5206 defined in the staple-forming surface 5202 has the same geometry. In other instances, the geometry of the pockets 5206 can vary row-to-row and/or longitudinally along the length of the anvil 5200. For example, in certain instances, the depth of the pockets 5206 can vary along the length of the anvil 5200 to accommodate for variations in gap distance between the anvil and the staple cartridge along the length of an end effector and/or tissue flow, as described herein.

The pockets 5206 can be configured to form staples to the same, or substantially the same, formed shape. As described herein, the pockets 5206 can be configured to form each staple to the same asymmetrical shape. In other instances, the pockets 5206 can be configured to form staples to different formed shapes, such as to different heights and/or configurations.

An exemplary intermediate pocket 5206b is shown in FIGS. 122-125C. The pocket 5206b has a first end, or proximal end, 5210 and a second end, or distal end, 5212. A pocket axis PA (FIG. 121) extends between the proximal end 5210 and the distal end 5212 of the pocket 5206b. The pocket 5206b includes a perimeter 5216, which defines the boundary of the pocket 5206b. The perimeter 5216 includes linear portions and contoured portions.

The pocket 5206b includes a proximal cup 5220, a distal cup 5222, and a neck 5224 extending between the proximal cup 5220 and the distal cup 5222. When a staple is driven into forming contact with the staple-forming surface 5202, the proximal cup 5220 is aligned with a proximal staple leg, and the distal cup 5222 is aligned with a distal staple leg. The cups 5220 and 5222 are configured to direct or funnel the staple legs toward the pocket axis PA and the central portion of the pocket 5206, such as the neck portion 5224, and to deform the staple legs into the formed configuration. In other instances, the cup 5222 can be proximal to the cup 5220.

Referring primarily to FIG. 119, each cup 5220 and 5222 of the pocket 5206b defines an entrance ramp 5240a and 5240b, respectively, and an exit ramp 5242a and 5242b, respectively. When forming a staple, the tip of a staple leg can enter the respective pocket 5220, 5222 along the entrance ramp 5240a, 5240b and exit the respective pocket 5220, 5222 along the exit ramp 5242a, 5242b. At an apex 5246a, 5246b, respectively, between the entrance ramp 5240a, 5240b and the exit ramp 5242a, 5242b, the tips of the staple legs are deformed toward the staple base to assume the formed configuration, such as a B-form or modified B-form, for example. The pocket 5206b also defines a bridge 5244 between the proximal cup 5220 and the distal cup 5222. The bridge 5244 is offset from the non-forming portion 5208. More specifically, the bridge 5244 is positioned below or recessed relative to the non-forming portion 5208.

Referring again to FIG. 122, the pocket 5206b is symmetric about the pocket axis PA. For example, the perimeter 5216 of the pocket 5206b is symmetric about the pocket axis PA. Moreover, the pocket 5206b is asymmetric about a central axis CA through the neck portion 5224 and perpendicular to the pocket axis PA. For example, the perimeter 5216 of the pocket 5206b is asymmetric about the central axis CA, and the proximal cup 5220 has a different geometry than the distal cup 5222. The asymmetry of the cups 5220 and 5222 is configured to form asymmetric staples. For example, referring again to FIG. 123, the distal depth $D_2$ is less than the proximal depth $D_1$, which is configured to form a staple having a greater formed height at the proximal leg than at the distal leg. The distal depth $D_2$ can be about 0.002 inches less than the proximal depth $D_1$. In other instances, the difference between the distal depth $D_2$ and the proximal depth $D_1$ can be greater than and/or less than 0.002 inches. In certain instances, the difference can be between one percent and ten percent of the staple diameter. For example, the difference can be about two percent of the staple diameter. In other instances, the formed height of the staple can be greater at the distal leg than the proximal leg. The length of each cup 5220, 5222 is also different. For example, the distal length $D_2$ is greater than the proximal length $D_1$ in FIG. 123. Additionally, the incline of the entrance ramps 5240a and 5240b in the pocket 5206b are different, and the incline of the exit ramps 5242a and 5242b in the pocket 5206b are also different.

In various instances, the reduced depth in a portion of the pocket 5206b can improve the stiffness of the anvil. For example, because the distal depth $D_2$ is less than the proximal depth $D_1$, the anvil 5200 is comprised of more material, which can increase the stiffness thereof. Moreover, because the increased material is in a distal portion of the anvil 5200, such portion can have an increased stiffness, which can limit bowing or deformation of the anvil toward the distal end.

The difference in geometry of the proximal and distal cups 5220 and 5222, respectively, can accommodate for tissue movement or flow. More specifically, when tissue is clamped against the anvil 5200, fluid in the clamped tissue can flow or move toward adjacent, unclamped tissue. The tissue can flow laterally toward the longitudinal sides of the anvil 5200, distally toward the distal end of the anvil 5200, and/or proximally toward the proximal end of the anvil 5200. In certain instances, tissue can flow relative to the anvil 5200 when the cutting edge is advanced distally through the tissue. In such instances, tissue may flow laterally, distally, and/or proximally, but it primarily flows distally due to the distal movement of the cutting edge. In instances where the cutting edge moves proximally to incise tissue, the movement or flow of the tissue would be generally proximal during the cutting stroke. The different geometries of the proximal and distal cups 5220 and 5222, respectively, can accommodate for the flow of the tissue, which can shift or skew the staple legs embedded therein.

Figure 124C:
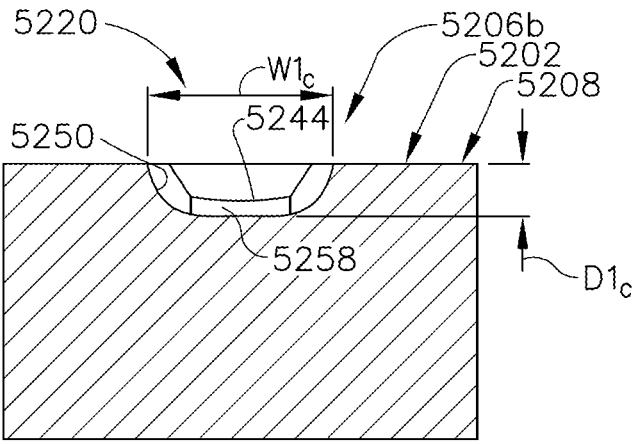
Figure 124B:
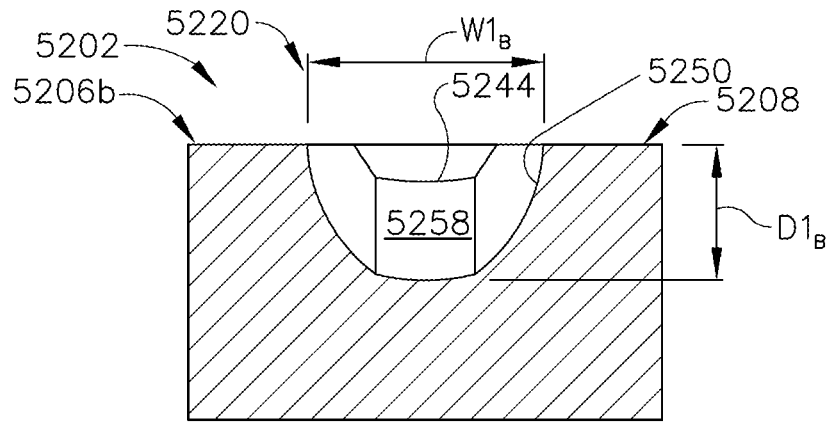
Figure 124A:
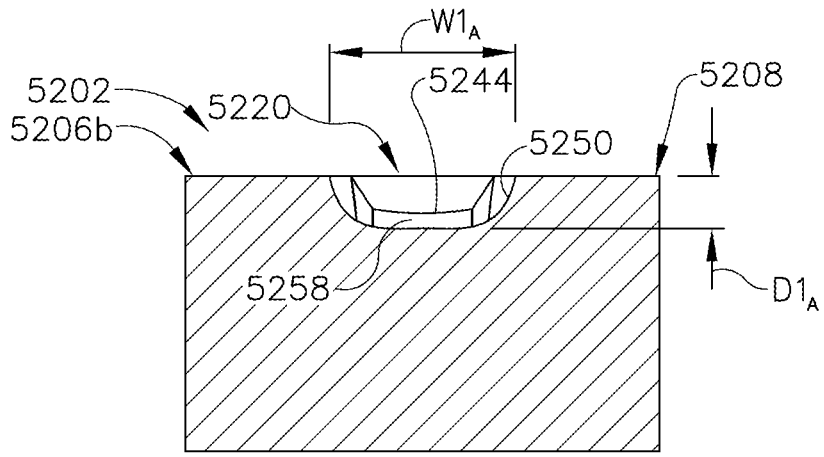

Referring primarily to FIGS. 124A-124C, the pocket 5206b includes sidewalls 5250, which extend from the non-forming portion 5208. The cups 5220, 5222 are configured to funnel and/or guide the staple legs and tips thereof toward and/or along the pocket axis PA and into a formed configuration. Owing to the different geometries of the proximal and distal cups 5220 and 5222, the path of the proximal staple leg can be different than the path of the distal staple leg when driven into forming contact with the pocket 5206b. In certain instances, the asymmetrical staple pockets 5206b can form asymmetrical staples from symmetrical unformed staples. Additionally or alternatively, asymmetrical unformed staples can be formed into asymmetrical formed staples by the staple pockets 5206b.

Figure 122:
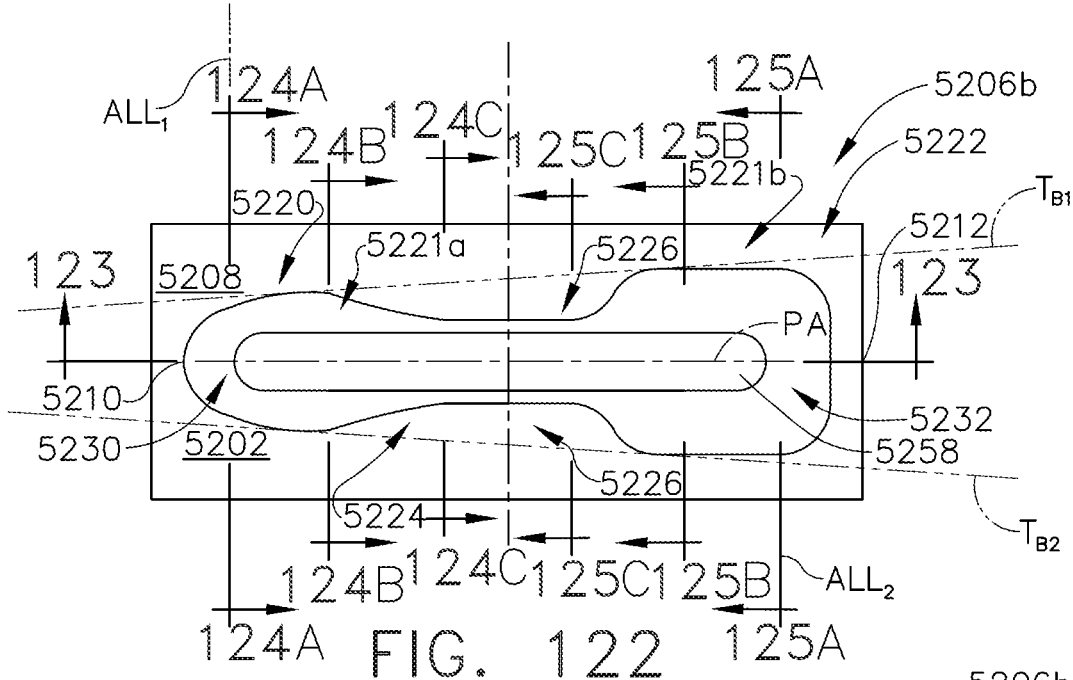
FIG. 122 is a detail view of a pocket of FIG. 121.
Figure 123:
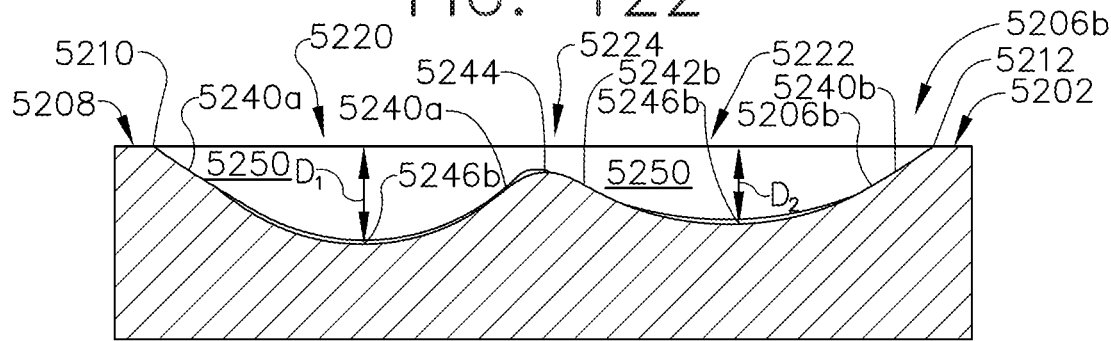
FIGS. 123, 124A, 124B, 124C, 125A, 125B, and 125C are cross-sectional views of the pocket of FIG. 122, taken along lines 123-123, 124A-124A, 124B-124B, 124C-124C, 125A-125A, 125B-125B, and 125C-125C.

FIG. 124A is taken along the plane $ALL_1$ in FIG. 122, which corresponds to the anticipated landing location of a proximal staple leg. For example, the tip of a proximal staple leg can be expected to land in the proximal cup 5220 at and/or near the intersection of the plane $ALL_1$ and the pocket axis PA. At the plane $ALL_1$, the proximal cup 5220 defines a width $W1_A$ and a depth $D1_A$. The cross-section in FIG. 124B is taken across a transition between the proximal cup 5220 and the neck 5224. FIG. 124B depicts the proximal cup 5220 defining a width $W1_B$ and a depth $D1_B$. The width $W1_B$ is greater than the width $W1_A$, and the depth $D1_B$ is greater than the depth $D1_A$. In other words, the proximal cup 5220 widens and deepens from the plane $ALL_1$ in the proximal cup 5220 toward the neck 5224. The cross-section in FIG. 124C is taken across a proximal end of the neck portion 5224. FIG. 124C depicts the pocket 5206b defining a width $W1_C$ and a depth $D1_C$. The width $W1_C$ is less than the width $W1_B$, and the depth $D1_C$ is less than the depth $D1_B$. In other words, the pocket 5206b continues to narrow, and becomes shallower in the neck 5224 across the bridge 5244.

Figure 125C:
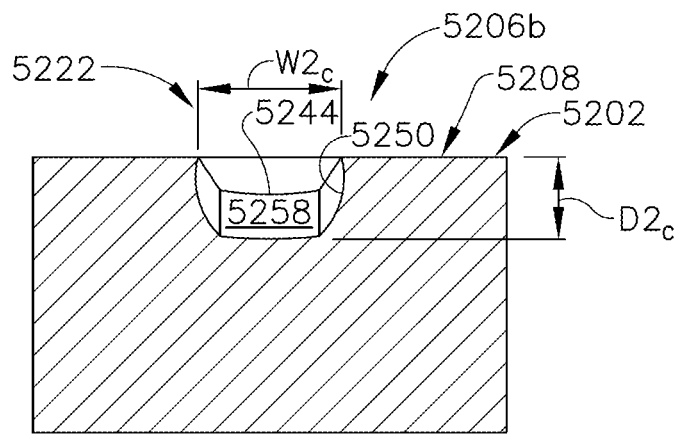
Figure 125B:
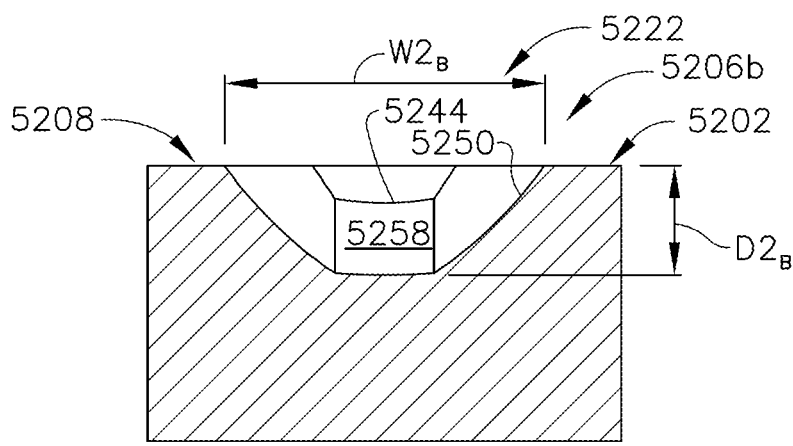
Figure 125A:
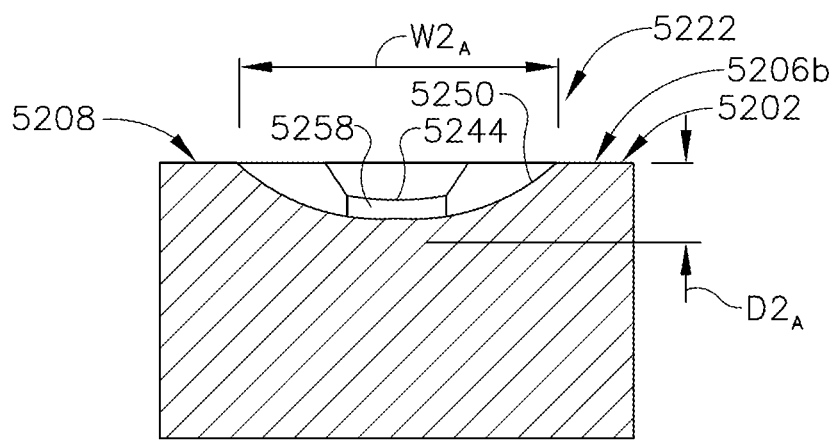

FIG. 125A is taken along the plane $ALL_2$ in FIG. 122, which corresponds to the anticipated landing location of a distal staple leg. For example, the tip of a distal staple leg can be expected to land in the distal cup 5222 at and/or near the intersection of the plane $ALL_2$ and the pocket axis PA. At the plane $ALL_2$, the distal cup 5222 defines a width $W2_A$ and a depth $D2_A$. The width $W2_A$ is different than the width $W1_A$, and the depth $D2_A$ is different than the depth $D1_A$. The cross-section in FIG. 125B is taken across a transition between the distal cup 5222 and the neck 5224. FIG. 125B depicts the distal cup 5222 defining a width $W2_B$ and a depth $D2_B$. The width $W2_B$ is different than the width $W1_B$, and the depth $D2_B$ is different than the depth $D1_B$. The width $W2_B$ is less than the width $W2_A$, and the depth $D2_B$ is greater than the depth $D2_A$. In other words, the distal cup 5222 narrows and deepens from the plane $ALL_2$ in the distal cup 5222 toward the neck 5224. The cross-section in FIG. 125C is taken across a distal end of the neck portion 5224. FIG. 125C depicts the pocket 5206b defining a width $W2_C$ and a depth $D2_C$. The width $W2_C$ is different than the width $W1_C$, and the depth $D2_C$ is different than the depth $D1_C$. The width $W2_C$ is less than the width $W2_B$, and the depth $D2_C$ is less than the depth $D2_B$. In other words, the pocket 5206b continues to narrow, and becomes shallower in the neck 5224 across the bridge 5244.

The bottom surface 5258 of the pocket 5206b is a flat surface. In other instances, the bottom surface 5258 can have a groove defined along at least a portion thereof. In still other instances, the bottom surface 5258 can form a trough and/or can include a hump or ridge along at least a portion thereof, such as across the bridge 5244, for example.

Referring primarily now to FIG. 122, the pocket 5206b includes a proximal extended landing zone 5230 and a distal extended landing zone 5232. The proximal extended landing zone 5230 is positioned in a proximal portion of the proximal cup 5220, and the distal extended landing zone 5232 is positioned in a distal portion of the distal cup 5222. More specifically, the extended landing zones 5230 and 5232 are positioned beyond the anticipated landing location of a staple. For example, the proximal extended landing zone 5230 is positioned proximal to the plane $ALL_1$ and, in instances where the tip of a staple leg lands beyond the plane $ALL_1$, the proximal extended landing zones 5230 can catch the staple leg and direct it toward the pocket axis PA and/or toward the neck portion 5224. The distal extended landing zone 5232 is positioned distal to the plane $ALL_2$ and, in instances where the tip of a staple leg lands beyond the plane $ALL_2$, the distal extended landing zones 5232 can catch the staple leg and direct it toward the pocket axis PA and/or toward the neck portion 5224. In certain instances, the geometry of the extended landing zones 5230, 5232 can be constrained or limited by the geometry of the adjacent, nested staple-forming pockets 5206.

Referring again to FIG. 122, the neck portion 5224 is narrower than the proximal and distal cups 5220 and 5222. The narrowed perimeter 5216 of the pocket 5206b at the neck portion 5224 defines a receiving peninsula 5226 between a portion of the proximal cup 5220 and a portion of the distal cup 5222. Receiving peninsulas 5226 are positioned on each side of the pocket 5206b. The receiving peninsulas 5226 are bounded by the perimeter 5216 of the pocket 5206b and a tangent axis (e.g., $T_{B1}$ and $T_{B2}$), which is tangential to the widest portions of the proximal and distal cups 5220 and 5222 on each side of the pocket 5206. A first tangent axis $T_{B1}$ is positioned on a first side of the pocket 5206b and a second tangent axis $T_{B2}$ is positioned on the opposite side of the pocket 5206b. The first and second tangent axes $T_{B1}$ and $T_{B2}$ depicted in FIG. 122 are skewed relative to the pocket axis PA. In other instances, one or both of the tangent axes $T_{B1}$ and $T_{B2}$ can be parallel to the pocket axis PA.

In various instances, the geometry of the pockets 5206 can facilitate the nesting and/or the close arrangement of the pockets 5206 in the staple-forming surface 5202. For example, the surface area of the staple-forming surface 5202 that is covered by the pockets 5206 can be optimized. The "forming ratio" of the staple-forming surface 5202 is the ratio of the non-forming portion 5208 to the forming portion, i.e., the pockets 5206. In at least one instance, the forming ratio can be at least 1:1, for example.

As described herein, the arrangement of staple cavities and staples in a staple cartridge for an end effector can correspond to or match the arrangement of staple-forming pockets in an anvil of the end effector. More specifically, the angular orientation and spacing of each staple cavity can match the angular orientation and spacing of a respective staple-forming pocket. For example, when the staple cavities are arranged in a herringbone pattern, the staple-forming pockets can be arranged in a corresponding herringbone pattern.

In certain instances, an end effector can include a staple cartridge having an arrangement of staple cavities and an anvil having a non-corresponding arrangement of staple-forming pockets. For example, the staple cavities can be obliquely oriented relative to a longitudinal axis and the staple-forming pockets can be oriented parallel to the longitudinal axis. In certain instances, an end effector can be configured to receive different staple cartridges having different arrangements of staple cavities, for example, and the anvil of the end effector may not be compatible with all of the different staple cartridges and permutations of staple cavities therein. In such instances, the anvil can be retrofit or adapted with an attachment, such as an anvil plate, having a suitable arrangement of staple-forming pockets.

Figure 126:
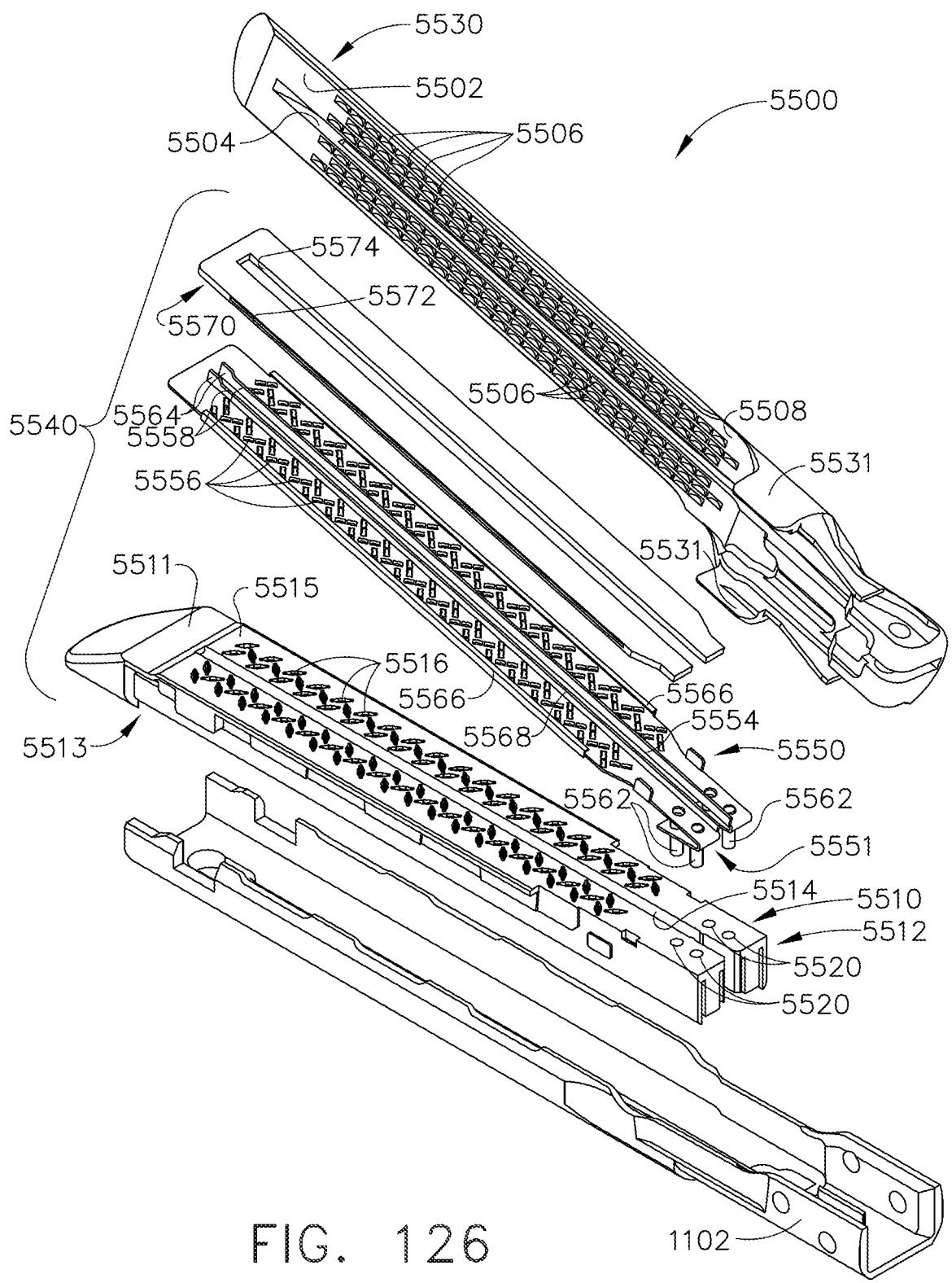
Figure 127:
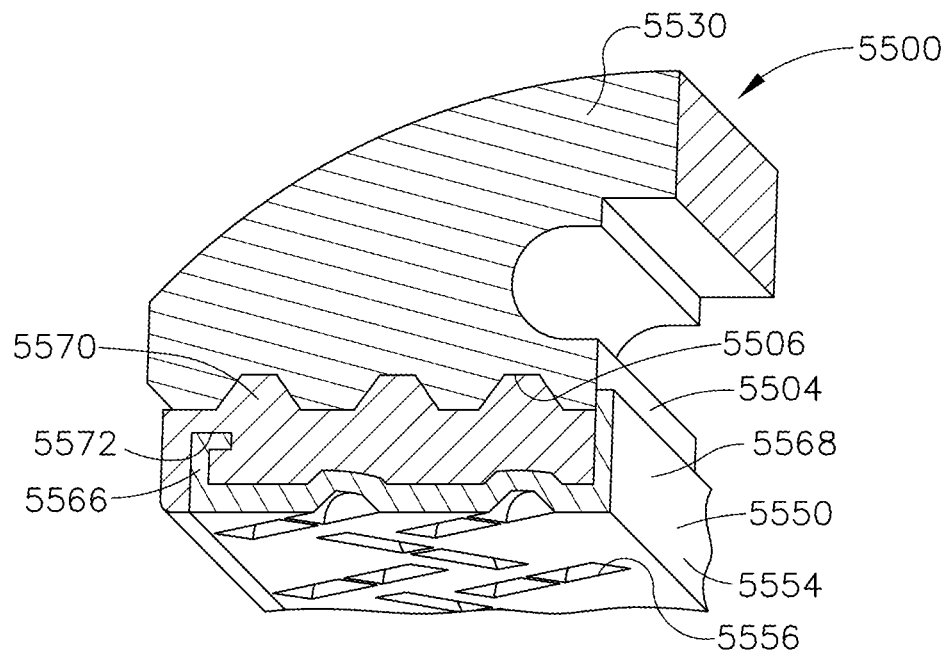
Figure 128:
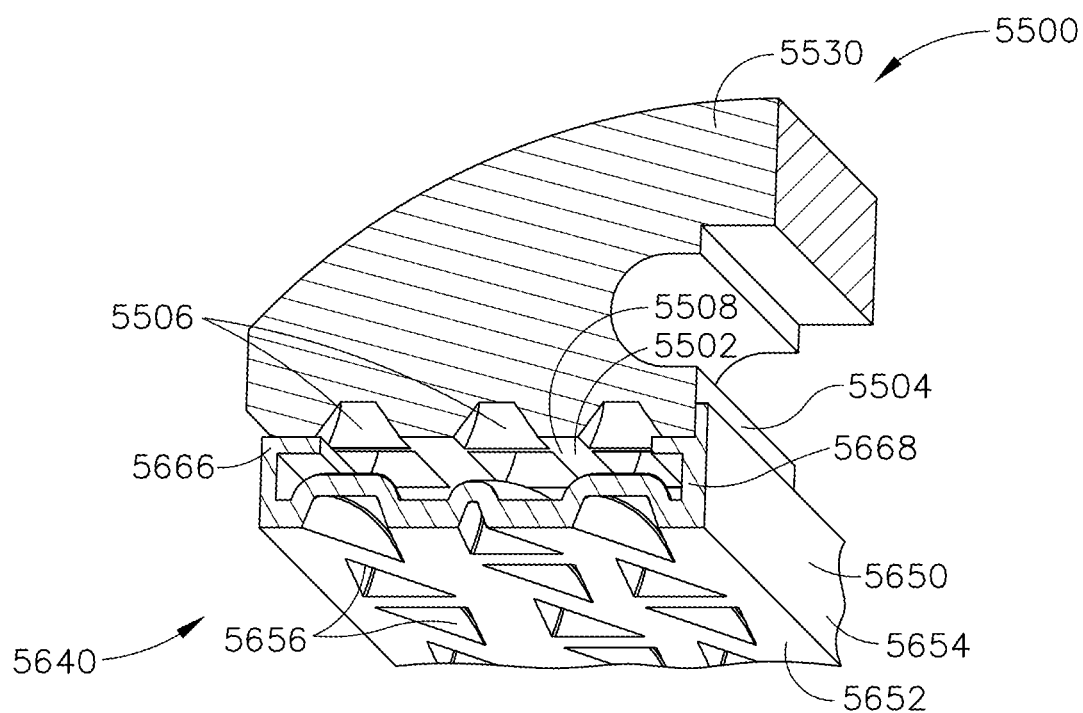

A surgical end effector 5500 is depicted in FIGS. 126-128. Similar to the end effector 1100 (FIGS. 1-4), the end effector 5500 includes the elongate channel 1102, which is configured to operably support a staple cartridge 5510 therein. The staple cartridge 5510 is similar in many aspects to the staple cartridge 1110. For example, the staple cartridge includes a staple cartridge body 5511 having a deck 5515. A longitudinal slot 5514 extends through the deck 5515 from a proximal end portion 5512 of the body 5511 toward a distal end portion 5513 of the body 5511. Angularly-oriented staple cavities 5516 are defined in the cartridge body 5511 and each staple cavity 5516 defines an opening in the deck 5515. The opening of each staple cavity 5516 is oriented at an oblique angle relative to the longitudinal slot 5514. The staple cavities 5516 are arranged in a herringbone pattern. Staples are removably positioned in the staple cavities.

The end effector 5500 also includes an anvil 5530 that is pivotally supported relative to the elongate channel 1102. The anvil 5530 is similar in many aspects to the anvil 1130. For example, the anvil 5530 includes a staple-forming surface 5502 and a longitudinal slot 5504. In certain instances, a firing element and/or a cutting element, such as the sled assembly 1120 and/or the firing member 1760 (FIG. 4), for example, can translate through the longitudinal slot 5504 during at least a portion of a firing stroke. Tissue stops 5531 extend downward toward the staple cartridge 5510 to control the positioning of tissue between the proximal end portion 5512 of the cartridge body 5511 and the anvil 5530. Staple-forming pockets 5506 are defined in the staple-forming surface 5502, which also includes a non-forming portion 5508 that extends around the pockets 5506. The staple-forming pockets 5506 are oriented parallel to the longitudinal slot 5504. In other words, the arrangement of staple-forming pockets 5506 does not match or correspond to the arrangement of staple cavities 5516. If staples were fired from the staple cartridge 5510 into forming contact with the anvil 5530, the majority of such staples would likely be unformed and/or malformed.

The end effector 5500 includes an adaptor assembly 5540, which is configured to adapt the anvil 5530 to a suitable arrangement of staple-forming pockets. The staple cartridge 5510 is part of the adaptor assembly 5540. The adaptor assembly 5540 also includes an anvil plate 5550 and connecting material 5570. A proximal portion of the anvil plate 5550 forms a spring 5551 at which the anvil plate 5550 is attached to the staple cartridge 5510. As such, the anvil plate 5550 is configured to pivot downward toward the staple cartridge 5510 at the proximal spring 5551 when a closing motion is applied to the anvil plate 5550, such as by the anvil 5530, for example. The spring 5551 can bias the anvil plate 5550 toward the configuration shown in FIG. 126, which can facilitate the releasable attachment of the adaptor assembly 5540 to the anvil 5530.

The arrangement of staple-forming pockets in the anvil plate 5550 corresponds to the arrangement of staple cavities 5516 in the staple cartridge. The anvil plate 5550 includes a staple-forming surface 5502 and a longitudinal slot 5554, which is aligned with the longitudinal slot 5504 in the anvil 5530 and the longitudinal slot 5514 in the staple cartridge 5510 when the adaptor assembly 5540 is installed in the end effector 5500. Staple-forming pockets 5556 are defined in the staple-forming surface 5502 and a non-forming portion 5558 (FIG. 126) extends around the staple-forming pockets 5556. In the illustrated embodiment, the staple-forming pockets 5556 are oriented at oblique angles relative to the longitudinal slot 5554. More specifically, the staple-forming pockets 5556 are arranged in a herringbone pattern, which corresponds to the herringbone pattern of the staple cavities 5516. The anvil plate 5550 can be a sheet of metal in which the arrangement of staple-forming pockets has been stamped.

The arrangement of staple-forming pockets 5556 in the anvil plate 5550 corresponds to the arrangement of staple cavities 5516 in the staple cartridge. In other words, each staple-forming pocket 5556 in the anvil plate 5550 corresponds to the angle and position of a staple cavity 5516. The reader will appreciate that a staple cartridge can include a variety of different arrangements of staple cavities, and various exemplary arrangements of staple cavities are described herein. For example, a staple cartridge can include a longitudinally-repetitive pattern of obliquely-oriented staple cavities and/or one or more parallel and/or angularly-offset staple cavities. Additionally or alternatively, a staple cartridge can include multiple distinct patterns of staple cavities. In still other instances, the arrangement of staple cavities can vary laterally and/or longitudinally along the cartridge body. Whatever the arrangement of staple cavities in a staple cartridge, a corresponding arrangement of staple-forming pockets can be provided by the complementary anvil plate 5550 of the adaptor assembly 5540.

The anvil plate 5500 is connectable to the staple cartridge 5510, and the connecting material 5570 is attached to the anvil plate 5500. In use, when the staple cartridge 5510 is inserted into the elongate channel 1102, the anvil plate 5500 and the connecting material 5570 of the adaptor assembly 5540 are also disposed between the elongate channel 1102 and the anvil 5530. In certain instances, the anvil 5530 can be pivoted downward toward the elongate channel 1102 to secure or otherwise attach the anvil plate 5550 to the staple-forming surface 5502 of the anvil 5530 with the connecting material 5570. Additionally or alternatively, the spring member 5551 can bias the anvil plate 5550 and the connecting material 5570 thereon into and/or toward attachment with the anvil 5530. When the adaptor assembly 5540 is installed in the end effector 5500, the anvil 5530 has effectively been retrofit or adapted for use with the staple cartridge 5510.

The staple cartridge 5510 and the anvil plate 5550 may include alignment features for aligning the staple cavities 5516 in the staple cartridge 5510 with the corresponding staple-forming pockets 5556 in the anvil plate 5500. For example, the staple cartridge 5510 includes alignment apertures 5520 (FIG. 126), and the anvil plate 5550 includes alignment posts or pins 5562. The alignment pins 5562 are received by the alignment apertures 5520 to position the anvil plate 5550 relative to the staple cartridge 5510. For example, the alignment pins 5562 can be press fit into the alignment apertures 5520. The connection between the alignment apertures 5520 and the alignment pins 5562 is configured to longitudinally align the staple cartridge 5510 and the anvil plate 5550, for example.

In certain instances, the manufacturer and/or distributor can provide the assembly 5540 pre-assembled. For example, the anvil plate 5550 can be press fit into engagement with the staple cartridge 5510 before a surgeon or assistant thereto obtains the assembly 5540 for a surgical procedure. In other instances, the surgeon and/or assistant thereto can assemble the assembly 5540.

The anvil plate 5550 also includes alignment features for aligning the anvil plate 5550 with the anvil 5530. For example, the anvil plate 5550 includes distal alignment flanges 5564. The distal alignment flanges 5564 are received by the longitudinal slot 5504 in the anvil 5530 to position the anvil plate 5550 relative to the anvil 5530. For example, the distal alignment flanges 5564 can be press fit into the longitudinal slot 5504. The connection between the alignment flanges 5564 and the longitudinal slot 5504 is configured to laterally align the anvil plate 5550 and the anvil 5530, for example.

The connecting material 5570 is a flexible material. For example, the connecting material 5570 can comprise an elastomer and/or low density polyethylene. In various instances, the connecting material 5570 can be an overmold on the anvil plate 5550. When adhered or otherwise secured to the anvil 5530, the connecting material 5570 is configured to assume a deformed configuration that matches the profile of the staple-forming surface 5502. For example, the unformed configuration of the connecting material 5570 is depicted in FIG. 126 and the formed configuration of the connecting material 5570 is depicted in FIG. 127. Referring primarily to FIG. 127, the connecting material 5570 flows into and fills the staple-forming pockets 5506. In other words, the staple-forming pockets 5506 imprint in the connecting material 5570. In such instances, the connecting material 5570 can fortify the anvil plate 5550 during a forming process. For example, the connecting material 5570 between the anvil plate 5550 and the anvil 5530 can provide a backing for the anvil plate 5550 to prevent and/or limit deformation of the anvil plate 5550 relative to the anvil 5530 when the anvil plate 5550 is impacted and subjected to other forces during use.

The connecting material 5570 includes a channel 5572. The channel 5572 extends along a portion of the length thereof. Although not shown in FIG. 126, a similar channel 5572 can be defined in the connecting material 5570 along the opposite side of the adaptor assembly 5540. A lip 5566 of the anvil plate 5550 is positioned in the channel 5572. The lip 5566 is substantially U-shaped. In other instances, the lip 5566 can be L-shaped, linear, and/or contoured, for example. The anvil plate 5500 also includes an inner ridge 5568, which is aligned with a longitudinal slot 5574 (FIG. 126) in the connecting material 5570 and the longitudinal slot 5504 in the anvil 5530. The ridge 5568 is configured to facilitate the alignment of the adaptor assembly 5540 along the length of the end effector 5500. In various instances, the connecting material 5570 can be molded over the anvil plate 5550. For example, the connecting material 5570 can be molded around the lip 5566 and/or the ridge 5568.

A portion of the end effector 5500 is also depicted in FIG. 128. An adaptor assembly 5640 is installed in the end effector 5500 in FIG. 128. The adaptor assembly 5640 is similar in many aspects to the adaptor assembly 5540. For example, the adaptor assembly 5640 includes an anvil plate 5650 having a staple-forming surface 5652 and a longitudinal slot 5654, which is aligned with the longitudinal slot 5504 in the anvil 5530. Staple-forming pockets 5656 are defined in the staple-forming surface 5652 and a non-forming portion 5658 extends around the staple-forming pockets 5656. The staple-forming pockets 5656 are oriented at oblique angles relative to the longitudinal slot 5654. More specifically, the staple-forming pockets 5656 are arranged in a herringbone pattern, which corresponds to the herringbone pattern of the staple cavities 5516 (FIG. 126). The anvil plate 5650 can be a sheet of metal in which the arrangement of staple-forming pockets has been stamped.

The adaptor assembly 5640 does not include a deformable material, such as the deformable material 5570. Rather, the anvil plate 5650 is configured to directly engage the anvil 5530. The anvil plate 5650 includes a lip 5666, which is positioned against the staple-forming surface 5502. The lip 5666 is substantially U-shaped. In other instances, the lip 5666 can be L-shaped, linear, and/or contoured, for example. The anvil plate 5600 also includes an inner ridge 5668, which is aligned with the longitudinal slot 5504 in the anvil 5530. The ridge 5668 is configured to facilitate the alignment of the adaptor assembly 5640 along the length of the end effector 5600.

In other instances, the anvil plate 5650 can be embedded in the staple-forming surface 5502 of the anvil 5530. For example, staple-forming pockets 5656 of the anvil plate 5650 can at least partially nest within the staple-forming pockets 5506 in the anvil 5530. Although the arrangement, quantity, and/or geometry of the staple-forming pockets 5656 are different than the arrangement, quantity, and/or geometry of the staple-forming pockets 5506, portions of the staple-forming pockets 5656 can be positioned within portions of the staple-forming pockets 5506.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures or characteristics illustrated or described in connection with one embodiment may be combined in whole or in part, with the features, structures, or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method, comprising:
    obtaining a staple cartridge comprising cartridge body comprising a plurality of surgical staples stored therein, wherein the cartridge body further comprises an active tissue stop arrangement movably coupled thereto, wherein the active tissue stop arrangement comprises;
    a pair of movable tissue stops, wherein one movable tissue stop is movably coupled to one side of the cartridge body and another movable tissue stop is movably coupled to another side of the cartridge body, wherein each movable tissue stop comprises:
        a lower tissue stop portion defining a lower cavity therein;
        an upper tissue stop portion movably supported in each lower cavity, wherein each lower tissue stop portion and corresponding upper tissue stop portion are pivotally supported on a corresponding side of the staple cartridge for pivotal travel relative thereto about a common pivot axis; and
        a biaser for biasing each upper tissue stop out of the corresponding lower cavity, and wherein said method further comprises installing the staple cartridge in an end effector, wherein the end effector comprises an anvil comprising a fixed tissue stop arrangement such that when the staple cartridge is installed in the end effector, the active tissue stop arrangement and the fixed tissue stop arrangement prevents tissue from extending proximally beyond a proximal-most surgical staple stored in the cartridge body.

2. The method of claim 1, wherein the anvil is movably supported relative to an elongate channel and is movable relative thereto between an open and closed position, and wherein said installing comprises removably seating the staple cartridge in the elongate channel.

3. The method of claim 1, further comprising retaining the movable tissue stops in a collapsed orientation during said installing of the staple cartridge in the end effector.

4. The method of claim 3, further comprising permitting the movable tissue stops to expand to an expanded orientation after the staple cartridge has been installed in the end effector and the anvil is moved to an open position.

5. The method of claim 4, wherein the staple cartridge further comprises a removable staple cover attached to the cartridge body, wherein the removable staple cover retains the surgical staples in the cartridge body and further retains the movable tissue stops in the collapsed orientation, and wherein said permitting the movable tissue stops to expand to the expanded orientation comprises removing the removable staple cover from the cartridge body.

6. The method of claim 4, wherein each of the movable tissue stops is biased into the expanded position.

7. The method of claim 6, wherein the staple cartridge further comprises means for preventing each of the movable tissue stops from expanding beyond a predetermined fully expanded orientation.

8. The method of claim 4, wherein when the movable tissue stops are in a fully expanded position and the anvil is in a fully open position, each of the movable tissue stops contact a corresponding portion of the anvil.

9. The method of claim 1, wherein the staple cartridge comprises a plurality of staple cavities arranged in a herringbone pattern.

10. A method, comprising:
    obtaining a staple cartridge comprising cartridge body that defines a cartridge deck surface, wherein the cartridge body comprises a plurality of surgical staples stored therein, wherein the cartridge body further comprises a pair of upstanding cartridge tissue stops that extend upward from a proximal end of the cartridge deck surface; and
    installing the staple cartridge in an end effector, wherein the end effector comprises an anvil comprising a pair of anvil tissue stops protruding downward from a proximal end of the anvil such that when the staple cartridge is installed in the end effector, the upstanding cartridge tissue stops cooperate with the anvil tissue stops to prevent tissue from extending proximally beyond a proximal-most surgical staple stored in the cartridge body, and wherein when the anvil is in a fully closed position, an upper end of each of the cartridge tissue stops is received in a corresponding tissue stop cavity formed in the anvil.

11. The method of claim 10, wherein the anvil further comprises a pair of distal tissue stops located distal to the anvil tissue stops and the cartridge tissue stops.

12. The method of claim 11, wherein when the anvil is in the fully closed position, the distal tissue stops do not extend below the cartridge deck surface.

13. The method of claim 10, wherein the staple cartridge comprises a plurality of staple cavities arranged in a herringbone pattern.

14. A method of operating a surgical stapler, wherein the surgical stapler comprises an elongate channel and an anvil movably supported relative to the elongate channel, wherein the anvil comprises a pair of fixed tissue stops protruding therefrom, and wherein said method comprises:
    installing a staple cartridge in the elongate channel when the anvil is in an open position, wherein the staple cartridge comprises a cartridge body comprising a movable tissue stop corresponding to each fixed tissue stop on the anvil, wherein each said movable tissue stop comprises:
        a first movable tissue stop portion movably coupled to the cartridge body, wherein the first movable tissue stop portion is configured to be received within a corresponding cavity in the cartridge body; and a second movable tissue stop portion corresponding to each first movable tissue stop portion and being movable relative thereto between a collapsed orientation in which the second movable tissue stop is received within the corresponding first tissue stop portion and an expanded orientation in which the second movable tissue stop portion extends out of the corresponding first tissue stop portion, and wherein said method further comprises:

positioning a target tissue between the anvil and the staple cartridge such that the fixed tissue stops and each movable tissue stop prevents the target tissue from extending proximally beyond a proximal-most staple in the staple cartridge; and moving the anvil to a closed position.

15. A method for operating a surgical stapler, comprising:

installing a surgical staple cartridge into a channel of the surgical stapler when an anvil of the surgical stapler is in an open position;

abutting a target tissue against fixed tissue stops protruding from the anvil and movable tissue stops protruding out of the surgical staple cartridge, wherein each movable tissue stop comprises a first portion and a second portion, wherein each first portion and each second portion is movable relative to each other between an expanded orientation and a collapsed orientation;

moving the anvil to a closed position to clamp the target tissue between the anvil and the surgical staple cartridge such that movable tissue stops are moved to the collapsed orientation; and actuating the surgical stapler to drive surgical staples stored in the surgical staple cartridge through the target tissue and into forming contact with the anvil.

16. The method of claim 15, further comprising:
returning the anvil to the open position; and
returning the movable tissue stops to the expanded orientation.

17. The method of claim 16, wherein each movable tissue stop comprises a biaser configured to bias the second portion into the expanded orientation.

* * * * *